United States Patent
Kobilka et al.

(10) Patent No.: US 7,912,654 B2
(45) Date of Patent: Mar. 22, 2011

(54) CRYSTAL STRUCTURE $\beta_2$ ADRENORECEPTOR

(75) Inventors: Brian K. Kobilka, Palo Alto, CA (US); Gebhard F. X. Schertler, Cambridge (GB)

(73) Assignees: The Board of Trustees of the Leland Stanford Junior University, Palo Alto, CA (US); Heptares Therapeutics Limited, Welwyn Garden, Hertfordshire (DE)

( * ) Notice: Subject to any disclaimer, the term of this patent is extended or adjusted under 35 U.S.C. 154(b) by 0 days.

(21) Appl. No.: 12/283,988

(22) Filed: Sep. 16, 2008

(65) Prior Publication Data

US 2009/0271162 A1    Oct. 29, 2009

Related U.S. Application Data

(60) Provisional application No. 60/960,300, filed on Sep. 21, 2007.

(51) Int. Cl.
G01N 33/50 (2006.01)
G01N 33/00 (2006.01)

(52) U.S. Cl. .............................. 702/19; 702/27; 436/86

(58) Field of Classification Search ........................ None
See application file for complete search history.

(56) References Cited

U.S. PATENT DOCUMENTS

2005/0203131 A1    9/2005    Mammen et al.

FOREIGN PATENT DOCUMENTS

WO    01/81627    11/2001

OTHER PUBLICATIONS

Cohen et al. Molecular Modeling software and material for medicinal chemmistry. J. Med. Chem. 1990, 33 (3), 883-894.*
Spina et al. beta2-Adrenoceptor agonist. In Drugs for the Treatment of Respiratory Diseases (2003) Editor(s): Spina, Domenico pp. 56-104, Cambridge University Press: Cambridge, UK.*
Wiencek, J. M. New Strategies for Protein Crystal Growth. Ann. Rev. Biomed. Eng. 1999, 1, 505-534).*
Cherezov; et al., "High-resolution crystal structure of an engineered human beta2-adrenergic G protein-coupled receptor", Science, Nov. 23, 2007, 318(5854):1258-65.
Rasmussen; et al., "Crystal structure of the human beta2 adrenergic G-protein-coupled receptor", Nature, Nov. 15, 2007, 450(7168):383-7.
Rosenbaum; et al., "GPCR Engineering Yields High-Resolution Structural Insights into b2-Adrenergic Receptor Function", Science, Nov. 23, 2007, 318:1266-1273.

* cited by examiner

*Primary Examiner* — Nashaat T Nashed
(74) *Attorney, Agent, or Firm* — Bozicevic, Field & Francis LLP; James S. Keddie

(57) ABSTRACT

A computer readable medium comprising atomic coordinates for the human $\beta_2$ adrenoreceptor is provided. The computer readable medium programming for displaying a molecular model of the human $\beta_2$ adrenoreceptor, programming for identifying a compound that binds to said human $\beta_2$ adrenoreceptor and/or a database of structures of known test compounds. Also provided is a method comprising computationally identifying a compound that binds to the human $\beta_2$ adrenoreceptor using the atomic coordinates.

6 Claims, 8 Drawing Sheets
(7 of 8 Drawing Sheet(s) Filed in Color)

US 7,912,654 B2

CRYSTAL STRUCTURE β₂ ADRENORECEPTOR

GOVERNMENT RIGHTS

This work was supported in part by federal grant numbers GM082028-01 from the National Institutes of Health, GM56169 from the National Institute of General Medical Sciences and NS28471 from the National Institute of Neurological Disorders and Stroke. The federal government has certain rights in this invention.

BACKGROUND

GPCRs are remarkably versatile signaling molecules that are responsible for the majority of transmembrane signal transduction in response to hormones and neurotransmitters. They share a common structural signature of seven membrane-spanning helices with an extracellular amino terminus and an intracellular carboxyl terminus (FIG. 1). Our understanding of GPCR structure has been based largely on the crystal structures of the inactive state of rhodopsin. Rhodopsin is better suited for structural studies than most other GPCRs because it is possible to obtain large quantities of functional protein from bovine retina. Rhodopsin is also a remarkably stable GPCR, retaining function under conditions that denature other GPCRs.

The β₂AR is one of the most extensively characterized members of this large family of membrane proteins. The sites of interactions between agonists and the receptor have been characterized by mutagenesis studies, and biophysical methods have been used to study the conformational changes associated with agonist binding and activation. The β₂AR is efficiently expressed in Sf9 cells and can be purified to homogeneity using antibody and ligand affinity chromatography. The β₂AR is biochemically pure following chromatography using an antibody resin that binds to an amino terminal Flag epitope; however, more than half of the receptor is not functional. Affinity chromatography, an important early development in GPCR biochemistry, may be used to isolate functional β₂AR protein. Purified β₂AR bound to an antagonist remains stable and soluble at concentrations up to 50 mg/ml for up to a week at room temperature in the detergent dodecylmaltoside. However, the β₂AR is unstable in detergents used to obtain crystals of bovine rhodopsin. Extensive sparse matrix screening (over 2000 conditions at 4° and 20°) failed to produce diffraction-quality crystals of wild type β₂AR.

This disclosure provides the atomic coordinates of human wild type β₂AR.

SUMMARY OF THE INVENTION

A computer readable medium comprising atomic coordinates for the human β₂ adrenoreceptor is provided. The computer readable medium may further contain programming for displaying a molecular model of the human β₂ adrenoreceptor, programming for identifying a compound that binds to the human β₂ adrenoreceptor and/or a database of structures of known test compounds, for example. In certain cases, the atomic coordinates are set forth in Table 2. The amino acid sequences shown in Table 2 are set forth in the accompanying Sequence Listing as SEQ ID NOS:1 and 2.

A method is also provided. In general terms, the method comprises computationally identifying a compound that binds to the β₂ adrenoreceptor using the atomic coordinates.

BRIEF DESCRIPTION OF THE FIGURES

The patent or application file contains at least one drawing executed in color. Copies of this patent or patent application publication with color drawing(s) will be provided by the Office upon request and payment of the necessary fee.

DEFINITIONS

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with general dictionaries of many of the terms used in this disclosure. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Figure 1:
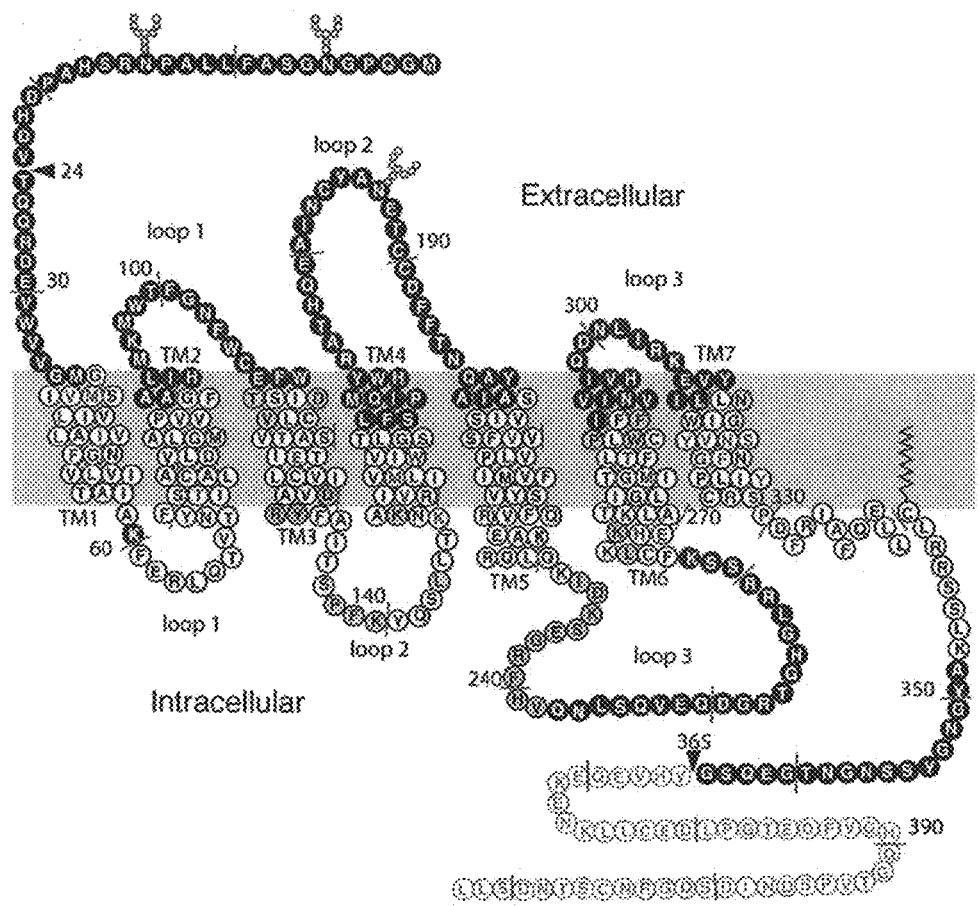
FIG. 1. Diagram of the secondary structure and predicted membrane topology for the β₂AR. The membrane bilayer is indicated by the blue box. Black circles with white letters indicate disordered residues not included in the model. Grey letters and circles indicate residues not included in the β₂AR365 truncation used for crystallography. Red letters indicate amino acids for which side chain electron density was not modeled. Yellow residues indicate amino acids implicated in ligand binding from mutagenesis studies. Orange residues indicate the conserved DRY sequence. Green residues form the Fab5 epitope, and pink residues are packed against the Fab5 constant domain in the lattice. Small blue circles indicate glycosylation sites. Glycosylation was removed enzymatically with PNGaseF. Red lines indicate ten amino acid increments.

"G-protein coupled receptors", or "GPCRs" are polypeptides that share a common structural motif, having seven regions of between 22 to 24 hydrophobic amino acids that form seven alpha helices, each of which spans a membrane. As illustrated in FIG. 1, each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. GPCR structure and classification is generally well known in the art, and further discussion of GPCRs may be found in Probst, DNA Cell Biol. 1992 11:1-20; Marchese et al Genomics 23: 609-618, 1994; and the following books: Jürgen Wess (Ed) Structure-Function Analysis of G Protein-Coupled Receptors published by Wiley-Liss (1st edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994). A schematic representation of an exemplary GPCR is shown in FIG. 1.

The term "$\beta_2$ adrenoreceptor" is the beta-adrenergic receptor. In the human genome, the $\beta_2$ adrenoreceptor is encoded by the following locus: Chr 5: 148.19-148.19 Mb. In addition to the human $\beta_2$ adrenoreceptor, (e.g., the sequence described by Genbank accession number NP_000015), the mouse $\beta_2$ adrenoreceptor (e.g., as described by Genbank accession no. NM_007420) or other mammalian $\beta_2$ adrenoreceptor may be employed. When the term "$\beta_2$ adrenoreceptor" is associated with a part particular species, e.g., as in "the human $\beta_2$ adrenoreceptor", the term is intended to encompass wild-type polymorphic variants and certain other active variants of the $\beta_2$ adrenoreceptor from that species. A "human $\beta_2$ adrenoreceptor" has an amino acid sequence that is at least 95% identical to (e.g., at least 95% or at least 98% identical to) the "human $\beta_2$ adrenoreceptor" of Genbank accession number NP_000015.

The term "atomic coordinates" refers to the Cartesian coordinates corresponding to an atom's spatial relationship to other atoms in a molecule or molecular complex. Atomic coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The atomic coordinates of the present invention may be modified from the original set provided in Table 2 is by mathematical manipulation, such as by inversion or integer additions or subtractions. As such, it is recognized that the structural coordinates of the present invention are relative, and are in no way specifically limited by the actual x, y, z coordinates of Table 2.

"Root mean square deviation" is the square root of the arithmetic mean of the squares of the deviations from the mean, and is a way of expressing deviation or variation from the structural coordinates described herein. The present invention includes all embodiments comprising conservative substitutions of the noted amino acid residues resulting in same structural coordinates within the stated root mean square deviation. It will be obvious to the skilled practitioner that the numbering of the amino acid residues of $\beta_2$ AR may be different than that set forth herein, and may contain certain conservative amino acid substitutions that yield the same three dimensional structures as those defined by Table 2. Corresponding amino acids and conservative substitutions in other isoforms or analogues are easily identified by visual inspection of the relevant amino acid sequences or by using commercially available homology software programs (e.g., MODELLAR, MSI, San Diego, Calif.).

The terms "system" and "computer-based system" refer to the hardware means, software means, and data storage means used to analyze the information of the present invention. The minimum hardware of the computer-based systems of the present invention comprises a central processing unit (CPU), input means, output means, and data storage means. As such, any convenient computer-based system may be employed in the present invention. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Computer readable medium" as used herein refers to any storage or transmission medium that participates in providing instructions and/or data to a computer for execution and/or processing. Examples of storage media include floppy disks, magnetic tape, UBS, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. A file may be stored in permanent memory. A computer readable medium is physical and is not a signal.

With respect to computer readable media, "permanent memory" refers to memory that is permanently stored on a data storage medium. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

To "record" data, programming or other information on a computer readable medium refers to a process for storing information, using any convenient method. Any convenient data storage structure may be chosen, based on the means used to access the stored information. A variety of data processor programs and formats can be used for storage, e.g. word processing text file, database format, etc.

A "memory" or "memory unit" refers to any device which can store information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

In certain embodiments, a system includes hardware components which take the form of one or more platforms, e.g., in the form of servers, such that any functional elements of the system, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any convenient type of computer platform, e.g., such as a server, main-frame computer, a work station, etc. Where more than one platform is present, the platforms may be connected via any convenient type of connection, e.g., cabling or other communication system including wireless systems, either networked or otherwise. Where more than one platform is present, the platforms may be co-located or they may be physically separated. Various operating systems may be employed on any of the computer platforms, where representative operating systems include Windows, MacOS, Sun Solaris, Linux, OS/400, Compaq Tru64 Unix, SGI IRIX, Siemens Reliant Unix, and others. The functional elements of system may also be implemented in accordance with a variety of software facilitators, platforms, or other convenient method.

Items of data are "linked" to one another in a memory when the same data input (for example, filename or directory name or search term) retrieves the linked items (in a same file or not) or an input of one or more of the linked items retrieves one or more of the others.

Subject computer readable media may be at a "remote location", where "remote location," means a location other than the location at which the MALDI ionization and detection apparatus. For example, a remote location could be another location (e.g., office, lab, etc.) in the same city, another location in a different city, another location in a different state, another location in a different country, etc. As such, when one item is indicated as being "remote" from another, what is meant is that the two items may be in the same room but separated, or at least in different rooms or different buildings, and may be at least one mile, ten miles, or at least one hundred miles apart.

"Communicating" information references transmitting the data representing that information as, e.g., electrical or optical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the Internet or Intranets including email transmissions and information recorded on websites and the like.

DETAILED DESCRIPTION OF EXEMPLARY EMBODIMENTS

As noted above, a computer readable medium comprising atomic coordinates for the $\beta_2$ adrenoreceptor is provided, as well as a method of computationally identifying a compound that binds to the $\beta_2$ adrenoreceptor using the atomic coordinates. In the following description, the computer readable medium is described first, followed by a discussion of methods in which the computer readable medium may be employed.

Computer Models and Computer Systems

In certain embodiments, the above-described computer readable medium may further comprise programming for displaying a molecular model of the human $\beta_2$ adrenoreceptor, programming for identifying a compound that binds to the human β2 adrenoreceptor and/or a database of structures of known test compounds, for example. In certain embodiments, the atomic coordinates of the computer readable medium may be the atomic coordinates set forth in Table 2 below. A computer system comprising the computer-readable medium is also provided. The model may be displayed to a user via a display, e.g., a computer monitor, for example.

As noted above, the atomic coordinates may be employed in conjunction with a modeling program to provide a model of $\beta_2$ AR. As used herein, the term "model" refers to a representation in a tangible medium of the three dimensional structure of $\beta_2$ AR. For example, a model can be a representation of the three dimensional structure in an electronic file, on a display, e.g., a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate is the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, backbone traces, ribbon diagrams, and electron density maps. Exemplary modeling programs include, but are not limited to PYMOL, GRASP, or O software, for example.

In another embodiment, the invention provides a computer system having a memory comprising the above-described atomic coordinates; and a processor in communication with the memory, wherein the processor generates a molecular model having a three dimensional structure representative of $\beta_2$ AR. The processor can be adapted for identifying a candidate compound having a structure that is capable of binding to $\beta_2$ AR for example.

In the present disclosure, the processor may execute a modeling program which accesses data representative of the $\beta_2$ AR structure. In addition, the processor also can execute another program, a compound modeling program, which uses the three-dimensional model of $\beta_2$ AR to identify compounds having a chemical structure that binds to $\beta_2$ AR. In one embodiment the compound identification program and the structure modeling program are the same program. In another embodiment, the compound identification program and the structure modeling program are different programs, which programs may be stored on the same or different storage medium.

A number of exemplary public and commercial sources of libraries of compound structures are available, for example the Cambridge Structural Database (CSD), the Chemical Directory (ACD) from the company MDL (US), ZINC (Irwin and Shoichet, J. Chem. Inf Model. (2005) 45:177-82) as well as various electronic catalogues of publicly available compounds such as the National Cancer Institute (NCI, US) catalogue, ComGenex catalogue (Budapest, Hungary), and Asinex (Moscow, Russia). Such libraries may be used to allow computer-based docking of many compounds in order to identify those with potential to interact with the human $\beta_2$ adrenoreceptor using the atomic coordinates described herein.

Methods

In certain cases, the method may further comprise a testing a compound to determine if it binds and/or modulates the $\beta_2$ adrenoreceptor, using the atomic coordinates provided herein. In some embodiments, the method may further comprise obtaining the compound (e.g., purchasing or synthesizing the compound) and testing the compound to determine if it modulates (e.g., activates or inhibits) the $\beta_2$ adrenoreceptor (e.g., acts an agonist, antagonist or inverse agonist of the human $\beta_2$ adrenoreceptor).

In some embodiments, the method employs a docking program that computationally tests known compounds for binding to the human $\beta_2$ adrenoreceptor. Structural databases of known compounds are known in the art. In certain cases, compounds that are known to bind and modulate $\beta_2$ AR may be computationally tested for binding to $\beta_2$ AR, e.g., in order to identify a binding site and/or facilitate the identification of active variants of an existing compound. Such compounds include compounds that are know to be $\beta_2$ AR agonists such as, for example: albuterol, albuterol sulfate, salbutamol (CAS RN 35763-26-9), clenbuterol, adrafinil, and SR58611A (described in Simiand et al., Eur J Pharmacol, 219:193-201 (1992)), clonidine (CAS RN 4205-90-7), yohimbine (CAS RN 146-48-5) or yohimbine hydrochloride, arbutamine; befunolol; BRL 26830A; BRL 35135; BRL 37344; bromoacetylalprenololmenthane; broxaterol; carvedilol; CGP 12177; cimaterol; cirazoline; CL 316243; Clenbuterol; denopamine; dexmedetomidine or dexmedetomidine hydrochloride; Dobutamine, dopexamine, Ephedrine, Epinephrine, Etilefrine; Fenoterol; formoterol; formoterol fumarate; Hexoprenaline; higenamine; ICI D7114; Isoetharine; Isoproterenol; Isoxsuprine; levalbuterol tartrate hydrofluoroalkane; lidamidine; mabuterol; methoxyphenamine; modafinil; Nylidrin; Orciprenaline; Oxyfedrine; pirbuterol; Prenalterol; Procaterol; ractopamine; reproterol; Ritodrine; Ro 363; salmeterol; salmeterol xinafoate; Terbutaline; tetramethylpyrazine; tizanidine or tizanidine hydrochloride; Tretoquinol; tulobuterol; Xamoterol; or zinterol. Additional non-limiting examples include Apraclonidine, Bitolterol Mesylate, Brimonidine or Brimonidine tartrate, Dipivefrin (which is converted to epinephrine in vivo), Epinephrine, Ergotamine, Guanabenz, guanfacine, Metaproterenol, Metaraminol, Methoxamine, Methyldopa, Midodrine (a prodrug which is metabolized to the major metabolite desglymidodrine formed by deglycination of midodrine), Oxymetazoline, Phenylephrine, Phenylpropanolamine, Pseudoephedrine, alphamethylnoradrenaline, mivazerol, natural ephedrine or D(−)ephedrine, any one or any mixture of two, three, or four of the optically active forms of ephedrine, CHF1035 or nolomirole hydrochloride (CAS RN 138531-51-8), AJ-9677 or TAK677 ([3-[(2R)-[[(2R)-(3-chlorophenyl)-2-hydroxyethyl]amino] propyl]-1H-indol-7-1-yloxy]acetic acid), MN-221 or KUR-1246 ((−)-bis(2-{[(2S)-2-({(2R)-2-hydroxy-2-[4-hydroxy-3-(2-hydroxyethyl)phenyl-1]ethyl}amino)-1,2,3,4-tetrahydronaphthalen-7-yl]oxy}-N,N-dimethylacetamide) monosulfate or bis(2-[[(2S)-2-([(2R)-2-hydroxy-2-[4-hydroxy-3-(2-hydroxyethyl)-phenyl]ethyl]amino)-1,2,3,4-tetrahydronaphthalen-7-yl]oxy]-N,N-dimethylacetamide) sulfate or CAS RN 194785-31-4), levosalbutamol (CAS RN 34391-04-3), lofexidine (CAS RN 31036-80-3) or TQ-1016 (from TheraQuest Biosciences, LLC). Compounds that are know to be $\beta_2$ AR antagonists such as, for example: alpha-methylpropranolol, IPS 339, ICI 118,551, S 37-429, S 32-468, ICI 78,462, H35/25, butoxamine, propranolol, timolol, atenolol, practolol, acebutolol, butoxamine, carteolol, esmolol, labetolol, metoprolol, nadolol, penbutolol, propranolol, and timolol, may also be tested.

In other cases, the method may include designing a compound that binds to the human $\beta_2$ adrenoreceptor, either de novo, or by modifying an existing compound that is known to bind to the human $\beta_2$ adrenoreceptor.

In particular embodiments, the method may comprise computationally identifying a compound that binds to the human $\beta_2$ adrenoreceptor using the atomic coordinates set forth in Table 2. In other embodiments, the method may comprise computationally identifying a compound that binds to the ligand binding site of human $\beta_2$ adrenoreceptor, wherein the ligand binding site contains the following amino acids Asp113, V114, Phe 289, Phe290 and Asn 312 of SEQ ID NO:1, as well as those atoms that are close thereto, e.g., within 5 Å, within 10 Å, within 20 Å or within 30 Å of those amino acids.

A method that comprises receiving a set of atomic coordinates for the human $\beta_2$ adrenoreceptor; and identifying a compound that binds to said human $\beta_2$ adrenoreceptor using the coordinates is also provided, as is a method comprising: forwarding to a remote location a set of atomic coordinates for the human $\beta_2$ adrenoreceptor; and receiving the identity of a compound that binds to the human $\beta_2$ adrenoreceptor.

In certain embodiments, a computer system comprising a memory comprising the atomic coordinates of $\beta_2$-AR is provided. The atomic coordinates are useful as models for rationally identifying compounds that bind $\beta_2$-AR. Such compounds may be designed either de novo, or by modification of a known compound, for example. In other cases, binding compounds may be identified by testing known compounds to determine if the "dock" with a molecular model of $\beta_2$-AR. Such docking methods are generally well known in the art.

The structure data provided herein can be used in conjunction with computer-modeling techniques to develop models of ligand-binding sites on $\beta_2$-AR selected by analysis of the crystal structure data. The site models characterize the three-dimensional topography of site surface, as well as factors including van der Waals contacts, electrostatic interactions, and hydrogen-bonding opportunities. Computer simulation techniques are then used to map interaction positions for functional groups including but not limited to protons, hydroxyl groups, amine groups, divalent cations, aromatic and aliphatic functional groups, amide groups, alcohol groups, etc. that are designed to interact with the model site. These groups may be designed into a candidate compound with the expectation that the candidate compound will specifically bind to the site.

The ability of a candidate compound to bind to $\beta_2$-AR can be analyzed prior to actual synthesis using computer modeling techniques. Only those candidates that are indicated by computer modeling to bind the target with sufficient binding energy (i.e., binding energy corresponding to a dissociation constant with the target on the order of $10^{-2}$ M or tighter) may be synthesized and tested for their ability to bind to and modulate $\beta_2$-AR. Such assays are known to those of skill in the art. The computational evaluation step thus avoids the unnecessary synthesis of compounds that are unlikely to bind $\beta_2$-AR with adequate affinity.

A candidate compound may be computationally identified by means of a series of steps in which chemical entities or fragments are screened and selected for their ability to associate with individual binding target sites on $\beta_2$-AR. One skilled in the art may use one of several methods to screen chemical entities or fragments for their ability to associate with $\beta_2$-AR, and more particularly with target sites on $\beta_2$-AR. The process may begin by visual inspection of, for example a target site on a computer screen, based on $\beta_2$-AR coordinates, or a subset of those coordinates. Selected fragments or chemical entities may then be positioned in a variety of orientations or "docked" within a target site of $\beta_2$-AR as defined from analysis of the crystal structure data. Docking may be accomplished using software such as Quanta (Molecular Simulations, Inc., San Diego, Calif.) and Sybyl (Tripos, Inc. St. Louis, Mo.) followed by energy minimization and molecular dynamics with standard molecular mechanics forcefields such as CHARMM (Molecular Simulations, Inc., San Diego, Calif.) and AMBER (University of California at San Francisco).

Specialized computer programs may also assist in the process of selecting fragments or chemical entities. These include but are not limited to: GRID (Goodford, P. J., "A Computational Procedure for Determining Energetically Favorable Binding Sites on Biologically Important Macromolecules," J. Med. Chem., 28, pp. 849-857 (1985)); GRID is available from Oxford University, Oxford, UK; MCSS (Miranker, A. and M. Karplus, "Functionality Maps of Binding Sites: A Multiple Copy Simultaneous Search Method," Proteins: Structure, Function and Genetics, 11, pp. 29-34 (1991)); MCSS is available from Molecular Simulations, Inc., San Diego, Calif.; AUTODOCK (Goodsell, D. S, and A. J. Olsen, "Automated Docking of Substrates to Proteins by Simulated Annealing," Proteins: Structure, Function, and Genetics, 8, pp. 195-202 (1990)); AUTODOCK is available from Scripps Research Institute, La Jolla, Calif.; DOCK (Kunts, I. D., et al. "A Geometric Approach to Macromolecule-Ligand Interactions," J. Mol. Biol., 161, pp. 269-288 (1982)); DOCK is available from University of California, San Francisco, Calif.; CERIUS II (available from Molecular Simulations, Inc., San Diego, Calif.); and Flexx (Raret, et al. J. Mol. Biol. 261, pp. 470-489 (1996)).

After selecting suitable chemical entities or fragments, they can be assembled into a single compound. Assembly may proceed by visual inspection of the relationship of the fragments to each other on a three-dimensional image of the fragments in relation to the structure or portion thereof displayed on a computer screen. Visual inspection may be followed by manual model building using software such as the Quanta or Sybyl programs described above.

Software programs also may be used to aid one skilled in the art in connecting the individual chemical entities or fragments. These include, but are not limited to CAVEAT (Bartlett, P. A., et al. "CAVEAT: A Program to Facilitate the Structure-Derived Design of Biologically Active Molecules" In "Molecular Recognition in Chemical and Biological Problems," Special Publ, Royal Chem. Soc., 78, pp. 182-196 (1989)); CAVEAT is available from the University of California, Berkeley, Calif.; 3D Database systems such as MACCS-3D (MDL Information Systems, San Leandro, Calif.); this area is reviewed in Martin, Y. C., "3D Database Searching in Drug Design," J. Med. Chem., 35:2145-2154 (1992)); and HOOK (available from Molecular Simulations Inc., San Diego, Calif.).

As an alternative to building candidate pharmacophores or candidate compounds up from individual fragments or chemical entities, they may be designed de novo using the structure of $\beta_2$ AR, optionally, including information from known activators or inhibitor(s) that bind to a target site. De novo design may be included by programs including, but not limited to LUDI (Bohm, H. J., "The Computer Program LUDI: A New Method for the De Novo Design of Enzyme Inhibitors, J. Comp. Aid. Molec. Design, 6, pp. 61-78 (1992)); LUDI is available from Molecular Simulations, Inc., San Diego, Calif.; LEGEND (Nishibata, Y., and Itai, A., Tetrahedron 47, p. 8985 (1991); LEGEND is available from Molecular Simulations, San Diego, Calif.; and LeapFrog (available from Tripos Associates, St. Louis, Mo.).

The functional effects of known ligands also may be altered through the use of the molecular modeling and design techniques described herein. This may be carried out by docking the structure of the known ligands into a β2 AR model structure and modifying the structure and charge distribution of the ligand to optimize the binding interactions with the β2 AR. The modified structure may be synthesized or obtained from a library of compounds and tested for its binding affinity and/or effect on $\beta_2$ AR function. The structure provided in the present disclosure are especially well suited for the structure-based drug design and optimization of compounds that modulate β2 AR.

Additional molecular modeling techniques also may be employed in accordance with the invention. See, e.g., Cohen, N. C., et al. "Molecular Modeling Software and Methods for Medicinal Chemistry," J. Med. Chem., 33, pp. 883-894 (1990); Navia, M. A. and Murcko, M. A., "The Use of Structural Information in Drug Design," Curr. Opin. Biotechnol. 8, pp. 696-700 (1997); and Afshar, et al. "Structure-Based and Combinatorial Search for New RNA-Binding Drugs," Curr. Opin. Biotechnol. 10, pp. 59-63 (1999).

Following compound design or selection according to any of the above methods or other methods known to one skilled in the art, the efficiency with which a candidate compound may be tested and optimized using computational evaluation. A candidate compound may be optimized, e.g., so that in its bound state it would lack repulsive electrostatic interaction with the target site. These repulsive electrostatic interactions include repulsive charge-charge, dipole-dipole, and charge-dipole interactions.

Specific computer software is available in the art to evaluate compound deformation energy and electrostatic interactions. Examples of programs designed for such uses include, but are not limited to Gaussian 92, revision C (Frisch, M. J., Gaussian, Inc., Pittsburgh, Pa. (1992)); AMBER, version 4.0 (Kollman, P. A., University of California at San Francisco, (1994)); QUANTA/CHARMM (Molecular Simulations, Inc., San Diego, Calif. (1994)); and Insight II/Discover (Biosym Technologies Inc., San Diego, Calif. (1994)). These programs may be run, using, e.g., a Silicon Graphics workstation, Indigo, 02-R10000 or IBM RISC/6000 workstation model 550. Other hardware and software combinations may be used to carry out the above described functions, and are known to those of skill in the art.

Once a candidate compound has been identified, as described above, substitutions may then be made in some of its atoms or side groups to improve or modify its binding properties. Generally, initial substitutions are conservative in that the replacement group will have either approximately same size, or overall structure, or hydrophobicity, or charge as the original group. Components known in the art to alter conformation should be avoided in making substitutions. Substituted candidates may be analyzed for efficiency of fit to β2 AR using the same methods described above.

Once a candidate compound has been identified using any of the methods described above, it can be obtained (e.g., synthesized or purchased) and tested for biological activity. A variety of tests for assaying β2 AR function are known including, but not limited to cell free assays and cellular assays. In one embodiment the method includes contacting a compound with a cell comprising β2 AR, and determining whether intracellular cAMP levels are altered. This may be done by directly measuring cAMP, or using a cAMP-inducible reporter protein, for example. The contact step may be done in the presence or absence or a known agonist, inverse agonist, antagonist, or using a constitutively active β2 AR, for example.

TABLE 2

Atomic coordinates of b2 adrenoreceptor

| ATOM | 1 | C | GLY | A | 37 | 12.267 | 36.922 | 30.533 | 1.00 | 211.64 | A |
|---|---|---|---|---|---|---|---|---|---|---|---|
| ATOM | 2 | O | GLY | A | 37 | 13.195 | 37.070 | 31.329 | 1.00 | 211.64 | A |
| ATOM | 3 | N | GLY | A | 37 | 12.352 | 38.788 | 28.880 | 1.00 | 211.64 | A |
| ATOM | 4 | CA | GLY | A | 37 | 11.554 | 38.126 | 29.950 | 1.00 | 211.64 | A |
| ATOM | 5 | N | ILE | A | 38 | 11.831 | 35.728 | 30.140 | 1.00 | 225.51 | A |
| ATOM | 6 | CA | ILE | A | 38 | 12.440 | 34.492 | 30.621 | 1.00 | 225.51 | A |
| ATOM | 7 | CB | ILE | A | 38 | 11.732 | 33.251 | 30.034 | 1.00 | 147.61 | A |
| ATOM | 8 | CG2 | ILE | A | 38 | 10.353 | 33.094 | 30.661 | 1.00 | 147.61 | A |
| ATOM | 9 | CG1 | ILE | A | 38 | 11.636 | 33.377 | 28.510 | 1.00 | 147.61 | A |
| ATOM | 10 | CD1 | ILE | A | 38 | 10.938 | 32.215 | 27.830 | 1.00 | 147.61 | A |
| ATOM | 11 | C | ILE | A | 38 | 13.912 | 34.460 | 30.226 | 1.00 | 225.51 | A |
| ATOM | 12 | O | ILE | A | 38 | 14.671 | 33.600 | 30.674 | 1.00 | 225.51 | A |
| ATOM | 13 | N | ALA | A | 39 | 14.302 | 35.410 | 29.380 | 1.00 | 266.23 | A |
| ATOM | 14 | CA | ALA | A | 39 | 15.679 | 35.525 | 28.918 | 1.00 | 266.23 | A |
| ATOM | 15 | CB | ALA | A | 39 | 15.711 | 36.111 | 27.505 | 1.00 | 136.09 | A |
| ATOM | 16 | C | ALA | A | 39 | 16.446 | 36.427 | 29.882 | 1.00 | 266.23 | A |
| ATOM | 17 | O | ALA | A | 39 | 17.621 | 36.194 | 30.168 | 1.00 | 266.23 | A |
| ATOM | 18 | N | ALA | A | 40 | 15.768 | 37.455 | 30.382 | 1.00 | 236.67 | A |
| ATOM | 19 | CA | ALA | A | 40 | 16.371 | 38.398 | 31.315 | 1.00 | 236.67 | A |
| ATOM | 20 | CB | ALA | A | 40 | 15.568 | 39.695 | 31.339 | 1.00 | 51.30 | A |
| ATOM | 21 | C | ALA | A | 40 | 16.440 | 37.800 | 32.716 | 1.00 | 236.67 | A |
| ATOM | 22 | O | ALA | A | 40 | 17.030 | 38.388 | 33.620 | 1.00 | 236.67 | A |
| ATOM | 23 | N | SER | A | 41 | 15.833 | 36.630 | 32.890 | 1.00 | 183.65 | A |
| ATOM | 24 | CA | SER | A | 41 | 15.823 | 35.947 | 34.181 | 1.00 | 183.65 | A |
| ATOM | 25 | CB | SER | A | 41 | 15.114 | 34.595 | 34.060 | 1.00 | 159.24 | A |
| ATOM | 26 | OG | SER | A | 41 | 13.764 | 34.755 | 33.663 | 1.00 | 159.24 | A |
| ATOM | 27 | C | SER | A | 41 | 17.242 | 35.731 | 34.697 | 1.00 | 183.65 | A |
| ATOM | 28 | O | SER | A | 41 | 17.463 | 35.588 | 35.900 | 1.00 | 183.65 | A |
| ATOM | 29 | N | ALA | A | 42 | 18.200 | 35.705 | 33.777 | 1.00 | 224.20 | A |
| ATOM | 30 | CA | ALA | A | 42 | 19.596 | 35.507 | 34.135 | 1.00 | 224.20 | A |
| ATOM | 31 | CB | ALA | A | 42 | 20.391 | 35.091 | 32.906 | 1.00 | 106.74 | A |
| ATOM | 32 | C | ALA | A | 42 | 20.173 | 36.789 | 34.722 | 1.00 | 224.20 | A |
| ATOM | 33 | O | ALA | A | 42 | 21.318 | 36.816 | 35.174 | 1.00 | 224.20 | A |
| ATOM | 34 | N | ILE | A | 43 | 19.368 | 37.846 | 34.720 | 1.00 | 154.53 | A |
| ATOM | 35 | CA | ILE | A | 43 | 19.793 | 39.140 | 35.238 | 1.00 | 154.53 | A |
| ATOM | 36 | CB | ILE | A | 43 | 19.108 | 40.289 | 34.446 | 1.00 | 113.24 | A |
| ATOM | 37 | CG2 | ILE | A | 43 | 19.535 | 41.643 | 34.991 | 1.00 | 113.24 | A |
| ATOM | 38 | CG1 | ILE | A | 43 | 19.484 | 40.179 | 32.962 | 1.00 | 113.24 | A |
| ATOM | 39 | CD1 | ILE | A | 43 | 18.962 | 41.307 | 32.091 | 1.00 | 113.24 | A |
| ATOM | 40 | C | ILE | A | 43 | 19.537 | 39.302 | 36.742 | 1.00 | 154.53 | A |
| ATOM | 41 | O | ILE | A | 43 | 19.984 | 40.273 | 37.353 | 1.00 | 154.53 | A |
| ATOM | 42 | N | VAL | A | 44 | 18.828 | 38.348 | 37.341 | 1.00 | 159.82 | A |
| ATOM | 43 | CA | VAL | A | 44 | 18.546 | 38.402 | 38.776 | 1.00 | 159.82 | A |
| ATOM | 44 | CB | VAL | A | 44 | 17.185 | 37.767 | 39.123 | 1.00 | 137.78 | A |
| ATOM | 45 | CG1 | VAL | A | 44 | 16.907 | 37.913 | 40.615 | 1.00 | 137.78 | A |
| ATOM | 46 | CG2 | VAL | A | 44 | 16.090 | 38.422 | 38.312 | 1.00 | 137.78 | A |

TABLE 2-continued

Atomic coordinates of b2 adrenoreceptor

| ATOM | 47 | C | VAL | A | 44 | 19.629 | 37.650 | 39.540 | 1.00 | 159.82 | A |
|---|---|---|---|---|---|---|---|---|---|---|---|
| ATOM | 48 | O | VAL | A | 44 | 20.116 | 38.122 | 40.568 | 1.00 | 159.82 | A |
| ATOM | 49 | N | ALA | A | 45 | 19.998 | 36.475 | 39.036 | 1.00 | 152.90 | A |
| ATOM | 50 | CA | ALA | A | 45 | 21.038 | 35.668 | 39.663 | 1.00 | 152.90 | A |
| ATOM | 51 | CB | ALA | A | 45 | 21.237 | 34.369 | 38.890 | 1.00 | 156.69 | A |
| ATOM | 52 | C | ALA | A | 45 | 22.316 | 36.492 | 39.649 | 1.00 | 152.90 | A |
| ATOM | 53 | O | ALA | A | 45 | 23.265 | 36.207 | 40.375 | 1.00 | 308.44 | A |
| ATOM | 54 | N | ALA | A | 46 | 22.321 | 37.520 | 38.805 | 1.00 | 188.55 | A |
| ATOM | 55 | CA | ALA | A | 46 | 23.456 | 38.422 | 38.678 | 1.00 | 188.55 | A |
| ATOM | 56 | CB | ALA | A | 46 | 23.391 | 39.162 | 37.340 | 1.00 | 83.28 | A |
| ATOM | 57 | C | ALA | A | 46 | 23.419 | 39.416 | 39.834 | 1.00 | 188.55 | A |
| ATOM | 58 | O | ALA | A | 46 | 24.457 | 39.881 | 40.303 | 1.00 | 188.55 | A |
| ATOM | 59 | N | ALA | A | 47 | 22.210 | 39.737 | 40.288 | 1.00 | 149.52 | A |
| ATOM | 60 | CA | ALA | A | 47 | 22.021 | 40.666 | 41.395 | 1.00 | 149.52 | A |
| ATOM | 61 | CB | ALA | A | 47 | 20.795 | 41.534 | 41.144 | 1.00 | 75.11 | A |
| ATOM | 62 | C | ALA | A | 47 | 21.857 | 39.879 | 42.692 | 1.00 | 149.52 | A |
| ATOM | 63 | O | ALA | A | 47 | 21.411 | 40.413 | 43.711 | 1.00 | 149.52 | A |
| ATOM | 64 | N | VAL | A | 48 | 22.219 | 38.601 | 42.640 | 1.00 | 151.22 | A |
| ATOM | 65 | CA | VAL | A | 48 | 22.132 | 37.717 | 43.795 | 1.00 | 151.22 | A |
| ATOM | 66 | CB | VAL | A | 48 | 21.010 | 36.676 | 43.617 | 1.00 | 111.38 | A |
| ATOM | 67 | CG1 | VAL | A | 48 | 20.900 | 35.808 | 44.859 | 1.00 | 111.38 | A |
| ATOM | 68 | CG2 | VAL | A | 48 | 19.694 | 37.379 | 43.337 | 1.00 | 111.38 | A |
| ATOM | 69 | C | VAL | A | 48 | 23.458 | 36.983 | 43.960 | 1.00 | 151.22 | A |
| ATOM | 70 | O | VAL | A | 48 | 23.684 | 36.299 | 44.957 | 1.00 | 283.45 | A |
| ATOM | 71 | N | ALA | A | 49 | 24.333 | 37.136 | 42.971 | 1.00 | 213.35 | A |
| ATOM | 72 | CA | ALA | A | 49 | 25.642 | 36.495 | 42.990 | 1.00 | 213.35 | A |
| ATOM | 73 | CB | ALA | A | 49 | 25.868 | 35.734 | 41.688 | 1.00 | 124.18 | A |
| ATOM | 74 | C | ALA | A | 49 | 26.760 | 37.513 | 43.196 | 1.00 | 213.35 | A |
| ATOM | 75 | O | ALA | A | 49 | 27.426 | 37.516 | 44.231 | 1.00 | 347.17 | A |
| ATOM | 76 | N | GLY | A | 50 | 26.958 | 38.375 | 42.203 | 1.00 | 188.97 | A |
| ATOM | 77 | CA | GLY | A | 50 | 28.000 | 39.383 | 42.285 | 1.00 | 188.97 | A |
| ATOM | 78 | C | GLY | A | 50 | 27.967 | 40.237 | 43.539 | 1.00 | 188.97 | A |
| ATOM | 79 | O | GLY | A | 50 | 29.000 | 40.749 | 43.970 | 1.00 | 188.97 | A |
| ATOM | 80 | N | ASN | A | 51 | 26.785 | 40.393 | 44.127 | 1.00 | 138.02 | A |
| ATOM | 81 | CA | ASN | A | 51 | 26.628 | 41.196 | 45.335 | 1.00 | 138.02 | A |
| ATOM | 82 | CB | ASN | A | 51 | 25.231 | 41.815 | 45.374 | 1.00 | 209.31 | A |
| ATOM | 83 | CG | ASN | A | 51 | 24.975 | 42.740 | 44.202 | 1.00 | 209.31 | A |
| ATOM | 84 | OD1 | ASN | A | 51 | 25.667 | 43.742 | 44.025 | 1.00 | 209.31 | A |
| ATOM | 85 | ND2 | ASN | A | 51 | 23.980 | 42.405 | 43.390 | 1.00 | 209.31 | A |
| ATOM | 86 | C | ASN | A | 51 | 26.867 | 40.377 | 46.600 | 1.00 | 138.02 | A |
| ATOM | 87 | O | ASN | A | 51 | 26.945 | 40.925 | 47.698 | 1.00 | 138.02 | A |
| ATOM | 88 | N | VAL | A | 52 | 26.978 | 39.063 | 46.438 | 1.00 | 112.78 | A |
| ATOM | 89 | CA | VAL | A | 52 | 27.223 | 38.170 | 47.565 | 1.00 | 112.78 | A |
| ATOM | 90 | CB | VAL | A | 52 | 26.409 | 36.867 | 47.437 | 1.00 | 219.12 | A |
| ATOM | 91 | CG1 | VAL | A | 52 | 26.702 | 35.953 | 48.615 | 1.00 | 219.12 | A |
| ATOM | 92 | CG2 | VAL | A | 52 | 24.928 | 37.186 | 47.375 | 1.00 | 219.12 | A |
| ATOM | 93 | C | VAL | A | 52 | 28.707 | 37.822 | 47.614 | 1.00 | 112.78 | A |
| ATOM | 94 | O | VAL | A | 52 | 29.309 | 37.760 | 48.685 | 1.00 | 212.17 | A |
| ATOM | 95 | N | ALA | A | 53 | 29.290 | 37.590 | 46.443 | 1.00 | 191.31 | A |
| ATOM | 96 | CA | ALA | A | 53 | 30.706 | 37.265 | 46.352 | 1.00 | 191.31 | A |
| ATOM | 97 | CB | ALA | A | 53 | 31.099 | 37.038 | 44.899 | 1.00 | 145.79 | A |
| ATOM | 98 | C | ALA | A | 53 | 31.475 | 38.444 | 46.931 | 1.00 | 191.31 | A |
| ATOM | 99 | O | ALA | A | 53 | 32.635 | 38.319 | 47.330 | 1.00 | 191.31 | A |
| ATOM | 100 | N | VAL | A | 54 | 30.804 | 39.592 | 46.972 | 1.00 | 157.37 | A |
| ATOM | 101 | CA | VAL | A | 54 | 31.382 | 40.817 | 47.503 | 1.00 | 157.37 | A |
| ATOM | 102 | CB | VAL | A | 54 | 30.721 | 42.069 | 46.869 | 1.00 | 101.43 | A |
| ATOM | 103 | CG1 | VAL | A | 54 | 31.224 | 43.328 | 47.555 | 1.00 | 101.43 | A |
| ATOM | 104 | CG2 | VAL | A | 54 | 31.030 | 42.128 | 45.376 | 1.00 | 101.43 | A |
| ATOM | 105 | C | VAL | A | 54 | 31.196 | 40.870 | 49.017 | 1.00 | 157.37 | A |
| ATOM | 106 | O | VAL | A | 54 | 32.159 | 41.070 | 49.759 | 1.00 | 157.37 | A |
| ATOM | 107 | N | ILE | A | 55 | 29.958 | 40.687 | 49.471 | 1.00 | 108.96 | A |
| ATOM | 108 | CA | ILE | A | 55 | 29.658 | 40.721 | 50.901 | 1.00 | 108.96 | A |
| ATOM | 109 | CB | ILE | A | 55 | 28.171 | 40.388 | 51.186 | 1.00 | 178.57 | A |
| ATOM | 110 | CG2 | ILE | A | 55 | 27.271 | 41.403 | 50.504 | 1.00 | 178.57 | A |
| ATOM | 111 | CG1 | ILE | A | 55 | 27.848 | 38.970 | 50.712 | 1.00 | 178.57 | A |
| ATOM | 112 | CD1 | ILE | A | 55 | 26.430 | 38.532 | 50.993 | 1.00 | 178.57 | A |
| ATOM | 113 | C | ILE | A | 55 | 30.530 | 39.734 | 51.663 | 1.00 | 108.96 | A |
| ATOM | 114 | O | ILE | A | 55 | 30.968 | 40.008 | 52.780 | 1.00 | 211.54 | A |
| ATOM | 115 | N | THR | A | 56 | 30.773 | 38.579 | 51.055 | 1.00 | 133.34 | A |
| ATOM | 116 | CA | THR | A | 56 | 31.603 | 37.562 | 51.677 | 1.00 | 133.34 | A |
| ATOM | 117 | CB | THR | A | 56 | 31.416 | 36.190 | 50.987 | 1.00 | 195.37 | A |
| ATOM | 118 | OG1 | THR | A | 56 | 32.218 | 35.207 | 51.651 | 1.00 | 195.37 | A |
| ATOM | 119 | CG2 | THR | A | 56 | 31.815 | 36.264 | 49.520 | 1.00 | 195.37 | A |
| ATOM | 120 | C | THR | A | 56 | 33.056 | 38.008 | 51.557 | 1.00 | 133.34 | A |
| ATOM | 121 | O | THR | A | 56 | 33.839 | 37.866 | 52.498 | 1.00 | 133.34 | A |
| ATOM | 122 | N | ALA | A | 57 | 33.402 | 38.561 | 50.395 | 1.00 | 213.86 | A |
| ATOM | 123 | CA | ALA | A | 57 | 34.754 | 39.045 | 50.141 | 1.00 | 213.86 | A |
| ATOM | 124 | CB | ALA | A | 57 | 34.808 | 39.785 | 48.811 | 1.00 | 146.97 | A |

TABLE 2-continued

Atomic coordinates of b2 adrenoreceptor

| ATOM | 125 | C | ALA | A | 57 | 35.165 | 39.972 | 51.275 | 1.00 | 213.86 | A |
|---|---|---|---|---|---|---|---|---|---|---|---|
| ATOM | 126 | O | ALA | A | 57 | 36.277 | 39.881 | 51.789 | 1.00 | 213.86 | A |
| ATOM | 127 | N | ILE | A | 58 | 34.260 | 40.867 | 51.659 | 1.00 | 95.92 | A |
| ATOM | 128 | CA | ILE | A | 58 | 34.524 | 41.793 | 52.753 | 1.00 | 95.92 | A |
| ATOM | 129 | CB | ILE | A | 58 | 33.595 | 43.055 | 52.668 | 1.00 | 110.93 | A |
| ATOM | 130 | CG2 | ILE | A | 58 | 32.166 | 42.636 | 52.382 | 1.00 | 110.93 | A |
| ATOM | 131 | CG1 | ILE | A | 58 | 33.692 | 43.894 | 53.953 | 1.00 | 110.93 | A |
| ATOM | 132 | CD1 | ILE | A | 58 | 32.778 | 43.454 | 55.101 | 1.00 | 110.93 | A |
| ATOM | 133 | C | ILE | A | 58 | 34.338 | 41.070 | 54.089 | 1.00 | 95.92 | A |
| ATOM | 134 | O | ILE | A | 58 | 35.304 | 40.858 | 54.820 | 1.00 | 95.92 | A |
| ATOM | 135 | N | ALA | A | 59 | 33.104 | 40.673 | 54.393 | 1.00 | 160.99 | A |
| ATOM | 136 | CA | ALA | A | 59 | 32.799 | 39.979 | 55.644 | 1.00 | 160.99 | A |
| ATOM | 137 | CB | ALA | A | 59 | 31.355 | 39.487 | 55.629 | 1.00 | 121.47 | A |
| ATOM | 138 | C | ALA | A | 59 | 33.746 | 38.808 | 55.895 | 1.00 | 160.99 | A |
| ATOM | 139 | O | ALA | A | 59 | 33.887 | 38.343 | 57.028 | 1.00 | 160.99 | A |
| ATOM | 140 | N | PHE | A | 61 | 37.528 | 39.018 | 53.832 | 1.00 | 174.57 | A |
| ATOM | 141 | CA | PHE | A | 61 | 38.933 | 38.837 | 54.168 | 1.00 | 175.09 | A |
| ATOM | 142 | CB | PHE | A | 61 | 39.758 | 38.592 | 52.901 | 1.00 | 139.18 | A |
| ATOM | 143 | CG | PHE | A | 61 | 39.347 | 37.363 | 52.131 | 1.00 | 139.13 | A |
| ATOM | 144 | CD1 | PHE | A | 61 | 38.121 | 37.311 | 51.473 | 1.00 | 138.65 | A |
| ATOM | 145 | CD2 | PHE | A | 61 | 40.196 | 36.263 | 52.048 | 1.00 | 139.24 | A |
| ATOM | 146 | CE1 | PHE | A | 61 | 37.748 | 36.182 | 50.741 | 1.00 | 138.54 | A |
| ATOM | 147 | CE2 | PHE | A | 61 | 39.832 | 35.129 | 51.318 | 1.00 | 138.31 | A |
| ATOM | 148 | CZ | PHE | A | 61 | 38.607 | 35.090 | 50.664 | 1.00 | 138.29 | A |
| ATOM | 149 | C | PHE | A | 61 | 39.485 | 40.050 | 54.911 | 1.00 | 175.64 | A |
| ATOM | 150 | O | PHE | A | 61 | 39.131 | 41.193 | 54.619 | 1.00 | 175.70 | A |
| ATOM | 151 | N | GLU | A | 62 | 40.359 | 39.777 | 55.874 | 1.00 | 220.77 | A |
| ATOM | 152 | CA | GLU | A | 62 | 40.988 | 40.804 | 56.696 | 1.00 | 221.47 | A |
| ATOM | 153 | CB | GLU | A | 62 | 42.221 | 40.208 | 57.388 | 1.00 | 175.65 | A |
| ATOM | 154 | CG | GLU | A | 62 | 42.934 | 41.125 | 58.381 | 1.00 | 176.45 | A |
| ATOM | 155 | CD | GLU | A | 62 | 42.089 | 41.454 | 59.598 | 1.00 | 176.75 | A |
| ATOM | 156 | OE1 | GLU | A | 62 | 41.494 | 40.524 | 60.181 | 1.00 | 177.71 | A |
| ATOM | 157 | OE2 | GLU | A | 62 | 42.031 | 42.642 | 59.978 | 1.00 | 178.16 | A |
| ATOM | 158 | C | GLU | A | 62 | 41.385 | 42.055 | 55.905 | 1.00 | 221.41 | A |
| ATOM | 159 | O | GLU | A | 62 | 40.884 | 43.148 | 56.167 | 1.00 | 221.41 | A |
| ATOM | 160 | N | ARG | A | 63 | 42.275 | 41.886 | 54.933 | 1.00 | 164.31 | A |
| ATOM | 161 | CA | ARG | A | 63 | 42.758 | 43.003 | 54.126 | 1.00 | 164.34 | A |
| ATOM | 162 | CB | ARG | A | 63 | 43.789 | 42.505 | 53.109 | 1.00 | 195.65 | A |
| ATOM | 163 | CG | ARG | A | 63 | 44.572 | 43.612 | 52.408 | 1.00 | 197.93 | A |
| ATOM | 164 | CD | ARG | A | 63 | 45.523 | 44.331 | 53.367 | 1.00 | 201.43 | A |
| ATOM | 165 | NE | ARG | A | 63 | 46.355 | 45.320 | 52.681 | 1.00 | 203.36 | A |
| ATOM | 166 | CZ | ARG | A | 63 | 47.323 | 46.023 | 53.264 | 1.00 | 204.62 | A |
| ATOM | 167 | NH1 | ARG | A | 63 | 47.591 | 45.852 | 54.551 | 1.00 | 204.96 | A |
| ATOM | 168 | NH2 | ARG | A | 63 | 48.029 | 46.896 | 52.558 | 1.00 | 204.88 | A |
| ATOM | 169 | C | ARG | A | 63 | 41.659 | 43.776 | 53.397 | 1.00 | 163.68 | A |
| ATOM | 170 | O | ARG | A | 63 | 41.832 | 44.955 | 53.083 | 1.00 | 163.72 | A |
| ATOM | 171 | N | LEU | A | 64 | 40.532 | 43.122 | 53.128 | 1.00 | 119.72 | A |
| ATOM | 172 | CA | LEU | A | 64 | 39.433 | 43.779 | 52.424 | 1.00 | 118.80 | A |
| ATOM | 173 | CB | LEU | A | 64 | 38.602 | 42.748 | 51.656 | 1.00 | 115.48 | A |
| ATOM | 174 | CG | LEU | A | 64 | 39.147 | 42.268 | 50.307 | 1.00 | 115.27 | A |
| ATOM | 175 | CD1 | LEU | A | 64 | 38.210 | 41.220 | 49.720 | 1.00 | 114.70 | A |
| ATOM | 176 | CD2 | LEU | A | 64 | 39.278 | 43.450 | 49.353 | 1.00 | 115.00 | A |
| ATOM | 177 | C | LEU | A | 64 | 38.518 | 44.594 | 53.331 | 1.00 | 118.35 | A |
| ATOM | 178 | O | LEU | A | 64 | 37.547 | 45.193 | 52.866 | 1.00 | 118.46 | A |
| ATOM | 179 | N | GLN | A | 65 | 38.838 | 44.631 | 54.619 | 1.00 | 117.77 | A |
| ATOM | 180 | CA | GLN | A | 65 | 38.033 | 45.364 | 55.590 | 1.00 | 117.23 | A |
| ATOM | 181 | CB | GLN | A | 65 | 38.055 | 44.617 | 56.919 | 1.00 | 169.16 | A |
| ATOM | 182 | CG | GLN | A | 65 | 37.598 | 43.172 | 56.807 | 1.00 | 169.48 | A |
| ATOM | 183 | CD | GLN | A | 65 | 37.767 | 42.416 | 58.105 | 1.00 | 170.11 | A |
| ATOM | 184 | OE1 | GLN | A | 65 | 37.845 | 43.017 | 59.176 | 1.00 | 171.77 | A |
| ATOM | 185 | NE2 | GLN | A | 65 | 37.817 | 41.089 | 58.021 | 1.00 | 171.27 | A |
| ATOM | 186 | C | GLN | A | 65 | 38.504 | 46.806 | 55.795 | 1.00 | 116.27 | A |
| ATOM | 187 | O | GLN | A | 65 | 39.488 | 47.053 | 56.491 | 1.00 | 116.46 | A |
| ATOM | 188 | N | THR | A | 66 | 37.788 | 47.750 | 55.185 | 1.00 | 142.99 | A |
| ATOM | 189 | CA | THR | A | 66 | 38.113 | 49.174 | 55.284 | 1.00 | 141.64 | A |
| ATOM | 190 | CB | THR | A | 66 | 39.153 | 49.583 | 54.217 | 1.00 | 153.27 | A |
| ATOM | 191 | OG1 | THR | A | 66 | 38.668 | 49.232 | 52.915 | 1.00 | 153.40 | A |
| ATOM | 192 | CG2 | THR | A | 66 | 40.477 | 48.877 | 54.461 | 1.00 | 152.75 | A |
| ATOM | 193 | C | THR | A | 66 | 36.867 | 50.051 | 55.110 | 1.00 | 140.73 | A |
| ATOM | 194 | O | THR | A | 66 | 35.843 | 49.590 | 54.606 | 1.00 | 140.70 | A |
| ATOM | 195 | N | VAL | A | 67 | 36.961 | 51.312 | 55.527 | 1.00 | 172.21 | A |
| ATOM | 196 | CA | VAL | A | 67 | 35.841 | 52.245 | 55.415 | 1.00 | 172.21 | A |
| ATOM | 197 | CB | VAL | A | 67 | 36.243 | 53.673 | 55.883 | 1.00 | 84.67 | A |
| ATOM | 198 | CG1 | VAL | A | 67 | 35.232 | 54.708 | 55.387 | 1.00 | 84.67 | A |
| ATOM | 199 | CG2 | VAL | A | 67 | 36.308 | 53.710 | 57.401 | 1.00 | 84.67 | A |
| ATOM | 200 | C | VAL | A | 67 | 35.290 | 52.321 | 53.996 | 1.00 | 172.21 | A |
| ATOM | 201 | O | VAL | A | 67 | 34.077 | 52.380 | 53.799 | 1.00 | 172.21 | A |
| ATOM | 202 | N | THR | A | 68 | 36.180 | 52.323 | 53.008 | 1.00 | 124.57 | A |

TABLE 2-continued

Atomic coordinates of b2 adrenoreceptor

| ATOM | 203 | CA | THR | A | 68 | 35.755 | 52.390 | 51.614 | 1.00 | 124.57 | A |
| ATOM | 204 | CB | THR | A | 68 | 36.963 | 52.525 | 50.662 | 1.00 | 205.49 | A |
| ATOM | 205 | OG1 | THR | A | 68 | 37.688 | 53.720 | 50.979 | 1.00 | 205.49 | A |
| ATOM | 206 | CG2 | THR | A | 68 | 36.498 | 52.589 | 49.210 | 1.00 | 205.49 | A |
| ATOM | 207 | C | THR | A | 68 | 34.971 | 51.135 | 51.242 | 1.00 | 124.57 | A |
| ATOM | 208 | O | THR | A | 68 | 33.819 | 51.215 | 50.817 | 1.00 | 124.57 | A |
| ATOM | 209 | N | ASN | A | 69 | 35.596 | 49.974 | 51.411 | 1.00 | 217.80 | A |
| ATOM | 210 | CA | ASN | A | 69 | 34.946 | 48.710 | 51.087 | 1.00 | 217.80 | A |
| ATOM | 211 | CB | ASN | A | 69 | 35.990 | 47.598 | 50.978 | 1.00 | 88.48 | A |
| ATOM | 212 | CG | ASN | A | 69 | 37.065 | 47.909 | 49.952 | 1.00 | 88.48 | A |
| ATOM | 213 | OD1 | ASN | A | 69 | 36.764 | 48.287 | 48.818 | 1.00 | 88.48 | A |
| ATOM | 214 | ND2 | ASN | A | 69 | 38.327 | 47.749 | 50.344 | 1.00 | 88.48 | A |
| ATOM | 215 | C | ASN | A | 69 | 33.886 | 48.342 | 52.122 | 1.00 | 217.80 | A |
| ATOM | 216 | O | ASN | A | 69 | 33.402 | 47.210 | 52.159 | 1.00 | 217.80 | A |
| ATOM | 217 | N | TYR | A | 70 | 33.531 | 49.314 | 52.956 | 1.00 | 125.17 | A |
| ATOM | 218 | CA | TYR | A | 70 | 32.526 | 49.131 | 53.995 | 1.00 | 125.17 | A |
| ATOM | 219 | CB | TYR | A | 70 | 32.984 | 49.787 | 55.294 | 1.00 | 150.31 | A |
| ATOM | 220 | CG | TYR | A | 70 | 32.839 | 48.907 | 56.504 | 1.00 | 150.31 | A |
| ATOM | 221 | CD1 | TYR | A | 70 | 33.633 | 47.772 | 56.661 | 1.00 | 150.31 | A |
| ATOM | 222 | CE1 | TYR | A | 70 | 33.508 | 46.954 | 57.781 | 1.00 | 150.31 | A |
| ATOM | 223 | CD2 | TYR | A | 70 | 31.910 | 49.207 | 57.498 | 1.00 | 150.31 | A |
| ATOM | 224 | CE2 | TYR | A | 70 | 31.775 | 48.396 | 58.625 | 1.00 | 150.31 | A |
| ATOM | 225 | CZ | TYR | A | 70 | 32.577 | 47.272 | 58.759 | 1.00 | 150.31 | A |
| ATOM | 226 | OH | TYR | A | 70 | 32.447 | 46.468 | 59.869 | 1.00 | 150.31 | A |
| ATOM | 227 | C | TYR | A | 70 | 31.244 | 49.798 | 53.525 | 1.00 | 125.17 | A |
| ATOM | 228 | O | TYR | A | 70 | 30.150 | 49.457 | 53.969 | 1.00 | 125.17 | A |
| ATOM | 229 | N | PHE | A | 71 | 31.402 | 50.769 | 52.633 | 1.00 | 113.36 | A |
| ATOM | 230 | CA | PHE | A | 71 | 30.272 | 51.496 | 52.075 | 1.00 | 113.36 | A |
| ATOM | 231 | CB | PHE | A | 71 | 30.596 | 52.985 | 51.942 | 1.00 | 122.12 | A |
| ATOM | 232 | CG | PHE | A | 71 | 30.838 | 53.680 | 53.253 | 1.00 | 122.12 | A |
| ATOM | 233 | CD1 | PHE | A | 71 | 31.188 | 55.027 | 53.281 | 1.00 | 122.12 | A |
| ATOM | 234 | CD2 | PHE | A | 71 | 30.730 | 52.992 | 54.459 | 1.00 | 122.12 | A |
| ATOM | 235 | CE1 | PHE | A | 71 | 31.429 | 55.678 | 54.486 | 1.00 | 122.12 | A |
| ATOM | 236 | CE2 | PHE | A | 71 | 30.969 | 53.635 | 55.670 | 1.00 | 122.12 | A |
| ATOM | 237 | CZ | PHE | A | 71 | 31.321 | 54.983 | 55.683 | 1.00 | 122.12 | A |
| ATOM | 238 | C | PHE | A | 71 | 29.971 | 50.917 | 50.705 | 1.00 | 113.36 | A |
| ATOM | 239 | O | PHE | A | 71 | 28.854 | 51.037 | 50.205 | 1.00 | 113.36 | A |
| ATOM | 240 | N | ILE | A | 72 | 30.977 | 50.300 | 50.091 | 1.00 | 182.96 | A |
| ATOM | 241 | CA | ILE | A | 72 | 30.782 | 49.688 | 48.786 | 1.00 | 182.96 | A |
| ATOM | 242 | CB | ILE | A | 72 | 32.124 | 49.477 | 48.027 | 1.00 | 49.63 | A |
| ATOM | 243 | CG2 | ILE | A | 72 | 32.897 | 48.299 | 48.610 | 1.00 | 49.63 | A |
| ATOM | 244 | CG1 | ILE | A | 72 | 31.838 | 49.198 | 46.549 | 1.00 | 49.63 | A |
| ATOM | 245 | CD1 | ILE | A | 72 | 32.500 | 50.180 | 45.599 | 1.00 | 49.63 | A |
| ATOM | 246 | C | ILE | A | 72 | 30.120 | 48.345 | 49.060 | 1.00 | 182.96 | A |
| ATOM | 247 | O | ILE | A | 72 | 29.379 | 47.820 | 48.229 | 1.00 | 182.96 | A |
| ATOM | 248 | N | ALA | A | 73 | 30.391 | 47.806 | 50.246 | 1.00 | 153.97 | A |
| ATOM | 249 | CA | ALA | A | 73 | 29.815 | 46.537 | 50.673 | 1.00 | 153.97 | A |
| ATOM | 250 | CB | ALA | A | 73 | 30.633 | 45.943 | 51.819 | 1.00 | 99.35 | A |
| ATOM | 251 | C | ALA | A | 73 | 28.388 | 46.828 | 51.127 | 1.00 | 153.97 | A |
| ATOM | 252 | O | ALA | A | 73 | 27.595 | 45.920 | 51.371 | 1.00 | 306.64 | A |
| ATOM | 253 | N | SER | A | 74 | 28.084 | 48.117 | 51.238 | 1.00 | 149.89 | A |
| ATOM | 254 | CA | SER | A | 74 | 26.764 | 48.586 | 51.636 | 1.00 | 149.89 | A |
| ATOM | 255 | CB | SER | A | 74 | 26.847 | 50.036 | 52.119 | 1.00 | 101.35 | A |
| ATOM | 256 | OG | SER | A | 74 | 25.565 | 50.638 | 52.174 | 1.00 | 101.35 | A |
| ATOM | 257 | C | SER | A | 74 | 25.839 | 48.500 | 50.431 | 1.00 | 149.89 | A |
| ATOM | 258 | O | SER | A | 74 | 24.701 | 48.045 | 50.539 | 1.00 | 149.89 | A |
| ATOM | 259 | N | LEU | A | 75 | 26.341 | 48.943 | 49.283 | 1.00 | 102.13 | A |
| ATOM | 260 | CA | LEU | A | 75 | 25.578 | 48.914 | 48.042 | 1.00 | 102.13 | A |
| ATOM | 261 | CB | LEU | A | 75 | 26.293 | 49.739 | 46.969 | 1.00 | 135.64 | A |
| ATOM | 262 | CG | LEU | A | 75 | 26.193 | 51.264 | 47.075 | 1.00 | 135.64 | A |
| ATOM | 263 | CD1 | LEU | A | 75 | 26.518 | 51.727 | 48.483 | 1.00 | 135.64 | A |
| ATOM | 264 | CD2 | LEU | A | 75 | 27.139 | 51.895 | 46.067 | 1.00 | 135.64 | A |
| ATOM | 265 | C | LEU | A | 75 | 25.398 | 47.478 | 47.560 | 1.00 | 102.13 | A |
| ATOM | 266 | O | LEU | A | 75 | 24.934 | 47.237 | 46.445 | 1.00 | 102.13 | A |
| ATOM | 267 | N | ALA | A | 76 | 25.777 | 46.528 | 48.408 | 1.00 | 285.40 | A |
| ATOM | 268 | CA | ALA | A | 76 | 25.646 | 45.112 | 48.088 | 1.00 | 285.40 | A |
| ATOM | 269 | CB | ALA | A | 76 | 26.740 | 44.313 | 48.786 | 1.00 | 110.66 | A |
| ATOM | 270 | C | ALA | A | 76 | 24.276 | 44.651 | 48.564 | 1.00 | 285.40 | A |
| ATOM | 271 | O | ALA | A | 76 | 23.584 | 43.894 | 47.881 | 1.00 | 285.40 | A |
| ATOM | 272 | N | CYS | A | 77 | 23.894 | 45.125 | 49.745 | 1.00 | 231.81 | A |
| ATOM | 273 | CA | CYS | A | 77 | 22.609 | 44.787 | 50.340 | 1.00 | 231.81 | A |
| ATOM | 274 | CB | CYS | A | 77 | 22.661 | 45.023 | 51.852 | 1.00 | 140.09 | A |
| ATOM | 275 | SG | CYS | A | 77 | 24.045 | 44.177 | 52.682 | 1.00 | 140.09 | A |
| ATOM | 276 | C | CYS | A | 77 | 21.526 | 45.652 | 49.703 | 1.00 | 231.81 | A |
| ATOM | 277 | O | CYS | A | 77 | 20.334 | 45.388 | 49.851 | 1.00 | 231.81 | A |
| ATOM | 278 | N | ALA | A | 78 | 21.961 | 46.691 | 48.995 | 1.00 | 123.96 | A |
| ATOM | 279 | CA | ALA | A | 78 | 21.052 | 47.602 | 48.305 | 1.00 | 123.96 | A |
| ATOM | 280 | CB | ALA | A | 78 | 21.512 | 49.049 | 48.479 | 1.00 | 110.68 | A |

TABLE 2-continued

Atomic coordinates of b2 adrenoreceptor

| ATOM | 281 | C | ALA | A | 78 | 21.047 | 47.224 | 46.828 | 1.00 | 123.96 | A |
|---|---|---|---|---|---|---|---|---|---|---|---|
| ATOM | 282 | O | ALA | A | 78 | 20.851 | 48.067 | 45.947 | 1.00 | 123.96 | A |
| ATOM | 283 | N | ASP | A | 79 | 21.278 | 45.938 | 46.577 | 1.00 | 145.69 | A |
| ATOM | 284 | CA | ASP | A | 79 | 21.303 | 45.398 | 45.227 | 1.00 | 145.69 | A |
| ATOM | 285 | CB | ASP | A | 79 | 22.708 | 45.523 | 44.638 | 1.00 | 182.75 | A |
| ATOM | 286 | CG | ASP | A | 79 | 22.697 | 45.624 | 43.129 | 1.00 | 182.75 | A |
| ATOM | 287 | OD1 | ASP | A | 79 | 22.138 | 46.613 | 42.608 | 1.00 | 182.75 | A |
| ATOM | 288 | OD2 | ASP | A | 79 | 23.243 | 44.719 | 42.465 | 1.00 | 182.75 | A |
| ATOM | 289 | C | ASP | A | 79 | 20.888 | 43.931 | 45.298 | 1.00 | 145.69 | A |
| ATOM | 290 | O | ASP | A | 79 | 20.271 | 43.400 | 44.374 | 1.00 | 145.69 | A |
| ATOM | 291 | N | LEU | A | 80 | 21.236 | 43.281 | 46.404 | 1.00 | 209.18 | A |
| ATOM | 292 | CA | LEU | A | 80 | 20.877 | 41.885 | 46.616 | 1.00 | 209.18 | A |
| ATOM | 293 | CB | LEU | A | 80 | 21.844 | 41.226 | 47.604 | 1.00 | 132.62 | A |
| ATOM | 294 | CG | LEU | A | 80 | 21.455 | 39.857 | 48.176 | 1.00 | 132.62 | A |
| ATOM | 295 | CD1 | LEU | A | 80 | 22.696 | 39.134 | 48.660 | 1.00 | 132.62 | A |
| ATOM | 296 | CD2 | LEU | A | 80 | 20.458 | 40.027 | 49.317 | 1.00 | 132.62 | A |
| ATOM | 297 | C | LEU | A | 80 | 19.459 | 41.852 | 47.166 | 1.00 | 209.18 | A |
| ATOM | 298 | O | LEU | A | 80 | 18.628 | 41.058 | 46.724 | 1.00 | 209.18 | A |
| ATOM | 299 | N | VAL | A | 81 | 19.190 | 42.718 | 48.139 | 1.00 | 238.66 | A |
| ATOM | 300 | CA | VAL | A | 81 | 17.866 | 42.803 | 48.739 | 1.00 | 238.66 | A |
| ATOM | 301 | CB | VAL | A | 81 | 17.864 | 43.748 | 49.963 | 1.00 | 140.89 | A |
| ATOM | 302 | CG1 | VAL | A | 81 | 16.453 | 43.897 | 50.511 | 1.00 | 140.89 | A |
| ATOM | 303 | CG2 | VAL | A | 81 | 18.790 | 43.198 | 51.039 | 1.00 | 140.89 | A |
| ATOM | 304 | C | VAL | A | 81 | 16.903 | 43.336 | 47.684 | 1.00 | 238.66 | A |
| ATOM | 305 | O | VAL | A | 81 | 15.731 | 42.961 | 47.652 | 1.00 | 238.66 | A |
| ATOM | 306 | N | MET | A | 82 | 17.410 | 44.208 | 46.817 | 1.00 | 119.48 | A |
| ATOM | 307 | CA | MET | A | 82 | 16.603 | 44.784 | 45.749 | 1.00 | 119.48 | A |
| ATOM | 308 | CB | MET | A | 82 | 17.120 | 46.174 | 45.377 | 1.00 | 145.77 | A |
| ATOM | 309 | CG | MET | A | 82 | 16.176 | 46.947 | 44.474 | 1.00 | 145.77 | A |
| ATOM | 310 | SD | MET | A | 82 | 16.902 | 48.434 | 43.775 | 1.00 | 145.77 | A |
| ATOM | 311 | CE | MET | A | 82 | 17.194 | 47.891 | 42.085 | 1.00 | 145.77 | A |
| ATOM | 312 | C | MET | A | 82 | 16.667 | 43.871 | 44.525 | 1.00 | 119.48 | A |
| ATOM | 313 | O | MET | A | 82 | 16.560 | 44.330 | 43.384 | 1.00 | 119.48 | A |
| ATOM | 314 | N | GLY | A | 83 | 16.849 | 42.577 | 44.778 | 1.00 | 198.83 | A |
| ATOM | 315 | CA | GLY | A | 83 | 16.929 | 41.597 | 43.707 | 1.00 | 198.83 | A |
| ATOM | 316 | C | GLY | A | 83 | 16.335 | 40.271 | 44.144 | 1.00 | 198.83 | A |
| ATOM | 317 | O | GLY | A | 83 | 15.942 | 39.445 | 43.320 | 1.00 | 198.83 | A |
| ATOM | 318 | N | LEU | A | 84 | 16.286 | 40.071 | 45.456 | 1.00 | 157.08 | A |
| ATOM | 319 | CA | LEU | A | 84 | 15.728 | 38.862 | 46.045 | 1.00 | 157.08 | A |
| ATOM | 320 | CB | LEU | A | 84 | 16.754 | 38.180 | 46.951 | 1.00 | 185.78 | A |
| ATOM | 321 | CG | LEU | A | 84 | 17.918 | 37.467 | 46.262 | 1.00 | 185.78 | A |
| ATOM | 322 | CD1 | LEU | A | 84 | 18.927 | 36.999 | 47.300 | 1.00 | 185.78 | A |
| ATOM | 323 | CD2 | LEU | A | 84 | 17.383 | 36.289 | 45.460 | 1.00 | 185.78 | A |
| ATOM | 324 | C | LEU | A | 84 | 14.514 | 39.269 | 46.862 | 1.00 | 157.08 | A |
| ATOM | 325 | O | LEU | A | 84 | 14.018 | 38.505 | 47.690 | 1.00 | 335.10 | A |
| ATOM | 326 | N | ALA | A | 85 | 14.045 | 40.489 | 46.621 | 1.00 | 181.65 | A |
| ATOM | 327 | CA | ALA | A | 85 | 12.891 | 41.021 | 47.327 | 1.00 | 181.65 | A |
| ATOM | 328 | CB | ALA | A | 85 | 13.331 | 41.633 | 48.649 | 1.00 | 101.08 | A |
| ATOM | 329 | C | ALA | A | 85 | 12.150 | 42.058 | 46.486 | 1.00 | 181.65 | A |
| ATOM | 330 | O | ALA | A | 85 | 10.974 | 42.330 | 46.723 | 1.00 | 181.65 | A |
| ATOM | 331 | N | VAL | A | 86 | 12.835 | 42.637 | 45.504 | 1.00 | 148.93 | A |
| ATOM | 332 | CA | VAL | A | 86 | 12.218 | 43.638 | 44.638 | 1.00 | 148.93 | A |
| ATOM | 333 | CB | VAL | A | 86 | 13.015 | 44.963 | 44.650 | 1.00 | 174.85 | A |
| ATOM | 334 | CG1 | VAL | A | 86 | 12.392 | 45.959 | 43.678 | 1.00 | 174.85 | A |
| ATOM | 335 | CG2 | VAL | A | 86 | 13.032 | 45.542 | 46.056 | 1.00 | 174.85 | A |
| ATOM | 336 | C | VAL | A | 86 | 12.109 | 43.144 | 43.199 | 1.00 | 148.93 | A |
| ATOM | 337 | O | VAL | A | 86 | 11.052 | 43.248 | 42.576 | 1.00 | 249.68 | A |
| ATOM | 338 | N | VAL | A | 87 | 13.207 | 42.606 | 42.677 | 1.00 | 190.10 | A |
| ATOM | 339 | CA | VAL | A | 87 | 13.233 | 42.092 | 41.313 | 1.00 | 190.10 | A |
| ATOM | 340 | CB | VAL | A | 87 | 14.673 | 41.722 | 40.887 | 1.00 | 168.93 | A |
| ATOM | 341 | CG1 | VAL | A | 87 | 14.678 | 41.216 | 39.458 | 1.00 | 168.93 | A |
| ATOM | 342 | CG2 | VAL | A | 87 | 15.578 | 42.935 | 41.011 | 1.00 | 168.93 | A |
| ATOM | 343 | C | VAL | A | 87 | 12.328 | 40.867 | 41.138 | 1.00 | 190.10 | A |
| ATOM | 344 | O | VAL | A | 87 | 11.642 | 40.736 | 40.122 | 1.00 | 190.10 | A |
| ATOM | 345 | N | PRO | A | 88 | 12.312 | 39.953 | 42.127 | 1.00 | 273.74 | A |
| ATOM | 346 | CD | PRO | A | 88 | 12.994 | 39.964 | 43.434 | 1.00 | 158.35 | A |
| ATOM | 347 | CA | PRO | A | 88 | 11.459 | 38.767 | 42.004 | 1.00 | 273.74 | A |
| ATOM | 348 | CB | PRO | A | 88 | 11.762 | 37.989 | 43.283 | 1.00 | 158.35 | A |
| ATOM | 349 | CG | PRO | A | 88 | 12.107 | 39.067 | 44.259 | 1.00 | 158.35 | A |
| ATOM | 350 | C | PRO | A | 88 | 9.983 | 39.131 | 41.873 | 1.00 | 273.74 | A |
| ATOM | 351 | O | PRO | A | 88 | 9.370 | 38.883 | 40.836 | 1.00 | 273.74 | A |
| ATOM | 352 | N | PHE | A | 89 | 9.420 | 39.724 | 42.923 | 1.00 | 221.00 | A |
| ATOM | 353 | CA | PHE | A | 89 | 8.016 | 40.125 | 42.911 | 1.00 | 221.00 | A |
| ATOM | 354 | CB | PHE | A | 89 | 7.625 | 40.781 | 44.241 | 1.00 | 134.34 | A |
| ATOM | 355 | CG | PHE | A | 89 | 7.656 | 39.842 | 45.420 | 1.00 | 134.34 | A |
| ATOM | 356 | CD1 | PHE | A | 89 | 6.947 | 38.644 | 45.396 | 1.00 | 134.34 | A |
| ATOM | 357 | CD2 | PHE | A | 89 | 8.381 | 40.165 | 46.562 | 1.00 | 134.34 | A |
| ATOM | 358 | CE1 | PHE | A | 89 | 6.958 | 37.782 | 46.496 | 1.00 | 134.34 | A |

TABLE 2-continued

Atomic coordinates of b2 adrenoreceptor

| ATOM | 359 | CE2 | PHE | A | 89 | 8.398 | 39.310 | 47.666 | 1.00 | 134.34 | A |
|---|---|---|---|---|---|---|---|---|---|---|---|
| ATOM | 360 | CZ | PHE | A | 89 | 7.685 | 38.117 | 47.631 | 1.00 | 134.34 | A |
| ATOM | 361 | C | PHE | A | 89 | 7.750 | 41.102 | 41.771 | 1.00 | 221.00 | A |
| ATOM | 362 | O | PHE | A | 89 | 6.606 | 41.478 | 41.518 | 1.00 | 221.00 | A |
| ATOM | 363 | N | GLY | A | 90 | 8.814 | 41.510 | 41.087 | 1.00 | 113.68 | A |
| ATOM | 364 | CA | GLY | A | 90 | 8.677 | 42.435 | 39.979 | 1.00 | 113.68 | A |
| ATOM | 365 | C | GLY | A | 90 | 9.409 | 41.956 | 38.741 | 1.00 | 113.68 | A |
| ATOM | 366 | O | GLY | A | 90 | 9.613 | 42.719 | 37.797 | 1.00 | 113.68 | A |
| ATOM | 367 | N | PHE | A | 108 | 4.424 | 46.981 | 50.260 | 1.00 | 211.62 | A |
| ATOM | 368 | CA | PHE | A | 108 | 5.703 | 46.672 | 50.893 | 1.00 | 210.27 | A |
| ATOM | 369 | CB | PHE | A | 108 | 5.571 | 45.396 | 51.733 | 1.00 | 161.77 | A |
| ATOM | 370 | CG | PHE | A | 108 | 6.572 | 45.291 | 52.858 | 1.00 | 162.07 | A |
| ATOM | 371 | CD1 | PHE | A | 108 | 6.598 | 46.240 | 53.878 | 1.00 | 162.56 | A |
| ATOM | 372 | CD2 | PHE | A | 108 | 7.462 | 44.221 | 52.919 | 1.00 | 162.04 | A |
| ATOM | 373 | CE1 | PHE | A | 108 | 7.494 | 46.122 | 54.944 | 1.00 | 162.44 | A |
| ATOM | 374 | CE2 | PHE | A | 108 | 8.363 | 44.092 | 53.982 | 1.00 | 162.05 | A |
| ATOM | 375 | CZ | PHE | A | 108 | 8.376 | 45.048 | 54.998 | 1.00 | 162.37 | A |
| ATOM | 376 | C | PHE | A | 108 | 6.747 | 46.475 | 49.798 | 1.00 | 209.13 | A |
| ATOM | 377 | O | PHE | A | 108 | 7.945 | 46.622 | 50.032 | 1.00 | 208.99 | A |
| ATOM | 378 | N | ALA | A | 109 | 6.272 | 46.141 | 48.599 | 1.00 | 185.03 | A |
| ATOM | 379 | CA | ALA | A | 109 | 7.142 | 45.919 | 47.446 | 1.00 | 183.72 | A |
| ATOM | 380 | CB | ALA | A | 109 | 6.400 | 45.136 | 46.361 | 1.00 | 162.79 | A |
| ATOM | 381 | C | ALA | A | 109 | 7.642 | 47.250 | 46.880 | 1.00 | 183.03 | A |
| ATOM | 382 | O | ALA | A | 109 | 8.670 | 47.292 | 46.201 | 1.00 | 182.88 | A |
| ATOM | 383 | N | THR | A | 110 | 6.914 | 48.334 | 47.155 | 1.00 | 231.68 | A |
| ATOM | 384 | CA | THR | A | 110 | 7.301 | 49.664 | 46.672 | 1.00 | 230.88 | A |
| ATOM | 385 | CB | THR | A | 110 | 6.103 | 50.438 | 46.108 | 1.00 | 146.66 | A |
| ATOM | 386 | OG1 | THR | A | 110 | 5.597 | 49.749 | 44.960 | 1.00 | 146.55 | A |
| ATOM | 387 | CG2 | THR | A | 110 | 6.518 | 51.847 | 45.666 | 1.00 | 146.34 | A |
| ATOM | 388 | C | THR | A | 110 | 7.911 | 50.436 | 47.827 | 1.00 | 230.53 | A |
| ATOM | 389 | O | THR | A | 110 | 8.384 | 51.578 | 47.690 | 1.00 | 230.87 | A |
| ATOM | 390 | N | SER | A | 111 | 7.931 | 49.769 | 48.972 | 1.00 | 185.34 | A |
| ATOM | 391 | CA | SER | A | 111 | 8.517 | 50.343 | 50.169 | 1.00 | 184.87 | A |
| ATOM | 392 | CB | SER | A | 111 | 7.928 | 49.677 | 51.414 | 1.00 | 163.64 | A |
| ATOM | 393 | OG | SER | A | 111 | 6.527 | 49.617 | 51.305 | 1.00 | 164.12 | A |
| ATOM | 394 | C | SER | A | 111 | 10.012 | 50.126 | 50.117 | 1.00 | 184.43 | A |
| ATOM | 395 | O | SER | A | 111 | 10.798 | 51.068 | 50.172 | 1.00 | 184.46 | A |
| ATOM | 396 | N | ALA | A | 112 | 10.410 | 48.869 | 50.007 | 1.00 | 255.77 | A |
| ATOM | 397 | CA | ALA | A | 112 | 11.840 | 48.574 | 49.933 | 1.00 | 255.36 | A |
| ATOM | 398 | CB | ALA | A | 112 | 12.083 | 47.110 | 50.226 | 1.00 | 170.87 | A |
| ATOM | 399 | C | ALA | A | 112 | 12.449 | 48.966 | 48.573 | 1.00 | 254.79 | A |
| ATOM | 400 | O | ALA | A | 112 | 13.667 | 48.869 | 48.383 | 1.00 | 254.60 | A |
| ATOM | 401 | N | ASP | A | 113 | 11.603 | 49.427 | 47.644 | 1.00 | 176.96 | A |
| ATOM | 402 | CA | ASP | A | 113 | 12.072 | 49.871 | 46.314 | 1.00 | 176.31 | A |
| ATOM | 403 | CB | ASP | A | 113 | 10.919 | 49.923 | 45.301 | 1.00 | 158.20 | A |
| ATOM | 404 | CG | ASP | A | 113 | 11.350 | 50.427 | 43.907 | 1.00 | 158.62 | A |
| ATOM | 405 | OD1 | ASP | A | 113 | 11.035 | 49.715 | 42.922 | 1.00 | 158.95 | A |
| ATOM | 406 | OD2 | ASP | A | 113 | 11.971 | 51.511 | 43.778 | 1.00 | 158.72 | A |
| ATOM | 407 | C | ASP | A | 113 | 12.667 | 51.273 | 46.433 | 1.00 | 175.82 | A |
| ATOM | 408 | O | ASP | A | 113 | 13.510 | 51.661 | 45.620 | 1.00 | 175.63 | A |
| ATOM | 409 | N | VAL | A | 114 | 12.216 | 52.035 | 47.427 | 1.00 | 183.24 | A |
| ATOM | 410 | CA | VAL | A | 114 | 12.716 | 53.381 | 47.633 | 1.00 | 182.80 | A |
| ATOM | 411 | CB | VAL | A | 114 | 11.576 | 54.318 | 48.130 | 1.00 | 168.51 | A |
| ATOM | 412 | CG1 | VAL | A | 114 | 12.109 | 55.731 | 48.371 | 1.00 | 168.37 | A |
| ATOM | 413 | CG2 | VAL | A | 114 | 10.449 | 54.363 | 47.108 | 1.00 | 168.53 | A |
| ATOM | 414 | C | VAL | A | 114 | 13.856 | 53.376 | 48.645 | 1.00 | 182.54 | A |
| ATOM | 415 | O | VAL | A | 114 | 14.899 | 53.995 | 48.439 | 1.00 | 182.48 | A |
| ATOM | 416 | N | LEU | A | 115 | 13.642 | 52.647 | 49.733 | 1.00 | 155.26 | A |
| ATOM | 417 | CA | LEU | A | 115 | 14.620 | 52.518 | 50.808 | 1.00 | 154.83 | A |
| ATOM | 418 | CB | LEU | A | 115 | 14.110 | 51.567 | 51.900 | 1.00 | 119.82 | A |
| ATOM | 419 | CG | LEU | A | 115 | 15.126 | 51.129 | 52.976 | 1.00 | 119.79 | A |
| ATOM | 420 | CD1 | LEU | A | 115 | 15.580 | 52.345 | 53.750 | 1.00 | 120.59 | A |
| ATOM | 421 | CD2 | LEU | A | 115 | 14.506 | 50.095 | 53.906 | 1.00 | 119.63 | A |
| ATOM | 422 | C | LEU | A | 115 | 15.933 | 51.969 | 50.259 | 1.00 | 154.53 | A |
| ATOM | 423 | O | LEU | A | 115 | 16.987 | 52.103 | 50.882 | 1.00 | 154.24 | A |
| ATOM | 424 | N | CYS | A | 116 | 15.859 | 51.365 | 49.077 | 1.00 | 153.92 | A |
| ATOM | 425 | CA | CYS | A | 116 | 17.013 | 50.790 | 48.409 | 1.00 | 153.92 | A |
| ATOM | 426 | CB | CYS | A | 116 | 16.582 | 49.554 | 47.603 | 1.00 | 151.47 | A |
| ATOM | 427 | SG | CYS | A | 116 | 16.296 | 48.060 | 48.595 | 1.00 | 151.47 | A |
| ATOM | 428 | C | CYS | A | 116 | 17.722 | 51.793 | 47.501 | 1.00 | 153.92 | A |
| ATOM | 429 | O | CYS | A | 116 | 18.942 | 51.947 | 47.582 | 1.00 | 153.92 | A |
| ATOM | 430 | N | VAL | A | 117 | 16.962 | 52.467 | 46.643 | 1.00 | 113.96 | A |
| ATOM | 431 | CA | VAL | A | 117 | 17.552 | 53.434 | 45.737 | 1.00 | 113.96 | A |
| ATOM | 432 | CB | VAL | A | 117 | 16.690 | 53.603 | 44.478 | 1.00 | 86.65 | A |
| ATOM | 433 | CG1 | VAL | A | 117 | 17.349 | 54.575 | 43.515 | 1.00 | 86.65 | A |
| ATOM | 434 | CG2 | VAL | A | 117 | 16.483 | 52.249 | 43.808 | 1.00 | 86.65 | A |
| ATOM | 435 | C | VAL | A | 117 | 17.807 | 54.808 | 46.364 | 1.00 | 113.96 | A |
| ATOM | 436 | O | VAL | A | 117 | 18.568 | 55.610 | 45.823 | 1.00 | 113.96 | A |

TABLE 2-continued

Atomic coordinates of b2 adrenoreceptor

| ATOM | 437 | N | THR | A | 118 | 17.180 | 55.078 | 47.506 | 1.00 | 241.70 | A |
|---|---|---|---|---|---|---|---|---|---|---|---|
| ATOM | 438 | CA | THR | A | 118 | 17.371 | 56.354 | 48.199 | 1.00 | 241.70 | A |
| ATOM | 439 | CB | THR | A | 118 | 16.107 | 56.776 | 48.969 | 1.00 | 188.36 | A |
| ATOM | 440 | OG1 | THR | A | 118 | 15.774 | 55.770 | 49.932 | 1.00 | 188.36 | A |
| ATOM | 441 | CG2 | THR | A | 118 | 14.950 | 56.959 | 48.005 | 1.00 | 188.36 | A |
| ATOM | 442 | C | THR | A | 118 | 18.533 | 56.240 | 49.185 | 1.00 | 241.70 | A |
| ATOM | 443 | O | THR | A | 118 | 18.961 | 57.228 | 49.784 | 1.00 | 241.70 | A |
| ATOM | 444 | N | ALA | A | 119 | 19.033 | 55.020 | 49.349 | 1.00 | 199.21 | A |
| ATOM | 445 | CA | ALA | A | 119 | 20.157 | 54.757 | 50.240 | 1.00 | 199.21 | A |
| ATOM | 446 | CB | ALA | A | 119 | 19.950 | 53.433 | 50.982 | 1.00 | 54.74 | A |
| ATOM | 447 | C | ALA | A | 119 | 21.432 | 54.696 | 49.406 | 1.00 | 199.21 | A |
| ATOM | 448 | O | ALA | A | 119 | 22.535 | 54.883 | 49.920 | 1.00 | 199.21 | A |
| ATOM | 449 | N | SER | A | 120 | 21.268 | 54.440 | 48.111 | 1.00 | 152.13 | A |
| ATOM | 450 | CA | SER | A | 120 | 22.397 | 54.352 | 47.194 | 1.00 | 152.13 | A |
| ATOM | 451 | CB | SER | A | 120 | 21.959 | 53.728 | 45.865 | 1.00 | 129.00 | A |
| ATOM | 452 | OG | SER | A | 120 | 21.637 | 52.356 | 46.020 | 1.00 | 129.00 | A |
| ATOM | 453 | C | SER | A | 120 | 23.028 | 55.712 | 46.937 | 1.00 | 152.13 | A |
| ATOM | 454 | O | SER | A | 120 | 24.143 | 55.972 | 47.385 | 1.00 | 152.13 | A |
| ATOM | 455 | N | ILE | A | 121 | 22.317 | 56.579 | 46.219 | 1.00 | 119.74 | A |
| ATOM | 456 | CA | ILE | A | 121 | 22.830 | 57.913 | 45.908 | 1.00 | 119.74 | A |
| ATOM | 457 | CB | ILE | A | 121 | 21.845 | 58.684 | 44.972 | 1.00 | 127.99 | A |
| ATOM | 458 | CG2 | ILE | A | 121 | 20.851 | 59.486 | 45.802 | 1.00 | 127.99 | A |
| ATOM | 459 | CG1 | ILE | A | 121 | 22.618 | 59.595 | 44.002 | 1.00 | 127.99 | A |
| ATOM | 460 | CD1 | ILE | A | 121 | 23.158 | 60.883 | 44.599 | 1.00 | 127.99 | A |
| ATOM | 461 | C | ILE | A | 121 | 23.078 | 58.704 | 47.201 | 1.00 | 119.74 | A |
| ATOM | 462 | O | ILE | A | 121 | 23.520 | 59.855 | 47.168 | 1.00 | 119.74 | A |
| ATOM | 463 | N | ALA | A | 122 | 22.785 | 58.079 | 48.340 | 1.00 | 173.88 | A |
| ATOM | 464 | CA | ALA | A | 122 | 23.010 | 58.701 | 49.643 | 1.00 | 173.88 | A |
| ATOM | 465 | CB | ALA | A | 122 | 21.952 | 58.251 | 50.640 | 1.00 | 118.62 | A |
| ATOM | 466 | C | ALA | A | 122 | 24.389 | 58.248 | 50.101 | 1.00 | 173.88 | A |
| ATOM | 467 | O | ALA | A | 122 | 25.194 | 59.045 | 50.583 | 1.00 | 316.39 | A |
| ATOM | 468 | N | THR | A | 123 | 24.649 | 56.953 | 49.942 | 1.00 | 139.17 | A |
| ATOM | 469 | CA | THR | A | 123 | 25.935 | 56.378 | 50.303 | 1.00 | 139.17 | A |
| ATOM | 470 | CB | THR | A | 123 | 25.918 | 54.847 | 50.167 | 1.00 | 174.52 | A |
| ATOM | 471 | OG1 | THR | A | 123 | 24.908 | 54.303 | 51.026 | 1.00 | 174.52 | A |
| ATOM | 472 | CG2 | THR | A | 123 | 27.266 | 54.264 | 50.553 | 1.00 | 174.52 | A |
| ATOM | 473 | C | THR | A | 123 | 26.970 | 56.959 | 49.348 | 1.00 | 139.17 | A |
| ATOM | 474 | O | THR | A | 123 | 28.089 | 57.266 | 49.746 | 1.00 | 139.17 | A |
| ATOM | 475 | N | LEU | A | 124 | 26.585 | 57.110 | 48.083 | 1.00 | 157.28 | A |
| ATOM | 476 | CA | LEU | A | 124 | 27.469 | 57.685 | 47.074 | 1.00 | 157.28 | A |
| ATOM | 477 | CB | LEU | A | 124 | 26.765 | 57.750 | 45.714 | 1.00 | 105.76 | A |
| ATOM | 478 | CG | LEU | A | 124 | 26.776 | 56.513 | 44.804 | 1.00 | 105.76 | A |
| ATOM | 479 | CD1 | LEU | A | 124 | 27.937 | 56.606 | 43.833 | 1.00 | 105.76 | A |
| ATOM | 480 | CD2 | LEU | A | 124 | 26.846 | 55.233 | 45.638 | 1.00 | 105.76 | A |
| ATOM | 481 | C | LEU | A | 124 | 27.854 | 59.089 | 47.515 | 1.00 | 157.28 | A |
| ATOM | 482 | O | LEU | A | 124 | 28.915 | 59.595 | 47.157 | 1.00 | 157.28 | A |
| ATOM | 483 | N | CYS | A | 125 | 26.978 | 59.717 | 48.291 | 1.00 | 169.53 | A |
| ATOM | 484 | CA | CYS | A | 125 | 27.242 | 61.055 | 48.795 | 1.00 | 169.53 | A |
| ATOM | 485 | CB | CYS | A | 125 | 25.941 | 61.718 | 49.249 | 1.00 | 168.07 | A |
| ATOM | 486 | SG | CYS | A | 125 | 26.139 | 63.413 | 49.843 | 1.00 | 168.07 | A |
| ATOM | 487 | C | CYS | A | 125 | 28.196 | 60.921 | 49.975 | 1.00 | 169.53 | A |
| ATOM | 488 | O | CYS | A | 125 | 29.046 | 61.779 | 50.206 | 1.00 | 169.53 | A |
| ATOM | 489 | N | VAL | A | 126 | 28.049 | 59.824 | 50.711 | 1.00 | 138.00 | A |
| ATOM | 490 | CA | VAL | A | 126 | 28.886 | 59.547 | 51.872 | 1.00 | 138.00 | A |
| ATOM | 491 | CB | VAL | A | 126 | 28.463 | 58.236 | 52.549 | 1.00 | 111.76 | A |
| ATOM | 492 | CG1 | VAL | A | 126 | 29.343 | 57.967 | 53.755 | 1.00 | 111.76 | A |
| ATOM | 493 | CG2 | VAL | A | 126 | 27.001 | 58.315 | 52.950 | 1.00 | 111.76 | A |
| ATOM | 494 | C | VAL | A | 126 | 30.357 | 59.437 | 51.494 | 1.00 | 138.00 | A |
| ATOM | 495 | O | VAL | A | 126 | 31.167 | 60.285 | 51.863 | 1.00 | 138.00 | A |
| ATOM | 496 | N | ILE | A | 127 | 30.694 | 58.379 | 50.764 | 1.00 | 87.26 | A |
| ATOM | 497 | CA | ILE | A | 127 | 32.064 | 58.145 | 50.324 | 1.00 | 87.26 | A |
| ATOM | 498 | CB | ILE | A | 127 | 32.135 | 56.985 | 49.302 | 1.00 | 151.63 | A |
| ATOM | 499 | CG2 | ILE | A | 127 | 33.547 | 56.851 | 48.765 | 1.00 | 151.63 | A |
| ATOM | 500 | CG1 | ILE | A | 127 | 31.702 | 55.672 | 49.957 | 1.00 | 151.63 | A |
| ATOM | 501 | CD1 | ILE | A | 127 | 30.223 | 55.558 | 50.173 | 1.00 | 151.63 | A |
| ATOM | 502 | C | ILE | A | 127 | 32.682 | 59.391 | 49.689 | 1.00 | 87.26 | A |
| ATOM | 503 | O | ILE | A | 127 | 33.759 | 59.826 | 50.098 | 1.00 | 87.26 | A |
| ATOM | 504 | N | ALA | A | 128 | 32.005 | 59.958 | 48.694 | 1.00 | 116.45 | A |
| ATOM | 505 | CA | ALA | A | 128 | 32.499 | 61.154 | 48.016 | 1.00 | 116.45 | A |
| ATOM | 506 | CB | ALA | A | 128 | 31.387 | 61.789 | 47.197 | 1.00 | 138.13 | A |
| ATOM | 507 | C | ALA | A | 128 | 33.045 | 62.159 | 49.028 | 1.00 | 116.45 | A |
| ATOM | 508 | O | ALA | A | 128 | 33.996 | 62.886 | 48.747 | 1.00 | 116.45 | A |
| ATOM | 509 | N | VAL | A | 129 | 32.433 | 62.193 | 50.206 | 1.00 | 103.72 | A |
| ATOM | 510 | CA | VAL | A | 129 | 32.860 | 63.086 | 51.274 | 1.00 | 103.72 | A |
| ATOM | 511 | CB | VAL | A | 129 | 31.671 | 63.471 | 52.181 | 1.00 | 100.86 | A |
| ATOM | 512 | CG1 | VAL | A | 129 | 32.162 | 64.214 | 53.419 | 1.00 | 100.86 | A |
| ATOM | 513 | CG2 | VAL | A | 129 | 30.699 | 64.331 | 51.404 | 1.00 | 100.86 | A |
| ATOM | 514 | C | VAL | A | 129 | 33.930 | 62.399 | 52.118 | 1.00 | 103.72 | A |

TABLE 2-continued

Atomic coordinates of b2 adrenoreceptor

| ATOM | 515 | O | VAL | A | 129 | 34.958 | 62.992 | 52.434 | 1.00 | 103.72 | A |
| ATOM | 516 | N | ASP | A | 130 | 33.681 | 61.145 | 52.483 | 1.00 | 87.93 | A |
| ATOM | 517 | CA | ASP | A | 130 | 34.626 | 60.379 | 53.282 | 1.00 | 87.93 | A |
| ATOM | 518 | CB | ASP | A | 130 | 34.134 | 58.940 | 53.459 | 1.00 | 155.04 | A |
| ATOM | 519 | CG | ASP | A | 130 | 35.214 | 58.016 | 53.987 | 1.00 | 155.04 | A |
| ATOM | 520 | OD1 | ASP | A | 130 | 36.147 | 57.691 | 53.222 | 1.00 | 155.04 | A |
| ATOM | 521 | OD2 | ASP | A | 130 | 35.133 | 57.617 | 55.166 | 1.00 | 155.04 | A |
| ATOM | 522 | C | ASP | A | 130 | 35.983 | 60.377 | 52.610 | 1.00 | 87.93 | A |
| ATOM | 523 | O | ASP | A | 130 | 36.987 | 60.740 | 53.220 | 1.00 | 87.93 | A |
| ATOM | 524 | N | ARG | A | 131 | 36.004 | 59.962 | 51.347 | 1.00 | 115.23 | A |
| ATOM | 525 | CA | ARG | A | 131 | 37.240 | 59.918 | 50.580 | 1.00 | 115.23 | A |
| ATOM | 526 | CB | ARG | A | 131 | 36.972 | 59.446 | 49.149 | 1.00 | 117.81 | A |
| ATOM | 527 | CG | ARG | A | 131 | 36.641 | 57.963 | 49.017 | 1.00 | 117.81 | A |
| ATOM | 528 | CD | ARG | A | 131 | 37.803 | 57.077 | 49.438 | 1.00 | 117.81 | A |
| ATOM | 529 | NE | ARG | A | 131 | 37.894 | 56.925 | 50.888 | 1.00 | 117.81 | A |
| ATOM | 530 | CZ | ARG | A | 131 | 38.890 | 56.302 | 51.517 | 1.00 | 117.81 | A |
| ATOM | 531 | NH1 | ARG | A | 131 | 39.892 | 55.772 | 50.826 | 1.00 | 117.81 | A |
| ATOM | 532 | NH2 | ARG | A | 131 | 38.882 | 56.199 | 52.841 | 1.00 | 117.81 | A |
| ATOM | 533 | C | ARG | A | 131 | 37.879 | 61.299 | 50.557 | 1.00 | 115.23 | A |
| ATOM | 534 | O | ARG | A | 131 | 39.102 | 61.425 | 50.590 | 1.00 | 227.48 | A |
| ATOM | 535 | N | TYR | A | 132 | 37.050 | 62.336 | 50.498 | 1.00 | 88.84 | A |
| ATOM | 536 | CA | TYR | A | 132 | 37.560 | 63.700 | 50.495 | 1.00 | 88.84 | A |
| ATOM | 537 | CB | TYR | A | 132 | 36.414 | 64.702 | 50.395 | 1.00 | 97.78 | A |
| ATOM | 538 | CG | TYR | A | 132 | 36.845 | 66.149 | 50.492 | 1.00 | 97.78 | A |
| ATOM | 539 | CD1 | TYR | A | 132 | 37.243 | 66.855 | 49.357 | 1.00 | 97.78 | A |
| ATOM | 540 | CE1 | TYR | A | 132 | 37.599 | 68.200 | 49.435 | 1.00 | 97.78 | A |
| ATOM | 541 | CD2 | TYR | A | 132 | 36.822 | 66.822 | 51.717 | 1.00 | 97.78 | A |
| ATOM | 542 | CE2 | TYR | A | 132 | 37.178 | 68.167 | 51.809 | 1.00 | 97.78 | A |
| ATOM | 543 | CZ | TYR | A | 132 | 37.561 | 68.854 | 50.662 | 1.00 | 97.78 | A |
| ATOM | 544 | OH | TYR | A | 132 | 37.866 | 70.201 | 50.731 | 1.00 | 97.78 | A |
| ATOM | 545 | C | TYR | A | 132 | 38.298 | 63.910 | 51.809 | 1.00 | 88.84 | A |
| ATOM | 546 | O | TYR | A | 132 | 39.507 | 64.121 | 51.819 | 1.00 | 88.84 | A |
| ATOM | 547 | N | PHE | A | 133 | 37.562 | 63.846 | 52.915 | 1.00 | 90.21 | A |
| ATOM | 548 | CA | PHE | A | 133 | 38.148 | 64.018 | 54.237 | 1.00 | 90.21 | A |
| ATOM | 549 | CB | PHE | A | 133 | 37.146 | 63.605 | 55.318 | 1.00 | 148.01 | A |
| ATOM | 550 | CG | PHE | A | 133 | 36.199 | 64.702 | 55.715 | 1.00 | 148.01 | A |
| ATOM | 551 | CD1 | PHE | A | 133 | 35.526 | 65.445 | 54.750 | 1.00 | 148.01 | A |
| ATOM | 552 | CD2 | PHE | A | 133 | 35.982 | 64.996 | 57.059 | 1.00 | 148.01 | A |
| ATOM | 553 | CE1 | PHE | A | 133 | 34.651 | 66.465 | 55.116 | 1.00 | 148.01 | A |
| ATOM | 554 | CE2 | PHE | A | 133 | 35.109 | 66.014 | 57.437 | 1.00 | 148.01 | A |
| ATOM | 555 | CZ | PHE | A | 133 | 34.443 | 66.750 | 56.464 | 1.00 | 148.01 | A |
| ATOM | 556 | C | PHE | A | 133 | 39.428 | 63.205 | 54.375 | 1.00 | 90.21 | A |
| ATOM | 557 | O | PHE | A | 133 | 40.270 | 63.506 | 55.216 | 1.00 | 90.21 | A |
| ATOM | 558 | N | ALA | A | 134 | 39.568 | 62.176 | 53.543 | 1.00 | 102.21 | A |
| ATOM | 559 | CA | ALA | A | 134 | 40.754 | 61.326 | 53.559 | 1.00 | 102.21 | A |
| ATOM | 560 | CB | ALA | A | 134 | 40.464 | 60.004 | 52.864 | 1.00 | 139.38 | A |
| ATOM | 561 | C | ALA | A | 134 | 41.905 | 62.039 | 52.865 | 1.00 | 102.21 | A |
| ATOM | 562 | O | ALA | A | 134 | 43.030 | 62.026 | 53.357 | 1.00 | 102.21 | A |
| ATOM | 563 | N | ILE | A | 135 | 41.624 | 62.660 | 51.722 | 1.00 | 115.57 | A |
| ATOM | 564 | CA | ILE | A | 135 | 42.651 | 63.385 | 50.980 | 1.00 | 115.57 | A |
| ATOM | 565 | CB | ILE | A | 135 | 42.258 | 63.569 | 49.497 | 1.00 | 82.63 | A |
| ATOM | 566 | CG2 | ILE | A | 135 | 42.966 | 64.790 | 48.908 | 1.00 | 82.63 | A |
| ATOM | 567 | CG1 | ILE | A | 135 | 42.605 | 62.299 | 48.717 | 1.00 | 82.63 | A |
| ATOM | 568 | CD1 | ILE | A | 135 | 42.541 | 62.454 | 47.202 | 1.00 | 82.63 | A |
| ATOM | 569 | C | ILE | A | 135 | 42.954 | 64.755 | 51.585 | 1.00 | 115.57 | A |
| ATOM | 570 | O | ILE | A | 135 | 44.114 | 65.082 | 51.838 | 1.00 | 82.02 | A |
| ATOM | 571 | N | THR | A | 136 | 41.917 | 65.556 | 51.808 | 1.00 | 165.83 | A |
| ATOM | 572 | CA | THR | A | 136 | 42.096 | 66.881 | 52.393 | 1.00 | 165.83 | A |
| ATOM | 573 | CB | THR | A | 136 | 40.741 | 67.575 | 52.640 | 1.00 | 212.61 | A |
| ATOM | 574 | OG1 | THR | A | 136 | 40.962 | 68.847 | 53.263 | 1.00 | 212.61 | A |
| ATOM | 575 | CG2 | THR | A | 136 | 39.861 | 66.724 | 53.541 | 1.00 | 212.61 | A |
| ATOM | 576 | C | THR | A | 136 | 42.833 | 66.749 | 53.723 | 1.00 | 165.83 | A |
| ATOM | 577 | O | THR | A | 136 | 43.413 | 67.711 | 54.228 | 1.00 | 285.35 | A |
| ATOM | 578 | N | SER | A | 137 | 42.800 | 65.541 | 54.279 | 1.00 | 131.01 | A |
| ATOM | 579 | CA | SER | A | 137 | 43.459 | 65.240 | 55.542 | 1.00 | 131.01 | A |
| ATOM | 580 | CB | SER | A | 137 | 43.220 | 63.777 | 55.924 | 1.00 | 193.42 | A |
| ATOM | 581 | OG | SER | A | 137 | 44.008 | 63.399 | 57.040 | 1.00 | 193.42 | A |
| ATOM | 582 | C | SER | A | 137 | 44.957 | 65.495 | 55.449 | 1.00 | 131.01 | A |
| ATOM | 583 | O | SER | A | 137 | 45.572 | 65.280 | 54.404 | 1.00 | 131.01 | A |
| ATOM | 584 | N | PRO | A | 138 | 45.564 | 65.961 | 56.550 | 1.00 | 117.34 | A |
| ATOM | 585 | CD | PRO | A | 138 | 44.919 | 66.345 | 57.820 | 1.00 | 174.21 | A |
| ATOM | 586 | CA | PRO | A | 138 | 47.001 | 66.245 | 56.590 | 1.00 | 117.34 | A |
| ATOM | 587 | CB | PRO | A | 138 | 47.145 | 67.075 | 57.859 | 1.00 | 174.21 | A |
| ATOM | 588 | CG | PRO | A | 138 | 46.099 | 66.479 | 58.755 | 1.00 | 174.21 | A |
| ATOM | 589 | C | PRO | A | 138 | 47.850 | 64.977 | 56.632 | 1.00 | 117.34 | A |
| ATOM | 590 | O | PRO | A | 138 | 49.046 | 65.016 | 56.341 | 1.00 | 117.34 | A |
| ATOM | 591 | N | PHE | A | 139 | 47.228 | 63.857 | 56.992 | 1.00 | 128.93 | A |
| ATOM | 592 | CA | PHE | A | 139 | 47.948 | 62.593 | 57.077 | 1.00 | 128.93 | A |

TABLE 2-continued

Atomic coordinates of b2 adrenoreceptor

| ATOM | 593 | CB | PHE | A | 139 | 47.780 | 61.973 | 58.471 | 1.00 | 121.70 | A |
|------|-----|------|-----|---|-----|--------|--------|--------|------|--------|---|
| ATOM | 594 | CG | PHE | A | 139 | 49.030 | 61.305 | 58.991 | 1.00 | 121.70 | A |
| ATOM | 595 | CD1 | PHE | A | 139 | 48.946 | 60.282 | 59.928 | 1.00 | 121.70 | A |
| ATOM | 596 | CD2 | PHE | A | 139 | 50.296 | 61.720 | 58.559 | 1.00 | 121.70 | A |
| ATOM | 597 | CE1 | PHE | A | 139 | 50.100 | 59.680 | 60.428 | 1.00 | 121.70 | A |
| ATOM | 598 | CE2 | PHE | A | 139 | 51.457 | 61.124 | 59.054 | 1.00 | 121.70 | A |
| ATOM | 599 | CZ | PHE | A | 139 | 51.359 | 60.105 | 59.987 | 1.00 | 121.70 | A |
| ATOM | 600 | C | PHE | A | 139 | 47.533 | 61.579 | 56.011 | 1.00 | 128.93 | A |
| ATOM | 601 | O | PHE | A | 139 | 46.739 | 61.889 | 55.123 | 1.00 | 128.93 | A |
| ATOM | 602 | N | LYS | A | 140 | 48.079 | 60.366 | 56.123 | 1.00 | 196.19 | A |
| ATOM | 603 | CA | LYS | A | 140 | 47.835 | 59.263 | 55.185 | 1.00 | 196.19 | A |
| ATOM | 604 | CB | LYS | A | 140 | 48.116 | 57.918 | 55.866 | 1.00 | 139.21 | A |
| ATOM | 605 | CG | LYS | A | 140 | 49.326 | 57.887 | 56.802 | 1.00 | 139.21 | A |
| ATOM | 606 | CD | LYS | A | 140 | 50.586 | 58.496 | 56.200 | 1.00 | 139.21 | A |
| ATOM | 607 | CE | LYS | A | 140 | 51.740 | 58.411 | 57.197 | 1.00 | 139.21 | A |
| ATOM | 608 | NZ | LYS | A | 140 | 52.847 | 59.368 | 56.911 | 1.00 | 139.21 | A |
| ATOM | 609 | C | LYS | A | 140 | 46.448 | 59.218 | 54.539 | 1.00 | 196.19 | A |
| ATOM | 610 | O | LYS | A | 140 | 45.503 | 59.860 | 55.005 | 1.00 | 196.19 | A |
| ATOM | 611 | N | TYR | A | 141 | 46.338 | 58.432 | 53.472 | 1.00 | 159.19 | A |
| ATOM | 612 | CA | TYR | A | 141 | 45.095 | 58.287 | 52.720 | 1.00 | 159.19 | A |
| ATOM | 613 | CB | TYR | A | 141 | 45.428 | 58.053 | 51.239 | 1.00 | 124.79 | A |
| ATOM | 614 | CG | TYR | A | 141 | 44.228 | 57.998 | 50.321 | 1.00 | 124.79 | A |
| ATOM | 615 | CD1 | TYR | A | 141 | 43.271 | 56.990 | 50.439 | 1.00 | 124.79 | A |
| ATOM | 616 | CE1 | TYR | A | 141 | 42.203 | 56.916 | 49.558 | 1.00 | 124.79 | A |
| ATOM | 617 | CD2 | TYR | A | 141 | 44.078 | 58.933 | 49.302 | 1.00 | 124.79 | A |
| ATOM | 618 | CE2 | TYR | A | 141 | 43.025 | 58.869 | 48.421 | 1.00 | 124.79 | A |
| ATOM | 619 | CZ | TYR | A | 141 | 42.089 | 57.856 | 48.549 | 1.00 | 124.79 | A |
| ATOM | 620 | OH | TYR | A | 141 | 41.057 | 57.768 | 47.648 | 1.00 | 124.79 | A |
| ATOM | 621 | C | TYR | A | 141 | 44.204 | 57.141 | 53.233 | 1.00 | 159.19 | A |
| ATOM | 622 | O | TYR | A | 141 | 44.420 | 55.985 | 52.896 | 1.00 | 323.05 | A |
| ATOM | 623 | N | GLN | A | 142 | 43.214 | 57.499 | 54.048 | 1.00 | 126.04 | A |
| ATOM | 624 | CA | GLN | A | 142 | 42.232 | 56.587 | 54.632 | 1.00 | 126.04 | A |
| ATOM | 625 | CB | GLN | A | 142 | 42.916 | 55.376 | 55.276 | 1.00 | 178.01 | A |
| ATOM | 626 | CG | GLN | A | 142 | 42.693 | 54.050 | 54.518 | 1.00 | 178.01 | A |
| ATOM | 627 | CD | GLN | A | 142 | 41.237 | 53.638 | 54.412 | 1.00 | 178.01 | A |
| ATOM | 628 | OE1 | GLN | A | 142 | 40.448 | 54.290 | 53.750 | 1.00 | 178.01 | A |
| ATOM | 629 | NE2 | GLN | A | 142 | 40.877 | 52.535 | 55.079 | 1.00 | 178.01 | A |
| ATOM | 630 | C | GLN | A | 142 | 41.460 | 57.381 | 55.672 | 1.00 | 126.04 | A |
| ATOM | 631 | O | GLN | A | 142 | 41.932 | 57.590 | 56.804 | 1.00 | 126.04 | A |
| ATOM | 632 | N | SER | A | 143 | 40.295 | 57.863 | 55.241 | 1.00 | 131.20 | A |
| ATOM | 633 | CA | SER | A | 143 | 39.384 | 58.679 | 56.041 | 1.00 | 131.20 | A |
| ATOM | 634 | CB | SER | A | 143 | 37.945 | 58.510 | 55.534 | 1.00 | 141.27 | A |
| ATOM | 635 | OG | SER | A | 143 | 37.054 | 59.445 | 56.110 | 1.00 | 141.27 | A |
| ATOM | 636 | C | SER | A | 143 | 39.448 | 58.327 | 57.515 | 1.00 | 131.20 | A |
| ATOM | 637 | O | SER | A | 143 | 39.847 | 57.224 | 57.885 | 1.00 | 131.20 | A |
| ATOM | 638 | N | LEU | A | 144 | 39.034 | 59.272 | 58.350 | 1.00 | 166.55 | A |
| ATOM | 639 | CA | LEU | A | 144 | 39.055 | 59.096 | 59.791 | 1.00 | 166.55 | A |
| ATOM | 640 | CB | LEU | A | 144 | 39.212 | 60.459 | 60.473 | 1.00 | 83.81 | A |
| ATOM | 641 | CG | LEU | A | 144 | 40.113 | 61.501 | 59.794 | 1.00 | 83.81 | A |
| ATOM | 642 | CD1 | LEU | A | 144 | 40.413 | 62.637 | 60.771 | 1.00 | 83.81 | A |
| ATOM | 643 | CD2 | LEU | A | 144 | 41.401 | 60.857 | 59.326 | 1.00 | 83.81 | A |
| ATOM | 644 | C | LEU | A | 144 | 37.814 | 58.389 | 60.349 | 1.00 | 166.55 | A |
| ATOM | 645 | O | LEU | A | 144 | 37.802 | 57.977 | 61.515 | 1.00 | 166.55 | A |
| ATOM | 646 | N | LEU | A | 145 | 36.766 | 58.269 | 59.536 | 1.00 | 174.87 | A |
| ATOM | 647 | CA | LEU | A | 145 | 35.540 | 57.600 | 59.968 | 1.00 | 174.87 | A |
| ATOM | 648 | CB | LEU | A | 145 | 34.586 | 57.404 | 58.780 | 1.00 | 99.32 | A |
| ATOM | 649 | CG | LEU | A | 145 | 33.497 | 58.418 | 58.395 | 1.00 | 99.32 | A |
| ATOM | 650 | CD1 | LEU | A | 145 | 32.419 | 58.480 | 59.466 | 1.00 | 99.32 | A |
| ATOM | 651 | CD2 | LEU | A | 145 | 34.113 | 59.780 | 58.160 | 1.00 | 99.32 | A |
| ATOM | 652 | C | LEU | A | 145 | 35.909 | 56.246 | 60.563 | 1.00 | 174.87 | A |
| ATOM | 653 | O | LEU | A | 145 | 36.111 | 55.277 | 59.835 | 1.00 | 174.87 | A |
| ATOM | 654 | N | THR | A | 146 | 35.993 | 56.185 | 61.889 | 1.00 | 200.16 | A |
| ATOM | 655 | CA | THR | A | 146 | 36.349 | 54.950 | 62.586 | 1.00 | 200.16 | A |
| ATOM | 656 | CB | THR | A | 146 | 36.195 | 55.109 | 64.115 | 1.00 | 186.40 | A |
| ATOM | 657 | OG1 | THR | A | 146 | 34.827 | 55.375 | 64.434 | 1.00 | 186.40 | A |
| ATOM | 658 | CG2 | THR | A | 146 | 37.048 | 56.260 | 64.619 | 1.00 | 186.40 | A |
| ATOM | 659 | C | THR | A | 146 | 35.513 | 53.755 | 62.127 | 1.00 | 200.16 | A |
| ATOM | 660 | O | THR | A | 146 | 34.476 | 53.925 | 61.491 | 1.00 | 200.16 | A |
| ATOM | 661 | N | ALA | A | 147 | 35.973 | 52.549 | 62.454 | 1.00 | 151.25 | A |
| ATOM | 662 | CA | ALA | A | 147 | 35.275 | 51.323 | 62.065 | 1.00 | 151.25 | A |
| ATOM | 663 | CB | ALA | A | 147 | 36.071 | 50.095 | 62.522 | 1.00 | 111.02 | A |
| ATOM | 664 | C | ALA | A | 147 | 33.854 | 51.259 | 62.620 | 1.00 | 151.25 | A |
| ATOM | 665 | O | ALA | A | 147 | 32.913 | 50.909 | 61.905 | 1.00 | 277.00 | A |
| ATOM | 666 | N | ASN | A | 148 | 33.706 | 51.593 | 63.897 | 1.00 | 195.48 | A |
| ATOM | 667 | CA | ASN | A | 148 | 32.399 | 51.573 | 64.537 | 1.00 | 195.48 | A |
| ATOM | 668 | CB | ASN | A | 148 | 32.555 | 51.522 | 66.066 | 1.00 | 175.69 | A |
| ATOM | 669 | CG | ASN | A | 148 | 33.507 | 52.580 | 66.604 | 1.00 | 175.69 | A |
| ATOM | 670 | OD1 | ASN | A | 148 | 33.763 | 52.640 | 67.806 | 1.00 | 175.69 | A |

TABLE 2-continued

Atomic coordinates of b2 adrenoreceptor

| ATOM | 671 | ND2 | ASN | A | 148 | 34.035 | 53.416 | 65.721 | 1.00 | 175.69 | A |
|---|---|---|---|---|---|---|---|---|---|---|---|
| ATOM | 672 | C | ASN | A | 148 | 31.537 | 52.765 | 64.124 | 1.00 | 195.48 | A |
| ATOM | 673 | O | ASN | A | 148 | 30.350 | 52.606 | 63.837 | 1.00 | 195.48 | A |
| ATOM | 674 | N | LYS | A | 149 | 32.134 | 53.953 | 64.086 | 1.00 | 119.46 | A |
| ATOM | 675 | CA | LYS | A | 149 | 31.410 | 55.161 | 63.698 | 1.00 | 119.46 | A |
| ATOM | 676 | CB | LYS | A | 149 | 32.227 | 56.409 | 64.052 | 1.00 | 143.14 | A |
| ATOM | 677 | CG | LYS | A | 149 | 32.506 | 56.566 | 65.544 | 1.00 | 143.14 | A |
| ATOM | 678 | CD | LYS | A | 149 | 33.448 | 57.731 | 65.809 | 1.00 | 143.14 | A |
| ATOM | 679 | CE | LYS | A | 149 | 33.819 | 57.833 | 67.281 | 1.00 | 143.14 | A |
| ATOM | 680 | NZ | LYS | A | 149 | 34.700 | 59.007 | 67.544 | 1.00 | 143.14 | A |
| ATOM | 681 | C | LYS | A | 149 | 31.105 | 55.134 | 62.199 | 1.00 | 119.46 | A |
| ATOM | 682 | O | LYS | A | 149 | 30.458 | 56.038 | 61.664 | 1.00 | 119.46 | A |
| ATOM | 683 | N | ALA | A | 150 | 31.591 | 54.093 | 61.527 | 1.00 | 182.22 | A |
| ATOM | 684 | CA | ALA | A | 150 | 31.350 | 53.915 | 60.099 | 1.00 | 182.22 | A |
| ATOM | 685 | CB | ALA | A | 150 | 32.483 | 53.125 | 59.461 | 1.00 | 149.79 | A |
| ATOM | 686 | C | ALA | A | 150 | 30.058 | 53.124 | 60.031 | 1.00 | 182.22 | A |
| ATOM | 687 | O | ALA | A | 150 | 29.234 | 53.316 | 59.138 | 1.00 | 182.22 | A |
| ATOM | 688 | N | ARG | A | 151 | 29.899 | 52.227 | 60.997 | 1.00 | 147.39 | A |
| ATOM | 689 | CA | ARG | A | 151 | 28.705 | 51.409 | 61.095 | 1.00 | 147.39 | A |
| ATOM | 690 | CB | ARG | A | 151 | 28.940 | 50.228 | 62.045 | 1.00 | 137.86 | A |
| ATOM | 691 | CG | ARG | A | 151 | 29.892 | 49.167 | 61.509 | 1.00 | 137.86 | A |
| ATOM | 692 | CD | ARG | A | 151 | 29.918 | 47.943 | 62.416 | 1.00 | 137.86 | A |
| ATOM | 693 | NE | ARG | A | 151 | 30.609 | 46.813 | 61.797 | 1.00 | 137.86 | A |
| ATOM | 694 | CZ | ARG | A | 151 | 30.681 | 45.595 | 62.328 | 1.00 | 137.86 | A |
| ATOM | 695 | NH1 | ARG | A | 151 | 30.105 | 45.339 | 63.495 | 1.00 | 137.86 | A |
| ATOM | 696 | NH2 | ARG | A | 151 | 31.325 | 44.629 | 61.687 | 1.00 | 137.86 | A |
| ATOM | 697 | C | ARG | A | 151 | 27.592 | 52.299 | 61.633 | 1.00 | 147.39 | A |
| ATOM | 698 | O | ARG | A | 151 | 26.498 | 52.342 | 61.075 | 1.00 | 147.39 | A |
| ATOM | 699 | N | ALA | A | 152 | 27.887 | 53.014 | 62.717 | 1.00 | 190.94 | A |
| ATOM | 700 | CA | ALA | A | 152 | 26.918 | 53.915 | 63.334 | 1.00 | 190.94 | A |
| ATOM | 701 | CB | ALA | A | 152 | 27.548 | 54.630 | 64.542 | 1.00 | 45.08 | A |
| ATOM | 702 | C | ALA | A | 152 | 26.452 | 54.931 | 62.294 | 1.00 | 190.94 | A |
| ATOM | 703 | O | ALA | A | 152 | 25.302 | 55.371 | 62.309 | 1.00 | 190.94 | A |
| ATOM | 704 | N | ALA | A | 153 | 27.358 | 55.295 | 61.391 | 1.00 | 106.72 | A |
| ATOM | 705 | CA | ALA | A | 153 | 27.044 | 56.241 | 60.328 | 1.00 | 106.72 | A |
| ATOM | 706 | CB | ALA | A | 153 | 28.324 | 56.884 | 59.793 | 1.00 | 138.35 | A |
| ATOM | 707 | C | ALA | A | 153 | 26.344 | 55.462 | 59.223 | 1.00 | 106.72 | A |
| ATOM | 708 | O | ALA | A | 153 | 25.550 | 56.011 | 58.466 | 1.00 | 106.72 | A |
| ATOM | 709 | N | ALA | A | 154 | 26.649 | 54.171 | 59.144 | 1.00 | 250.16 | A |
| ATOM | 710 | CA | ALA | A | 154 | 26.048 | 53.300 | 58.146 | 1.00 | 250.16 | A |
| ATOM | 711 | CB | ALA | A | 154 | 26.812 | 51.973 | 58.079 | 1.00 | 66.70 | A |
| ATOM | 712 | C | ALA | A | 154 | 24.589 | 53.050 | 58.514 | 1.00 | 250.16 | A |
| ATOM | 713 | O | ALA | A | 154 | 23.696 | 53.152 | 57.673 | 1.00 | 250.16 | A |
| ATOM | 714 | N | ALA | A | 155 | 24.360 | 52.733 | 59.784 | 1.00 | 140.86 | A |
| ATOM | 715 | CA | ALA | A | 155 | 23.021 | 52.457 | 60.292 | 1.00 | 140.86 | A |
| ATOM | 716 | CB | ALA | A | 155 | 23.097 | 52.124 | 61.781 | 1.00 | 75.07 | A |
| ATOM | 717 | C | ALA | A | 155 | 22.061 | 53.623 | 60.066 | 1.00 | 140.86 | A |
| ATOM | 718 | O | ALA | A | 155 | 20.891 | 53.416 | 59.743 | 1.00 | 140.86 | A |
| ATOM | 719 | N | ALA | A | 156 | 22.565 | 54.844 | 60.229 | 1.00 | 167.04 | A |
| ATOM | 720 | CA | ALA | A | 156 | 21.754 | 56.048 | 60.066 | 1.00 | 167.04 | A |
| ATOM | 721 | CB | ALA | A | 156 | 22.407 | 57.216 | 60.809 | 1.00 | 103.48 | A |
| ATOM | 722 | C | ALA | A | 156 | 21.483 | 56.443 | 58.615 | 1.00 | 167.04 | A |
| ATOM | 723 | O | ALA | A | 156 | 20.802 | 57.436 | 58.358 | 1.00 | 167.04 | A |
| ATOM | 724 | N | VAL | A | 157 | 22.014 | 55.676 | 57.668 | 1.00 | 190.00 | A |
| ATOM | 725 | CA | VAL | A | 157 | 21.802 | 55.972 | 56.252 | 1.00 | 190.00 | A |
| ATOM | 726 | CB | VAL | A | 157 | 23.029 | 55.569 | 55.394 | 1.00 | 136.88 | A |
| ATOM | 727 | CG1 | VAL | A | 157 | 22.830 | 56.014 | 53.948 | 1.00 | 136.88 | A |
| ATOM | 728 | CG2 | VAL | A | 157 | 24.289 | 56.190 | 55.964 | 1.00 | 136.88 | A |
| ATOM | 729 | C | VAL | A | 157 | 20.582 | 55.208 | 55.745 | 1.00 | 190.00 | A |
| ATOM | 730 | O | VAL | A | 157 | 19.991 | 55.562 | 54.725 | 1.00 | 347.17 | A |
| ATOM | 731 | N | ALA | A | 158 | 20.209 | 54.162 | 56.476 | 1.00 | 264.69 | A |
| ATOM | 732 | CA | ALA | A | 158 | 19.069 | 53.329 | 56.112 | 1.00 | 264.69 | A |
| ATOM | 733 | CB | ALA | A | 158 | 19.302 | 51.901 | 56.586 | 1.00 | 187.17 | A |
| ATOM | 734 | C | ALA | A | 158 | 17.753 | 53.857 | 56.679 | 1.00 | 264.69 | A |
| ATOM | 735 | O | ALA | A | 158 | 16.794 | 54.063 | 55.938 | 1.00 | 347.17 | A |
| ATOM | 736 | N | ILE | A | 159 | 17.706 | 54.067 | 57.992 | 1.00 | 164.48 | A |
| ATOM | 737 | CA | ILE | A | 159 | 16.495 | 54.567 | 58.634 | 1.00 | 164.48 | A |
| ATOM | 738 | CB | ILE | A | 159 | 16.676 | 54.695 | 60.164 | 1.00 | 99.62 | A |
| ATOM | 739 | CG2 | ILE | A | 159 | 16.867 | 53.312 | 60.781 | 1.00 | 99.62 | A |
| ATOM | 740 | CG1 | ILE | A | 159 | 17.862 | 55.610 | 60.479 | 1.00 | 99.62 | A |
| ATOM | 741 | CD1 | ILE | A | 159 | 18.130 | 55.783 | 61.969 | 1.00 | 99.62 | A |
| ATOM | 742 | C | ILE | A | 159 | 16.079 | 55.917 | 58.062 | 1.00 | 164.48 | A |
| ATOM | 743 | O | ILE | A | 159 | 14.891 | 56.215 | 57.971 | 1.00 | 164.48 | A |
| ATOM | 744 | N | VAL | A | 160 | 17.058 | 56.732 | 57.681 | 1.00 | 95.04 | A |
| ATOM | 745 | CA | VAL | A | 160 | 16.774 | 58.038 | 57.091 | 1.00 | 95.04 | A |
| ATOM | 746 | CB | VAL | A | 160 | 18.002 | 58.970 | 57.138 | 1.00 | 137.66 | A |
| ATOM | 747 | CG1 | VAL | A | 160 | 17.695 | 60.276 | 56.419 | 1.00 | 137.66 | A |
| ATOM | 748 | CG2 | VAL | A | 160 | 18.381 | 59.247 | 58.580 | 1.00 | 137.66 | A |

TABLE 2-continued

Atomic coordinates of b2 adrenoreceptor

| ATOM | 749 | C   | VAL | A | 160 | 16.389 | 57.803 | 55.637 | 1.00 | 95.04  | A |
|------|-----|-----|-----|---|-----|--------|--------|--------|------|--------|---|
| ATOM | 750 | O   | VAL | A | 160 | 15.790 | 58.660 | 54.985 | 1.00 | 95.04  | A |
| ATOM | 751 | N   | SER | A | 161 | 16.751 | 56.627 | 55.137 | 1.00 | 228.73 | A |
| ATOM | 752 | CA  | SER | A | 161 | 16.429 | 56.233 | 53.775 | 1.00 | 228.73 | A |
| ATOM | 753 | CB  | SER | A | 161 | 17.469 | 55.239 | 53.256 | 1.00 | 208.98 | A |
| ATOM | 754 | OG  | SER | A | 161 | 17.209 | 54.876 | 51.913 | 1.00 | 208.98 | A |
| ATOM | 755 | C   | SER | A | 161 | 15.055 | 55.575 | 53.852 | 1.00 | 228.73 | A |
| ATOM | 756 | O   | SER | A | 161 | 14.376 | 55.386 | 52.841 | 1.00 | 228.73 | A |
| ATOM | 757 | N   | GLY | A | 162 | 14.661 | 55.230 | 55.076 | 1.00 | 223.63 | A |
| ATOM | 758 | CA  | GLY | A | 162 | 13.372 | 54.609 | 55.311 | 1.00 | 223.63 | A |
| ATOM | 759 | C   | GLY | A | 162 | 12.359 | 55.675 | 55.673 | 1.00 | 223.63 | A |
| ATOM | 760 | O   | GLY | A | 162 | 11.187 | 55.583 | 55.308 | 1.00 | 223.63 | A |
| ATOM | 761 | N   | LEU | A | 163 | 12.814 | 56.690 | 56.401 | 1.00 | 150.56 | A |
| ATOM | 762 | CA  | LEU | A | 163 | 11.952 | 57.796 | 56.795 | 1.00 | 150.56 | A |
| ATOM | 763 | CB  | LEU | A | 163 | 12.513 | 58.520 | 58.029 | 1.00 | 143.97 | A |
| ATOM | 764 | CG  | LEU | A | 163 | 12.614 | 57.762 | 59.360 | 1.00 | 143.97 | A |
| ATOM | 765 | CD1 | LEU | A | 163 | 13.249 | 58.657 | 60.416 | 1.00 | 143.97 | A |
| ATOM | 766 | CD2 | LEU | A | 163 | 11.234 | 57.313 | 59.809 | 1.00 | 143.97 | A |
| ATOM | 767 | C   | LEU | A | 163 | 11.877 | 58.768 | 55.621 | 1.00 | 150.56 | A |
| ATOM | 768 | O   | LEU | A | 163 | 11.570 | 59.947 | 55.797 | 1.00 | 150.56 | A |
| ATOM | 769 | N   | THR | A | 164 | 12.174 | 58.263 | 54.424 | 1.00 | 150.27 | A |
| ATOM | 770 | CA  | THR | A | 164 | 12.136 | 59.069 | 53.206 | 1.00 | 150.27 | A |
| ATOM | 771 | CB  | THR | A | 164 | 13.558 | 59.472 | 52.737 | 1.00 | 174.50 | A |
| ATOM | 772 | OG1 | THR | A | 164 | 13.460 | 60.406 | 51.654 | 1.00 | 174.50 | A |
| ATOM | 773 | CG2 | THR | A | 164 | 14.331 | 58.256 | 52.257 | 1.00 | 174.50 | A |
| ATOM | 774 | C   | THR | A | 164 | 11.456 | 58.292 | 52.080 | 1.00 | 150.27 | A |
| ATOM | 775 | O   | THR | A | 164 | 11.324 | 58.787 | 50.961 | 1.00 | 150.27 | A |
| ATOM | 776 | N   | SER | A | 203 | 10.428 | 64.492 | 46.394 | 1.00 | 195.00 | A |
| ATOM | 777 | CA  | SER | A | 203 | 11.547 | 63.848 | 47.070 | 1.00 | 195.00 | A |
| ATOM | 778 | CB  | SER | A | 203 | 11.154 | 62.437 | 47.519 | 1.00 | 177.78 | A |
| ATOM | 779 | OG  | SER | A | 203 | 12.209 | 61.812 | 48.232 | 1.00 | 177.78 | A |
| ATOM | 780 | C   | SER | A | 203 | 12.761 | 63.775 | 46.152 | 1.00 | 195.00 | A |
| ATOM | 781 | O   | SER | A | 203 | 13.878 | 63.532 | 46.606 | 1.00 | 195.00 | A |
| ATOM | 782 | N   | SER | A | 204 | 12.537 | 63.983 | 44.858 | 1.00 | 247.95 | A |
| ATOM | 783 | CA  | SER | A | 204 | 13.620 | 63.944 | 43.883 | 1.00 | 247.95 | A |
| ATOM | 784 | CB  | SER | A | 204 | 13.074 | 64.166 | 42.473 | 1.00 | 121.64 | A |
| ATOM | 785 | OG  | SER | A | 204 | 12.188 | 63.125 | 42.104 | 1.00 | 121.64 | A |
| ATOM | 786 | C   | SER | A | 204 | 14.661 | 65.008 | 44.202 | 1.00 | 247.95 | A |
| ATOM | 787 | O   | SER | A | 204 | 15.786 | 64.958 | 43.707 | 1.00 | 247.95 | A |
| ATOM | 788 | N   | ILE | A | 205 | 14.272 | 65.975 | 45.026 | 1.00 | 176.88 | A |
| ATOM | 789 | CA  | ILE | A | 205 | 15.172 | 67.046 | 45.427 | 1.00 | 176.88 | A |
| ATOM | 790 | CB  | ILE | A | 205 | 14.437 | 68.405 | 45.499 | 1.00 | 163.70 | A |
| ATOM | 791 | CG2 | ILE | A | 205 | 15.348 | 69.465 | 46.106 | 1.00 | 163.70 | A |
| ATOM | 792 | CG1 | ILE | A | 205 | 13.981 | 68.829 | 44.098 | 1.00 | 163.70 | A |
| ATOM | 793 | CD1 | ILE | A | 205 | 15.114 | 69.031 | 43.100 | 1.00 | 163.70 | A |
| ATOM | 794 | C   | ILE | A | 205 | 15.747 | 66.710 | 46.795 | 1.00 | 176.88 | A |
| ATOM | 795 | O   | ILE | A | 205 | 16.785 | 67.232 | 47.191 | 1.00 | 176.88 | A |
| ATOM | 796 | N   | VAL | A | 206 | 15.066 | 65.822 | 47.510 | 1.00 | 169.14 | A |
| ATOM | 797 | CA  | VAL | A | 206 | 15.511 | 65.411 | 48.833 | 1.00 | 169.14 | A |
| ATOM | 798 | CB  | VAL | A | 206 | 14.309 | 65.137 | 49.763 | 1.00 | 119.32 | A |
| ATOM | 799 | CG1 | VAL | A | 206 | 14.795 | 64.650 | 51.123 | 1.00 | 119.32 | A |
| ATOM | 800 | CG2 | VAL | A | 206 | 13.480 | 66.400 | 49.915 | 1.00 | 119.32 | A |
| ATOM | 801 | C   | VAL | A | 206 | 16.373 | 64.153 | 48.769 | 1.00 | 169.14 | A |
| ATOM | 802 | O   | VAL | A | 206 | 17.481 | 64.122 | 49.307 | 1.00 | 169.14 | A |
| ATOM | 803 | N   | SER | A | 207 | 15.865 | 63.123 | 48.099 | 1.00 | 184.35 | A |
| ATOM | 804 | CA  | SER | A | 207 | 16.579 | 61.858 | 47.989 | 1.00 | 184.35 | A |
| ATOM | 805 | CB  | SER | A | 207 | 15.603 | 60.697 | 48.184 | 1.00 | 182.59 | A |
| ATOM | 806 | OG  | SER | A | 207 | 16.284 | 59.459 | 48.124 | 1.00 | 182.59 | A |
| ATOM | 807 | C   | SER | A | 207 | 17.352 | 61.653 | 46.687 | 1.00 | 184.35 | A |
| ATOM | 808 | O   | SER | A | 207 | 17.892 | 60.572 | 46.453 | 1.00 | 184.35 | A |
| ATOM | 809 | N   | PHE | A | 208 | 17.409 | 62.676 | 45.841 | 1.00 | 209.37 | A |
| ATOM | 810 | CA  | PHE | A | 208 | 18.142 | 62.561 | 44.583 | 1.00 | 209.37 | A |
| ATOM | 811 | CB  | PHE | A | 208 | 17.186 | 62.299 | 43.417 | 1.00 | 158.79 | A |
| ATOM | 812 | CG  | PHE | A | 208 | 17.836 | 62.414 | 42.064 | 1.00 | 158.79 | A |
| ATOM | 813 | CD1 | PHE | A | 208 | 17.910 | 63.644 | 41.414 | 1.00 | 158.79 | A |
| ATOM | 814 | CD2 | PHE | A | 208 | 18.396 | 61.298 | 41.450 | 1.00 | 158.79 | A |
| ATOM | 815 | CE1 | PHE | A | 208 | 18.531 | 63.761 | 40.173 | 1.00 | 158.79 | A |
| ATOM | 816 | CE2 | PHE | A | 208 | 19.021 | 61.403 | 40.208 | 1.00 | 158.79 | A |
| ATOM | 817 | CZ  | PHE | A | 208 | 19.088 | 62.638 | 39.568 | 1.00 | 158.79 | A |
| ATOM | 818 | C   | PHE | A | 208 | 18.996 | 63.783 | 44.275 | 1.00 | 209.37 | A |
| ATOM | 819 | O   | PHE | A | 208 | 20.220 | 63.684 | 44.181 | 1.00 | 209.37 | A |
| ATOM | 820 | N   | ALA | A | 209 | 18.352 | 64.932 | 44.102 | 1.00 | 176.50 | A |
| ATOM | 821 | CA  | ALA | A | 209 | 19.074 | 66.162 | 43.803 | 1.00 | 176.50 | A |
| ATOM | 822 | CB  | ALA | A | 209 | 18.107 | 67.335 | 43.720 | 1.00 | 195.40 | A |
| ATOM | 823 | C   | ALA | A | 209 | 20.122 | 66.415 | 44.880 | 1.00 | 176.50 | A |
| ATOM | 824 | O   | ALA | A | 209 | 21.313 | 66.231 | 44.644 | 1.00 | 325.58 | A |
| ATOM | 825 | N   | VAL | A | 210 | 19.670 | 66.826 | 46.062 | 1.00 | 251.26 | A |
| ATOM | 826 | CA  | VAL | A | 210 | 20.568 | 67.101 | 47.181 | 1.00 | 251.26 | A |

TABLE 2-continued

Atomic coordinates of b2 adrenoreceptor

| ATOM | 827 | CB | VAL | A | 210 | 19.798 | 67.075 | 48.536 | 1.00 | 126.57 | A |
|---|---|---|---|---|---|---|---|---|---|---|---|
| ATOM | 828 | CG1 | VAL | A | 210 | 20.770 | 67.011 | 49.705 | 1.00 | 126.57 | A |
| ATOM | 829 | CG2 | VAL | A | 210 | 18.942 | 68.319 | 48.663 | 1.00 | 126.57 | A |
| ATOM | 830 | C | VAL | A | 210 | 21.746 | 66.126 | 47.244 | 1.00 | 251.26 | A |
| ATOM | 831 | O | VAL | A | 210 | 22.903 | 66.547 | 47.245 | 1.00 | 251.26 | A |
| ATOM | 832 | N | PRO | A | 211 | 21.470 | 64.811 | 47.284 | 1.00 | 188.95 | A |
| ATOM | 833 | CD | PRO | A | 211 | 20.164 | 64.133 | 47.357 | 1.00 | 161.29 | A |
| ATOM | 834 | CA | PRO | A | 211 | 22.565 | 63.837 | 47.346 | 1.00 | 188.95 | A |
| ATOM | 835 | CB | PRO | A | 211 | 21.840 | 62.515 | 47.597 | 1.00 | 161.29 | A |
| ATOM | 836 | CG | PRO | A | 211 | 20.515 | 62.727 | 46.951 | 1.00 | 161.29 | A |
| ATOM | 837 | C | PRO | A | 211 | 23.487 | 63.792 | 46.123 | 1.00 | 188.95 | A |
| ATOM | 838 | O | PRO | A | 211 | 24.633 | 63.367 | 46.234 | 1.00 | 188.95 | A |
| ATOM | 839 | N | LEU | A | 212 | 22.995 | 64.222 | 44.964 | 1.00 | 124.70 | A |
| ATOM | 840 | CA | LEU | A | 212 | 23.822 | 64.233 | 43.759 | 1.00 | 124.70 | A |
| ATOM | 841 | CB | LEU | A | 212 | 23.044 | 63.702 | 42.544 | 1.00 | 89.09 | A |
| ATOM | 842 | CG | LEU | A | 212 | 23.782 | 63.773 | 41.189 | 1.00 | 89.09 | A |
| ATOM | 843 | CD1 | LEU | A | 212 | 23.271 | 62.682 | 40.257 | 1.00 | 89.09 | A |
| ATOM | 844 | CD2 | LEU | A | 212 | 23.623 | 65.162 | 40.552 | 1.00 | 89.09 | A |
| ATOM | 845 | C | LEU | A | 212 | 24.341 | 65.640 | 43.461 | 1.00 | 124.70 | A |
| ATOM | 846 | O | LEU | A | 212 | 25.339 | 65.805 | 42.761 | 1.00 | 124.70 | A |
| ATOM | 847 | N | VAL | A | 213 | 23.666 | 66.653 | 43.993 | 1.00 | 161.66 | A |
| ATOM | 848 | CA | VAL | A | 213 | 24.078 | 68.036 | 43.773 | 1.00 | 161.66 | A |
| ATOM | 849 | CB | VAL | A | 213 | 23.063 | 69.030 | 44.387 | 1.00 | 247.24 | A |
| ATOM | 850 | CG1 | VAL | A | 213 | 23.577 | 70.455 | 44.242 | 1.00 | 247.24 | A |
| ATOM | 851 | CG2 | VAL | A | 213 | 21.716 | 68.893 | 43.698 | 1.00 | 247.24 | A |
| ATOM | 852 | C | VAL | A | 213 | 25.456 | 68.305 | 44.373 | 1.00 | 161.66 | A |
| ATOM | 853 | O | VAL | A | 213 | 26.294 | 68.963 | 43.755 | 1.00 | 161.66 | A |
| ATOM | 854 | N | ILE | A | 214 | 25.687 | 67.794 | 45.578 | 1.00 | 185.98 | A |
| ATOM | 855 | CA | ILE | A | 214 | 26.965 | 67.983 | 46.253 | 1.00 | 185.98 | A |
| ATOM | 856 | CB | ILE | A | 214 | 26.785 | 68.083 | 47.784 | 1.00 | 120.31 | A |
| ATOM | 857 | CG2 | ILE | A | 214 | 26.004 | 69.341 | 48.136 | 1.00 | 120.31 | A |
| ATOM | 858 | CG1 | ILE | A | 214 | 26.084 | 66.827 | 48.311 | 1.00 | 120.31 | A |
| ATOM | 859 | CD1 | ILE | A | 214 | 26.003 | 66.756 | 49.821 | 1.00 | 120.31 | A |
| ATOM | 860 | C | ILE | A | 214 | 27.933 | 66.841 | 45.957 | 1.00 | 185.98 | A |
| ATOM | 861 | O | ILE | A | 214 | 29.114 | 67.070 | 45.698 | 1.00 | 185.98 | A |
| ATOM | 862 | N | MET | A | 215 | 27.422 | 65.613 | 45.994 | 1.00 | 123.05 | A |
| ATOM | 863 | CA | MET | A | 215 | 28.231 | 64.426 | 45.744 | 1.00 | 123.05 | A |
| ATOM | 864 | CB | MET | A | 215 | 27.323 | 63.193 | 45.658 | 1.00 | 125.22 | A |
| ATOM | 865 | CG | MET | A | 215 | 28.036 | 61.890 | 45.330 | 1.00 | 125.22 | A |
| ATOM | 866 | SD | MET | A | 215 | 28.238 | 61.593 | 43.553 | 1.00 | 125.22 | A |
| ATOM | 867 | CE | MET | A | 215 | 27.346 | 60.034 | 43.360 | 1.00 | 125.22 | A |
| ATOM | 868 | C | MET | A | 215 | 29.104 | 64.528 | 44.493 | 1.00 | 123.05 | A |
| ATOM | 869 | O | MET | A | 215 | 30.196 | 63.964 | 44.453 | 1.00 | 123.05 | A |
| ATOM | 870 | N | VAL | A | 216 | 28.634 | 65.252 | 43.480 | 1.00 | 153.98 | A |
| ATOM | 871 | CA | VAL | A | 216 | 29.390 | 65.405 | 42.238 | 1.00 | 153.98 | A |
| ATOM | 872 | CB | VAL | A | 216 | 28.460 | 65.777 | 41.058 | 1.00 | 120.80 | A |
| ATOM | 873 | CG1 | VAL | A | 216 | 29.277 | 66.051 | 39.801 | 1.00 | 120.80 | A |
| ATOM | 874 | CG2 | VAL | A | 216 | 27.484 | 64.644 | 40.803 | 1.00 | 120.80 | A |
| ATOM | 875 | C | VAL | A | 216 | 30.499 | 66.450 | 42.336 | 1.00 | 153.98 | A |
| ATOM | 876 | O | VAL | A | 216 | 31.446 | 66.429 | 41.550 | 1.00 | 153.98 | A |
| ATOM | 877 | N | PHE | A | 217 | 30.389 | 67.357 | 43.300 | 1.00 | 166.03 | A |
| ATOM | 878 | CA | PHE | A | 217 | 31.401 | 68.393 | 43.468 | 1.00 | 166.03 | A |
| ATOM | 879 | CB | PHE | A | 217 | 30.728 | 69.751 | 43.657 | 1.00 | 202.37 | A |
| ATOM | 880 | CG | PHE | A | 217 | 29.946 | 70.198 | 42.455 | 1.00 | 202.37 | A |
| ATOM | 881 | CD1 | PHE | A | 217 | 28.817 | 69.496 | 42.043 | 1.00 | 202.37 | A |
| ATOM | 882 | CD2 | PHE | A | 217 | 30.357 | 71.298 | 41.710 | 1.00 | 202.37 | A |
| ATOM | 883 | CE1 | PHE | A | 217 | 28.110 | 69.880 | 40.907 | 1.00 | 202.37 | A |
| ATOM | 884 | CE2 | PHE | A | 217 | 29.657 | 71.691 | 40.571 | 1.00 | 202.37 | A |
| ATOM | 885 | CZ | PHE | A | 217 | 28.531 | 70.980 | 40.169 | 1.00 | 202.37 | A |
| ATOM | 886 | C | PHE | A | 217 | 32.362 | 68.089 | 44.612 | 1.00 | 166.03 | A |
| ATOM | 887 | O | PHE | A | 217 | 33.532 | 68.474 | 44.561 | 1.00 | 166.03 | A |
| ATOM | 888 | N | VAL | A | 218 | 31.873 | 67.401 | 45.642 | 1.00 | 160.18 | A |
| ATOM | 889 | CA | VAL | A | 218 | 32.731 | 67.020 | 46.759 | 1.00 | 160.18 | A |
| ATOM | 890 | CB | VAL | A | 218 | 31.933 | 66.302 | 47.888 | 1.00 | 103.99 | A |
| ATOM | 891 | CG1 | VAL | A | 218 | 32.865 | 65.478 | 48.761 | 1.00 | 103.99 | A |
| ATOM | 892 | CG2 | VAL | A | 218 | 31.227 | 67.338 | 48.756 | 1.00 | 103.99 | A |
| ATOM | 893 | C | VAL | A | 218 | 33.753 | 66.067 | 46.149 | 1.00 | 160.18 | A |
| ATOM | 894 | O | VAL | A | 218 | 34.907 | 66.013 | 46.574 | 1.00 | 160.18 | A |
| ATOM | 895 | N | TYR | A | 219 | 33.309 | 65.327 | 45.136 | 1.00 | 90.42 | A |
| ATOM | 896 | CA | TYR | A | 219 | 34.171 | 64.394 | 44.425 | 1.00 | 90.42 | A |
| ATOM | 897 | CB | TYR | A | 219 | 33.344 | 63.298 | 43.746 | 1.00 | 153.40 | A |
| ATOM | 898 | CG | TYR | A | 219 | 34.174 | 62.308 | 42.950 | 1.00 | 153.40 | A |
| ATOM | 899 | CD1 | TYR | A | 219 | 33.663 | 61.704 | 41.801 | 1.00 | 153.40 | A |
| ATOM | 900 | CE1 | TYR | A | 219 | 34.423 | 60.799 | 41.062 | 1.00 | 153.40 | A |
| ATOM | 901 | CD2 | TYR | A | 219 | 35.471 | 61.975 | 43.344 | 1.00 | 153.40 | A |
| ATOM | 902 | CE2 | TYR | A | 219 | 36.238 | 61.070 | 42.613 | 1.00 | 153.40 | A |
| ATOM | 903 | CZ | TYR | A | 219 | 35.707 | 60.488 | 41.475 | 1.00 | 153.40 | A |
| ATOM | 904 | OH | TYR | A | 219 | 36.464 | 59.605 | 40.746 | 1.00 | 153.40 | A |

TABLE 2-continued

Atomic coordinates of b2 adrenoreceptor

| ATOM | 905 | C | TYR | A | 219 | 34.961 | 65.168 | 43.363 | 1.00 | 90.42 | A |
|---|---|---|---|---|---|---|---|---|---|---|---|
| ATOM | 906 | O | TYR | A | 219 | 36.162 | 64.957 | 43.200 | 1.00 | 90.42 | A |
| ATOM | 907 | N | SER | A | 220 | 34.288 | 66.057 | 42.638 | 1.00 | 125.18 | A |
| ATOM | 908 | CA | SER | A | 220 | 34.969 | 66.849 | 41.620 | 1.00 | 125.18 | A |
| ATOM | 909 | CB | SER | A | 220 | 34.056 | 67.950 | 41.085 | 1.00 | 125.45 | A |
| ATOM | 910 | OG | SER | A | 220 | 34.708 | 68.685 | 40.064 | 1.00 | 125.45 | A |
| ATOM | 911 | C | SER | A | 220 | 36.188 | 67.473 | 42.284 | 1.00 | 125.18 | A |
| ATOM | 912 | O | SER | A | 220 | 37.308 | 67.357 | 41.786 | 1.00 | 125.18 | A |
| ATOM | 913 | N | ARG | A | 221 | 35.960 | 68.132 | 43.417 | 1.00 | 121.38 | A |
| ATOM | 914 | CA | ARG | A | 221 | 37.043 | 68.749 | 44.170 | 1.00 | 121.38 | A |
| ATOM | 915 | CB | ARG | A | 221 | 36.562 | 69.138 | 45.572 | 1.00 | 106.88 | A |
| ATOM | 916 | CG | ARG | A | 221 | 37.683 | 69.531 | 46.522 | 1.00 | 106.88 | A |
| ATOM | 917 | CD | ARG | A | 221 | 38.019 | 71.012 | 46.454 | 1.00 | 106.88 | A |
| ATOM | 918 | NE | ARG | A | 221 | 37.040 | 71.815 | 47.183 | 1.00 | 106.88 | A |
| ATOM | 919 | CZ | ARG | A | 221 | 37.120 | 73.132 | 47.353 | 1.00 | 106.88 | A |
| ATOM | 920 | NH1 | ARG | A | 221 | 38.141 | 73.810 | 46.843 | 1.00 | 106.88 | A |
| ATOM | 921 | NH2 | ARG | A | 221 | 36.178 | 73.773 | 48.035 | 1.00 | 106.88 | A |
| ATOM | 922 | C | ARG | A | 221 | 38.157 | 67.715 | 44.291 | 1.00 | 121.38 | A |
| ATOM | 923 | O | ARG | A | 221 | 39.303 | 67.969 | 43.926 | 1.00 | 114.46 | A |
| ATOM | 924 | N | VAL | A | 222 | 37.790 | 66.540 | 44.793 | 1.00 | 81.85 | A |
| ATOM | 925 | CA | VAL | A | 222 | 38.719 | 65.434 | 44.994 | 1.00 | 81.85 | A |
| ATOM | 926 | CB | VAL | A | 222 | 37.984 | 64.206 | 45.606 | 1.00 | 65.87 | A |
| ATOM | 927 | CG1 | VAL | A | 222 | 38.901 | 62.993 | 45.631 | 1.00 | 65.87 | A |
| ATOM | 928 | CG2 | VAL | A | 222 | 37.522 | 64.530 | 47.022 | 1.00 | 65.87 | A |
| ATOM | 929 | C | VAL | A | 222 | 39.470 | 65.013 | 43.729 | 1.00 | 81.85 | A |
| ATOM | 930 | O | VAL | A | 222 | 40.671 | 65.237 | 43.631 | 1.00 | 81.85 | A |
| ATOM | 931 | N | PHE | A | 223 | 38.782 | 64.409 | 42.764 | 1.00 | 129.84 | A |
| ATOM | 932 | CA | PHE | A | 223 | 39.446 | 63.974 | 41.535 | 1.00 | 129.84 | A |
| ATOM | 933 | CB | PHE | A | 223 | 38.423 | 63.617 | 40.450 | 1.00 | 118.25 | A |
| ATOM | 934 | CG | PHE | A | 223 | 39.036 | 63.029 | 39.194 | 1.00 | 118.25 | A |
| ATOM | 935 | CD1 | PHE | A | 223 | 39.323 | 61.667 | 39.112 | 1.00 | 118.25 | A |
| ATOM | 936 | CD2 | PHE | A | 223 | 39.330 | 63.840 | 38.098 | 1.00 | 118.25 | A |
| ATOM | 937 | CE1 | PHE | A | 223 | 39.890 | 61.123 | 37.960 | 1.00 | 118.25 | A |
| ATOM | 938 | CE2 | PHE | A | 223 | 39.897 | 63.305 | 36.943 | 1.00 | 118.25 | A |
| ATOM | 939 | CZ | PHE | A | 223 | 40.177 | 61.944 | 36.875 | 1.00 | 118.25 | A |
| ATOM | 940 | C | PHE | A | 223 | 40.375 | 65.055 | 40.993 | 1.00 | 129.84 | A |
| ATOM | 941 | O | PHE | A | 223 | 41.274 | 64.766 | 40.203 | 1.00 | 118.22 | A |
| ATOM | 942 | N | GLN | A | 224 | 40.159 | 66.299 | 41.412 | 1.00 | 124.20 | A |
| ATOM | 943 | CA | GLN | A | 224 | 40.992 | 67.401 | 40.947 | 1.00 | 124.20 | A |
| ATOM | 944 | CB | GLN | A | 224 | 40.159 | 68.685 | 40.833 | 1.00 | 145.39 | A |
| ATOM | 945 | CG | GLN | A | 224 | 38.981 | 68.596 | 39.863 | 1.00 | 145.39 | A |
| ATOM | 946 | CD | GLN | A | 224 | 39.387 | 68.215 | 38.445 | 1.00 | 145.39 | A |
| ATOM | 947 | OE1 | GLN | A | 224 | 40.570 | 68.074 | 38.134 | 1.00 | 145.39 | A |
| ATOM | 948 | NE2 | GLN | A | 224 | 38.396 | 68.049 | 37.575 | 1.00 | 145.39 | A |
| ATOM | 949 | C | GLN | A | 224 | 42.222 | 67.648 | 41.830 | 1.00 | 124.20 | A |
| ATOM | 950 | O | GLN | A | 224 | 43.358 | 67.513 | 41.369 | 1.00 | 124.20 | A |
| ATOM | 951 | N | GLU | A | 225 | 42.003 | 68.003 | 43.094 | 1.00 | 120.06 | A |
| ATOM | 952 | CA | GLU | A | 225 | 43.114 | 68.267 | 44.007 | 1.00 | 120.06 | A |
| ATOM | 953 | CB | GLU | A | 225 | 42.605 | 68.910 | 45.305 | 1.00 | 124.75 | A |
| ATOM | 954 | CG | GLU | A | 225 | 43.707 | 69.523 | 46.166 | 1.00 | 124.75 | A |
| ATOM | 955 | CD | GLU | A | 225 | 43.172 | 70.363 | 47.319 | 1.00 | 124.75 | A |
| ATOM | 956 | OE1 | GLU | A | 225 | 42.384 | 71.303 | 47.066 | 1.00 | 124.75 | A |
| ATOM | 957 | OE2 | GLU | A | 225 | 43.546 | 70.090 | 48.480 | 1.00 | 124.75 | A |
| ATOM | 958 | C | GLU | A | 225 | 43.880 | 66.984 | 44.321 | 1.00 | 120.06 | A |
| ATOM | 959 | O | GLU | A | 225 | 44.720 | 66.950 | 45.215 | 1.00 | 113.48 | A |
| ATOM | 960 | N | ALA | A | 226 | 43.573 | 65.926 | 43.579 | 1.00 | 110.10 | A |
| ATOM | 961 | CA | ALA | A | 226 | 44.239 | 64.643 | 43.748 | 1.00 | 110.10 | A |
| ATOM | 962 | CB | ALA | A | 226 | 43.234 | 63.509 | 43.657 | 1.00 | 153.01 | A |
| ATOM | 963 | C | ALA | A | 226 | 45.249 | 64.540 | 42.620 | 1.00 | 110.10 | A |
| ATOM | 964 | O | ALA | A | 226 | 46.078 | 63.631 | 42.589 | 1.00 | 110.10 | A |
| ATOM | 965 | N | LYS | A | 227 | 45.155 | 65.486 | 41.689 | 1.00 | 128.87 | A |
| ATOM | 966 | CA | LYS | A | 227 | 46.053 | 65.557 | 40.542 | 1.00 | 128.87 | A |
| ATOM | 967 | CB | LYS | A | 227 | 45.327 | 66.142 | 39.327 | 1.00 | 133.60 | A |
| ATOM | 968 | CG | LYS | A | 227 | 44.658 | 65.103 | 38.434 | 1.00 | 133.60 | A |
| ATOM | 969 | CD | LYS | A | 227 | 45.695 | 64.256 | 37.704 | 1.00 | 133.60 | A |
| ATOM | 970 | CE | LYS | A | 227 | 45.045 | 63.233 | 36.790 | 1.00 | 133.60 | A |
| ATOM | 971 | NZ | LYS | A | 227 | 46.063 | 62.391 | 36.107 | 1.00 | 133.60 | A |
| ATOM | 972 | C | LYS | A | 227 | 47.257 | 66.421 | 40.884 | 1.00 | 128.87 | A |
| ATOM | 973 | O | LYS | A | 227 | 48.396 | 66.061 | 40.583 | 1.00 | 287.78 | A |
| ATOM | 974 | N | ARG | A | 228 | 47.000 | 67.563 | 41.512 | 1.00 | 106.99 | A |
| ATOM | 975 | CA | ARG | A | 228 | 48.078 | 68.458 | 41.900 | 1.00 | 106.99 | A |
| ATOM | 976 | CB | ARG | A | 228 | 47.549 | 69.622 | 42.750 | 1.00 | 148.97 | A |
| ATOM | 977 | CG | ARG | A | 228 | 46.734 | 70.641 | 41.965 | 1.00 | 148.97 | A |
| ATOM | 978 | CD | ARG | A | 228 | 46.494 | 71.931 | 42.748 | 1.00 | 148.97 | A |
| ATOM | 979 | NE | ARG | A | 228 | 45.881 | 72.958 | 41.905 | 1.00 | 148.97 | A |
| ATOM | 980 | CZ | ARG | A | 228 | 45.656 | 74.214 | 42.280 | 1.00 | 148.97 | A |
| ATOM | 981 | NH1 | ARG | A | 228 | 45.991 | 74.618 | 43.496 | 1.00 | 148.97 | A |
| ATOM | 982 | NH2 | ARG | A | 228 | 45.101 | 75.069 | 41.433 | 1.00 | 148.97 | A |

TABLE 2-continued

Atomic coordinates of b2 adrenoreceptor

| ATOM | 983 | C | ARG | A | 228 | 49.089 | 67.653 | 42.697 | 1.00 | 106.99 | A |
| ATOM | 984 | O | ARG | A | 228 | 50.297 | 67.763 | 42.480 | 1.00 | 240.41 | A |
| ATOM | 985 | N | GLN | A | 229 | 48.589 | 66.830 | 43.614 | 1.00 | 122.70 | A |
| ATOM | 986 | CA | GLN | A | 229 | 49.468 | 66.006 | 44.428 | 1.00 | 122.70 | A |
| ATOM | 987 | CB | GLN | A | 229 | 48.700 | 65.341 | 45.576 | 1.00 | 125.44 | A |
| ATOM | 988 | CG | GLN | A | 229 | 49.568 | 64.361 | 46.370 | 1.00 | 125.44 | A |
| ATOM | 989 | CD | GLN | A | 229 | 48.829 | 63.652 | 47.488 | 1.00 | 125.44 | A |
| ATOM | 990 | OE1 | GLN | A | 229 | 47.612 | 63.775 | 47.625 | 1.00 | 125.44 | A |
| ATOM | 991 | NE2 | GLN | A | 229 | 49.569 | 62.893 | 48.295 | 1.00 | 125.44 | A |
| ATOM | 992 | C | GLN | A | 229 | 50.106 | 64.924 | 43.573 | 1.00 | 122.70 | A |
| ATOM | 993 | O | GLN | A | 229 | 51.327 | 64.763 | 43.569 | 1.00 | 122.70 | A |
| ATOM | 994 | N | LEU | A | 230 | 49.267 | 64.197 | 42.843 | 1.00 | 182.57 | A |
| ATOM | 995 | CA | LEU | A | 230 | 49.725 | 63.102 | 42.000 | 1.00 | 182.57 | A |
| ATOM | 996 | CB | LEU | A | 230 | 48.765 | 62.879 | 40.831 | 1.00 | 105.00 | A |
| ATOM | 997 | CG | LEU | A | 230 | 48.942 | 61.512 | 40.158 | 1.00 | 105.00 | A |
| ATOM | 998 | CD1 | LEU | A | 230 | 48.498 | 60.425 | 41.126 | 1.00 | 105.00 | A |
| ATOM | 999 | CD2 | LEU | A | 230 | 48.140 | 61.437 | 38.866 | 1.00 | 105.00 | A |
| ATOM | 1000 | C | LEU | A | 230 | 51.145 | 63.279 | 41.473 | 1.00 | 182.57 | A |
| ATOM | 1001 | O | LEU | A | 230 | 51.918 | 62.323 | 41.471 | 1.00 | 182.57 | A |
| ATOM | 1002 | N | GLN | A | 231 | 51.504 | 64.479 | 41.022 | 1.00 | 122.04 | A |
| ATOM | 1003 | CA | GLN | A | 231 | 52.865 | 64.656 | 40.535 | 1.00 | 122.04 | A |
| ATOM | 1004 | CB | GLN | A | 231 | 52.897 | 64.843 | 39.015 | 1.00 | 119.44 | A |
| ATOM | 1005 | CG | GLN | A | 231 | 54.277 | 64.535 | 38.387 | 1.00 | 119.44 | A |
| ATOM | 1006 | CD | GLN | A | 231 | 54.735 | 63.080 | 38.579 | 1.00 | 119.44 | A |
| ATOM | 1007 | OE1 | GLN | A | 231 | 54.061 | 62.280 | 39.226 | 1.00 | 119.44 | A |
| ATOM | 1008 | NE2 | GLN | A | 231 | 55.889 | 62.744 | 38.013 | 1.00 | 119.44 | A |
| ATOM | 1009 | C | GLN | A | 231 | 53.655 | 65.766 | 41.219 | 1.00 | 122.04 | A |
| ATOM | 1010 | O | GLN | A | 231 | 54.728 | 66.154 | 40.751 | 1.00 | 122.04 | A |
| ATOM | 1011 | N | LYS | A | 232 | 53.132 | 66.285 | 42.326 | 1.00 | 91.57 | A |
| ATOM | 1012 | CA | LYS | A | 232 | 53.876 | 67.287 | 43.075 | 1.00 | 91.57 | A |
| ATOM | 1013 | CB | LYS | A | 232 | 53.008 | 67.922 | 44.159 | 1.00 | 171.10 | A |
| ATOM | 1014 | CG | LYS | A | 232 | 53.434 | 69.335 | 44.538 | 1.00 | 171.10 | A |
| ATOM | 1015 | CD | LYS | A | 232 | 54.892 | 69.407 | 44.970 | 1.00 | 171.10 | A |
| ATOM | 1016 | CE | LYS | A | 232 | 55.313 | 70.841 | 45.258 | 1.00 | 171.10 | A |
| ATOM | 1017 | NZ | LYS | A | 232 | 56.736 | 70.931 | 45.684 | 1.00 | 171.10 | A |
| ATOM | 1018 | C | LYS | A | 232 | 54.926 | 66.374 | 43.704 | 1.00 | 91.57 | A |
| ATOM | 1019 | O | LYS | A | 232 | 55.774 | 66.791 | 44.486 | 1.00 | 101.47 | A |
| ATOM | 1020 | N | ILE | A | 233 | 54.812 | 65.100 | 43.337 | 1.00 | 70.92 | A |
| ATOM | 1021 | CA | ILE | A | 233 | 55.688 | 64.015 | 43.751 | 1.00 | 70.92 | A |
| ATOM | 1022 | CB | ILE | A | 233 | 55.155 | 62.662 | 43.229 | 1.00 | 25.15 | A |
| ATOM | 1023 | CG2 | ILE | A | 233 | 56.190 | 61.563 | 43.439 | 1.00 | 25.15 | A |
| ATOM | 1024 | CG1 | ILE | A | 233 | 53.828 | 62.329 | 43.908 | 1.00 | 25.15 | A |
| ATOM | 1025 | CD1 | ILE | A | 233 | 53.283 | 60.964 | 43.561 | 1.00 | 25.15 | A |
| ATOM | 1026 | C | ILE | A | 233 | 57.040 | 64.243 | 43.101 | 1.00 | 70.92 | A |
| ATOM | 1027 | O | ILE | A | 233 | 57.175 | 65.100 | 42.227 | 1.00 | 70.92 | A |
| ATOM | 1028 | N | ASP | A | 234 | 58.033 | 63.465 | 43.520 | 1.00 | 51.96 | A |
| ATOM | 1029 | CA | ASP | A | 234 | 59.371 | 63.567 | 42.955 | 1.00 | 51.96 | A |
| ATOM | 1030 | CB | ASP | A | 234 | 60.396 | 63.014 | 43.939 | 1.00 | 102.71 | A |
| ATOM | 1031 | CG | ASP | A | 234 | 61.809 | 63.100 | 43.413 | 1.00 | 102.71 | A |
| ATOM | 1032 | OD1 | ASP | A | 234 | 62.741 | 62.778 | 44.175 | 1.00 | 102.71 | A |
| ATOM | 1033 | OD2 | ASP | A | 234 | 61.988 | 63.489 | 42.239 | 1.00 | 102.71 | A |
| ATOM | 1034 | C | ASP | A | 234 | 59.402 | 62.751 | 41.670 | 1.00 | 51.96 | A |
| ATOM | 1035 | O | ASP | A | 234 | 59.203 | 61.538 | 41.706 | 1.00 | 51.96 | A |
| ATOM | 1036 | N | LYS | A | 235 | 59.636 | 63.407 | 40.536 | 1.00 | 60.49 | A |
| ATOM | 1037 | CA | LYS | A | 235 | 59.678 | 62.688 | 39.270 | 1.00 | 60.49 | A |
| ATOM | 1038 | CB | LYS | A | 235 | 60.241 | 63.575 | 38.159 | 1.00 | 71.41 | A |
| ATOM | 1039 | CG | LYS | A | 235 | 59.369 | 63.676 | 36.899 | 1.00 | 71.41 | A |
| ATOM | 1040 | CD | LYS | A | 235 | 58.121 | 64.542 | 37.111 | 1.00 | 71.41 | A |
| ATOM | 1041 | CE | LYS | A | 235 | 57.370 | 64.849 | 35.784 | 1.00 | 71.41 | A |
| ATOM | 1042 | NZ | LYS | A | 235 | 56.723 | 63.708 | 35.039 | 1.00 | 71.41 | A |
| ATOM | 1043 | C | LYS | A | 235 | 60.569 | 61.463 | 39.469 | 1.00 | 60.49 | A |
| ATOM | 1044 | O | LYS | A | 235 | 60.120 | 60.338 | 39.287 | 1.00 | 60.49 | A |
| ATOM | 1045 | N | SER | A | 236 | 61.820 | 61.696 | 39.873 | 1.00 | 32.54 | A |
| ATOM | 1046 | CA | SER | A | 236 | 62.805 | 60.631 | 40.120 | 1.00 | 32.54 | A |
| ATOM | 1047 | CB | SER | A | 236 | 63.956 | 61.161 | 40.982 | 1.00 | 52.55 | A |
| ATOM | 1048 | OG | SER | A | 236 | 64.569 | 62.292 | 40.394 | 1.00 | 52.55 | A |
| ATOM | 1049 | C | SER | A | 236 | 62.200 | 59.420 | 40.820 | 1.00 | 32.54 | A |
| ATOM | 1050 | O | SER | A | 236 | 62.573 | 58.276 | 40.564 | 1.00 | 32.54 | A |
| ATOM | 1051 | N | GLU | A | 237 | 61.281 | 59.689 | 41.732 | 1.00 | 44.42 | A |
| ATOM | 1052 | CA | GLU | A | 237 | 60.615 | 58.633 | 42.466 | 1.00 | 44.42 | A |
| ATOM | 1053 | CB | GLU | A | 237 | 59.527 | 59.238 | 43.360 | 1.00 | 78.65 | A |
| ATOM | 1054 | CG | GLU | A | 237 | 59.738 | 59.082 | 44.850 | 1.00 | 78.65 | A |
| ATOM | 1055 | CD | GLU | A | 237 | 59.333 | 57.715 | 45.364 | 1.00 | 78.65 | A |
| ATOM | 1056 | OE1 | GLU | A | 237 | 59.240 | 57.555 | 46.598 | 1.00 | 78.65 | A |
| ATOM | 1057 | OE2 | GLU | A | 237 | 59.106 | 56.797 | 44.548 | 1.00 | 78.65 | A |
| ATOM | 1058 | C | GLU | A | 237 | 59.978 | 57.699 | 41.446 | 1.00 | 44.42 | A |
| ATOM | 1059 | O | GLU | A | 237 | 59.108 | 58.111 | 40.680 | 1.00 | 44.42 | A |
| ATOM | 1060 | N | GLY | A | 238 | 60.423 | 56.452 | 41.408 | 1.00 | 26.01 | A |

TABLE 2-continued

Atomic coordinates of b2 adrenoreceptor

| ATOM | 1061 | CA | GLY | A | 238 | 59.808 | 55.517 | 40.488 | 1.00 | 26.01 | A |
|---|---|---|---|---|---|---|---|---|---|---|---|
| ATOM | 1062 | C | GLY | A | 238 | 60.635 | 55.130 | 39.295 | 1.00 | 26.01 | A |
| ATOM | 1063 | O | GLY | A | 238 | 60.280 | 54.185 | 38.578 | 1.00 | 26.01 | A |
| ATOM | 1064 | N | ARG | A | 239 | 61.735 | 55.855 | 39.085 | 1.00 | 35.02 | A |
| ATOM | 1065 | CA | ARG | A | 239 | 62.641 | 55.593 | 37.974 | 1.00 | 35.02 | A |
| ATOM | 1066 | CB | ARG | A | 239 | 62.383 | 56.581 | 36.839 | 1.00 | 30.52 | A |
| ATOM | 1067 | CG | ARG | A | 239 | 62.445 | 58.049 | 37.233 | 1.00 | 30.52 | A |
| ATOM | 1068 | CD | ARG | A | 239 | 61.064 | 58.659 | 37.415 | 1.00 | 30.52 | A |
| ATOM | 1069 | NE | ARG | A | 239 | 60.241 | 58.544 | 36.218 | 1.00 | 30.52 | A |
| ATOM | 1070 | CZ | ARG | A | 239 | 59.108 | 59.207 | 36.027 | 1.00 | 30.52 | A |
| ATOM | 1071 | NH1 | ARG | A | 239 | 58.658 | 60.040 | 36.955 | 1.00 | 30.52 | A |
| ATOM | 1072 | NH2 | ARG | A | 239 | 58.416 | 59.028 | 34.913 | 1.00 | 30.52 | A |
| ATOM | 1073 | C | ARG | A | 239 | 64.114 | 55.649 | 38.373 | 1.00 | 35.02 | A |
| ATOM | 1074 | O | ARG | A | 239 | 64.987 | 55.422 | 37.544 | 1.00 | 35.02 | A |
| ATOM | 1075 | N | PHE | A | 240 | 64.392 | 55.962 | 39.633 | 1.00 | 56.16 | A |
| ATOM | 1076 | CA | PHE | A | 240 | 65.770 | 56.015 | 40.124 | 1.00 | 56.16 | A |
| ATOM | 1077 | CB | PHE | A | 240 | 66.354 | 57.424 | 39.960 | 1.00 | 23.84 | A |
| ATOM | 1078 | CG | PHE | A | 240 | 66.437 | 57.885 | 38.538 | 1.00 | 23.84 | A |
| ATOM | 1079 | CD1 | PHE | A | 240 | 67.558 | 57.604 | 37.765 | 1.00 | 23.84 | A |
| ATOM | 1080 | CD2 | PHE | A | 240 | 65.368 | 58.575 | 37.952 | 1.00 | 23.84 | A |
| ATOM | 1081 | CE1 | PHE | A | 240 | 67.614 | 58.003 | 36.420 | 1.00 | 23.84 | A |
| ATOM | 1082 | CE2 | PHE | A | 240 | 65.408 | 58.976 | 36.613 | 1.00 | 23.84 | A |
| ATOM | 1083 | CZ | PHE | A | 240 | 66.532 | 58.690 | 35.844 | 1.00 | 23.84 | A |
| ATOM | 1084 | C | PHE | A | 240 | 65.800 | 55.606 | 41.603 | 1.00 | 56.16 | A |
| ATOM | 1085 | O | PHE | A | 240 | 66.865 | 55.318 | 42.158 | 1.00 | 56.16 | A |
| ATOM | 1086 | N | HIS | A | 241 | 64.619 | 55.589 | 42.221 | 1.00 | 137.86 | A |
| ATOM | 1087 | CA | HIS | A | 241 | 64.426 | 55.208 | 43.624 | 1.00 | 137.86 | A |
| ATOM | 1088 | CB | HIS | A | 241 | 63.602 | 53.916 | 43.673 | 1.00 | 106.39 | A |
| ATOM | 1089 | CG | HIS | A | 241 | 62.522 | 53.915 | 44.708 | 1.00 | 106.39 | A |
| ATOM | 1090 | CD2 | HIS | A | 241 | 62.500 | 54.381 | 45.980 | 1.00 | 106.39 | A |
| ATOM | 1091 | ND1 | HIS | A | 241 | 61.281 | 53.361 | 44.482 | 1.00 | 106.39 | A |
| ATOM | 1092 | CE1 | HIS | A | 241 | 60.538 | 53.488 | 45.568 | 1.00 | 106.39 | A |
| ATOM | 1093 | NE2 | HIS | A | 241 | 61.254 | 54.104 | 46.491 | 1.00 | 106.39 | A |
| ATOM | 1094 | C | HIS | A | 241 | 65.738 | 55.022 | 44.394 | 1.00 | 137.86 | A |
| ATOM | 1095 | O | HIS | A | 241 | 66.081 | 55.827 | 45.265 | 1.00 | 137.86 | A |
| ATOM | 1096 | N | VAL | A | 242 | 66.463 | 53.956 | 44.061 | 1.00 | 125.85 | A |
| ATOM | 1097 | CA | VAL | A | 242 | 67.738 | 53.641 | 44.697 | 1.00 | 125.85 | A |
| ATOM | 1098 | CB | VAL | A | 242 | 68.301 | 52.295 | 44.165 | 1.00 | 115.77 | A |
| ATOM | 1099 | CG1 | VAL | A | 242 | 69.563 | 51.908 | 44.931 | 1.00 | 115.77 | A |
| ATOM | 1100 | CG2 | VAL | A | 242 | 67.247 | 51.206 | 44.290 | 1.00 | 115.77 | A |
| ATOM | 1101 | C | VAL | A | 242 | 68.765 | 54.752 | 44.448 | 1.00 | 125.85 | A |
| ATOM | 1102 | O | VAL | A | 242 | 69.564 | 54.692 | 43.509 | 1.00 | 125.85 | A |
| ATOM | 1103 | N | PHE | A | 264 | 49.999 | 59.321 | 48.794 | 1.00 | 68.58 | A |
| ATOM | 1104 | CA | PHE | A | 264 | 49.200 | 59.161 | 47.579 | 1.00 | 68.58 | A |
| ATOM | 1105 | CB | PHE | A | 264 | 48.278 | 60.369 | 47.380 | 1.00 | 114.21 | A |
| ATOM | 1106 | CG | PHE | A | 264 | 47.326 | 60.229 | 46.217 | 1.00 | 114.21 | A |
| ATOM | 1107 | CD1 | PHE | A | 264 | 46.218 | 59.390 | 46.302 | 1.00 | 114.21 | A |
| ATOM | 1108 | CD2 | PHE | A | 264 | 47.533 | 60.939 | 45.037 | 1.00 | 114.21 | A |
| ATOM | 1109 | CE1 | PHE | A | 264 | 45.328 | 59.260 | 45.232 | 1.00 | 114.21 | A |
| ATOM | 1110 | CE2 | PHE | A | 264 | 46.649 | 60.815 | 43.961 | 1.00 | 114.21 | A |
| ATOM | 1111 | CZ | PHE | A | 264 | 45.544 | 59.973 | 44.062 | 1.00 | 114.21 | A |
| ATOM | 1112 | C | PHE | A | 264 | 50.087 | 59.010 | 46.349 | 1.00 | 68.58 | A |
| ATOM | 1113 | O | PHE | A | 264 | 50.966 | 59.836 | 46.098 | 1.00 | 124.63 | A |
| ATOM | 1114 | N | CYS | A | 265 | 49.846 | 57.948 | 45.588 | 1.00 | 81.01 | A |
| ATOM | 1115 | CA | CYS | A | 265 | 50.607 | 57.672 | 44.374 | 1.00 | 81.01 | A |
| ATOM | 1116 | CB | CYS | A | 265 | 51.602 | 56.527 | 44.611 | 1.00 | 135.59 | A |
| ATOM | 1117 | SG | CYS | A | 265 | 50.857 | 54.920 | 45.010 | 1.00 | 135.59 | A |
| ATOM | 1118 | C | CYS | A | 265 | 49.644 | 57.298 | 43.251 | 1.00 | 81.01 | A |
| ATOM | 1119 | O | CYS | A | 265 | 48.430 | 57.255 | 43.454 | 1.00 | 81.01 | A |
| ATOM | 1120 | N | LEU | A | 266 | 50.187 | 57.025 | 42.069 | 1.00 | 146.67 | A |
| ATOM | 1121 | CA | LEU | A | 266 | 49.361 | 56.662 | 40.925 | 1.00 | 146.67 | A |
| ATOM | 1122 | CB | LEU | A | 266 | 50.238 | 56.351 | 39.712 | 1.00 | 126.31 | A |
| ATOM | 1123 | CG | LEU | A | 266 | 49.462 | 55.941 | 38.457 | 1.00 | 126.31 | A |
| ATOM | 1124 | CD1 | LEU | A | 266 | 48.486 | 57.048 | 38.069 | 1.00 | 126.31 | A |
| ATOM | 1125 | CD2 | LEU | A | 266 | 50.433 | 55.652 | 37.325 | 1.00 | 126.31 | A |
| ATOM | 1126 | C | LEU | A | 266 | 48.454 | 55.470 | 41.215 | 1.00 | 146.67 | A |
| ATOM | 1127 | O | LEU | A | 266 | 47.454 | 55.263 | 40.526 | 1.00 | 146.67 | A |
| ATOM | 1128 | N | LYS | A | 267 | 48.800 | 54.680 | 42.226 | 1.00 | 130.43 | A |
| ATOM | 1129 | CA | LYS | A | 267 | 47.977 | 53.530 | 42.572 | 1.00 | 130.43 | A |
| ATOM | 1130 | CB | LYS | A | 267 | 48.694 | 52.624 | 43.579 | 1.00 | 104.32 | A |
| ATOM | 1131 | CG | LYS | A | 267 | 48.039 | 51.248 | 43.739 | 1.00 | 104.32 | A |
| ATOM | 1132 | CD | LYS | A | 267 | 46.588 | 51.352 | 44.210 | 1.00 | 104.32 | A |
| ATOM | 1133 | CE | LYS | A | 267 | 45.840 | 50.042 | 44.053 | 1.00 | 104.32 | A |
| ATOM | 1134 | NZ | LYS | A | 267 | 44.395 | 50.196 | 44.382 | 1.00 | 104.32 | A |
| ATOM | 1135 | C | LYS | A | 267 | 46.665 | 54.029 | 43.171 | 1.00 | 130.43 | A |
| ATOM | 1136 | O | LYS | A | 267 | 45.592 | 53.805 | 42.608 | 1.00 | 130.43 | A |
| ATOM | 1137 | N | GLU | A | 268 | 46.755 | 54.704 | 44.316 | 1.00 | 121.24 | A |
| ATOM | 1138 | CA | GLU | A | 268 | 45.571 | 55.234 | 44.988 | 1.00 | 121.24 | A |

TABLE 2-continued

Atomic coordinates of b2 adrenoreceptor

| ATOM | 1139 | CB | GLU | A | 268 | 45.961 | 55.858 | 46.333 | 1.00 | 153.35 | A |
|---|---|---|---|---|---|---|---|---|---|---|---|
| ATOM | 1140 | CG | GLU | A | 268 | 46.680 | 54.904 | 47.288 | 1.00 | 153.35 | A |
| ATOM | 1141 | CD | GLU | A | 268 | 45.811 | 53.737 | 47.742 | 1.00 | 153.35 | A |
| ATOM | 1142 | OE1 | GLU | A | 268 | 45.316 | 52.983 | 46.877 | 1.00 | 153.35 | A |
| ATOM | 1143 | OE2 | GLU | A | 268 | 45.628 | 53.567 | 48.967 | 1.00 | 153.35 | A |
| ATOM | 1144 | C | GLU | A | 268 | 44.893 | 56.277 | 44.102 | 1.00 | 121.24 | A |
| ATOM | 1145 | O | GLU | A | 268 | 43.899 | 56.891 | 44.485 | 1.00 | 121.24 | A |
| ATOM | 1146 | N | HIS | A | 269 | 45.451 | 56.471 | 42.913 | 1.00 | 151.07 | A |
| ATOM | 1147 | CA | HIS | A | 269 | 44.916 | 57.416 | 41.946 | 1.00 | 151.07 | A |
| ATOM | 1148 | CB | HIS | A | 269 | 46.054 | 57.965 | 41.081 | 1.00 | 116.47 | A |
| ATOM | 1149 | CG | HIS | A | 269 | 45.635 | 59.045 | 40.134 | 1.00 | 116.47 | A |
| ATOM | 1150 | CD2 | HIS | A | 269 | 45.676 | 59.111 | 38.782 | 1.00 | 116.47 | A |
| ATOM | 1151 | ND1 | HIS | A | 269 | 45.123 | 60.251 | 40.562 | 1.00 | 116.47 | A |
| ATOM | 1152 | CE1 | HIS | A | 269 | 44.867 | 61.014 | 39.514 | 1.00 | 116.47 | A |
| ATOM | 1153 | NE2 | HIS | A | 269 | 45.195 | 60.346 | 38.422 | 1.00 | 116.47 | A |
| ATOM | 1154 | C | HIS | A | 269 | 43.912 | 56.666 | 41.078 | 1.00 | 151.07 | A |
| ATOM | 1155 | O | HIS | A | 269 | 43.051 | 57.269 | 40.442 | 1.00 | 151.07 | A |
| ATOM | 1156 | N | LYS | A | 270 | 44.037 | 55.342 | 41.060 | 1.00 | 97.21 | A |
| ATOM | 1157 | CA | LYS | A | 270 | 43.146 | 54.489 | 40.284 | 1.00 | 97.21 | A |
| ATOM | 1158 | CB | LYS | A | 270 | 43.926 | 53.316 | 39.680 | 1.00 | 140.25 | A |
| ATOM | 1159 | CG | LYS | A | 270 | 44.980 | 53.729 | 38.661 | 1.00 | 140.25 | A |
| ATOM | 1160 | CD | LYS | A | 270 | 44.353 | 54.371 | 37.425 | 1.00 | 140.25 | A |
| ATOM | 1161 | CE | LYS | A | 270 | 45.409 | 54.775 | 36.399 | 1.00 | 140.25 | A |
| ATOM | 1162 | NZ | LYS | A | 270 | 44.805 | 55.367 | 35.172 | 1.00 | 140.25 | A |
| ATOM | 1163 | C | LYS | A | 270 | 42.023 | 53.964 | 41.177 | 1.00 | 97.21 | A |
| ATOM | 1164 | O | LYS | A | 270 | 40.970 | 53.558 | 40.694 | 1.00 | 291.71 | A |
| ATOM | 1165 | N | ALA | A | 271 | 42.268 | 53.966 | 42.484 | 1.00 | 133.65 | A |
| ATOM | 1166 | CA | ALA | A | 271 | 41.279 | 53.513 | 43.457 | 1.00 | 133.65 | A |
| ATOM | 1167 | CB | ALA | A | 271 | 41.890 | 53.484 | 44.853 | 1.00 | 77.39 | A |
| ATOM | 1168 | C | ALA | A | 271 | 40.117 | 54.500 | 43.410 | 1.00 | 133.65 | A |
| ATOM | 1169 | O | ALA | A | 271 | 38.987 | 54.176 | 43.776 | 1.00 | 133.65 | A |
| ATOM | 1170 | N | LEU | A | 272 | 40.417 | 55.715 | 42.962 | 1.00 | 133.18 | A |
| ATOM | 1171 | CA | LEU | A | 272 | 39.419 | 56.763 | 42.831 | 1.00 | 133.18 | A |
| ATOM | 1172 | CB | LEU | A | 272 | 40.037 | 58.135 | 43.111 | 1.00 | 90.98 | A |
| ATOM | 1173 | CG | LEU | A | 272 | 40.444 | 58.376 | 44.572 | 1.00 | 90.98 | A |
| ATOM | 1174 | CD1 | LEU | A | 272 | 41.205 | 59.687 | 44.707 | 1.00 | 90.98 | A |
| ATOM | 1175 | CD2 | LEU | A | 272 | 39.200 | 58.389 | 45.442 | 1.00 | 90.98 | A |
| ATOM | 1176 | C | LEU | A | 272 | 38.881 | 56.703 | 41.412 | 1.00 | 133.18 | A |
| ATOM | 1177 | O | LEU | A | 272 | 37.958 | 57.433 | 41.056 | 1.00 | 133.18 | A |
| ATOM | 1178 | N | LYS | A | 273 | 39.477 | 55.828 | 40.606 | 1.00 | 104.92 | A |
| ATOM | 1179 | CA | LYS | A | 273 | 39.044 | 55.623 | 39.226 | 1.00 | 104.92 | A |
| ATOM | 1180 | CB | LYS | A | 273 | 40.191 | 55.069 | 38.368 | 1.00 | 135.03 | A |
| ATOM | 1181 | CG | LYS | A | 273 | 39.750 | 54.484 | 37.019 | 1.00 | 135.03 | A |
| ATOM | 1182 | CD | LYS | A | 273 | 40.886 | 53.727 | 36.322 | 1.00 | 135.03 | A |
| ATOM | 1183 | CE | LYS | A | 273 | 40.396 | 53.008 | 35.069 | 1.00 | 135.03 | A |
| ATOM | 1184 | NZ | LYS | A | 273 | 39.317 | 52.032 | 35.391 | 1.00 | 135.03 | A |
| ATOM | 1185 | C | LYS | A | 273 | 37.923 | 54.595 | 39.305 | 1.00 | 104.92 | A |
| ATOM | 1186 | O | LYS | A | 273 | 36.906 | 54.703 | 38.618 | 1.00 | 221.81 | A |
| ATOM | 1187 | N | THR | A | 274 | 38.126 | 53.599 | 40.163 | 1.00 | 155.07 | A |
| ATOM | 1188 | CA | THR | A | 274 | 37.150 | 52.539 | 40.369 | 1.00 | 155.07 | A |
| ATOM | 1189 | CB | THR | A | 274 | 37.761 | 51.385 | 41.207 | 1.00 | 143.09 | A |
| ATOM | 1190 | OG1 | THR | A | 274 | 36.775 | 50.370 | 41.423 | 1.00 | 143.09 | A |
| ATOM | 1191 | CG2 | THR | A | 274 | 38.264 | 51.891 | 42.538 | 1.00 | 143.09 | A |
| ATOM | 1192 | C | THR | A | 274 | 35.937 | 53.139 | 41.077 | 1.00 | 155.07 | A |
| ATOM | 1193 | O | THR | A | 274 | 34.793 | 52.823 | 40.748 | 1.00 | 155.07 | A |
| ATOM | 1194 | N | LEU | A | 275 | 36.196 | 54.011 | 42.048 | 1.00 | 104.67 | A |
| ATOM | 1195 | CA | LEU | A | 275 | 35.128 | 54.690 | 42.776 | 1.00 | 104.67 | A |
| ATOM | 1196 | CB | LEU | A | 275 | 35.626 | 55.208 | 44.135 | 1.00 | 117.55 | A |
| ATOM | 1197 | CG | LEU | A | 275 | 36.067 | 54.226 | 45.227 | 1.00 | 117.55 | A |
| ATOM | 1198 | CD1 | LEU | A | 275 | 36.592 | 55.008 | 46.425 | 1.00 | 117.55 | A |
| ATOM | 1199 | CD2 | LEU | A | 275 | 34.901 | 53.343 | 45.645 | 1.00 | 117.55 | A |
| ATOM | 1200 | C | LEU | A | 275 | 34.686 | 55.874 | 41.920 | 1.00 | 104.67 | A |
| ATOM | 1201 | O | LEU | A | 275 | 33.682 | 56.516 | 42.204 | 1.00 | 104.67 | A |
| ATOM | 1202 | N | GLY | A | 276 | 35.450 | 56.151 | 40.867 | 1.00 | 132.79 | A |
| ATOM | 1203 | CA | GLY | A | 276 | 35.135 | 57.259 | 39.984 | 1.00 | 132.79 | A |
| ATOM | 1204 | C | GLY | A | 276 | 34.161 | 56.889 | 38.885 | 1.00 | 132.79 | A |
| ATOM | 1205 | O | GLY | A | 276 | 33.562 | 57.765 | 38.262 | 1.00 | 132.79 | A |
| ATOM | 1206 | N | ILE | A | 277 | 34.009 | 55.591 | 38.636 | 1.00 | 153.38 | A |
| ATOM | 1207 | CA | ILE | A | 277 | 33.085 | 55.122 | 37.614 | 1.00 | 153.38 | A |
| ATOM | 1208 | CB | ILE | A | 277 | 33.717 | 54.022 | 36.733 | 1.00 | 123.15 | A |
| ATOM | 1209 | CG2 | ILE | A | 277 | 34.909 | 54.588 | 35.976 | 1.00 | 123.15 | A |
| ATOM | 1210 | CG1 | ILE | A | 277 | 34.136 | 52.831 | 37.594 | 1.00 | 123.15 | A |
| ATOM | 1211 | CD1 | ILE | A | 277 | 34.631 | 51.651 | 36.793 | 1.00 | 123.15 | A |
| ATOM | 1212 | C | ILE | A | 277 | 31.820 | 54.576 | 38.269 | 1.00 | 153.38 | A |
| ATOM | 1213 | O | ILE | A | 277 | 30.736 | 54.645 | 37.691 | 1.00 | 297.67 | A |
| ATOM | 1214 | N | ILE | A | 278 | 31.964 | 54.036 | 39.477 | 1.00 | 116.16 | A |
| ATOM | 1215 | CA | ILE | A | 278 | 30.820 | 53.503 | 40.211 | 1.00 | 116.16 | A |
| ATOM | 1216 | CB | ILE | A | 278 | 31.255 | 52.854 | 41.553 | 1.00 | 121.09 | A |

TABLE 2-continued

Atomic coordinates of b2 adrenoreceptor

| ATOM | 1217 | CG2 | ILE | A | 278 | 32.013 | 53.856 | 42.399 | 1.00 | 121.09 | A |
|---|---|---|---|---|---|---|---|---|---|---|---|
| ATOM | 1218 | CG1 | ILE | A | 278 | 30.027 | 52.365 | 42.321 | 1.00 | 121.09 | A |
| ATOM | 1219 | CD1 | ILE | A | 278 | 30.358 | 51.635 | 43.602 | 1.00 | 121.09 | A |
| ATOM | 1220 | C | ILE | A | 278 | 29.851 | 54.652 | 40.490 | 1.00 | 116.16 | A |
| ATOM | 1221 | O | ILE | A | 278 | 28.634 | 54.466 | 40.508 | 1.00 | 116.16 | A |
| ATOM | 1222 | N | MET | A | 279 | 30.410 | 55.840 | 40.707 | 1.00 | 148.24 | A |
| ATOM | 1223 | CA | MET | A | 279 | 29.620 | 57.038 | 40.961 | 1.00 | 148.24 | A |
| ATOM | 1224 | CB | MET | A | 279 | 30.421 | 58.059 | 41.784 | 1.00 | 153.05 | A |
| ATOM | 1225 | CG | MET | A | 279 | 30.939 | 57.559 | 43.133 | 1.00 | 153.05 | A |
| ATOM | 1226 | SD | MET | A | 279 | 31.650 | 58.874 | 44.183 | 1.00 | 153.05 | A |
| ATOM | 1227 | CE | MET | A | 279 | 33.399 | 58.491 | 44.154 | 1.00 | 153.05 | A |
| ATOM | 1228 | C | MET | A | 279 | 29.271 | 57.653 | 39.609 | 1.00 | 148.24 | A |
| ATOM | 1229 | O | MET | A | 279 | 28.362 | 58.474 | 39.503 | 1.00 | 148.24 | A |
| ATOM | 1230 | N | GLY | A | 280 | 30.008 | 57.245 | 38.578 | 1.00 | 157.87 | A |
| ATOM | 1231 | CA | GLY | A | 280 | 29.785 | 57.762 | 37.239 | 1.00 | 157.87 | A |
| ATOM | 1232 | C | GLY | A | 280 | 28.921 | 56.874 | 36.362 | 1.00 | 157.87 | A |
| ATOM | 1233 | O | GLY | A | 280 | 28.727 | 57.160 | 35.180 | 1.00 | 157.87 | A |
| ATOM | 1234 | N | THR | A | 281 | 28.409 | 55.790 | 36.934 | 1.00 | 186.52 | A |
| ATOM | 1235 | CA | THR | A | 281 | 27.547 | 54.872 | 36.197 | 1.00 | 186.52 | A |
| ATOM | 1236 | CB | THR | A | 281 | 28.074 | 53.429 | 36.261 | 1.00 | 130.88 | A |
| ATOM | 1237 | OG1 | THR | A | 281 | 27.208 | 52.570 | 35.508 | 1.00 | 130.88 | A |
| ATOM | 1238 | CG2 | THR | A | 281 | 28.128 | 52.947 | 37.707 | 1.00 | 130.88 | A |
| ATOM | 1239 | C | THR | A | 281 | 26.159 | 54.909 | 36.821 | 1.00 | 186.52 | A |
| ATOM | 1240 | O | THR | A | 281 | 25.154 | 54.665 | 36.155 | 1.00 | 186.52 | A |
| ATOM | 1241 | N | PHE | A | 282 | 26.124 | 55.222 | 38.111 | 1.00 | 115.26 | A |
| ATOM | 1242 | CA | PHE | A | 282 | 24.879 | 55.304 | 38.861 | 1.00 | 115.26 | A |
| ATOM | 1243 | CB | PHE | A | 282 | 25.163 | 55.226 | 40.360 | 1.00 | 129.81 | A |
| ATOM | 1244 | CG | PHE | A | 282 | 23.948 | 54.956 | 41.194 | 1.00 | 129.81 | A |
| ATOM | 1245 | CD1 | PHE | A | 282 | 23.338 | 53.704 | 41.167 | 1.00 | 129.81 | A |
| ATOM | 1246 | CD2 | PHE | A | 282 | 23.415 | 55.948 | 42.014 | 1.00 | 129.81 | A |
| ATOM | 1247 | CE1 | PHE | A | 282 | 22.217 | 53.443 | 41.947 | 1.00 | 129.81 | A |
| ATOM | 1248 | CE2 | PHE | A | 282 | 22.292 | 55.698 | 42.798 | 1.00 | 129.81 | A |
| ATOM | 1249 | CZ | PHE | A | 282 | 21.692 | 54.443 | 42.764 | 1.00 | 129.81 | A |
| ATOM | 1250 | C | PHE | A | 282 | 24.197 | 56.627 | 38.547 | 1.00 | 115.26 | A |
| ATOM | 1251 | O | PHE | A | 282 | 23.095 | 56.891 | 39.016 | 1.00 | 115.26 | A |
| ATOM | 1252 | N | THR | A | 283 | 24.867 | 57.463 | 37.762 | 1.00 | 197.10 | A |
| ATOM | 1253 | CA | THR | A | 283 | 24.310 | 58.753 | 37.382 | 1.00 | 197.10 | A |
| ATOM | 1254 | CB | THR | A | 283 | 25.404 | 59.843 | 37.310 | 1.00 | 122.24 | A |
| ATOM | 1255 | OG1 | THR | A | 283 | 24.841 | 61.063 | 36.808 | 1.00 | 122.24 | A |
| ATOM | 1256 | CG2 | THR | A | 283 | 26.537 | 59.401 | 36.410 | 1.00 | 122.24 | A |
| ATOM | 1257 | C | THR | A | 283 | 23.635 | 58.622 | 36.025 | 1.00 | 197.10 | A |
| ATOM | 1258 | O | THR | A | 283 | 22.520 | 59.101 | 35.831 | 1.00 | 197.10 | A |
| ATOM | 1259 | N | LEU | A | 284 | 24.306 | 57.960 | 35.088 | 1.00 | 148.47 | A |
| ATOM | 1260 | CA | LEU | A | 284 | 23.742 | 57.772 | 33.758 | 1.00 | 148.47 | A |
| ATOM | 1261 | CB | LEU | A | 284 | 24.850 | 57.552 | 32.727 | 1.00 | 118.29 | A |
| ATOM | 1262 | CG | LEU | A | 284 | 25.459 | 58.828 | 32.135 | 1.00 | 118.29 | A |
| ATOM | 1263 | CD1 | LEU | A | 284 | 26.116 | 59.642 | 33.233 | 1.00 | 118.29 | A |
| ATOM | 1264 | CD2 | LEU | A | 284 | 26.460 | 58.462 | 31.055 | 1.00 | 118.29 | A |
| ATOM | 1265 | C | LEU | A | 284 | 22.765 | 56.607 | 33.718 | 1.00 | 148.47 | A |
| ATOM | 1266 | O | LEU | A | 284 | 22.265 | 56.239 | 32.654 | 1.00 | 148.47 | A |
| ATOM | 1267 | N | CYS | A | 285 | 22.496 | 56.027 | 34.882 | 1.00 | 218.82 | A |
| ATOM | 1268 | CA | CYS | A | 285 | 21.563 | 54.915 | 34.971 | 1.00 | 218.82 | A |
| ATOM | 1269 | CB | CYS | A | 285 | 22.201 | 53.748 | 35.730 | 1.00 | 181.12 | A |
| ATOM | 1270 | SG | CYS | A | 285 | 23.504 | 52.879 | 34.810 | 1.00 | 181.12 | A |
| ATOM | 1271 | C | CYS | A | 285 | 20.260 | 55.330 | 35.651 | 1.00 | 218.82 | A |
| ATOM | 1272 | O | CYS | A | 285 | 19.194 | 54.805 | 35.334 | 1.00 | 218.82 | A |
| ATOM | 1273 | N | TRP | A | 286 | 20.349 | 56.273 | 36.586 | 1.00 | 157.71 | A |
| ATOM | 1274 | CA | TRP | A | 286 | 19.165 | 56.741 | 37.296 | 1.00 | 157.68 | A |
| ATOM | 1275 | CB | TRP | A | 286 | 19.293 | 56.482 | 38.797 | 1.00 | 187.69 | A |
| ATOM | 1276 | CG | TRP | A | 286 | 19.298 | 55.031 | 39.167 | 1.00 | 187.27 | A |
| ATOM | 1277 | CD2 | TRP | A | 286 | 18.188 | 54.263 | 39.653 | 1.00 | 187.08 | A |
| ATOM | 1278 | CE2 | TRP | A | 286 | 18.651 | 52.944 | 39.855 | 1.00 | 186.79 | A |
| ATOM | 1279 | CE3 | TRP | A | 286 | 16.849 | 54.561 | 39.937 | 1.00 | 187.50 | A |
| ATOM | 1280 | CD1 | TRP | A | 286 | 20.354 | 54.172 | 39.094 | 1.00 | 186.75 | A |
| ATOM | 1281 | NE1 | TRP | A | 286 | 19.974 | 52.916 | 39.507 | 1.00 | 186.82 | A |
| ATOM | 1282 | CZ2 | TRP | A | 286 | 17.820 | 51.921 | 40.328 | 1.00 | 187.57 | A |
| ATOM | 1283 | CZ3 | TRP | A | 286 | 16.022 | 53.541 | 40.408 | 1.00 | 187.26 | A |
| ATOM | 1284 | CH2 | TRP | A | 286 | 16.514 | 52.237 | 40.598 | 1.00 | 187.12 | A |
| ATOM | 1285 | C | TRP | A | 286 | 18.869 | 58.216 | 37.069 | 1.00 | 157.96 | A |
| ATOM | 1286 | O | TRP | A | 286 | 18.151 | 58.835 | 37.846 | 1.00 | 158.07 | A |
| ATOM | 1287 | N | LEU | A | 287 | 19.422 | 58.796 | 36.012 | 1.00 | 228.94 | A |
| ATOM | 1288 | CA | LEU | A | 287 | 19.147 | 60.212 | 35.737 | 1.00 | 229.21 | A |
| ATOM | 1289 | CB | LEU | A | 287 | 20.367 | 60.924 | 35.162 | 1.00 | 144.29 | A |
| ATOM | 1290 | CG | LEU | A | 287 | 20.707 | 62.335 | 35.669 | 1.00 | 145.14 | A |
| ATOM | 1291 | CD1 | LEU | A | 287 | 21.703 | 62.999 | 34.723 | 1.00 | 145.69 | A |
| ATOM | 1292 | CD2 | LEU | A | 287 | 19.451 | 63.167 | 35.790 | 1.00 | 145.08 | A |
| ATOM | 1293 | C | LEU | A | 287 | 18.017 | 60.304 | 34.740 | 1.00 | 229.34 | A |
| ATOM | 1294 | O | LEU | A | 287 | 17.030 | 60.993 | 34.958 | 1.00 | 229.51 | A |

TABLE 2-continued

Atomic coordinates of b2 adrenoreceptor

| ATOM | 1295 | N | PRO | A | 288 | 18.153 | 59.602 | 33.613 | 1.00 | 234.86 | A |
|---|---|---|---|---|---|---|---|---|---|---|---|
| ATOM | 1296 | CD | PRO | A | 288 | 19.274 | 58.757 | 33.156 | 1.00 | 166.89 | A |
| ATOM | 1297 | CA | PRO | A | 288 | 17.087 | 59.642 | 32.610 | 1.00 | 234.97 | A |
| ATOM | 1298 | CB | PRO | A | 288 | 17.599 | 58.660 | 31.544 | 1.00 | 166.97 | A |
| ATOM | 1299 | CG | PRO | A | 288 | 19.114 | 58.791 | 31.670 | 1.00 | 166.81 | A |
| ATOM | 1300 | C | PRO | A | 288 | 15.710 | 59.248 | 33.195 | 1.00 | 235.30 | A |
| ATOM | 1301 | O | PRO | A | 288 | 14.664 | 59.447 | 32.569 | 1.00 | 235.22 | A |
| ATOM | 1302 | N | PHE | A | 289 | 15.749 | 58.690 | 34.406 | 1.00 | 202.26 | A |
| ATOM | 1303 | CA | PHE | A | 289 | 14.553 | 58.264 | 35.151 | 1.00 | 202.58 | A |
| ATOM | 1304 | CB | PHE | A | 289 | 14.840 | 57.026 | 36.024 | 1.00 | 158.63 | A |
| ATOM | 1305 | CG | PHE | A | 289 | 13.671 | 56.588 | 36.888 | 1.00 | 158.55 | A |
| ATOM | 1306 | CD1 | PHE | A | 289 | 13.622 | 56.917 | 38.240 | 1.00 | 158.22 | A |
| ATOM | 1307 | CD2 | PHE | A | 289 | 12.638 | 55.823 | 36.347 | 1.00 | 158.16 | A |
| ATOM | 1308 | CE1 | PHE | A | 289 | 12.562 | 56.492 | 39.042 | 1.00 | 158.61 | A |
| ATOM | 1309 | CE2 | PHE | A | 289 | 11.582 | 55.400 | 37.138 | 1.00 | 158.66 | A |
| ATOM | 1310 | CZ | PHE | A | 289 | 11.545 | 55.733 | 38.488 | 1.00 | 158.80 | A |
| ATOM | 1311 | C | PHE | A | 289 | 14.057 | 59.374 | 36.064 | 1.00 | 203.13 | A |
| ATOM | 1312 | O | PHE | A | 289 | 12.855 | 59.608 | 36.172 | 1.00 | 203.11 | A |
| ATOM | 1313 | N | PHE | A | 290 | 14.988 | 60.048 | 36.735 | 1.00 | 184.77 | A |
| ATOM | 1314 | CA | PHE | A | 290 | 14.612 | 61.138 | 37.633 | 1.00 | 185.62 | A |
| ATOM | 1315 | CB | PHE | A | 290 | 15.665 | 61.377 | 38.733 | 1.00 | 180.41 | A |
| ATOM | 1316 | CG | PHE | A | 290 | 15.653 | 60.339 | 39.839 | 1.00 | 180.30 | A |
| ATOM | 1317 | CD1 | PHE | A | 290 | 16.084 | 59.044 | 39.593 | 1.00 | 180.30 | A |
| ATOM | 1318 | CD2 | PHE | A | 290 | 15.219 | 60.659 | 41.127 | 1.00 | 180.12 | A |
| ATOM | 1319 | CE1 | PHE | A | 290 | 16.091 | 58.073 | 40.606 | 1.00 | 180.71 | A |
| ATOM | 1320 | CE2 | PHE | A | 290 | 15.222 | 59.692 | 42.154 | 1.00 | 180.67 | A |
| ATOM | 1321 | CZ | PHE | A | 290 | 15.660 | 58.397 | 41.889 | 1.00 | 180.42 | A |
| ATOM | 1322 | C | PHE | A | 290 | 14.390 | 62.431 | 36.862 | 1.00 | 186.21 | A |
| ATOM | 1323 | O | PHE | A | 290 | 13.928 | 63.427 | 37.425 | 1.00 | 186.31 | A |
| ATOM | 1324 | N | ILE | A | 291 | 14.731 | 62.416 | 35.576 | 1.00 | 212.97 | A |
| ATOM | 1325 | CA | ILE | A | 291 | 14.546 | 63.585 | 34.721 | 1.00 | 214.05 | A |
| ATOM | 1326 | CB | ILE | A | 291 | 15.480 | 63.551 | 33.476 | 1.00 | 148.16 | A |
| ATOM | 1327 | CG2 | ILE | A | 291 | 15.035 | 64.583 | 32.457 | 1.00 | 147.77 | A |
| ATOM | 1328 | CG1 | ILE | A | 291 | 16.920 | 63.865 | 33.892 | 1.00 | 148.03 | A |
| ATOM | 1329 | CD1 | ILE | A | 291 | 17.892 | 63.978 | 32.723 | 1.00 | 148.27 | A |
| ATOM | 1330 | C | ILE | A | 291 | 13.101 | 63.657 | 34.239 | 1.00 | 214.91 | A |
| ATOM | 1331 | O | ILE | A | 291 | 12.533 | 64.742 | 34.130 | 1.00 | 215.17 | A |
| ATOM | 1332 | N | LEU | A | 311 | 12.595 | 53.083 | 30.970 | 1.00 | 169.33 | A |
| ATOM | 1333 | CA | LEU | A | 311 | 13.816 | 53.617 | 31.554 | 1.00 | 168.32 | A |
| ATOM | 1334 | CB | LEU | A | 311 | 13.820 | 55.144 | 31.477 | 1.00 | 131.29 | A |
| ATOM | 1335 | CG | LEU | A | 311 | 13.675 | 55.778 | 30.092 | 1.00 | 131.50 | A |
| ATOM | 1336 | CD1 | LEU | A | 311 | 13.788 | 57.289 | 30.217 | 1.00 | 131.63 | A |
| ATOM | 1337 | CD2 | LEU | A | 311 | 14.745 | 55.235 | 29.163 | 1.00 | 131.82 | A |
| ATOM | 1338 | C | LEU | A | 311 | 13.952 | 53.189 | 33.008 | 1.00 | 167.63 | A |
| ATOM | 1339 | O | LEU | A | 311 | 15.000 | 53.385 | 33.624 | 1.00 | 167.53 | A |
| ATOM | 1340 | N | ASN | A | 312 | 12.887 | 52.618 | 33.561 | 1.00 | 194.21 | A |
| ATOM | 1341 | CA | ASN | A | 312 | 12.910 | 52.168 | 34.945 | 1.00 | 193.49 | A |
| ATOM | 1342 | CB | ASN | A | 312 | 11.484 | 51.914 | 35.444 | 1.00 | 142.13 | A |
| ATOM | 1343 | CG | ASN | A | 312 | 11.390 | 51.895 | 36.962 | 1.00 | 141.91 | A |
| ATOM | 1344 | OD1 | ASN | A | 312 | 10.755 | 52.759 | 37.564 | 1.00 | 141.58 | A |
| ATOM | 1345 | ND2 | ASN | A | 312 | 12.025 | 50.913 | 37.585 | 1.00 | 141.45 | A |
| ATOM | 1346 | C | ASN | A | 312 | 13.729 | 50.882 | 35.022 | 1.00 | 193.14 | A |
| ATOM | 1347 | O | ASN | A | 312 | 14.159 | 50.467 | 36.099 | 1.00 | 193.30 | A |
| ATOM | 1348 | N | ALA | A | 313 | 13.944 | 50.259 | 33.866 | 1.00 | 168.44 | A |
| ATOM | 1349 | CA | ALA | A | 313 | 14.717 | 49.024 | 33.788 | 1.00 | 167.84 | A |
| ATOM | 1350 | CB | ALA | A | 313 | 14.260 | 48.193 | 32.598 | 1.00 | 155.01 | A |
| ATOM | 1351 | C | ALA | A | 313 | 16.212 | 49.337 | 33.671 | 1.00 | 167.35 | A |
| ATOM | 1352 | O | ALA | A | 313 | 17.055 | 48.520 | 34.051 | 1.00 | 167.34 | A |
| ATOM | 1353 | N | ILE | A | 314 | 16.536 | 50.516 | 33.144 | 1.00 | 229.65 | A |
| ATOM | 1354 | CA | ILE | A | 314 | 17.927 | 50.935 | 32.998 | 1.00 | 229.18 | A |
| ATOM | 1355 | CB | ILE | A | 314 | 18.050 | 52.269 | 32.224 | 1.00 | 121.34 | A |
| ATOM | 1356 | CG2 | ILE | A | 314 | 19.514 | 52.692 | 32.140 | 1.00 | 120.98 | A |
| ATOM | 1357 | CG1 | ILE | A | 314 | 17.453 | 52.122 | 30.823 | 1.00 | 120.97 | A |
| ATOM | 1358 | CD1 | ILE | A | 314 | 17.506 | 53.394 | 30.002 | 1.00 | 120.98 | A |
| ATOM | 1359 | C | ILE | A | 314 | 18.538 | 51.138 | 34.378 | 1.00 | 228.95 | A |
| ATOM | 1360 | O | ILE | A | 314 | 19.719 | 50.882 | 34.588 | 1.00 | 228.82 | A |
| ATOM | 1361 | N | GLY | A | 315 | 17.731 | 51.609 | 35.322 | 1.00 | 187.67 | A |
| ATOM | 1362 | CA | GLY | A | 315 | 18.226 | 51.831 | 36.671 | 1.00 | 187.41 | A |
| ATOM | 1363 | C | GLY | A | 315 | 18.616 | 50.537 | 37.357 | 1.00 | 187.24 | A |
| ATOM | 1364 | O | GLY | A | 315 | 19.554 | 50.502 | 38.152 | 1.00 | 187.12 | A |
| ATOM | 1365 | N | TYR | A | 316 | 17.884 | 49.471 | 37.052 | 1.00 | 158.32 | A |
| ATOM | 1366 | CA | TYR | A | 316 | 18.151 | 48.154 | 37.637 | 1.00 | 158.23 | A |
| ATOM | 1367 | CB | TYR | A | 316 | 17.068 | 47.151 | 37.202 | 1.00 | 203.24 | A |
| ATOM | 1368 | CG | TYR | A | 316 | 15.656 | 47.441 | 37.675 | 1.00 | 203.57 | A |
| ATOM | 1369 | CD1 | TYR | A | 316 | 14.588 | 46.644 | 37.254 | 1.00 | 204.14 | A |
| ATOM | 1370 | CE1 | TYR | A | 316 | 13.290 | 46.880 | 37.706 | 1.00 | 203.69 | A |
| ATOM | 1371 | CD2 | TYR | A | 316 | 15.388 | 48.487 | 38.560 | 1.00 | 203.45 | A |
| ATOM | 1372 | CE2 | TYR | A | 316 | 14.090 | 48.729 | 39.018 | 1.00 | 203.49 | A |

TABLE 2-continued

Atomic coordinates of b2 adrenoreceptor

| ATOM | 1373 | CZ | TYR | A | 316 | 13.050 | 47.923 | 38.589 | 1.00 | 203.89 | A |
| ATOM | 1374 | OH | TYR | A | 316 | 11.777 | 48.155 | 39.059 | 1.00 | 203.78 | A |
| ATOM | 1375 | C | TYR | A | 316 | 19.509 | 47.649 | 37.168 | 1.00 | 158.15 | A |
| ATOM | 1376 | O | TYR | A | 316 | 20.173 | 46.874 | 37.859 | 1.00 | 158.05 | A |
| ATOM | 1377 | N | VAL | A | 317 | 19.908 | 48.117 | 35.989 | 1.00 | 217.34 | A |
| ATOM | 1378 | CA | VAL | A | 317 | 21.168 | 47.728 | 35.359 | 1.00 | 217.24 | A |
| ATOM | 1379 | CB | VAL | A | 317 | 21.370 | 48.507 | 34.024 | 1.00 | 136.45 | A |
| ATOM | 1380 | CG1 | VAL | A | 317 | 22.665 | 48.100 | 33.357 | 1.00 | 136.77 | A |
| ATOM | 1381 | CG2 | VAL | A | 317 | 20.183 | 48.253 | 33.090 | 1.00 | 136.60 | A |
| ATOM | 1382 | C | VAL | A | 317 | 22.404 | 47.908 | 36.245 | 1.00 | 217.09 | A |
| ATOM | 1383 | O | VAL | A | 317 | 23.344 | 47.111 | 36.179 | 1.00 | 216.91 | A |
| ATOM | 1384 | N | ALA | A | 318 | 22.404 | 48.952 | 37.069 | 1.00 | 142.59 | A |
| ATOM | 1385 | CA | ALA | A | 318 | 23.530 | 49.217 | 37.961 | 1.00 | 142.59 | A |
| ATOM | 1386 | CB | ALA | A | 318 | 23.415 | 50.624 | 38.538 | 1.00 | 86.95 | A |
| ATOM | 1387 | C | ALA | A | 318 | 23.606 | 48.190 | 39.090 | 1.00 | 142.59 | A |
| ATOM | 1388 | O | ALA | A | 318 | 24.219 | 48.440 | 40.129 | 1.00 | 296.78 | A |
| ATOM | 1389 | N | ALA | A | 319 | 22.967 | 47.041 | 38.883 | 1.00 | 170.21 | A |
| ATOM | 1390 | CA | ALA | A | 319 | 22.962 | 45.968 | 39.872 | 1.00 | 170.21 | A |
| ATOM | 1391 | CB | ALA | A | 319 | 21.590 | 45.307 | 39.921 | 1.00 | 160.46 | A |
| ATOM | 1392 | C | ALA | A | 319 | 24.028 | 44.933 | 39.529 | 1.00 | 170.21 | A |
| ATOM | 1393 | O | ALA | A | 319 | 24.457 | 44.154 | 40.380 | 1.00 | 346.56 | A |
| ATOM | 1394 | N | GLY | A | 320 | 24.444 | 44.929 | 38.270 | 1.00 | 192.95 | A |
| ATOM | 1395 | CA | GLY | A | 320 | 25.464 | 43.996 | 37.832 | 1.00 | 192.95 | A |
| ATOM | 1396 | C | GLY | A | 320 | 26.579 | 44.755 | 37.147 | 1.00 | 192.95 | A |
| ATOM | 1397 | O | GLY | A | 320 | 27.269 | 44.222 | 36.278 | 1.00 | 192.95 | A |
| ATOM | 1398 | N | ALA | A | 321 | 26.753 | 46.012 | 37.542 | 1.00 | 219.60 | A |
| ATOM | 1399 | CA | ALA | A | 321 | 27.784 | 46.857 | 36.957 | 1.00 | 219.60 | A |
| ATOM | 1400 | CB | ALA | A | 321 | 27.157 | 48.145 | 36.428 | 1.00 | 63.81 | A |
| ATOM | 1401 | C | ALA | A | 321 | 28.907 | 47.178 | 37.947 | 1.00 | 219.60 | A |
| ATOM | 1402 | O | ALA | A | 321 | 30.036 | 47.456 | 37.540 | 1.00 | 219.60 | A |
| ATOM | 1403 | N | ASN | A | 322 | 28.600 | 47.140 | 39.242 | 1.00 | 178.87 | A |
| ATOM | 1404 | CA | ASN | A | 322 | 29.603 | 47.427 | 40.264 | 1.00 | 178.87 | A |
| ATOM | 1405 | CB | ASN | A | 322 | 28.931 | 47.779 | 41.592 | 1.00 | 175.55 | A |
| ATOM | 1406 | CG | ASN | A | 322 | 28.140 | 49.064 | 41.515 | 1.00 | 175.55 | A |
| ATOM | 1407 | OD1 | ASN | A | 322 | 28.681 | 50.117 | 41.183 | 1.00 | 175.55 | A |
| ATOM | 1408 | ND2 | ASN | A | 322 | 26.852 | 48.985 | 41.818 | 1.00 | 175.55 | A |
| ATOM | 1409 | C | ASN | A | 322 | 30.554 | 46.253 | 40.459 | 1.00 | 178.87 | A |
| ATOM | 1410 | O | ASN | A | 322 | 31.772 | 46.418 | 40.391 | 1.00 | 178.87 | A |
| ATOM | 1411 | N | PRO | A | 323 | 30.013 | 45.049 | 40.711 | 1.00 | 146.14 | A |
| ATOM | 1412 | CD | PRO | A | 323 | 28.599 | 44.662 | 40.866 | 1.00 | 154.90 | A |
| ATOM | 1413 | CA | PRO | A | 323 | 30.891 | 43.892 | 40.897 | 1.00 | 146.14 | A |
| ATOM | 1414 | CB | PRO | A | 323 | 29.947 | 42.838 | 41.460 | 1.00 | 154.90 | A |
| ATOM | 1415 | CG | PRO | A | 323 | 28.664 | 43.154 | 40.761 | 1.00 | 154.90 | A |
| ATOM | 1416 | C | PRO | A | 323 | 31.496 | 43.486 | 39.554 | 1.00 | 146.14 | A |
| ATOM | 1417 | O | PRO | A | 323 | 32.138 | 42.444 | 39.438 | 1.00 | 146.14 | A |
| ATOM | 1418 | N | LEU | A | 324 | 31.274 | 44.328 | 38.546 | 1.00 | 149.27 | A |
| ATOM | 1419 | CA | LEU | A | 324 | 31.783 | 44.104 | 37.194 | 1.00 | 149.27 | A |
| ATOM | 1420 | CB | LEU | A | 324 | 30.673 | 44.367 | 36.162 | 1.00 | 158.78 | A |
| ATOM | 1421 | CG | LEU | A | 324 | 30.976 | 44.258 | 34.658 | 1.00 | 158.78 | A |
| ATOM | 1422 | CD1 | LEU | A | 324 | 29.670 | 44.136 | 33.890 | 1.00 | 158.78 | A |
| ATOM | 1423 | CD2 | LEU | A | 324 | 31.768 | 45.471 | 34.178 | 1.00 | 158.78 | A |
| ATOM | 1424 | C | LEU | A | 324 | 32.971 | 45.027 | 36.931 | 1.00 | 149.27 | A |
| ATOM | 1425 | O | LEU | A | 324 | 33.922 | 44.658 | 36.238 | 1.00 | 149.27 | A |
| ATOM | 1426 | N | ALA | A | 325 | 32.907 | 46.232 | 37.486 | 1.00 | 157.69 | A |
| ATOM | 1427 | CA | ALA | A | 325 | 33.974 | 47.209 | 37.318 | 1.00 | 157.69 | A |
| ATOM | 1428 | CB | ALA | A | 325 | 33.407 | 48.619 | 37.434 | 1.00 | 139.29 | A |
| ATOM | 1429 | C | ALA | A | 325 | 35.057 | 46.988 | 38.369 | 1.00 | 157.69 | A |
| ATOM | 1430 | O | ALA | A | 325 | 36.157 | 47.529 | 38.265 | 1.00 | 278.86 | A |
| ATOM | 1431 | N | ALA | A | 326 | 34.736 | 46.184 | 39.379 | 1.00 | 107.81 | A |
| ATOM | 1432 | CA | ALA | A | 326 | 35.676 | 45.892 | 40.454 | 1.00 | 107.81 | A |
| ATOM | 1433 | CB | ALA | A | 326 | 34.925 | 45.513 | 41.721 | 1.00 | 53.82 | A |
| ATOM | 1434 | C | ALA | A | 326 | 36.661 | 44.791 | 40.078 | 1.00 | 107.81 | A |
| ATOM | 1435 | O | ALA | A | 326 | 37.615 | 44.527 | 40.812 | 1.00 | 107.81 | A |
| ATOM | 1436 | N | CYS | A | 327 | 36.429 | 44.148 | 38.938 | 1.00 | 161.23 | A |
| ATOM | 1437 | CA | CYS | A | 327 | 37.317 | 43.089 | 38.471 | 1.00 | 161.23 | A |
| ATOM | 1438 | CB | CYS | A | 327 | 36.589 | 42.159 | 37.491 | 1.00 | 121.56 | A |
| ATOM | 1439 | SG | CYS | A | 327 | 35.396 | 41.014 | 38.240 | 1.00 | 121.56 | A |
| ATOM | 1440 | C | CYS | A | 327 | 38.542 | 43.696 | 37.793 | 1.00 | 161.23 | A |
| ATOM | 1441 | O | CYS | A | 327 | 39.662 | 43.540 | 38.275 | 1.00 | 161.23 | A |
| ATOM | 1442 | N | ARG | A | 328 | 38.323 | 44.395 | 36.680 | 1.00 | 185.65 | A |
| ATOM | 1443 | CA | ARG | A | 328 | 39.414 | 45.023 | 35.938 | 1.00 | 185.65 | A |
| ATOM | 1444 | CB | ARG | A | 328 | 39.133 | 44.989 | 34.433 | 1.00 | 125.20 | A |
| ATOM | 1445 | CG | ARG | A | 328 | 39.508 | 43.682 | 33.763 | 1.00 | 125.20 | A |
| ATOM | 1446 | CD | ARG | A | 328 | 39.459 | 43.834 | 32.254 | 1.00 | 125.20 | A |
| ATOM | 1447 | NE | ARG | A | 328 | 40.084 | 42.713 | 31.558 | 1.00 | 125.20 | A |
| ATOM | 1448 | CZ | ARG | A | 328 | 40.284 | 42.668 | 30.242 | 1.00 | 125.20 | A |
| ATOM | 1449 | NH1 | ARG | A | 328 | 39.906 | 43.685 | 29.475 | 1.00 | 125.20 | A |
| ATOM | 1450 | NH2 | ARG | A | 328 | 40.867 | 41.608 | 29.692 | 1.00 | 125.20 | A |

TABLE 2-continued

Atomic coordinates of b2 adrenoreceptor

| ATOM | 1451 | C | ARG | A | 328 | 39.715 | 46.458 | 36.358 | 1.00 | 185.65 | A |
|---|---|---|---|---|---|---|---|---|---|---|---|
| ATOM | 1452 | O | ARG | A | 328 | 39.921 | 47.332 | 35.512 | 1.00 | 185.65 | A |
| ATOM | 1453 | N | SER | A | 329 | 39.736 | 46.694 | 37.666 | 1.00 | 245.64 | A |
| ATOM | 1454 | CA | SER | A | 329 | 40.041 | 48.013 | 38.207 | 1.00 | 245.64 | A |
| ATOM | 1455 | CB | SER | A | 329 | 38.792 | 48.910 | 38.199 | 1.00 | 93.21 | A |
| ATOM | 1456 | OG | SER | A | 329 | 38.463 | 49.337 | 36.887 | 1.00 | 93.21 | A |
| ATOM | 1457 | C | SER | A | 329 | 40.641 | 47.915 | 39.617 | 1.00 | 245.64 | A |
| ATOM | 1458 | O | SER | A | 329 | 41.786 | 48.314 | 39.830 | 1.00 | 245.64 | A |
| ATOM | 1459 | N | PRO | A | 330 | 39.884 | 47.389 | 40.599 | 1.00 | 132.20 | A |
| ATOM | 1460 | CD | PRO | A | 330 | 38.413 | 47.332 | 40.669 | 1.00 | 203.11 | A |
| ATOM | 1461 | CA | PRO | A | 330 | 40.452 | 47.289 | 41.947 | 1.00 | 132.20 | A |
| ATOM | 1462 | CB | PRO | A | 330 | 39.298 | 47.742 | 42.824 | 1.00 | 203.11 | A |
| ATOM | 1463 | CG | PRO | A | 330 | 38.152 | 47.088 | 42.154 | 1.00 | 203.11 | A |
| ATOM | 1464 | C | PRO | A | 330 | 40.938 | 45.882 | 42.312 | 1.00 | 132.20 | A |
| ATOM | 1465 | O | PRO | A | 330 | 40.781 | 44.936 | 41.539 | 1.00 | 132.20 | A |
| ATOM | 1466 | N | ASP | A | 331 | 41.520 | 45.764 | 43.504 | 1.00 | 242.71 | A |
| ATOM | 1467 | CA | ASP | A | 331 | 42.052 | 44.500 | 44.012 | 1.00 | 242.71 | A |
| ATOM | 1468 | CB | ASP | A | 331 | 42.560 | 44.688 | 45.446 | 1.00 | 203.10 | A |
| ATOM | 1469 | CG | ASP | A | 331 | 43.057 | 43.394 | 46.067 | 1.00 | 203.10 | A |
| ATOM | 1470 | OD1 | ASP | A | 331 | 42.249 | 42.454 | 46.231 | 1.00 | 203.10 | A |
| ATOM | 1471 | OD2 | ASP | A | 331 | 44.259 | 43.317 | 46.394 | 1.00 | 203.10 | A |
| ATOM | 1472 | C | ASP | A | 331 | 41.048 | 43.353 | 43.981 | 1.00 | 242.71 | A |
| ATOM | 1473 | O | ASP | A | 331 | 41.431 | 42.199 | 43.783 | 1.00 | 242.71 | A |
| ATOM | 1474 | N | ALA | A | 332 | 39.774 | 43.672 | 44.190 | 1.00 | 104.31 | A |
| ATOM | 1475 | CA | ALA | A | 332 | 38.710 | 42.673 | 44.190 | 1.00 | 104.31 | A |
| ATOM | 1476 | CB | ALA | A | 332 | 37.379 | 43.335 | 43.846 | 1.00 | 109.64 | A |
| ATOM | 1477 | C | ALA | A | 332 | 39.002 | 41.539 | 43.208 | 1.00 | 104.31 | A |
| ATOM | 1478 | O | ALA | A | 332 | 38.793 | 40.369 | 43.526 | 1.00 | 234.64 | A |
| ATOM | 1479 | N | ARG | A | 333 | 39.484 | 41.903 | 42.019 | 1.00 | 99.48 | A |
| ATOM | 1480 | CA | ARG | A | 333 | 39.834 | 40.954 | 40.961 | 1.00 | 99.48 | A |
| ATOM | 1481 | CB | ARG | A | 333 | 41.071 | 41.460 | 40.213 | 1.00 | 198.20 | A |
| ATOM | 1482 | CG | ARG | A | 333 | 41.106 | 41.148 | 38.728 | 1.00 | 198.20 | A |
| ATOM | 1483 | CD | ARG | A | 333 | 40.916 | 39.674 | 38.437 | 1.00 | 198.20 | A |
| ATOM | 1484 | NE | ARG | A | 333 | 41.113 | 39.368 | 37.021 | 1.00 | 198.20 | A |
| ATOM | 1485 | CZ | ARG | A | 333 | 40.454 | 39.950 | 36.023 | 1.00 | 198.20 | A |
| ATOM | 1486 | NH1 | ARG | A | 333 | 39.543 | 40.882 | 36.276 | 1.00 | 198.20 | A |
| ATOM | 1487 | NH2 | ARG | A | 333 | 40.704 | 39.601 | 34.766 | 1.00 | 198.20 | A |
| ATOM | 1488 | C | ARG | A | 333 | 40.131 | 39.588 | 41.576 | 1.00 | 99.48 | A |
| ATOM | 1489 | O | ARG | A | 333 | 39.331 | 38.661 | 41.475 | 1.00 | 99.48 | A |
| ATOM | 1490 | N | ILE | A | 334 | 41.284 | 39.480 | 42.229 | 1.00 | 201.77 | A |
| ATOM | 1491 | CA | ILE | A | 334 | 41.689 | 38.236 | 42.875 | 1.00 | 201.77 | A |
| ATOM | 1492 | CB | ILE | A | 334 | 43.178 | 38.297 | 43.336 | 1.00 | 122.43 | A |
| ATOM | 1493 | CG2 | ILE | A | 334 | 43.521 | 37.061 | 44.153 | 1.00 | 122.43 | A |
| ATOM | 1494 | CG1 | ILE | A | 334 | 44.109 | 38.403 | 42.123 | 1.00 | 122.43 | A |
| ATOM | 1495 | CD1 | ILE | A | 334 | 45.593 | 38.406 | 42.473 | 1.00 | 122.43 | A |
| ATOM | 1496 | C | ILE | A | 334 | 40.807 | 37.959 | 44.097 | 1.00 | 201.77 | A |
| ATOM | 1497 | O | ILE | A | 334 | 40.289 | 36.854 | 44.265 | 1.00 | 201.77 | A |
| ATOM | 1498 | N | ALA | A | 335 | 40.639 | 38.979 | 44.935 | 1.00 | 130.58 | A |
| ATOM | 1499 | CA | ALA | A | 335 | 39.847 | 38.888 | 46.159 | 1.00 | 130.58 | A |
| ATOM | 1500 | CB | ALA | A | 335 | 39.403 | 40.285 | 46.587 | 1.00 | 116.45 | A |
| ATOM | 1501 | C | ALA | A | 335 | 38.636 | 37.961 | 46.081 | 1.00 | 130.58 | A |
| ATOM | 1502 | O | ALA | A | 335 | 38.393 | 37.174 | 46.998 | 1.00 | 130.58 | A |
| ATOM | 1503 | N | PHE | A | 336 | 37.876 | 38.052 | 44.992 | 1.00 | 174.31 | A |
| ATOM | 1504 | CA | PHE | A | 336 | 36.690 | 37.216 | 44.844 | 1.00 | 174.31 | A |
| ATOM | 1505 | CB | PHE | A | 336 | 35.413 | 38.086 | 44.834 | 1.00 | 120.87 | A |
| ATOM | 1506 | CG | PHE | A | 336 | 35.290 | 39.030 | 43.645 | 1.00 | 120.87 | A |
| ATOM | 1507 | CD1 | PHE | A | 336 | 34.189 | 39.879 | 43.544 | 1.00 | 120.87 | A |
| ATOM | 1508 | CD2 | PHE | A | 336 | 36.252 | 39.074 | 42.635 | 1.00 | 120.87 | A |
| ATOM | 1509 | CE1 | PHE | A | 336 | 34.048 | 40.752 | 42.464 | 1.00 | 120.87 | A |
| ATOM | 1510 | CE2 | PHE | A | 336 | 36.119 | 39.944 | 41.551 | 1.00 | 120.87 | A |
| ATOM | 1511 | CZ | PHE | A | 336 | 35.015 | 40.783 | 41.468 | 1.00 | 120.87 | A |
| ATOM | 1512 | C | PHE | A | 336 | 36.679 | 36.268 | 43.645 | 1.00 | 174.31 | A |
| ATOM | 1513 | O | PHE | A | 336 | 35.969 | 35.263 | 43.663 | 1.00 | 174.31 | A |
| ATOM | 1514 | N | GLN | A | 337 | 37.459 | 36.571 | 42.611 | 1.00 | 214.43 | A |
| ATOM | 1515 | CA | GLN | A | 337 | 37.484 | 35.712 | 41.431 | 1.00 | 214.43 | A |
| ATOM | 1516 | CB | GLN | A | 337 | 38.095 | 36.447 | 40.232 | 1.00 | 148.23 | A |
| ATOM | 1517 | CG | GLN | A | 337 | 37.887 | 35.726 | 38.903 | 1.00 | 148.23 | A |
| ATOM | 1518 | CD | GLN | A | 337 | 38.376 | 36.524 | 37.707 | 1.00 | 148.23 | A |
| ATOM | 1519 | OE1 | GLN | A | 337 | 38.804 | 37.667 | 37.843 | 1.00 | 148.23 | A |
| ATOM | 1520 | NE2 | GLN | A | 337 | 38.307 | 35.922 | 36.525 | 1.00 | 148.23 | A |
| ATOM | 1521 | C | GLN | A | 337 | 38.261 | 34.434 | 41.714 | 1.00 | 214.43 | A |
| ATOM | 1522 | O | GLN | A | 337 | 37.985 | 33.387 | 41.129 | 1.00 | 214.43 | A |
| ATOM | 1523 | N | GLU | A | 338 | 39.233 | 34.518 | 42.616 | 1.00 | 196.91 | A |
| ATOM | 1524 | CA | GLU | A | 338 | 40.023 | 33.349 | 42.973 | 1.00 | 196.91 | A |
| ATOM | 1525 | CB | GLU | A | 338 | 41.487 | 33.735 | 43.215 | 1.00 | 250.94 | A |
| ATOM | 1526 | CG | GLU | A | 338 | 42.216 | 34.236 | 41.972 | 1.00 | 250.94 | A |
| ATOM | 1527 | CD | GLU | A | 338 | 43.714 | 34.396 | 42.187 | 1.00 | 250.94 | A |
| ATOM | 1528 | OE1 | GLU | A | 338 | 44.406 | 34.862 | 41.256 | 1.00 | 250.94 | A |

TABLE 2-continued

Atomic coordinates of b2 adrenoreceptor

| ATOM | 1529 | OE2 | GLU | A | 338 | 44.202 | 34.052 | 43.284 | 1.00 | 250.94 | A |
| ATOM | 1530 | C | GLU | A | 338 | 39.445 | 32.679 | 44.217 | 1.00 | 196.91 | A |
| ATOM | 1531 | O | GLU | A | 338 | 39.882 | 31.595 | 44.602 | 1.00 | 196.91 | A |
| ATOM | 1532 | N | LEU | A | 339 | 38.460 | 33.321 | 44.843 | 1.00 | 211.59 | A |
| ATOM | 1533 | CA | LEU | A | 339 | 37.833 | 32.757 | 46.035 | 1.00 | 211.59 | A |
| ATOM | 1534 | CB | LEU | A | 339 | 36.891 | 33.776 | 46.696 | 1.00 | 160.31 | A |
| ATOM | 1535 | CG | LEU | A | 339 | 35.471 | 34.016 | 46.168 | 1.00 | 160.31 | A |
| ATOM | 1536 | CD1 | LEU | A | 339 | 34.579 | 32.823 | 46.485 | 1.00 | 160.31 | A |
| ATOM | 1537 | CD2 | LEU | A | 339 | 34.900 | 35.267 | 46.824 | 1.00 | 160.31 | A |
| ATOM | 1538 | C | LEU | A | 339 | 37.058 | 31.514 | 45.613 | 1.00 | 211.59 | A |
| ATOM | 1539 | O | LEU | A | 339 | 36.843 | 30.599 | 46.410 | 1.00 | 211.59 | A |
| ATOM | 1540 | N | LEU | A | 340 | 36.637 | 31.498 | 44.351 | 1.00 | 248.34 | A |
| ATOM | 1541 | CA | LEU | A | 340 | 35.902 | 30.369 | 43.791 | 1.00 | 248.34 | A |
| ATOM | 1542 | CB | LEU | A | 340 | 35.077 | 30.812 | 42.575 | 1.00 | 166.64 | A |
| ATOM | 1543 | CG | LEU | A | 340 | 33.906 | 31.778 | 42.790 | 1.00 | 166.64 | A |
| ATOM | 1544 | CD1 | LEU | A | 340 | 33.356 | 32.224 | 41.440 | 1.00 | 166.64 | A |
| ATOM | 1545 | CD2 | LEU | A | 340 | 32.822 | 31.102 | 43.618 | 1.00 | 166.64 | A |
| ATOM | 1546 | C | LEU | A | 340 | 36.913 | 29.310 | 43.364 | 1.00 | 248.34 | A |
| ATOM | 1547 | O | LEU | A | 340 | 37.037 | 28.998 | 42.178 | 1.00 | 248.34 | A |
| ATOM | 1548 | N | CYS | A | 341 | 37.635 | 28.771 | 44.342 | 1.00 | 247.73 | A |
| ATOM | 1549 | CA | CYS | A | 341 | 38.652 | 27.752 | 44.102 | 1.00 | 247.73 | A |
| ATOM | 1550 | CB | CYS | A | 341 | 38.000 | 26.373 | 43.942 | 1.00 | 228.60 | A |
| ATOM | 1551 | SG | CYS | A | 341 | 36.833 | 26.222 | 42.570 | 1.00 | 228.60 | A |
| ATOM | 1552 | C | CYS | A | 341 | 39.502 | 28.075 | 42.875 | 1.00 | 247.73 | A |
| ATOM | 1553 | O | CYS | A | 341 | 39.505 | 27.332 | 41.893 | 1.00 | 247.73 | A |
| ATOM | 1554 | N | LEU | A | 342 | 40.224 | 29.191 | 42.948 | 1.00 | 236.27 | A |
| ATOM | 1555 | CA | LEU | A | 342 | 41.090 | 29.646 | 41.863 | 1.00 | 236.27 | A |
| ATOM | 1556 | CB | LEU | A | 342 | 42.371 | 28.802 | 41.816 | 1.00 | 134.01 | A |
| ATOM | 1557 | CG | LEU | A | 342 | 43.377 | 28.959 | 42.971 | 1.00 | 134.01 | A |
| ATOM | 1558 | CD1 | LEU | A | 342 | 43.730 | 30.429 | 43.147 | 1.00 | 134.01 | A |
| ATOM | 1559 | CD2 | LEU | A | 342 | 42.800 | 28.403 | 44.259 | 1.00 | 134.01 | A |
| ATOM | 1560 | C | LEU | A | 342 | 40.390 | 29.628 | 40.504 | 1.00 | 236.27 | A |
| ATOM | 1561 | O | LEU | A | 342 | 40.246 | 28.581 | 39.871 | 1.00 | 236.27 | A |
| ATOM | 1562 | N | ARG | A | 343 | 39.967 | 30.810 | 40.068 | 1.00 | 231.57 | A |
| ATOM | 1563 | CA | ARG | A | 343 | 39.265 | 30.990 | 38.802 | 1.00 | 231.57 | A |
| ATOM | 1564 | CB | ARG | A | 343 | 38.976 | 32.480 | 38.591 | 1.00 | 159.44 | A |
| ATOM | 1565 | CG | ARG | A | 343 | 38.498 | 32.868 | 37.193 | 1.00 | 159.44 | A |
| ATOM | 1566 | CD | ARG | A | 343 | 37.095 | 32.374 | 36.874 | 1.00 | 159.44 | A |
| ATOM | 1567 | NE | ARG | A | 343 | 36.660 | 32.861 | 35.565 | 1.00 | 159.44 | A |
| ATOM | 1568 | CZ | ARG | A | 343 | 35.434 | 32.716 | 35.073 | 1.00 | 159.44 | A |
| ATOM | 1569 | NH1 | ARG | A | 343 | 34.503 | 32.091 | 35.781 | 1.00 | 159.44 | A |
| ATOM | 1570 | NH2 | ARG | A | 343 | 35.137 | 33.199 | 33.874 | 1.00 | 159.44 | A |
| ATOM | 1571 | C | ARG | A | 343 | 39.973 | 30.433 | 37.569 | 1.00 | 231.57 | A |
| ATOM | 1572 | O | ARG | A | 343 | 39.812 | 29.260 | 37.228 | 1.00 | 231.57 | A |
| ATOM | 1573 | N | ARG | A | 344 | 40.758 | 31.280 | 36.908 | 1.00 | 161.08 | A |
| ATOM | 1574 | CA | ARG | A | 344 | 41.449 | 30.894 | 35.683 | 1.00 | 161.08 | A |
| ATOM | 1575 | CB | ARG | A | 344 | 40.804 | 31.627 | 34.501 | 1.00 | 162.76 | A |
| ATOM | 1576 | CG | ARG | A | 344 | 41.392 | 31.311 | 33.141 | 1.00 | 162.76 | A |
| ATOM | 1577 | CD | ARG | A | 344 | 40.681 | 32.109 | 32.059 | 1.00 | 162.76 | A |
| ATOM | 1578 | NE | ARG | A | 344 | 39.239 | 31.873 | 32.075 | 1.00 | 162.76 | A |
| ATOM | 1579 | CZ | ARG | A | 344 | 38.379 | 32.423 | 31.223 | 1.00 | 162.76 | A |
| ATOM | 1580 | NH1 | ARG | A | 344 | 38.814 | 33.247 | 30.279 | 1.00 | 162.76 | A |
| ATOM | 1581 | NH2 | ARG | A | 344 | 37.083 | 32.147 | 31.312 | 1.00 | 162.76 | A |
| ATOM | 1582 | C | ARG | A | 344 | 42.953 | 31.160 | 35.697 | 1.00 | 161.08 | A |
| ATOM | 1583 | O | ARG | A | 344 | 43.752 | 30.225 | 35.741 | 1.00 | 321.32 | A |
| ATOM | 1584 | N | SER | A | 345 | 43.332 | 32.435 | 35.655 | 1.00 | 225.15 | A |
| ATOM | 1585 | CA | SER | A | 345 | 44.742 | 32.826 | 35.643 | 1.00 | 225.15 | A |
| ATOM | 1586 | CB | SER | A | 345 | 44.875 | 34.337 | 35.435 | 1.00 | 168.15 | A |
| ATOM | 1587 | OG | SER | A | 345 | 46.239 | 34.722 | 35.384 | 1.00 | 168.15 | A |
| ATOM | 1588 | C | SER | A | 345 | 45.496 | 32.424 | 36.905 | 1.00 | 225.15 | A |
| ATOM | 1589 | O | SER | A | 345 | 46.562 | 32.967 | 37.201 | 1.00 | 225.15 | A |
| ATOM | 1590 | N | SER | A | 346 | 44.935 | 31.478 | 37.650 | 1.00 | 269.98 | A |
| ATOM | 1591 | CA | SER | A | 346 | 45.571 | 30.988 | 38.864 | 1.00 | 269.98 | A |
| ATOM | 1592 | CB | SER | A | 346 | 44.601 | 30.096 | 39.644 | 1.00 | 123.96 | A |
| ATOM | 1593 | OG | SER | A | 346 | 45.238 | 29.494 | 40.757 | 1.00 | 123.96 | A |
| ATOM | 1594 | C | SER | A | 346 | 46.784 | 30.178 | 38.432 | 1.00 | 269.98 | A |
| ATOM | 1595 | O | SER | A | 346 | 46.950 | 29.029 | 38.840 | 1.00 | 269.98 | A |
| ATOM | 1596 | N | LEU | A | 347 | 47.628 | 30.784 | 37.601 | 1.00 | 218.44 | A |
| ATOM | 1597 | CA | LEU | A | 347 | 48.811 | 30.105 | 37.095 | 1.00 | 218.44 | A |
| ATOM | 1598 | CB | LEU | A | 347 | 49.750 | 29.737 | 38.253 | 1.00 | 124.08 | A |
| ATOM | 1599 | CG | LEU | A | 347 | 50.414 | 30.840 | 39.102 | 1.00 | 124.08 | A |
| ATOM | 1600 | CD1 | LEU | A | 347 | 51.403 | 31.614 | 38.248 | 1.00 | 124.08 | A |
| ATOM | 1601 | CD2 | LEU | A | 347 | 49.366 | 31.774 | 39.698 | 1.00 | 124.08 | A |
| ATOM | 1602 | C | LEU | A | 347 | 48.302 | 28.844 | 36.390 | 1.00 | 218.44 | A |
| ATOM | 1603 | O | LEU | A | 347 | 48.967 | 27.808 | 36.373 | 1.00 | 218.44 | A |
| ATOM | 1604 | N | LYS | A | 348 | 47.107 | 28.965 | 35.816 | 1.00 | 208.32 | A |
| ATOM | 1605 | CA | LYS | A | 348 | 46.421 | 27.883 | 35.106 | 1.00 | 208.32 | A |
| ATOM | 1606 | CB | LYS | A | 348 | 45.438 | 28.481 | 34.091 | 1.00 | 163.90 | A |

TABLE 2-continued

Atomic coordinates of b2 adrenoreceptor

| ATOM | 1607 | CG | LYS | A | 348 | 44.156 | 27.684 | 33.893 | 1.00 | 163.90 | A |
|---|---|---|---|---|---|---|---|---|---|---|---|
| ATOM | 1608 | CD | LYS | A | 348 | 43.210 | 28.406 | 32.940 | 1.00 | 163.90 | A |
| ATOM | 1609 | CE | LYS | A | 348 | 41.869 | 27.691 | 32.805 | 1.00 | 163.90 | A |
| ATOM | 1610 | NZ | LYS | A | 348 | 41.064 | 27.741 | 34.059 | 1.00 | 163.90 | A |
| ATOM | 1611 | C | LYS | A | 348 | 47.368 | 26.919 | 34.396 | 1.00 | 208.32 | A |
| ATOM | 1612 | O | LYS | A | 348 | 47.371 | 25.723 | 34.761 | 1.00 | 340.63 | A |
| ATOM | 1613 | OXT | LYS | A | 348 | 48.093 | 27.366 | 33.483 | 1.00 | 109.32 | A |
| ATOM | 1614 | CB | ASP | L | 1 | 58.843 | 68.155 | 22.719 | 1.00 | 104.97 | L |
| ATOM | 1615 | CG | ASP | L | 1 | 58.188 | 67.360 | 21.603 | 1.00 | 104.97 | L |
| ATOM | 1616 | OD1 | ASP | L | 1 | 56.985 | 67.576 | 21.331 | 1.00 | 104.97 | L |
| ATOM | 1617 | OD2 | ASP | L | 1 | 58.882 | 66.513 | 20.998 | 1.00 | 104.97 | L |
| ATOM | 1618 | C | ASP | L | 1 | 59.595 | 70.388 | 23.547 | 1.00 | 70.59 | L |
| ATOM | 1619 | O | ASP | L | 1 | 59.080 | 71.158 | 24.354 | 1.00 | 70.59 | L |
| ATOM | 1620 | N | ASP | L | 1 | 59.210 | 70.015 | 21.129 | 1.00 | 70.59 | L |
| ATOM | 1621 | CA | ASP | L | 1 | 58.748 | 69.667 | 22.502 | 1.00 | 70.59 | L |
| ATOM | 1622 | N | ILE | L | 2 | 60.897 | 70.131 | 23.534 | 1.00 | 33.06 | L |
| ATOM | 1623 | CA | ILE | L | 2 | 61.805 | 70.768 | 24.480 | 1.00 | 33.06 | L |
| ATOM | 1624 | CB | ILE | L | 2 | 61.501 | 70.346 | 25.967 | 1.00 | 40.05 | L |
| ATOM | 1625 | CG2 | ILE | L | 2 | 61.239 | 68.835 | 26.056 | 1.00 | 40.05 | L |
| ATOM | 1626 | CG1 | ILE | L | 2 | 62.656 | 70.803 | 26.884 | 1.00 | 40.05 | L |
| ATOM | 1627 | CD1 | ILE | L | 2 | 62.389 | 70.678 | 28.383 | 1.00 | 40.05 | L |
| ATOM | 1628 | C | ILE | L | 2 | 63.282 | 70.512 | 24.152 | 1.00 | 33.06 | L |
| ATOM | 1629 | O | ILE | L | 2 | 63.954 | 69.694 | 24.792 | 1.00 | 33.06 | L |
| ATOM | 1630 | N | LYS | L | 3 | 63.771 | 71.235 | 23.145 | 1.00 | 69.58 | L |
| ATOM | 1631 | CA | LYS | L | 3 | 65.156 | 71.143 | 22.693 | 1.00 | 69.58 | L |
| ATOM | 1632 | CB | LYS | L | 3 | 65.465 | 72.265 | 21.689 | 1.00 | 99.65 | L |
| ATOM | 1633 | CG | LYS | L | 3 | 64.995 | 72.029 | 20.252 | 1.00 | 99.65 | L |
| ATOM | 1634 | CD | LYS | L | 3 | 65.858 | 70.994 | 19.533 | 1.00 | 99.65 | L |
| ATOM | 1635 | CE | LYS | L | 3 | 65.454 | 70.846 | 18.072 | 1.00 | 99.65 | L |
| ATOM | 1636 | NZ | LYS | L | 3 | 66.197 | 69.747 | 17.398 | 1.00 | 99.65 | L |
| ATOM | 1637 | C | LYS | L | 3 | 66.124 | 71.253 | 23.861 | 1.00 | 69.58 | L |
| ATOM | 1638 | O | LYS | L | 3 | 65.899 | 72.024 | 24.799 | 1.00 | 69.58 | L |
| ATOM | 1639 | N | MET | L | 4 | 67.202 | 70.475 | 23.790 | 1.00 | 69.92 | L |
| ATOM | 1640 | CA | MET | L | 4 | 68.235 | 70.473 | 24.819 | 1.00 | 69.92 | L |
| ATOM | 1641 | CB | MET | L | 4 | 68.021 | 69.325 | 25.801 | 1.00 | 69.77 | L |
| ATOM | 1642 | CG | MET | L | 4 | 66.808 | 69.508 | 26.686 | 1.00 | 69.77 | L |
| ATOM | 1643 | SD | MET | L | 4 | 66.885 | 68.478 | 28.147 | 1.00 | 69.77 | L |
| ATOM | 1644 | CE | MET | L | 4 | 68.447 | 69.049 | 28.865 | 1.00 | 69.77 | L |
| ATOM | 1645 | C | MET | L | 4 | 69.613 | 70.338 | 24.199 | 1.00 | 69.92 | L |
| ATOM | 1646 | O | MET | L | 4 | 70.070 | 69.223 | 23.946 | 1.00 | 69.92 | L |
| ATOM | 1647 | N | THR | L | 5 | 70.269 | 71.474 | 23.950 | 1.00 | 47.75 | L |
| ATOM | 1648 | CA | THR | L | 5 | 71.609 | 71.479 | 23.362 | 1.00 | 47.75 | L |
| ATOM | 1649 | CB | THR | L | 5 | 72.027 | 72.900 | 22.940 | 1.00 | 191.35 | L |
| ATOM | 1650 | OG1 | THR | L | 5 | 73.321 | 72.855 | 22.326 | 1.00 | 191.35 | L |
| ATOM | 1651 | CG2 | THR | L | 5 | 72.060 | 73.825 | 24.143 | 1.00 | 191.35 | L |
| ATOM | 1652 | C | THR | L | 5 | 72.622 | 70.905 | 24.362 | 1.00 | 47.75 | L |
| ATOM | 1653 | O | THR | L | 5 | 72.305 | 70.709 | 25.538 | 1.00 | 47.75 | L |
| ATOM | 1654 | N | GLN | L | 6 | 73.846 | 70.657 | 23.912 | 1.00 | 47.00 | L |
| ATOM | 1655 | CA | GLN | L | 6 | 74.821 | 70.035 | 24.796 | 1.00 | 47.00 | L |
| ATOM | 1656 | CB | GLN | L | 6 | 74.444 | 68.547 | 24.909 | 1.00 | 57.42 | L |
| ATOM | 1657 | CG | GLN | L | 6 | 75.373 | 67.629 | 25.702 | 1.00 | 57.42 | L |
| ATOM | 1658 | CD | GLN | L | 6 | 74.856 | 66.192 | 25.727 | 1.00 | 57.42 | L |
| ATOM | 1659 | OE1 | GLN | L | 6 | 73.669 | 65.932 | 25.488 | 1.00 | 57.42 | L |
| ATOM | 1660 | NE2 | GLN | L | 6 | 75.747 | 65.256 | 26.025 | 1.00 | 57.42 | L |
| ATOM | 1661 | C | GLN | L | 6 | 76.275 | 70.173 | 24.344 | 1.00 | 47.00 | L |
| ATOM | 1662 | O | GLN | L | 6 | 76.814 | 69.256 | 23.722 | 1.00 | 47.00 | L |
| ATOM | 1663 | N | SER | L | 7 | 76.922 | 71.293 | 24.663 | 1.00 | 39.35 | L |
| ATOM | 1664 | CA | SER | L | 7 | 78.316 | 71.461 | 24.258 | 1.00 | 39.35 | L |
| ATOM | 1665 | CB | SER | L | 7 | 78.656 | 72.930 | 24.040 | 1.00 | 63.39 | L |
| ATOM | 1666 | OG | SER | L | 7 | 80.024 | 73.060 | 23.694 | 1.00 | 63.39 | L |
| ATOM | 1667 | C | SER | L | 7 | 79.279 | 70.876 | 25.283 | 1.00 | 39.35 | L |
| ATOM | 1668 | O | SER | L | 7 | 79.043 | 70.960 | 26.488 | 1.00 | 39.35 | L |
| ATOM | 1669 | N | PRO | L | 8 | 80.390 | 70.289 | 24.814 | 1.00 | 111.05 | L |
| ATOM | 1670 | CD | PRO | L | 8 | 81.455 | 69.727 | 25.664 | 1.00 | 14.97 | L |
| ATOM | 1671 | CA | PRO | L | 8 | 80.754 | 70.162 | 23.401 | 1.00 | 111.05 | L |
| ATOM | 1672 | CB | PRO | L | 8 | 82.248 | 69.907 | 23.464 | 1.00 | 14.97 | L |
| ATOM | 1673 | CG | PRO | L | 8 | 82.355 | 69.022 | 24.639 | 1.00 | 14.97 | L |
| ATOM | 1674 | C | PRO | L | 8 | 80.054 | 69.021 | 22.696 | 1.00 | 111.05 | L |
| ATOM | 1675 | O | PRO | L | 8 | 78.988 | 68.563 | 23.100 | 1.00 | 111.05 | L |
| ATOM | 1676 | N | SER | L | 9 | 80.696 | 68.568 | 21.629 | 1.00 | 48.18 | L |
| ATOM | 1677 | CA | SER | L | 9 | 80.215 | 67.464 | 20.826 | 1.00 | 48.18 | L |
| ATOM | 1678 | CB | SER | L | 9 | 79.870 | 67.949 | 19.426 | 1.00 | 43.62 | L |
| ATOM | 1679 | OG | SER | L | 9 | 79.612 | 66.848 | 18.581 | 1.00 | 43.62 | L |
| ATOM | 1680 | C | SER | L | 9 | 81.399 | 66.523 | 20.766 | 1.00 | 48.18 | L |
| ATOM | 1681 | O | SER | L | 9 | 81.341 | 65.392 | 21.236 | 1.00 | 48.18 | L |
| ATOM | 1682 | N | SER | L | 10 | 82.485 | 67.032 | 20.200 | 1.00 | 31.19 | L |
| ATOM | 1683 | CA | SER | L | 10 | 83.726 | 66.283 | 20.060 | 1.00 | 31.19 | L |
| ATOM | 1684 | CB | SER | L | 10 | 84.371 | 66.631 | 18.715 | 1.00 | 79.64 | L |

TABLE 2-continued

Atomic coordinates of b2 adrenoreceptor

| ATOM | 1685 | OG  | SER | L | 10 | 83.393 | 66.738 | 17.686 | 1.00 | 79.64  | L |
|------|------|-----|-----|---|----|--------|--------|--------|------|--------|---|
| ATOM | 1686 | C   | SER | L | 10 | 84.626 | 66.737 | 21.208 | 1.00 | 31.19  | L |
| ATOM | 1687 | O   | SER | L | 10 | 84.506 | 67.883 | 21.645 | 1.00 | 31.19  | L |
| ATOM | 1688 | N   | MET | L | 11 | 85.517 | 65.877 | 21.709 | 1.00 | 56.19  | L |
| ATOM | 1689 | CA  | MET | L | 11 | 86.379 | 66.297 | 22.827 | 1.00 | 56.19  | L |
| ATOM | 1690 | CB  | MET | L | 11 | 85.526 | 66.525 | 24.073 | 1.00 | 78.56  | L |
| ATOM | 1691 | CG  | MET | L | 11 | 85.916 | 67.746 | 24.864 | 1.00 | 78.56  | L |
| ATOM | 1692 | SD  | MET | L | 11 | 85.712 | 67.456 | 26.618 | 1.00 | 78.56  | L |
| ATOM | 1693 | CE  | MET | L | 11 | 87.430 | 67.133 | 27.082 | 1.00 | 78.56  | L |
| ATOM | 1694 | C   | MET | L | 11 | 87.519 | 65.340 | 23.185 | 1.00 | 56.19  | L |
| ATOM | 1695 | O   | MET | L | 11 | 87.290 | 64.152 | 23.418 | 1.00 | 56.19  | L |
| ATOM | 1696 | N   | TYR | L | 12 | 88.737 | 65.885 | 23.266 | 1.00 | 36.17  | L |
| ATOM | 1697 | CA  | TYR | L | 12 | 89.945 | 65.112 | 23.568 | 1.00 | 36.17  | L |
| ATOM | 1698 | CB  | TYR | L | 12 | 90.939 | 65.226 | 22.419 | 1.00 | 75.75  | L |
| ATOM | 1699 | CG  | TYR | L | 12 | 90.832 | 64.160 | 21.361 | 1.00 | 75.75  | L |
| ATOM | 1700 | CD1 | TYR | L | 12 | 89.977 | 64.310 | 20.268 | 1.00 | 75.75  | L |
| ATOM | 1701 | CE1 | TYR | L | 12 | 89.909 | 63.335 | 19.276 | 1.00 | 75.75  | L |
| ATOM | 1702 | CD2 | TYR | L | 12 | 91.616 | 63.006 | 21.441 | 1.00 | 75.75  | L |
| ATOM | 1703 | CE2 | TYR | L | 12 | 91.557 | 62.022 | 20.459 | 1.00 | 75.75  | L |
| ATOM | 1704 | CZ  | TYR | L | 12 | 90.704 | 62.188 | 19.378 | 1.00 | 75.75  | L |
| ATOM | 1705 | OH  | TYR | L | 12 | 90.653 | 61.203 | 18.413 | 1.00 | 75.75  | L |
| ATOM | 1706 | C   | TYR | L | 12 | 90.678 | 65.528 | 24.837 | 1.00 | 36.17  | L |
| ATOM | 1707 | O   | TYR | L | 12 | 91.331 | 66.563 | 24.863 | 1.00 | 36.17  | L |
| ATOM | 1708 | N   | ALA | L | 13 | 90.598 | 64.706 | 25.875 | 1.00 | 50.34  | L |
| ATOM | 1709 | CA  | ALA | L | 13 | 91.275 | 65.000 | 27.135 | 1.00 | 50.34  | L |
| ATOM | 1710 | CB  | ALA | L | 13 | 90.252 | 65.052 | 28.281 | 1.00 | 32.12  | L |
| ATOM | 1711 | C   | ALA | L | 13 | 92.320 | 63.927 | 27.415 | 1.00 | 50.34  | L |
| ATOM | 1712 | O   | ALA | L | 13 | 92.137 | 62.771 | 27.055 | 1.00 | 50.34  | L |
| ATOM | 1713 | N   | SER | L | 14 | 93.426 | 64.302 | 28.039 | 1.00 | 64.54  | L |
| ATOM | 1714 | CA  | SER | L | 14 | 94.445 | 63.311 | 28.356 | 1.00 | 64.54  | L |
| ATOM | 1715 | CB  | SER | L | 14 | 95.854 | 63.884 | 28.167 | 1.00 | 83.51  | L |
| ATOM | 1716 | OG  | SER | L | 14 | 96.011 | 65.106 | 28.863 | 1.00 | 83.51  | L |
| ATOM | 1717 | C   | SER | L | 14 | 94.231 | 62.885 | 29.798 | 1.00 | 64.54  | L |
| ATOM | 1718 | O   | SER | L | 14 | 93.632 | 63.624 | 30.576 | 1.00 | 64.54  | L |
| ATOM | 1719 | N   | LEU | L | 15 | 94.707 | 61.692 | 30.141 | 1.00 | 67.83  | L |
| ATOM | 1720 | CA  | LEU | L | 15 | 94.558 | 61.146 | 31.485 | 1.00 | 67.83  | L |
| ATOM | 1721 | CB  | LEU | L | 15 | 95.430 | 59.903 | 31.629 | 1.00 | 70.10  | L |
| ATOM | 1722 | CG  | LEU | L | 15 | 94.830 | 58.583 | 31.152 | 1.00 | 70.10  | L |
| ATOM | 1723 | CD1 | LEU | L | 15 | 94.161 | 58.763 | 29.799 | 1.00 | 70.10  | L |
| ATOM | 1724 | CD2 | LEU | L | 15 | 95.933 | 57.531 | 31.106 | 1.00 | 70.10  | L |
| ATOM | 1725 | C   | LEU | L | 15 | 94.894 | 62.115 | 32.609 | 1.00 | 67.83  | L |
| ATOM | 1726 | O   | LEU | L | 15 | 95.807 | 62.925 | 32.480 | 1.00 | 67.83  | L |
| ATOM | 1727 | N   | GLY | L | 16 | 94.155 | 62.031 | 33.712 | 1.00 | 103.45 | L |
| ATOM | 1728 | CA  | GLY | L | 16 | 94.427 | 62.897 | 34.848 | 1.00 | 103.45 | L |
| ATOM | 1729 | C   | GLY | L | 16 | 93.698 | 64.229 | 34.913 | 1.00 | 103.45 | L |
| ATOM | 1730 | O   | GLY | L | 16 | 93.256 | 64.634 | 35.988 | 1.00 | 103.45 | L |
| ATOM | 1731 | N   | GLU | L | 17 | 93.586 | 64.922 | 33.781 | 1.00 | 52.27  | L |
| ATOM | 1732 | CA  | GLU | L | 17 | 92.899 | 66.211 | 33.742 | 1.00 | 52.27  | L |
| ATOM | 1733 | CB  | GLU | L | 17 | 93.126 | 66.891 | 32.387 | 1.00 | 145.45 | L |
| ATOM | 1734 | CG  | GLU | L | 17 | 94.478 | 67.572 | 32.272 | 1.00 | 145.45 | L |
| ATOM | 1735 | CD  | GLU | L | 17 | 94.646 | 68.697 | 33.286 | 1.00 | 145.45 | L |
| ATOM | 1736 | OE1 | GLU | L | 17 | 93.968 | 69.740 | 33.147 | 1.00 | 145.45 | L |
| ATOM | 1737 | OE2 | GLU | L | 17 | 95.451 | 68.535 | 34.228 | 1.00 | 145.45 | L |
| ATOM | 1738 | C   | GLU | L | 17 | 91.401 | 66.075 | 34.016 | 1.00 | 52.27  | L |
| ATOM | 1739 | O   | GLU | L | 17 | 90.862 | 64.967 | 34.039 | 1.00 | 52.27  | L |
| ATOM | 1740 | N   | ARG | L | 18 | 90.741 | 67.206 | 34.258 | 1.00 | 64.28  | L |
| ATOM | 1741 | CA  | ARG | L | 18 | 89.307 | 67.207 | 34.514 | 1.00 | 64.28  | L |
| ATOM | 1742 | CB  | ARG | L | 18 | 88.965 | 68.073 | 35.722 | 1.00 | 76.65  | L |
| ATOM | 1743 | CG  | ARG | L | 18 | 89.552 | 69.462 | 35.658 | 1.00 | 76.65  | L |
| ATOM | 1744 | CD  | ARG | L | 18 | 89.244 | 70.237 | 36.927 | 1.00 | 76.65  | L |
| ATOM | 1745 | NE  | ARG | L | 18 | 87.958 | 70.924 | 36.867 | 1.00 | 76.65  | L |
| ATOM | 1746 | CZ  | ARG | L | 18 | 87.394 | 71.536 | 37.903 | 1.00 | 76.65  | L |
| ATOM | 1747 | NH1 | ARG | L | 18 | 87.998 | 71.539 | 39.088 | 1.00 | 76.65  | L |
| ATOM | 1748 | NH2 | ARG | L | 18 | 86.236 | 72.166 | 37.749 | 1.00 | 76.65  | L |
| ATOM | 1749 | C   | ARG | L | 18 | 88.601 | 67.740 | 33.284 | 1.00 | 64.28  | L |
| ATOM | 1750 | O   | ARG | L | 18 | 88.793 | 68.886 | 32.884 | 1.00 | 64.28  | L |
| ATOM | 1751 | N   | VAL | L | 19 | 87.796 | 66.879 | 32.679 | 1.00 | 79.97  | L |
| ATOM | 1752 | CA  | VAL | L | 19 | 87.046 | 67.208 | 31.480 | 1.00 | 79.97  | L |
| ATOM | 1753 | CB  | VAL | L | 19 | 86.988 | 65.970 | 30.551 | 1.00 | 77.26  | L |
| ATOM | 1754 | CG1 | VAL | L | 19 | 86.773 | 64.724 | 31.383 | 1.00 | 77.26  | L |
| ATOM | 1755 | CG2 | VAL | L | 19 | 85.867 | 66.104 | 29.540 | 1.00 | 77.26  | L |
| ATOM | 1756 | C   | VAL | L | 19 | 85.641 | 67.625 | 31.893 | 1.00 | 79.97  | L |
| ATOM | 1757 | O   | VAL | L | 19 | 85.199 | 67.289 | 32.992 | 1.00 | 79.97  | L |
| ATOM | 1758 | N   | THR | L | 20 | 84.938 | 68.350 | 31.024 | 1.00 | 115.14 | L |
| ATOM | 1759 | CA  | THR | L | 20 | 83.586 | 68.785 | 31.351 | 1.00 | 115.14 | L |
| ATOM | 1760 | CB  | THR | L | 20 | 83.620 | 70.032 | 32.226 | 1.00 | 30.28  | L |
| ATOM | 1761 | OG1 | THR | L | 20 | 84.242 | 69.709 | 33.471 | 1.00 | 30.28  | L |
| ATOM | 1762 | CG2 | THR | L | 20 | 82.205 | 70.545 | 32.493 | 1.00 | 30.28  | L |

TABLE 2-continued

Atomic coordinates of b2 adrenoreceptor

| ATOM | 1763 | C   | THR | L | 20 | 82.653 | 69.085 | 30.188 | 1.00 | 115.14 | L |
|------|------|-----|-----|---|----|--------|--------|--------|------|--------|---|
| ATOM | 1764 | O   | THR | L | 20 | 82.972 | 69.895 | 29.319 | 1.00 | 115.14 | L |
| ATOM | 1765 | N   | ILE | L | 21 | 81.493 | 68.432 | 30.185 | 1.00 | 36.42  | L |
| ATOM | 1766 | CA  | ILE | L | 21 | 80.495 | 68.675 | 29.155 | 1.00 | 36.42  | L |
| ATOM | 1767 | CB  | ILE | L | 21 | 79.987 | 67.347 | 28.534 | 1.00 | 53.75  | L |
| ATOM | 1768 | CG2 | ILE | L | 21 | 81.167 | 66.438 | 28.233 | 1.00 | 53.75  | L |
| ATOM | 1769 | CG1 | ILE | L | 21 | 79.044 | 66.622 | 29.493 | 1.00 | 53.75  | L |
| ATOM | 1770 | CD1 | ILE | L | 21 | 78.508 | 65.312 | 28.943 | 1.00 | 53.75  | L |
| ATOM | 1771 | C   | ILE | L | 21 | 79.350 | 69.445 | 29.845 | 1.00 | 36.42  | L |
| ATOM | 1772 | O   | ILE | L | 21 | 79.047 | 69.215 | 31.025 | 1.00 | 36.42  | L |
| ATOM | 1773 | N   | THR | L | 22 | 78.737 | 70.369 | 29.111 | 1.00 | 48.73  | L |
| ATOM | 1774 | CA  | THR | L | 22 | 77.663 | 71.197 | 29.648 | 1.00 | 48.73  | L |
| ATOM | 1775 | CB  | THR | L | 22 | 78.132 | 72.674 | 29.696 | 1.00 | 58.47  | L |
| ATOM | 1776 | OG1 | THR | L | 22 | 77.076 | 73.507 | 30.186 | 1.00 | 58.47  | L |
| ATOM | 1777 | CG2 | THR | L | 22 | 78.553 | 73.143 | 28.314 | 1.00 | 58.47  | L |
| ATOM | 1778 | C   | THR | L | 22 | 76.363 | 71.076 | 28.837 | 1.00 | 48.73  | L |
| ATOM | 1779 | O   | THR | L | 22 | 76.370 | 71.235 | 27.612 | 1.00 | 48.73  | L |
| ATOM | 1780 | N   | CYS | L | 23 | 75.255 | 70.820 | 29.537 | 1.00 | 67.88  | L |
| ATOM | 1781 | CA  | CYS | L | 23 | 73.918 | 70.637 | 28.938 | 1.00 | 67.88  | L |
| ATOM | 1782 | C   | CYS | L | 23 | 72.937 | 71.778 | 29.290 | 1.00 | 67.88  | L |
| ATOM | 1783 | O   | CYS | L | 23 | 72.758 | 72.084 | 30.468 | 1.00 | 67.88  | L |
| ATOM | 1784 | CB  | CYS | L | 23 | 73.368 | 69.297 | 29.449 | 1.00 | 61.55  | L |
| ATOM | 1785 | SG  | CYS | L | 23 | 71.711 | 68.698 | 28.961 | 1.00 | 61.55  | L |
| ATOM | 1786 | N   | LYS | L | 24 | 72.303 | 72.400 | 28.286 | 1.00 | 47.09  | L |
| ATOM | 1787 | CA  | LYS | L | 24 | 71.346 | 73.494 | 28.536 | 1.00 | 47.09  | L |
| ATOM | 1788 | CB  | LYS | L | 24 | 71.961 | 74.850 | 28.170 | 1.00 | 110.22 | L |
| ATOM | 1789 | CG  | LYS | L | 24 | 73.160 | 75.230 | 29.022 | 1.00 | 110.22 | L |
| ATOM | 1790 | CD  | LYS | L | 24 | 73.538 | 76.700 | 28.869 | 1.00 | 110.22 | L |
| ATOM | 1791 | CE  | LYS | L | 24 | 74.744 | 77.058 | 29.734 | 1.00 | 110.22 | L |
| ATOM | 1792 | NZ  | LYS | L | 24 | 75.175 | 78.470 | 29.536 | 1.00 | 110.22 | L |
| ATOM | 1793 | C   | LYS | L | 24 | 70.020 | 73.319 | 27.793 | 1.00 | 47.09  | L |
| ATOM | 1794 | O   | LYS | L | 24 | 69.953 | 73.467 | 26.572 | 1.00 | 47.09  | L |
| ATOM | 1795 | N   | ALA | L | 25 | 68.958 | 73.027 | 28.543 | 1.00 | 48.53  | L |
| ATOM | 1796 | CA  | ALA | L | 25 | 67.634 | 72.795 | 27.965 | 1.00 | 48.53  | L |
| ATOM | 1797 | CB  | ALA | L | 25 | 66.786 | 71.979 | 28.919 | 1.00 | 32.95  | L |
| ATOM | 1798 | C   | ALA | L | 25 | 66.879 | 74.044 | 27.584 | 1.00 | 48.53  | L |
| ATOM | 1799 | O   | ALA | L | 25 | 67.246 | 75.147 | 27.964 | 1.00 | 48.53  | L |
| ATOM | 1800 | N   | SER | L | 26 | 65.794 | 73.849 | 26.848 | 1.00 | 47.12  | L |
| ATOM | 1801 | CA  | SER | L | 26 | 64.955 | 74.952 | 26.398 | 1.00 | 47.12  | L |
| ATOM | 1802 | CB  | SER | L | 26 | 64.070 | 74.489 | 25.232 | 1.00 | 59.20  | L |
| ATOM | 1803 | OG  | SER | L | 26 | 63.366 | 73.306 | 25.555 | 1.00 | 59.20  | L |
| ATOM | 1804 | C   | SER | L | 26 | 64.084 | 75.544 | 27.502 | 1.00 | 47.12  | L |
| ATOM | 1805 | O   | SER | L | 26 | 64.024 | 76.754 | 27.663 | 1.00 | 47.12  | L |
| ATOM | 1806 | N   | GLN | L | 27 | 63.418 | 74.677 | 28.255 | 1.00 | 52.18  | L |
| ATOM | 1807 | CA  | GLN | L | 27 | 62.526 | 75.072 | 29.345 | 1.00 | 52.18  | L |
| ATOM | 1808 | CB  | GLN | L | 27 | 61.488 | 73.971 | 29.585 | 1.00 | 99.76  | L |
| ATOM | 1809 | CG  | GLN | L | 27 | 60.061 | 74.414 | 29.463 | 1.00 | 99.76  | L |
| ATOM | 1810 | CD  | GLN | L | 27 | 59.657 | 74.609 | 28.023 | 1.00 | 99.76  | L |
| ATOM | 1811 | OE1 | GLN | L | 27 | 60.494 | 74.564 | 27.114 | 1.00 | 99.76  | L |
| ATOM | 1812 | NE2 | GLN | L | 27 | 58.365 | 74.827 | 27.799 | 1.00 | 99.76  | L |
| ATOM | 1813 | C   | GLN | L | 27 | 63.245 | 75.312 | 30.670 | 1.00 | 52.18  | L |
| ATOM | 1814 | O   | GLN | L | 27 | 64.311 | 75.928 | 30.755 | 1.00 | 52.18  | L |
| ATOM | 1815 | N   | ASP | L | 28 | 62.602 | 74.807 | 31.711 | 1.00 | 56.74  | L |
| ATOM | 1816 | CA  | ASP | L | 28 | 63.103 | 74.878 | 33.060 | 1.00 | 56.74  | L |
| ATOM | 1817 | CB  | ASP | L | 28 | 62.475 | 76.040 | 33.823 | 1.00 | 128.63 | L |
| ATOM | 1818 | CG  | ASP | L | 28 | 62.751 | 75.972 | 35.316 | 1.00 | 128.63 | L |
| ATOM | 1819 | OD1 | ASP | L | 28 | 62.251 | 76.850 | 36.048 | 1.00 | 128.63 | L |
| ATOM | 1820 | OD2 | ASP | L | 28 | 63.462 | 75.042 | 35.762 | 1.00 | 128.63 | L |
| ATOM | 1821 | C   | ASP | L | 28 | 62.713 | 73.568 | 33.713 | 1.00 | 56.74  | L |
| ATOM | 1822 | O   | ASP | L | 28 | 61.625 | 73.428 | 34.279 | 1.00 | 56.74  | L |
| ATOM | 1823 | N   | ILE | L | 29 | 63.596 | 72.591 | 33.581 | 1.00 | 86.66  | L |
| ATOM | 1824 | CA  | ILE | L | 29 | 63.385 | 71.297 | 34.192 | 1.00 | 86.66  | L |
| ATOM | 1825 | CB  | ILE | L | 29 | 64.213 | 70.215 | 33.475 | 1.00 | 49.12  | L |
| ATOM | 1826 | CG2 | ILE | L | 29 | 63.634 | 69.977 | 32.088 | 1.00 | 49.12  | L |
| ATOM | 1827 | CG1 | ILE | L | 29 | 65.681 | 70.658 | 33.357 | 1.00 | 49.12  | L |
| ATOM | 1828 | CD1 | ILE | L | 29 | 66.635 | 69.587 | 32.836 | 1.00 | 49.12  | L |
| ATOM | 1829 | C   | ILE | L | 29 | 63.890 | 71.522 | 35.608 | 1.00 | 86.66  | L |
| ATOM | 1830 | O   | ILE | L | 29 | 64.944 | 72.113 | 35.807 | 1.00 | 86.66  | L |
| ATOM | 1831 | N   | ASN | L | 30 | 63.131 | 71.088 | 36.597 | 1.00 | 63.90  | L |
| ATOM | 1832 | CA  | ASN | L | 30 | 63.550 | 71.299 | 37.969 | 1.00 | 63.90  | L |
| ATOM | 1833 | CB  | ASN | L | 30 | 62.341 | 71.177 | 38.897 | 1.00 | 118.34 | L |
| ATOM | 1834 | CG  | ASN | L | 30 | 61.219 | 72.130 | 38.517 | 1.00 | 118.34 | L |
| ATOM | 1835 | OD1 | ASN | L | 30 | 60.115 | 72.057 | 39.061 | 1.00 | 118.34 | L |
| ATOM | 1836 | ND2 | ASN | L | 30 | 61.499 | 73.033 | 37.580 | 1.00 | 118.34 | L |
| ATOM | 1837 | C   | ASN | L | 30 | 64.629 | 70.290 | 38.342 | 1.00 | 63.90  | L |
| ATOM | 1838 | O   | ASN | L | 30 | 64.373 | 69.316 | 39.052 | 1.00 | 63.90  | L |
| ATOM | 1839 | N   | SER | L | 31 | 65.844 | 70.529 | 37.864 | 1.00 | 77.98  | L |
| ATOM | 1840 | CA  | SER | L | 31 | 66.952 | 69.624 | 38.138 | 1.00 | 77.98  | L |

TABLE 2-continued

Atomic coordinates of b2 adrenoreceptor

| ATOM | 1841 | CB | SER | L | 31 | 67.380 | 69.735 | 39.600 | 1.00 | 207.88 | L |
|---|---|---|---|---|---|---|---|---|---|---|---|
| ATOM | 1842 | OG | SER | L | 31 | 67.954 | 71.005 | 39.852 | 1.00 | 207.88 | L |
| ATOM | 1843 | C | SER | L | 31 | 66.560 | 68.181 | 37.806 | 1.00 | 77.98 | L |
| ATOM | 1844 | O | SER | L | 31 | 67.200 | 67.226 | 38.263 | 1.00 | 77.98 | L |
| ATOM | 1845 | N | TYR | L | 32 | 65.495 | 68.042 | 37.013 | 1.00 | 73.58 | L |
| ATOM | 1846 | CA | TYR | L | 32 | 64.999 | 66.743 | 36.566 | 1.00 | 73.58 | L |
| ATOM | 1847 | CB | TYR | L | 32 | 63.494 | 66.828 | 36.309 | 1.00 | 84.05 | L |
| ATOM | 1848 | CG | TYR | L | 32 | 62.647 | 66.635 | 37.556 | 1.00 | 84.05 | L |
| ATOM | 1849 | CD1 | TYR | L | 32 | 61.294 | 67.002 | 37.571 | 1.00 | 84.05 | L |
| ATOM | 1850 | CE1 | TYR | L | 32 | 60.486 | 66.771 | 38.698 | 1.00 | 84.05 | L |
| ATOM | 1851 | CD2 | TYR | L | 32 | 63.177 | 66.036 | 38.705 | 1.00 | 84.05 | L |
| ATOM | 1852 | CE2 | TYR | L | 32 | 62.380 | 65.799 | 39.837 | 1.00 | 84.05 | L |
| ATOM | 1853 | CZ | TYR | L | 32 | 61.036 | 66.167 | 39.823 | 1.00 | 84.05 | L |
| ATOM | 1854 | OH | TYR | L | 32 | 60.239 | 65.911 | 40.916 | 1.00 | 84.05 | L |
| ATOM | 1855 | C | TYR | L | 32 | 65.759 | 66.326 | 35.298 | 1.00 | 73.58 | L |
| ATOM | 1856 | O | TYR | L | 32 | 65.171 | 66.057 | 34.242 | 1.00 | 73.58 | L |
| ATOM | 1857 | N | LEU | L | 33 | 67.085 | 66.293 | 35.440 | 1.00 | 55.73 | L |
| ATOM | 1858 | CA | LEU | L | 33 | 68.016 | 65.928 | 34.376 | 1.00 | 55.73 | L |
| ATOM | 1859 | CB | LEU | L | 33 | 68.888 | 67.146 | 33.997 | 1.00 | 38.82 | L |
| ATOM | 1860 | CG | LEU | L | 33 | 70.184 | 66.927 | 33.192 | 1.00 | 38.82 | L |
| ATOM | 1861 | CD1 | LEU | L | 33 | 70.566 | 68.178 | 32.420 | 1.00 | 38.82 | L |
| ATOM | 1862 | CD2 | LEU | L | 33 | 71.307 | 66.517 | 34.143 | 1.00 | 38.82 | L |
| ATOM | 1863 | C | LEU | L | 33 | 68.897 | 64.752 | 34.822 | 1.00 | 55.73 | L |
| ATOM | 1864 | O | LEU | L | 33 | 69.113 | 64.544 | 36.018 | 1.00 | 55.73 | L |
| ATOM | 1865 | N | SER | L | 34 | 69.398 | 63.995 | 33.846 | 1.00 | 40.55 | L |
| ATOM | 1866 | CA | SER | L | 34 | 70.236 | 62.830 | 34.099 | 1.00 | 40.55 | L |
| ATOM | 1867 | CB | SER | L | 34 | 69.373 | 61.570 | 33.998 | 1.00 | 55.22 | L |
| ATOM | 1868 | OG | SER | L | 34 | 70.120 | 60.408 | 34.296 | 1.00 | 55.22 | L |
| ATOM | 1869 | C | SER | L | 34 | 71.424 | 62.746 | 33.119 | 1.00 | 40.55 | L |
| ATOM | 1870 | O | SER | L | 34 | 71.390 | 63.317 | 32.031 | 1.00 | 40.55 | L |
| ATOM | 1871 | N | TRP | L | 35 | 72.474 | 62.034 | 33.510 | 1.00 | 37.18 | L |
| ATOM | 1872 | CA | TRP | L | 35 | 73.654 | 61.895 | 32.667 | 1.00 | 37.18 | L |
| ATOM | 1873 | CB | TRP | L | 35 | 74.870 | 62.605 | 33.282 | 1.00 | 70.10 | L |
| ATOM | 1874 | CG | TRP | L | 35 | 74.797 | 64.097 | 33.345 | 1.00 | 70.10 | L |
| ATOM | 1875 | CD2 | TRP | L | 35 | 75.091 | 65.014 | 32.287 | 1.00 | 70.10 | L |
| ATOM | 1876 | CE2 | TRP | L | 35 | 74.914 | 66.316 | 32.801 | 1.00 | 70.10 | L |
| ATOM | 1877 | CE3 | TRP | L | 35 | 75.488 | 64.861 | 30.953 | 1.00 | 70.10 | L |
| ATOM | 1878 | CD1 | TRP | L | 35 | 74.460 | 64.858 | 34.427 | 1.00 | 70.10 | L |
| ATOM | 1879 | NE1 | TRP | L | 35 | 74.529 | 66.195 | 34.109 | 1.00 | 70.10 | L |
| ATOM | 1880 | CZ2 | TRP | L | 35 | 75.121 | 67.460 | 32.024 | 1.00 | 70.10 | L |
| ATOM | 1881 | CZ3 | TRP | L | 35 | 75.693 | 65.997 | 30.182 | 1.00 | 70.10 | L |
| ATOM | 1882 | CH2 | TRP | L | 35 | 75.510 | 67.279 | 30.720 | 1.00 | 70.10 | L |
| ATOM | 1883 | C | TRP | L | 35 | 74.028 | 60.436 | 32.514 | 1.00 | 37.18 | L |
| ATOM | 1884 | O | TRP | L | 35 | 74.199 | 59.739 | 33.518 | 1.00 | 37.18 | L |
| ATOM | 1885 | N | PHE | L | 36 | 74.165 | 59.972 | 31.272 | 1.00 | 44.91 | L |
| ATOM | 1886 | CA | PHE | L | 36 | 74.578 | 58.593 | 31.036 | 1.00 | 44.91 | L |
| ATOM | 1887 | CB | PHE | L | 36 | 73.371 | 57.705 | 30.688 | 1.00 | 47.06 | L |
| ATOM | 1888 | CG | PHE | L | 36 | 72.691 | 58.040 | 29.390 | 1.00 | 47.06 | L |
| ATOM | 1889 | CD1 | PHE | L | 36 | 73.204 | 57.589 | 28.180 | 1.00 | 47.06 | L |
| ATOM | 1890 | CD2 | PHE | L | 36 | 71.488 | 58.733 | 29.385 | 1.00 | 47.06 | L |
| ATOM | 1891 | CE1 | PHE | L | 36 | 72.523 | 57.816 | 26.991 | 1.00 | 47.06 | L |
| ATOM | 1892 | CE2 | PHE | L | 36 | 70.803 | 58.963 | 28.202 | 1.00 | 47.06 | L |
| ATOM | 1893 | CZ | PHE | L | 36 | 71.321 | 58.503 | 27.007 | 1.00 | 47.06 | L |
| ATOM | 1894 | C | PHE | L | 36 | 75.693 | 58.480 | 29.989 | 1.00 | 44.91 | L |
| ATOM | 1895 | O | PHE | L | 36 | 76.005 | 59.443 | 29.282 | 1.00 | 44.91 | L |
| ATOM | 1896 | N | GLN | L | 37 | 76.309 | 57.303 | 29.917 | 1.00 | 45.79 | L |
| ATOM | 1897 | CA | GLN | L | 37 | 77.411 | 57.064 | 28.996 | 1.00 | 45.79 | L |
| ATOM | 1898 | CB | GLN | L | 37 | 78.696 | 56.855 | 29.798 | 1.00 | 89.21 | L |
| ATOM | 1899 | CG | GLN | L | 37 | 79.598 | 55.744 | 29.282 | 1.00 | 89.21 | L |
| ATOM | 1900 | CD | GLN | L | 37 | 80.576 | 55.271 | 30.339 | 1.00 | 89.21 | L |
| ATOM | 1901 | OE1 | GLN | L | 37 | 80.262 | 55.277 | 31.524 | 1.00 | 89.21 | L |
| ATOM | 1902 | NE2 | GLN | L | 37 | 81.765 | 54.852 | 29.915 | 1.00 | 89.21 | L |
| ATOM | 1903 | C | GLN | L | 37 | 77.180 | 55.873 | 28.067 | 1.00 | 45.79 | L |
| ATOM | 1904 | O | GLN | L | 37 | 76.903 | 54.760 | 28.512 | 1.00 | 45.79 | L |
| ATOM | 1905 | N | GLN | L | 38 | 77.299 | 56.136 | 26.769 | 1.00 | 28.43 | L |
| ATOM | 1906 | CA | GLN | L | 38 | 77.147 | 55.128 | 25.730 | 1.00 | 28.43 | L |
| ATOM | 1907 | CB | GLN | L | 38 | 76.436 | 55.713 | 24.503 | 1.00 | 53.29 | L |
| ATOM | 1908 | CG | GLN | L | 38 | 75.025 | 55.187 | 24.249 | 1.00 | 53.29 | L |
| ATOM | 1909 | CD | GLN | L | 38 | 74.984 | 53.846 | 23.531 | 1.00 | 53.29 | L |
| ATOM | 1910 | OE1 | GLN | L | 38 | 75.763 | 52.955 | 23.832 | 1.00 | 53.29 | L |
| ATOM | 1911 | NE2 | GLN | L | 38 | 74.074 | 53.707 | 22.567 | 1.00 | 53.29 | L |
| ATOM | 1912 | C | GLN | L | 38 | 78.556 | 54.738 | 25.340 | 1.00 | 28.43 | L |
| ATOM | 1913 | O | GLN | L | 38 | 79.363 | 55.589 | 24.945 | 1.00 | 28.43 | L |
| ATOM | 1914 | N | LYS | L | 39 | 78.864 | 53.458 | 25.485 | 1.00 | 87.21 | L |
| ATOM | 1915 | CA | LYS | L | 39 | 80.173 | 52.955 | 25.115 | 1.00 | 87.21 | L |
| ATOM | 1916 | CB | LYS | L | 39 | 80.784 | 52.146 | 26.246 | 1.00 | 31.98 | L |
| ATOM | 1917 | CG | LYS | L | 39 | 82.023 | 52.779 | 26.856 | 1.00 | 31.98 | L |
| ATOM | 1918 | CD | LYS | L | 39 | 82.452 | 52.008 | 28.105 | 1.00 | 31.98 | L |

TABLE 2-continued

Atomic coordinates of b2 adrenoreceptor

| ATOM | 1919 | CE  | LYS | L | 39 | 83.677 | 52.605 | 28.787 | 1.00 | 31.98  | L |
|------|------|-----|-----|---|----|--------|--------|--------|------|--------|---|
| ATOM | 1920 | NZ  | LYS | L | 39 | 84.894 | 52.535 | 27.931 | 1.00 | 31.98  | L |
| ATOM | 1921 | C   | LYS | L | 39 | 79.944 | 52.059 | 23.924 | 1.00 | 87.21  | L |
| ATOM | 1922 | O   | LYS | L | 39 | 78.976 | 51.308 | 23.884 | 1.00 | 87.21  | L |
| ATOM | 1923 | N   | PRO | L | 40 | 80.836 | 52.116 | 22.937 | 1.00 | 47.59  | L |
| ATOM | 1924 | CD  | PRO | L | 40 | 82.214 | 52.627 | 23.021 | 1.00 | 48.65  | L |
| ATOM | 1925 | CA  | PRO | L | 40 | 80.668 | 51.274 | 21.753 | 1.00 | 47.59  | L |
| ATOM | 1926 | CB  | PRO | L | 40 | 81.949 | 51.532 | 20.974 | 1.00 | 48.65  | L |
| ATOM | 1927 | CG  | PRO | L | 40 | 82.950 | 51.702 | 22.071 | 1.00 | 48.65  | L |
| ATOM | 1928 | C   | PRO | L | 40 | 80.510 | 49.810 | 22.139 | 1.00 | 47.59  | L |
| ATOM | 1929 | O   | PRO | L | 40 | 81.272 | 49.294 | 22.964 | 1.00 | 47.59  | L |
| ATOM | 1930 | N   | GLY | L | 41 | 79.510 | 49.158 | 21.551 | 1.00 | 171.32 | L |
| ATOM | 1931 | CA  | GLY | L | 41 | 79.263 | 47.752 | 21.823 | 1.00 | 171.32 | L |
| ATOM | 1932 | C   | GLY | L | 41 | 78.640 | 47.442 | 23.172 | 1.00 | 171.32 | L |
| ATOM | 1933 | O   | GLY | L | 41 | 78.752 | 46.317 | 23.663 | 1.00 | 171.32 | L |
| ATOM | 1934 | N   | LYS | L | 42 | 77.982 | 48.427 | 23.775 | 1.00 | 185.83 | L |
| ATOM | 1935 | CA  | LYS | L | 42 | 77.350 | 48.227 | 25.073 | 1.00 | 185.83 | L |
| ATOM | 1936 | CB  | LYS | L | 42 | 78.320 | 48.574 | 26.202 | 1.00 | 148.24 | L |
| ATOM | 1937 | CG  | LYS | L | 42 | 79.670 | 47.893 | 26.119 | 1.00 | 148.24 | L |
| ATOM | 1938 | CD  | LYS | L | 42 | 80.607 | 48.457 | 27.175 | 1.00 | 148.24 | L |
| ATOM | 1939 | CE  | LYS | L | 42 | 82.043 | 48.012 | 26.952 | 1.00 | 148.24 | L |
| ATOM | 1940 | NZ  | LYS | L | 42 | 82.956 | 48.557 | 27.997 | 1.00 | 148.24 | L |
| ATOM | 1941 | C   | LYS | L | 42 | 76.104 | 49.083 | 25.232 | 1.00 | 185.83 | L |
| ATOM | 1942 | O   | LYS | L | 42 | 75.878 | 50.029 | 24.480 | 1.00 | 185.83 | L |
| ATOM | 1943 | N   | SER | L | 43 | 75.298 | 48.732 | 26.225 | 1.00 | 49.22  | L |
| ATOM | 1944 | CA  | SER | L | 43 | 74.081 | 49.460 | 26.537 | 1.00 | 49.22  | L |
| ATOM | 1945 | CB  | SER | L | 43 | 73.070 | 48.536 | 27.221 | 1.00 | 185.96 | L |
| ATOM | 1946 | OG  | SER | L | 43 | 73.644 | 47.902 | 28.350 | 1.00 | 185.96 | L |
| ATOM | 1947 | C   | SER | L | 43 | 74.489 | 50.592 | 27.472 | 1.00 | 49.22  | L |
| ATOM | 1948 | O   | SER | L | 43 | 75.398 | 50.441 | 28.295 | 1.00 | 49.22  | L |
| ATOM | 1949 | N   | PRO | L | 44 | 73.818 | 51.744 | 27.366 | 1.00 | 46.55  | L |
| ATOM | 1950 | CD  | PRO | L | 44 | 72.700 | 52.038 | 26.454 | 1.00 | 28.48  | L |
| ATOM | 1951 | CA  | PRO | L | 44 | 74.141 | 52.898 | 28.211 | 1.00 | 46.55  | L |
| ATOM | 1952 | CB  | PRO | L | 44 | 73.157 | 53.974 | 27.731 | 1.00 | 28.48  | L |
| ATOM | 1953 | CG  | PRO | L | 44 | 72.039 | 53.199 | 27.120 | 1.00 | 28.48  | L |
| ATOM | 1954 | C   | PRO | L | 44 | 74.110 | 52.686 | 29.720 | 1.00 | 46.55  | L |
| ATOM | 1955 | O   | PRO | L | 44 | 73.179 | 52.110 | 30.272 | 1.00 | 46.55  | L |
| ATOM | 1956 | N   | LYS | L | 45 | 75.157 | 53.157 | 30.380 | 1.00 | 34.34  | L |
| ATOM | 1957 | CA  | LYS | L | 45 | 75.259 | 53.040 | 31.820 | 1.00 | 34.34  | L |
| ATOM | 1958 | CB  | LYS | L | 45 | 76.648 | 52.525 | 32.184 | 1.00 | 92.14  | L |
| ATOM | 1959 | CG  | LYS | L | 45 | 76.883 | 52.339 | 33.664 | 1.00 | 92.14  | L |
| ATOM | 1960 | CD  | LYS | L | 45 | 78.369 | 52.158 | 33.932 | 1.00 | 92.14  | L |
| ATOM | 1961 | CE  | LYS | L | 45 | 78.698 | 52.309 | 35.408 | 1.00 | 92.14  | L |
| ATOM | 1962 | NZ  | LYS | L | 45 | 80.170 | 52.420 | 35.630 | 1.00 | 92.14  | L |
| ATOM | 1963 | C   | LYS | L | 45 | 75.018 | 54.439 | 32.404 | 1.00 | 34.34  | L |
| ATOM | 1964 | O   | LYS | L | 45 | 75.788 | 55.366 | 32.144 | 1.00 | 34.34  | L |
| ATOM | 1965 | N   | THR | L | 46 | 73.941 | 54.591 | 33.176 | 1.00 | 28.28  | L |
| ATOM | 1966 | CA  | THR | L | 46 | 73.590 | 55.878 | 33.786 | 1.00 | 28.28  | L |
| ATOM | 1967 | CB  | THR | L | 46 | 72.141 | 55.860 | 34.285 | 1.00 | 27.20  | L |
| ATOM | 1968 | OG1 | THR | L | 46 | 71.254 | 55.872 | 33.166 | 1.00 | 27.20  | L |
| ATOM | 1969 | CG2 | THR | L | 46 | 71.862 | 57.061 | 35.156 | 1.00 | 27.20  | L |
| ATOM | 1970 | C   | THR | L | 46 | 74.489 | 56.256 | 34.959 | 1.00 | 28.28  | L |
| ATOM | 1971 | O   | THR | L | 46 | 74.752 | 55.429 | 35.830 | 1.00 | 28.28  | L |
| ATOM | 1972 | N   | LEU | L | 47 | 74.944 | 57.506 | 34.993 | 1.00 | 33.78  | L |
| ATOM | 1973 | CA  | LEU | L | 47 | 75.819 | 57.957 | 36.076 | 1.00 | 33.78  | L |
| ATOM | 1974 | CB  | LEU | L | 47 | 77.041 | 58.736 | 35.557 | 1.00 | 29.08  | L |
| ATOM | 1975 | CG  | LEU | L | 47 | 77.798 | 58.445 | 34.254 | 1.00 | 29.08  | L |
| ATOM | 1976 | CD1 | LEU | L | 47 | 77.808 | 56.939 | 33.932 | 1.00 | 29.08  | L |
| ATOM | 1977 | CD2 | LEU | L | 47 | 77.136 | 59.256 | 33.148 | 1.00 | 29.08  | L |
| ATOM | 1978 | C   | LEU | L | 47 | 75.123 | 58.860 | 37.069 | 1.00 | 33.78  | L |
| ATOM | 1979 | O   | LEU | L | 47 | 75.276 | 58.693 | 38.269 | 1.00 | 33.78  | L |
| ATOM | 1980 | N   | ILE | L | 48 | 74.373 | 59.833 | 36.572 | 1.00 | 66.39  | L |
| ATOM | 1981 | CA  | ILE | L | 48 | 73.705 | 60.764 | 37.465 | 1.00 | 66.39  | L |
| ATOM | 1982 | CB  | ILE | L | 48 | 74.523 | 62.055 | 37.601 | 1.00 | 90.55  | L |
| ATOM | 1983 | CG2 | ILE | L | 48 | 73.838 | 63.019 | 38.548 | 1.00 | 90.55  | L |
| ATOM | 1984 | CG1 | ILE | L | 48 | 75.906 | 61.730 | 38.138 | 1.00 | 90.55  | L |
| ATOM | 1985 | CD1 | ILE | L | 48 | 76.759 | 62.955 | 38.344 | 1.00 | 90.55  | L |
| ATOM | 1986 | C   | ILE | L | 48 | 72.298 | 61.162 | 37.056 | 1.00 | 66.39  | L |
| ATOM | 1987 | O   | ILE | L | 48 | 71.958 | 61.166 | 35.877 | 1.00 | 66.39  | L |
| ATOM | 1988 | N   | TYR | L | 49 | 71.491 | 61.506 | 38.056 | 1.00 | 50.97  | L |
| ATOM | 1989 | CA  | TYR | L | 49 | 70.119 | 61.955 | 37.856 | 1.00 | 50.97  | L |
| ATOM | 1990 | CB  | TYR | L | 49 | 69.135 | 60.802 | 38.071 | 1.00 | 49.04  | L |
| ATOM | 1991 | CG  | TYR | L | 49 | 68.994 | 60.375 | 39.501 | 1.00 | 49.04  | L |
| ATOM | 1992 | CD1 | TYR | L | 49 | 68.106 | 61.015 | 40.342 | 1.00 | 49.04  | L |
| ATOM | 1993 | CE1 | TYR | L | 49 | 67.998 | 60.649 | 41.676 | 1.00 | 49.04  | L |
| ATOM | 1994 | CD2 | TYR | L | 49 | 69.775 | 59.350 | 40.019 | 1.00 | 49.04  | L |
| ATOM | 1995 | CE2 | TYR | L | 49 | 69.679 | 58.973 | 41.352 | 1.00 | 49.04  | L |
| ATOM | 1996 | CZ  | TYR | L | 49 | 68.786 | 59.628 | 42.180 | 1.00 | 49.04  | L |

TABLE 2-continued

Atomic coordinates of b2 adrenoreceptor

| ATOM | 1997 | OH | TYR | L | 49 | 68.673 | 59.275 | 43.513 | 1.00 | 49.04 | L |
| ATOM | 1998 | C | TYR | L | 49 | 69.877 | 63.084 | 38.860 | 1.00 | 50.97 | L |
| ATOM | 1999 | O | TYR | L | 49 | 70.774 | 63.422 | 39.640 | 1.00 | 50.97 | L |
| ATOM | 2000 | N | ARG | L | 50 | 68.675 | 63.658 | 38.856 | 1.00 | 44.13 | L |
| ATOM | 2001 | CA | ARG | L | 50 | 68.390 | 64.777 | 39.748 | 1.00 | 44.13 | L |
| ATOM | 2002 | CB | ARG | L | 50 | 68.247 | 64.314 | 41.198 | 1.00 | 110.84 | L |
| ATOM | 2003 | CG | ARG | L | 50 | 67.229 | 65.115 | 42.020 | 1.00 | 110.84 | L |
| ATOM | 2004 | CD | ARG | L | 50 | 67.484 | 66.634 | 42.046 | 1.00 | 110.84 | L |
| ATOM | 2005 | NE | ARG | L | 50 | 68.610 | 67.038 | 42.893 | 1.00 | 110.84 | L |
| ATOM | 2006 | CZ | ARG | L | 50 | 68.743 | 68.250 | 43.430 | 1.00 | 110.84 | L |
| ATOM | 2007 | NH1 | ARG | L | 50 | 67.819 | 69.176 | 43.214 | 1.00 | 110.84 | L |
| ATOM | 2008 | NH2 | ARG | L | 50 | 69.797 | 68.539 | 44.184 | 1.00 | 110.84 | L |
| ATOM | 2009 | C | ARG | L | 50 | 69.588 | 65.723 | 39.638 | 1.00 | 44.13 | L |
| ATOM | 2010 | O | ARG | L | 50 | 70.117 | 66.201 | 40.640 | 1.00 | 57.99 | L |
| ATOM | 2011 | N | ALA | L | 51 | 70.032 | 65.940 | 38.403 | 1.00 | 51.32 | L |
| ATOM | 2012 | CA | ALA | L | 51 | 71.146 | 66.830 | 38.092 | 1.00 | 51.32 | L |
| ATOM | 2013 | CB | ALA | L | 51 | 70.705 | 68.277 | 38.303 | 1.00 | 91.00 | L |
| ATOM | 2014 | C | ALA | L | 51 | 72.485 | 66.598 | 38.797 | 1.00 | 51.32 | L |
| ATOM | 2015 | O | ALA | L | 51 | 73.523 | 67.030 | 38.286 | 1.00 | 51.32 | L |
| ATOM | 2016 | N | ASN | L | 52 | 72.484 | 65.922 | 39.944 | 1.00 | 54.14 | L |
| ATOM | 2017 | CA | ASN | L | 52 | 73.737 | 65.711 | 40.679 | 1.00 | 54.14 | L |
| ATOM | 2018 | CB | ASN | L | 52 | 73.965 | 66.860 | 41.663 | 1.00 | 34.02 | L |
| ATOM | 2019 | CG | ASN | L | 52 | 72.847 | 66.974 | 42.683 | 1.00 | 34.02 | L |
| ATOM | 2020 | OD1 | ASN | L | 52 | 72.928 | 67.754 | 43.621 | 1.00 | 34.02 | L |
| ATOM | 2021 | ND2 | ASN | L | 52 | 71.792 | 66.193 | 42.495 | 1.00 | 34.02 | L |
| ATOM | 2022 | C | ASN | L | 52 | 73.837 | 64.415 | 41.470 | 1.00 | 54.14 | L |
| ATOM | 2023 | O | ASN | L | 52 | 74.937 | 64.005 | 41.853 | 1.00 | 54.14 | L |
| ATOM | 2024 | N | ARG | L | 53 | 72.696 | 63.785 | 41.730 | 1.00 | 34.48 | L |
| ATOM | 2025 | CA | ARG | L | 53 | 72.689 | 62.564 | 42.510 | 1.00 | 34.48 | L |
| ATOM | 2026 | CB | ARG | L | 53 | 71.292 | 62.326 | 43.077 | 1.00 | 114.60 | L |
| ATOM | 2027 | CG | ARG | L | 53 | 71.050 | 63.227 | 44.270 | 1.00 | 114.60 | L |
| ATOM | 2028 | CD | ARG | L | 53 | 69.636 | 63.201 | 44.802 | 1.00 | 114.60 | L |
| ATOM | 2029 | NE | ARG | L | 53 | 69.555 | 63.945 | 46.058 | 1.00 | 114.60 | L |
| ATOM | 2030 | CZ | ARG | L | 53 | 69.937 | 65.212 | 46.212 | 1.00 | 114.60 | L |
| ATOM | 2031 | NH1 | ARG | L | 53 | 70.429 | 65.897 | 45.189 | 1.00 | 114.60 | L |
| ATOM | 2032 | NH2 | ARG | L | 53 | 69.841 | 65.794 | 47.398 | 1.00 | 114.60 | L |
| ATOM | 2033 | C | ARG | L | 53 | 73.231 | 61.312 | 41.842 | 1.00 | 34.48 | L |
| ATOM | 2034 | O | ARG | L | 53 | 72.508 | 60.565 | 41.186 | 1.00 | 95.09 | L |
| ATOM | 2035 | N | LEU | L | 54 | 74.533 | 61.112 | 42.026 | 1.00 | 38.42 | L |
| ATOM | 2036 | CA | LEU | L | 54 | 75.243 | 59.956 | 41.515 | 1.00 | 38.42 | L |
| ATOM | 2037 | CB | LEU | L | 54 | 76.578 | 59.774 | 42.242 | 1.00 | 41.06 | L |
| ATOM | 2038 | CG | LEU | L | 54 | 77.843 | 60.252 | 41.536 | 1.00 | 41.06 | L |
| ATOM | 2039 | CD1 | LEU | L | 54 | 79.059 | 59.943 | 42.376 | 1.00 | 41.06 | L |
| ATOM | 2040 | CD2 | LEU | L | 54 | 77.957 | 59.575 | 40.194 | 1.00 | 41.06 | L |
| ATOM | 2041 | C | LEU | L | 54 | 74.441 | 58.690 | 41.729 | 1.00 | 38.42 | L |
| ATOM | 2042 | O | LEU | L | 54 | 73.875 | 58.465 | 42.802 | 1.00 | 38.42 | L |
| ATOM | 2043 | N | VAL | L | 55 | 74.413 | 57.856 | 40.700 | 1.00 | 45.07 | L |
| ATOM | 2044 | CA | VAL | L | 55 | 73.721 | 56.587 | 40.966 | 1.00 | 45.07 | L |
| ATOM | 2045 | CB | VAL | L | 55 | 73.572 | 55.984 | 39.362 | 1.00 | 51.74 | L |
| ATOM | 2046 | CG1 | VAL | L | 55 | 72.806 | 54.677 | 39.435 | 1.00 | 51.74 | L |
| ATOM | 2047 | CG2 | VAL | L | 55 | 72.868 | 56.988 | 38.443 | 1.00 | 51.74 | L |
| ATOM | 2048 | C | VAL | L | 55 | 74.622 | 55.708 | 41.618 | 1.00 | 45.07 | L |
| ATOM | 2049 | O | VAL | L | 55 | 75.801 | 56.025 | 41.798 | 1.00 | 45.07 | L |
| ATOM | 2050 | N | ASP | L | 56 | 74.061 | 54.626 | 42.152 | 1.00 | 87.21 | L |
| ATOM | 2051 | CA | ASP | L | 56 | 74.805 | 53.691 | 42.995 | 1.00 | 87.21 | L |
| ATOM | 2052 | CB | ASP | L | 56 | 73.831 | 52.779 | 43.742 | 1.00 | 204.14 | L |
| ATOM | 2053 | CG | ASP | L | 56 | 72.882 | 52.058 | 42.808 | 1.00 | 204.14 | L |
| ATOM | 2054 | OD1 | ASP | L | 56 | 72.129 | 52.742 | 42.082 | 1.00 | 204.14 | L |
| ATOM | 2055 | OD2 | ASP | L | 56 | 72.889 | 50.809 | 42.797 | 1.00 | 204.14 | L |
| ATOM | 2056 | C | ASP | L | 56 | 75.769 | 52.843 | 42.167 | 1.00 | 87.21 | L |
| ATOM | 2057 | O | ASP | L | 56 | 75.343 | 52.078 | 41.301 | 1.00 | 87.21 | L |
| ATOM | 2058 | N | GLY | L | 57 | 77.065 | 52.988 | 42.437 | 1.00 | 49.82 | L |
| ATOM | 2059 | CA | GLY | L | 57 | 78.069 | 52.233 | 41.707 | 1.00 | 49.82 | L |
| ATOM | 2060 | C | GLY | L | 57 | 78.985 | 53.112 | 40.877 | 1.00 | 49.82 | L |
| ATOM | 2061 | O | GLY | L | 57 | 80.142 | 52.765 | 40.619 | 1.00 | 49.82 | L |
| ATOM | 2062 | N | VAL | L | 58 | 78.461 | 54.258 | 40.457 | 1.00 | 42.50 | L |
| ATOM | 2063 | CA | VAL | L | 58 | 79.216 | 55.211 | 39.649 | 1.00 | 42.50 | L |
| ATOM | 2064 | CB | VAL | L | 58 | 78.327 | 56.402 | 39.216 | 1.00 | 27.60 | L |
| ATOM | 2065 | CG1 | VAL | L | 58 | 79.111 | 57.300 | 38.273 | 1.00 | 27.60 | L |
| ATOM | 2066 | CG2 | VAL | L | 58 | 77.040 | 55.916 | 38.562 | 1.00 | 27.60 | L |
| ATOM | 2067 | C | VAL | L | 58 | 80.411 | 55.785 | 40.419 | 1.00 | 42.50 | L |
| ATOM | 2068 | O | VAL | L | 58 | 80.261 | 56.284 | 41.532 | 1.00 | 42.50 | L |
| ATOM | 2069 | N | PRO | L | 59 | 81.616 | 55.728 | 39.836 | 1.00 | 56.23 | L |
| ATOM | 2070 | CD | PRO | L | 59 | 82.013 | 55.101 | 38.568 | 1.00 | 81.92 | L |
| ATOM | 2071 | CA | PRO | L | 59 | 82.779 | 56.275 | 40.545 | 1.00 | 56.23 | L |
| ATOM | 2072 | CB | PRO | L | 59 | 83.930 | 56.068 | 39.554 | 1.00 | 81.92 | L |
| ATOM | 2073 | CG | PRO | L | 59 | 83.243 | 55.875 | 38.229 | 1.00 | 81.92 | L |
| ATOM | 2074 | C | PRO | L | 59 | 82.621 | 57.736 | 40.994 | 1.00 | 56.23 | L |

TABLE 2-continued

Atomic coordinates of b2 adrenoreceptor

| ATOM | 2075 | O | PRO | L | 59 | 82.072 | 58.575 | 40.271 | 1.00 | 56.23 | L |
|---|---|---|---|---|---|---|---|---|---|---|---|
| ATOM | 2076 | N | SER | L | 60 | 83.117 | 58.010 | 42.200 | 1.00 | 78.13 | L |
| ATOM | 2077 | CA | SER | L | 60 | 83.050 | 59.318 | 42.854 | 1.00 | 78.13 | L |
| ATOM | 2078 | CB | SER | L | 60 | 83.556 | 59.195 | 44.288 | 1.00 | 90.69 | L |
| ATOM | 2079 | OG | SER | L | 60 | 84.927 | 58.834 | 44.299 | 1.00 | 90.69 | L |
| ATOM | 2080 | C | SER | L | 60 | 83.790 | 60.471 | 42.193 | 1.00 | 78.13 | L |
| ATOM | 2081 | O | SER | L | 60 | 83.843 | 61.571 | 42.757 | 1.00 | 78.13 | L |
| ATOM | 2082 | N | ARG | L | 61 | 84.375 | 60.234 | 41.021 | 1.00 | 58.74 | L |
| ATOM | 2083 | CA | ARG | L | 61 | 85.083 | 61.305 | 40.331 | 1.00 | 58.74 | L |
| ATOM | 2084 | CB | ARG | L | 61 | 86.364 | 60.791 | 39.669 | 1.00 | 67.65 | L |
| ATOM | 2085 | CG | ARG | L | 61 | 86.159 | 59.826 | 38.518 | 1.00 | 67.65 | L |
| ATOM | 2086 | CD | ARG | L | 61 | 87.483 | 59.531 | 37.824 | 1.00 | 67.65 | L |
| ATOM | 2087 | NE | ARG | L | 61 | 87.349 | 58.508 | 36.796 | 1.00 | 67.65 | L |
| ATOM | 2088 | CZ | ARG | L | 61 | 86.961 | 57.262 | 37.037 | 1.00 | 67.65 | L |
| ATOM | 2089 | NH1 | ARG | L | 61 | 86.664 | 56.877 | 38.271 | 1.00 | 67.65 | L |
| ATOM | 2090 | NH2 | ARG | L | 61 | 86.878 | 56.396 | 36.041 | 1.00 | 67.65 | L |
| ATOM | 2091 | C | ARG | L | 61 | 84.185 | 61.959 | 39.292 | 1.00 | 58.74 | L |
| ATOM | 2092 | O | ARG | L | 61 | 84.608 | 62.874 | 38.591 | 1.00 | 58.74 | L |
| ATOM | 2093 | N | PHE | L | 62 | 82.947 | 61.477 | 39.195 | 1.00 | 61.97 | L |
| ATOM | 2094 | CA | PHE | L | 62 | 81.966 | 62.035 | 38.270 | 1.00 | 61.97 | L |
| ATOM | 2095 | CB | PHE | L | 62 | 81.002 | 60.957 | 37.772 | 1.00 | 49.22 | L |
| ATOM | 2096 | CG | PHE | L | 62 | 81.576 | 60.076 | 36.705 | 1.00 | 49.22 | L |
| ATOM | 2097 | CD1 | PHE | L | 62 | 82.209 | 58.890 | 37.029 | 1.00 | 49.22 | L |
| ATOM | 2098 | CD2 | PHE | L | 62 | 81.500 | 60.449 | 35.369 | 1.00 | 49.22 | L |
| ATOM | 2099 | CE1 | PHE | L | 62 | 82.759 | 58.089 | 36.034 | 1.00 | 49.22 | L |
| ATOM | 2100 | CE2 | PHE | L | 62 | 82.050 | 59.652 | 34.371 | 1.00 | 49.22 | L |
| ATOM | 2101 | CZ | PHE | L | 62 | 82.680 | 58.470 | 34.706 | 1.00 | 49.22 | L |
| ATOM | 2102 | C | PHE | L | 62 | 81.179 | 63.093 | 39.026 | 1.00 | 61.97 | L |
| ATOM | 2103 | O | PHE | L | 62 | 80.852 | 62.907 | 40.198 | 1.00 | 61.97 | L |
| ATOM | 2104 | N | ILE | L | 63 | 80.856 | 64.199 | 38.370 | 1.00 | 55.57 | L |
| ATOM | 2105 | CA | ILE | L | 63 | 80.127 | 65.252 | 39.062 | 1.00 | 55.57 | L |
| ATOM | 2106 | CB | ILE | L | 63 | 81.121 | 66.238 | 39.728 | 1.00 | 23.50 | L |
| ATOM | 2107 | CG2 | ILE | L | 63 | 80.346 | 67.405 | 40.340 | 1.00 | 23.50 | L |
| ATOM | 2108 | CG1 | ILE | L | 63 | 81.960 | 65.507 | 40.789 | 1.00 | 23.50 | L |
| ATOM | 2109 | CD1 | ILE | L | 63 | 82.942 | 66.378 | 41.530 | 1.00 | 23.50 | L |
| ATOM | 2110 | C | ILE | L | 63 | 79.130 | 66.038 | 38.202 | 1.00 | 55.57 | L |
| ATOM | 2111 | O | ILE | L | 63 | 79.498 | 66.681 | 37.220 | 1.00 | 55.57 | L |
| ATOM | 2112 | N | GLY | L | 64 | 77.862 | 65.986 | 38.590 | 1.00 | 56.96 | L |
| ATOM | 2113 | CA | GLY | L | 64 | 76.840 | 66.693 | 37.845 | 1.00 | 56.96 | L |
| ATOM | 2114 | C | GLY | L | 64 | 76.355 | 67.878 | 38.645 | 1.00 | 56.96 | L |
| ATOM | 2115 | O | GLY | L | 64 | 75.957 | 67.722 | 39.798 | 1.00 | 56.96 | L |
| ATOM | 2116 | N | THR | L | 65 | 76.389 | 69.067 | 38.047 | 1.00 | 55.05 | L |
| ATOM | 2117 | CA | THR | L | 65 | 75.953 | 70.260 | 38.752 | 1.00 | 55.05 | L |
| ATOM | 2118 | CB | THR | L | 65 | 77.042 | 70.795 | 39.670 | 1.00 | 95.55 | L |
| ATOM | 2119 | OG1 | THR | L | 65 | 77.390 | 69.784 | 40.621 | 1.00 | 95.55 | L |
| ATOM | 2120 | CG2 | THR | L | 65 | 76.545 | 72.034 | 40.410 | 1.00 | 95.55 | L |
| ATOM | 2121 | C | THR | L | 65 | 75.502 | 71.402 | 37.876 | 1.00 | 55.05 | L |
| ATOM | 2122 | O | THR | L | 65 | 76.309 | 72.110 | 37.275 | 1.00 | 55.05 | L |
| ATOM | 2123 | N | GLY | L | 66 | 74.189 | 71.566 | 37.836 | 1.00 | 65.20 | L |
| ATOM | 2124 | CA | GLY | L | 66 | 73.560 | 72.628 | 37.086 | 1.00 | 65.20 | L |
| ATOM | 2125 | C | GLY | L | 66 | 72.344 | 72.988 | 37.914 | 1.00 | 65.20 | L |
| ATOM | 2126 | O | GLY | L | 66 | 72.276 | 72.619 | 39.086 | 1.00 | 65.20 | L |
| ATOM | 2127 | N | SER | L | 67 | 71.387 | 73.687 | 37.316 | 1.00 | 57.84 | L |
| ATOM | 2128 | CA | SER | L | 67 | 70.164 | 74.086 | 38.005 | 1.00 | 57.84 | L |
| ATOM | 2129 | CB | SER | L | 67 | 70.476 | 75.077 | 39.133 | 1.00 | 175.24 | L |
| ATOM | 2130 | OG | SER | L | 67 | 71.290 | 74.497 | 40.138 | 1.00 | 175.24 | L |
| ATOM | 2131 | C | SER | L | 67 | 69.214 | 74.748 | 37.013 | 1.00 | 57.84 | L |
| ATOM | 2132 | O | SER | L | 67 | 69.647 | 75.368 | 36.045 | 1.00 | 57.84 | L |
| ATOM | 2133 | N | GLY | L | 68 | 67.916 | 74.598 | 37.249 | 1.00 | 89.21 | L |
| ATOM | 2134 | CA | GLY | L | 68 | 66.912 | 75.216 | 36.396 | 1.00 | 89.21 | L |
| ATOM | 2135 | C | GLY | L | 68 | 66.931 | 75.088 | 34.878 | 1.00 | 89.21 | L |
| ATOM | 2136 | O | GLY | L | 68 | 65.986 | 74.537 | 34.308 | 1.00 | 89.21 | L |
| ATOM | 2137 | N | GLN | L | 69 | 67.967 | 75.602 | 34.211 | 1.00 | 61.91 | L |
| ATOM | 2138 | CA | GLN | L | 69 | 68.005 | 75.529 | 32.746 | 1.00 | 61.91 | L |
| ATOM | 2139 | CB | GLN | L | 69 | 67.455 | 76.829 | 32.158 | 1.00 | 95.48 | L |
| ATOM | 2140 | CG | GLN | L | 69 | 66.942 | 76.688 | 30.738 | 1.00 | 95.48 | L |
| ATOM | 2141 | CD | GLN | L | 69 | 66.291 | 77.955 | 30.240 | 1.00 | 95.48 | L |
| ATOM | 2142 | OE1 | GLN | L | 69 | 65.882 | 78.802 | 31.032 | 1.00 | 95.48 | L |
| ATOM | 2143 | NE2 | GLN | L | 69 | 66.180 | 78.090 | 28.923 | 1.00 | 95.48 | L |
| ATOM | 2144 | C | GLN | L | 69 | 69.349 | 75.205 | 32.083 | 1.00 | 61.91 | L |
| ATOM | 2145 | O | GLN | L | 69 | 69.440 | 75.118 | 30.853 | 1.00 | 61.91 | L |
| ATOM | 2146 | N | ASP | L | 70 | 70.387 | 75.024 | 32.891 | 1.00 | 67.80 | L |
| ATOM | 2147 | CA | ASP | L | 70 | 71.707 | 74.688 | 32.373 | 1.00 | 67.80 | L |
| ATOM | 2148 | CB | ASP | L | 70 | 72.476 | 75.959 | 32.001 | 1.00 | 111.64 | L |
| ATOM | 2149 | CG | ASP | L | 70 | 72.096 | 77.141 | 32.858 | 1.00 | 111.64 | L |
| ATOM | 2150 | OD1 | ASP | L | 70 | 70.907 | 77.530 | 32.843 | 1.00 | 111.64 | L |
| ATOM | 2151 | OD2 | ASP | L | 70 | 72.986 | 77.685 | 33.543 | 1.00 | 111.64 | L |
| ATOM | 2152 | C | ASP | L | 70 | 72.476 | 73.871 | 33.406 | 1.00 | 67.80 | L |

TABLE 2-continued

| | | | | | | | | | | |
|---|---|---|---|---|---|---|---|---|---|---|
| ATOM | 2153 | O | ASP | L | 70 | 72.550 | 74.241 | 34.574 | 1.00 | 67.80 L |
| ATOM | 2154 | N | TYR | L | 71 | 73.036 | 72.747 | 32.976 | 1.00 | 90.74 L |
| ATOM | 2155 | CA | TYR | L | 71 | 73.768 | 71.882 | 33.889 | 1.00 | 90.74 L |
| ATOM | 2156 | CB | TYR | L | 71 | 72.963 | 70.614 | 34.162 | 1.00 | 34.24 L |
| ATOM | 2157 | CG | TYR | L | 71 | 71.524 | 70.898 | 34.492 | 1.00 | 34.24 L |
| ATOM | 2158 | CD1 | TYR | L | 71 | 70.686 | 71.515 | 33.568 | 1.00 | 34.24 L |
| ATOM | 2159 | CE1 | TYR | L | 71 | 69.356 | 71.787 | 33.865 | 1.00 | 34.24 L |
| ATOM | 2160 | CD2 | TYR | L | 71 | 70.993 | 70.557 | 35.732 | 1.00 | 34.24 L |
| ATOM | 2161 | CE2 | TYR | L | 71 | 69.654 | 70.824 | 36.042 | 1.00 | 34.24 L |
| ATOM | 2162 | CZ | TYR | L | 71 | 68.849 | 71.439 | 35.099 | 1.00 | 34.24 L |
| ATOM | 2163 | OH | TYR | L | 71 | 67.536 | 71.696 | 35.387 | 1.00 | 34.24 L |
| ATOM | 2164 | C | TYR | L | 71 | 75.127 | 71.514 | 33.336 | 1.00 | 90.74 L |
| ATOM | 2165 | O | TYR | L | 71 | 75.651 | 72.190 | 32.451 | 1.00 | 90.74 L |
| ATOM | 2166 | N | SER | L | 72 | 75.693 | 70.430 | 33.849 | 1.00 | 38.37 L |
| ATOM | 2167 | CA | SER | L | 72 | 77.004 | 70.014 | 33.402 | 1.00 | 38.37 L |
| ATOM | 2168 | CB | SER | L | 72 | 77.985 | 71.169 | 33.567 | 1.00 | 56.29 L |
| ATOM | 2169 | OG | SER | L | 72 | 78.009 | 71.606 | 34.918 | 1.00 | 56.29 L |
| ATOM | 2170 | C | SER | L | 72 | 77.546 | 68.812 | 34.157 | 1.00 | 38.37 L |
| ATOM | 2171 | O | SER | L | 72 | 77.613 | 68.808 | 35.385 | 1.00 | 38.37 L |
| ATOM | 2172 | N | LEU | L | 73 | 77.937 | 67.792 | 33.408 | 1.00 | 29.02 L |
| ATOM | 2173 | CA | LEU | L | 73 | 78.526 | 66.599 | 33.989 | 1.00 | 29.02 L |
| ATOM | 2174 | CB | LEU | L | 73 | 78.203 | 65.386 | 33.119 | 1.00 | 45.31 L |
| ATOM | 2175 | CG | LEU | L | 73 | 78.965 | 64.108 | 33.445 | 1.00 | 45.31 L |
| ATOM | 2176 | CD1 | LEU | L | 73 | 78.712 | 63.733 | 34.902 | 1.00 | 45.31 L |
| ATOM | 2177 | CD2 | LEU | L | 73 | 78.549 | 62.996 | 32.472 | 1.00 | 45.31 L |
| ATOM | 2178 | C | LEU | L | 73 | 80.026 | 66.909 | 33.972 | 1.00 | 29.02 L |
| ATOM | 2179 | O | LEU | L | 73 | 80.527 | 67.534 | 33.020 | 1.00 | 29.02 L |
| ATOM | 2180 | N | THR | L | 74 | 80.735 | 66.500 | 35.023 | 1.00 | 42.12 L |
| ATOM | 2181 | CA | THR | L | 74 | 82.171 | 66.768 | 35.129 | 1.00 | 42.12 L |
| ATOM | 2182 | CB | THR | L | 74 | 82.442 | 68.134 | 35.798 | 1.00 | 98.20 L |
| ATOM | 2183 | OG1 | THR | L | 74 | 82.175 | 69.181 | 34.862 | 1.00 | 98.20 L |
| ATOM | 2184 | CG2 | THR | L | 74 | 83.886 | 68.238 | 36.267 | 1.00 | 98.20 L |
| ATOM | 2185 | C | THR | L | 74 | 82.931 | 65.726 | 35.919 | 1.00 | 42.12 L |
| ATOM | 2186 | O | THR | L | 74 | 82.427 | 65.178 | 36.899 | 1.00 | 42.12 L |
| ATOM | 2187 | N | ILE | L | 75 | 84.161 | 65.476 | 35.486 | 1.00 | 79.60 L |
| ATOM | 2188 | CA | ILE | L | 75 | 85.025 | 64.516 | 36.146 | 1.00 | 79.60 L |
| ATOM | 2189 | CB | ILE | L | 75 | 85.146 | 63.213 | 35.316 | 1.00 | 130.89 L |
| ATOM | 2190 | CG2 | ILE | L | 75 | 85.217 | 63.543 | 33.839 | 1.00 | 130.89 L |
| ATOM | 2191 | CG1 | ILE | L | 75 | 86.358 | 62.400 | 35.785 | 1.00 | 130.89 L |
| ATOM | 2192 | CD1 | ILE | L | 75 | 86.589 | 61.119 | 35.002 | 1.00 | 130.89 L |
| ATOM | 2193 | C | ILE | L | 75 | 86.415 | 65.098 | 36.391 | 1.00 | 79.60 L |
| ATOM | 2194 | O | ILE | L | 75 | 87.030 | 65.691 | 35.501 | 1.00 | 79.60 L |
| ATOM | 2195 | N | SER | L | 76 | 86.894 | 64.940 | 37.617 | 1.00 | 87.79 L |
| ATOM | 2196 | CA | SER | L | 76 | 88.211 | 65.423 | 37.989 | 1.00 | 87.79 L |
| ATOM | 2197 | CB | SER | L | 76 | 88.208 | 65.878 | 39.442 | 1.00 | 102.26 L |
| ATOM | 2198 | OG | SER | L | 76 | 87.829 | 64.805 | 40.288 | 1.00 | 102.26 L |
| ATOM | 2199 | C | SER | L | 76 | 89.103 | 64.217 | 37.857 | 1.00 | 87.79 L |
| ATOM | 2200 | O | SER | L | 76 | 88.668 | 63.109 | 38.144 | 1.00 | 87.79 L |
| ATOM | 2201 | N | SER | L | 77 | 90.337 | 64.407 | 37.422 | 1.00 | 53.08 L |
| ATOM | 2202 | CA | SER | L | 77 | 91.237 | 63.267 | 37.303 | 1.00 | 53.08 L |
| ATOM | 2203 | CB | SER | L | 77 | 91.481 | 62.655 | 38.690 | 1.00 | 112.99 L |
| ATOM | 2204 | OG | SER | L | 77 | 92.101 | 61.383 | 38.600 | 1.00 | 112.99 L |
| ATOM | 2205 | C | SER | L | 77 | 90.694 | 62.194 | 36.356 | 1.00 | 53.08 L |
| ATOM | 2206 | O | SER | L | 77 | 90.407 | 61.060 | 36.776 | 1.00 | 53.08 L |
| ATOM | 2207 | N | LEU | L | 78 | 90.567 | 62.562 | 35.082 | 1.00 | 84.74 L |
| ATOM | 2208 | CA | LEU | L | 78 | 90.073 | 61.663 | 34.037 | 1.00 | 84.74 L |
| ATOM | 2209 | CB | LEU | L | 78 | 90.175 | 62.338 | 32.667 | 1.00 | 37.46 L |
| ATOM | 2210 | CG | LEU | L | 78 | 89.940 | 61.431 | 31.455 | 1.00 | 37.46 L |
| ATOM | 2211 | CD1 | LEU | L | 78 | 88.483 | 61.017 | 31.429 | 1.00 | 37.46 L |
| ATOM | 2212 | CD2 | LEU | L | 78 | 90.321 | 62.154 | 30.167 | 1.00 | 37.46 L |
| ATOM | 2213 | C | LEU | L | 78 | 90.843 | 60.348 | 33.982 | 1.00 | 84.74 L |
| ATOM | 2214 | O | LEU | L | 78 | 92.064 | 60.349 | 33.814 | 1.00 | 84.74 L |
| ATOM | 2215 | N | ASP | L | 79 | 90.123 | 59.234 | 34.107 | 1.00 | 46.47 L |
| ATOM | 2216 | CA | ASP | L | 79 | 90.734 | 57.911 | 34.066 | 1.00 | 46.47 L |
| ATOM | 2217 | CB | ASP | L | 79 | 90.059 | 56.969 | 35.049 | 1.00 | 62.71 L |
| ATOM | 2218 | CG | ASP | L | 79 | 90.503 | 55.541 | 34.859 | 1.00 | 62.71 L |
| ATOM | 2219 | OD1 | ASP | L | 79 | 91.639 | 55.227 | 35.266 | 1.00 | 62.71 L |
| ATOM | 2220 | OD2 | ASP | L | 79 | 89.727 | 54.744 | 34.285 | 1.00 | 62.71 L |
| ATOM | 2221 | C | ASP | L | 79 | 90.620 | 57.317 | 32.673 | 1.00 | 46.47 L |
| ATOM | 2222 | O | ASP | L | 79 | 89.657 | 57.601 | 31.959 | 1.00 | 46.47 L |
| ATOM | 2223 | N | TYR | L | 80 | 91.588 | 56.469 | 32.312 | 1.00 | 54.42 L |
| ATOM | 2224 | CA | TYR | L | 80 | 91.635 | 55.852 | 30.985 | 1.00 | 54.42 L |
| ATOM | 2225 | CB | TYR | L | 80 | 92.782 | 54.831 | 30.901 | 1.00 | 118.53 L |
| ATOM | 2226 | CG | TYR | L | 80 | 92.568 | 53.558 | 31.686 | 1.00 | 118.53 L |
| ATOM | 2227 | CD1 | TYR | L | 80 | 91.628 | 52.613 | 31.279 | 1.00 | 118.53 L |
| ATOM | 2228 | CE1 | TYR | L | 80 | 91.410 | 51.452 | 32.008 | 1.00 | 118.53 L |
| ATOM | 2229 | CD2 | TYR | L | 80 | 93.295 | 53.306 | 32.846 | 1.00 | 118.53 L |
| ATOM | 2230 | CE2 | TYR | L | 80 | 93.088 | 52.145 | 33.585 | 1.00 | 118.53 L |

TABLE 2-continued

Atomic coordinates of b2 adrenoreceptor

| ATOM | 2231 | CZ  | TYR | L | 80 | 92.141 | 51.224 | 33.162 | 1.00 | 118.53 | L |
| ---- | ---- | --- | --- | - | -- | ------ | ------ | ------ | ---- | ------ | - |
| ATOM | 2232 | OH  | TYR | L | 80 | 91.909 | 50.091 | 33.908 | 1.00 | 118.53 | L |
| ATOM | 2233 | C   | TYR | L | 80 | 90.332 | 55.206 | 30.544 | 1.00 | 54.42  | L |
| ATOM | 2234 | O   | TYR | L | 80 | 89.912 | 55.354 | 29.397 | 1.00 | 54.42  | L |
| ATOM | 2235 | N   | ALA | L | 81 | 89.679 | 54.504 | 31.455 | 1.00 | 27.07  | L |
| ATOM | 2236 | CA  | ALA | L | 81 | 88.432 | 53.838 | 31.112 | 1.00 | 27.07  | L |
| ATOM | 2237 | CB  | ALA | L | 81 | 88.050 | 52.854 | 32.224 | 1.00 | 48.10  | L |
| ATOM | 2238 | C   | ALA | L | 81 | 87.291 | 54.828 | 30.866 | 1.00 | 27.07  | L |
| ATOM | 2239 | O   | ALA | L | 81 | 86.179 | 54.438 | 30.514 | 1.00 | 27.07  | L |
| ATOM | 2240 | N   | ASP | L | 82 | 87.567 | 56.115 | 31.025 | 1.00 | 61.35  | L |
| ATOM | 2241 | CA  | ASP | L | 82 | 86.523 | 57.118 | 30.849 | 1.00 | 61.35  | L |
| ATOM | 2242 | CB  | ASP | L | 82 | 86.779 | 58.279 | 31.814 | 1.00 | 55.82  | L |
| ATOM | 2243 | CG  | ASP | L | 82 | 86.886 | 57.823 | 33.258 | 1.00 | 55.82  | L |
| ATOM | 2244 | OD1 | ASP | L | 82 | 85.944 | 57.163 | 33.746 | 1.00 | 55.82  | L |
| ATOM | 2245 | OD2 | ASP | L | 82 | 87.909 | 58.131 | 33.898 | 1.00 | 55.82  | L |
| ATOM | 2246 | C   | ASP | L | 82 | 86.341 | 57.654 | 29.423 | 1.00 | 61.35  | L |
| ATOM | 2247 | O   | ASP | L | 82 | 86.141 | 58.857 | 29.225 | 1.00 | 61.35  | L |
| ATOM | 2248 | N   | MET | L | 83 | 86.370 | 56.755 | 28.441 | 1.00 | 60.67  | L |
| ATOM | 2249 | CA  | MET | L | 83 | 86.237 | 57.126 | 27.031 | 1.00 | 60.67  | L |
| ATOM | 2250 | CB  | MET | L | 83 | 87.369 | 56.490 | 26.235 | 1.00 | 100.10 | L |
| ATOM | 2251 | CG  | MET | L | 83 | 87.500 | 55.003 | 26.502 | 1.00 | 100.10 | L |
| ATOM | 2252 | SD  | MET | L | 83 | 88.851 | 54.250 | 25.604 | 1.00 | 100.10 | L |
| ATOM | 2253 | CE  | MET | L | 83 | 90.275 | 54.927 | 26.479 | 1.00 | 100.10 | L |
| ATOM | 2254 | C   | MET | L | 83 | 84.917 | 56.683 | 26.436 | 1.00 | 60.67  | L |
| ATOM | 2255 | O   | MET | L | 83 | 84.565 | 55.513 | 26.539 | 1.00 | 60.67  | L |
| ATOM | 2256 | N   | GLY | L | 84 | 84.197 | 57.607 | 25.800 | 1.00 | 44.27  | L |
| ATOM | 2257 | CA  | GLY | L | 84 | 82.919 | 57.250 | 25.194 | 1.00 | 44.27  | L |
| ATOM | 2258 | C   | GLY | L | 84 | 82.009 | 58.410 | 24.834 | 1.00 | 44.27  | L |
| ATOM | 2259 | O   | GLY | L | 84 | 82.490 | 59.479 | 24.464 | 1.00 | 44.27  | L |
| ATOM | 2260 | N   | ILE | L | 85 | 80.694 | 58.200 | 24.921 | 1.00 | 5.85   | L |
| ATOM | 2261 | CA  | ILE | L | 85 | 79.741 | 59.267 | 24.605 | 1.00 | 5.85   | L |
| ATOM | 2262 | CB  | ILE | L | 85 | 78.952 | 59.020 | 23.281 | 1.00 | 19.69  | L |
| ATOM | 2263 | CG2 | ILE | L | 85 | 78.366 | 60.344 | 22.768 | 1.00 | 19.69  | L |
| ATOM | 2264 | CG1 | ILE | L | 85 | 79.863 | 58.474 | 22.189 | 1.00 | 19.69  | L |
| ATOM | 2265 | CD1 | ILE | L | 85 | 79.078 | 57.972 | 21.008 | 1.00 | 19.69  | L |
| ATOM | 2266 | C   | ILE | L | 85 | 78.656 | 59.471 | 25.699 | 1.00 | 5.85   | L |
| ATOM | 2267 | O   | ILE | L | 85 | 77.793 | 58.647 | 25.873 | 1.00 | 5.85   | L |
| ATOM | 2268 | N   | TYR | L | 86 | 78.813 | 60.597 | 26.403 | 1.00 | 32.01  | L |
| ATOM | 2269 | CA  | TYR | L | 86 | 77.895 | 60.955 | 27.481 | 1.00 | 32.01  | L |
| ATOM | 2270 | CB  | TYR | L | 86 | 78.641 | 61.715 | 28.565 | 1.00 | 47.33  | L |
| ATOM | 2271 | CG  | TYR | L | 86 | 79.915 | 61.037 | 28.987 | 1.00 | 47.33  | L |
| ATOM | 2272 | CD1 | TYR | L | 86 | 81.003 | 60.961 | 28.118 | 1.00 | 47.33  | L |
| ATOM | 2273 | CE1 | TYR | L | 86 | 82.174 | 60.331 | 28.497 | 1.00 | 47.33  | L |
| ATOM | 2274 | CD2 | TYR | L | 86 | 80.031 | 60.462 | 30.251 | 1.00 | 47.33  | L |
| ATOM | 2275 | CE2 | TYR | L | 86 | 81.195 | 59.825 | 30.643 | 1.00 | 47.33  | L |
| ATOM | 2276 | CZ  | TYR | L | 86 | 82.264 | 59.763 | 29.762 | 1.00 | 47.33  | L |
| ATOM | 2277 | OH  | TYR | L | 86 | 83.426 | 59.132 | 30.141 | 1.00 | 47.33  | L |
| ATOM | 2278 | C   | TYR | L | 86 | 76.760 | 61.818 | 26.957 | 1.00 | 32.01  | L |
| ATOM | 2279 | O   | TYR | L | 86 | 76.984 | 62.748 | 26.182 | 1.00 | 32.01  | L |
| ATOM | 2280 | N   | TYR | L | 87 | 75.545 | 61.495 | 27.386 | 1.00 | 39.25  | L |
| ATOM | 2281 | CA  | TYR | L | 87 | 74.350 | 62.217 | 26.960 | 1.00 | 39.25  | L |
| ATOM | 2282 | CB  | TYR | L | 87 | 73.411 | 61.320 | 26.145 | 1.00 | 74.91  | L |
| ATOM | 2283 | CG  | TYR | L | 87 | 74.009 | 60.637 | 24.939 | 1.00 | 74.91  | L |
| ATOM | 2284 | CD1 | TYR | L | 87 | 75.030 | 59.701 | 25.082 | 1.00 | 74.91  | L |
| ATOM | 2285 | CE1 | TYR | L | 87 | 75.546 | 59.036 | 23.983 | 1.00 | 74.91  | L |
| ATOM | 2286 | CD2 | TYR | L | 87 | 73.518 | 60.894 | 23.655 | 1.00 | 74.91  | L |
| ATOM | 2287 | CE2 | TYR | L | 87 | 74.027 | 60.232 | 22.546 | 1.00 | 74.91  | L |
| ATOM | 2288 | CZ  | TYR | L | 87 | 75.041 | 59.303 | 22.717 | 1.00 | 74.91  | L |
| ATOM | 2289 | OH  | TYR | L | 87 | 75.556 | 58.630 | 21.631 | 1.00 | 74.91  | L |
| ATOM | 2290 | C   | TYR | L | 87 | 73.574 | 62.665 | 28.180 | 1.00 | 39.25  | L |
| ATOM | 2291 | O   | TYR | L | 87 | 73.632 | 62.007 | 29.219 | 1.00 | 39.25  | L |
| ATOM | 2292 | N   | CYS | L | 88 | 72.837 | 63.769 | 28.044 | 1.00 | 49.46  | L |
| ATOM | 2293 | CA  | CYS | L | 88 | 72.011 | 64.289 | 29.130 | 1.00 | 49.46  | L |
| ATOM | 2294 | C   | CYS | L | 88 | 70.550 | 64.121 | 28.755 | 1.00 | 49.46  | L |
| ATOM | 2295 | O   | CYS | L | 88 | 70.166 | 64.356 | 27.611 | 1.00 | 49.46  | L |
| ATOM | 2296 | CB  | CYS | L | 88 | 72.307 | 65.766 | 29.405 | 1.00 | 83.34  | L |
| ATOM | 2297 | SG  | CYS | L | 88 | 72.120 | 66.939 | 28.019 | 1.00 | 83.34  | L |
| ATOM | 2298 | N   | LEU | L | 89 | 69.743 | 63.702 | 29.725 | 1.00 | 74.44  | L |
| ATOM | 2299 | CA  | LEU | L | 89 | 68.322 | 63.482 | 29.506 | 1.00 | 74.44  | L |
| ATOM | 2300 | CB  | LEU | L | 89 | 68.016 | 61.983 | 29.589 | 1.00 | 32.48  | L |
| ATOM | 2301 | CG  | LEU | L | 89 | 66.546 | 61.576 | 29.743 | 1.00 | 32.48  | L |
| ATOM | 2302 | CD1 | LEU | L | 89 | 65.676 | 62.389 | 28.798 | 1.00 | 32.48  | L |
| ATOM | 2303 | CD2 | LEU | L | 89 | 66.388 | 60.092 | 29.461 | 1.00 | 32.48  | L |
| ATOM | 2304 | C   | LEU | L | 89 | 67.479 | 64.241 | 30.524 | 1.00 | 74.44  | L |
| ATOM | 2305 | O   | LEU | L | 89 | 67.873 | 64.365 | 31.679 | 1.00 | 74.44  | L |
| ATOM | 2306 | N   | GLN | L | 90 | 66.328 | 64.754 | 30.085 | 1.00 | 19.89  | L |
| ATOM | 2307 | CA  | GLN | L | 90 | 65.418 | 65.496 | 30.962 | 1.00 | 19.89  | L |
| ATOM | 2308 | CB  | GLN | L | 90 | 65.125 | 66.904 | 30.416 | 1.00 | 33.63  | L |

TABLE 2-continued

Atomic coordinates of b2 adrenoreceptor

| ATOM | 2309 | CG | GLN | L | 90 | 64.223 | 66.984 | 29.158 | 1.00 | 33.63 | L |
| ATOM | 2310 | CD | GLN | L | 90 | 62.727 | 66.874 | 29.457 | 1.00 | 33.63 | L |
| ATOM | 2311 | OE1 | GLN | L | 90 | 62.306 | 66.948 | 30.616 | 1.00 | 33.63 | L |
| ATOM | 2312 | NE2 | GLN | L | 90 | 61.918 | 66.704 | 28.405 | 1.00 | 33.63 | L |
| ATOM | 2313 | C | GLN | L | 90 | 64.126 | 64.734 | 31.034 | 1.00 | 19.89 | L |
| ATOM | 2314 | O | GLN | L | 90 | 63.621 | 64.275 | 30.002 | 1.00 | 19.89 | L |
| ATOM | 2315 | N | TYR | L | 91 | 63.591 | 64.600 | 32.246 | 1.00 | 44.92 | L |
| ATOM | 2316 | CA | TYR | L | 91 | 62.335 | 63.887 | 32.440 | 1.00 | 44.92 | L |
| ATOM | 2317 | CB | TYR | L | 91 | 62.563 | 62.562 | 33.172 | 1.00 | 38.39 | L |
| ATOM | 2318 | CG | TYR | L | 91 | 63.340 | 62.648 | 34.460 | 1.00 | 38.39 | L |
| ATOM | 2319 | CD1 | TYR | L | 91 | 64.668 | 63.020 | 34.460 | 1.00 | 38.39 | L |
| ATOM | 2320 | CE1 | TYR | L | 91 | 65.420 | 62.999 | 35.629 | 1.00 | 38.39 | L |
| ATOM | 2321 | CD2 | TYR | L | 91 | 62.764 | 62.266 | 35.670 | 1.00 | 38.39 | L |
| ATOM | 2322 | CE2 | TYR | L | 91 | 63.504 | 62.239 | 36.855 | 1.00 | 38.39 | L |
| ATOM | 2323 | CZ | TYR | L | 91 | 64.839 | 62.601 | 36.828 | 1.00 | 38.39 | L |
| ATOM | 2324 | OH | TYR | L | 91 | 65.618 | 62.519 | 37.975 | 1.00 | 38.39 | L |
| ATOM | 2325 | C | TYR | L | 91 | 61.329 | 64.728 | 33.194 | 1.00 | 44.92 | L |
| ATOM | 2326 | O | TYR | L | 91 | 60.404 | 64.207 | 33.821 | 1.00 | 44.92 | L |
| ATOM | 2327 | N | ASP | L | 92 | 61.525 | 66.037 | 33.110 | 1.00 | 46.92 | L |
| ATOM | 2328 | CA | ASP | L | 92 | 60.659 | 67.003 | 33.766 | 1.00 | 46.92 | L |
| ATOM | 2329 | CB | ASP | L | 92 | 61.216 | 68.416 | 33.549 | 1.00 | 79.69 | L |
| ATOM | 2330 | CG | ASP | L | 92 | 60.583 | 69.445 | 34.462 | 1.00 | 79.69 | L |
| ATOM | 2331 | OD1 | ASP | L | 92 | 60.745 | 69.324 | 35.690 | 1.00 | 79.69 | L |
| ATOM | 2332 | OD2 | ASP | L | 92 | 59.927 | 70.376 | 33.955 | 1.00 | 79.69 | L |
| ATOM | 2333 | C | ASP | L | 92 | 59.227 | 66.912 | 33.228 | 1.00 | 46.92 | L |
| ATOM | 2334 | O | ASP | L | 92 | 58.272 | 66.919 | 34.006 | 1.00 | 46.92 | L |
| ATOM | 2335 | N | GLU | L | 93 | 59.087 | 66.829 | 31.900 | 1.00 | 43.51 | L |
| ATOM | 2336 | CA | GLU | L | 93 | 57.777 | 66.731 | 31.244 | 1.00 | 43.51 | L |
| ATOM | 2337 | CB | GLU | L | 93 | 57.268 | 68.129 | 30.881 | 1.00 | 116.42 | L |
| ATOM | 2338 | CG | GLU | L | 93 | 58.337 | 69.072 | 30.354 | 1.00 | 116.42 | L |
| ATOM | 2339 | CD | GLU | L | 93 | 57.765 | 70.409 | 29.920 | 1.00 | 116.42 | L |
| ATOM | 2340 | OE1 | GLU | L | 93 | 57.127 | 70.466 | 28.845 | 1.00 | 116.42 | L |
| ATOM | 2341 | OE2 | GLU | L | 93 | 57.945 | 71.401 | 30.661 | 1.00 | 116.42 | L |
| ATOM | 2342 | C | GLU | L | 93 | 57.804 | 65.848 | 29.988 | 1.00 | 43.51 | L |
| ATOM | 2343 | O | GLU | L | 93 | 58.874 | 65.458 | 29.516 | 1.00 | 43.51 | L |
| ATOM | 2344 | N | PHE | L | 94 | 56.627 | 65.516 | 29.459 | 1.00 | 72.44 | L |
| ATOM | 2345 | CA | PHE | L | 94 | 56.547 | 64.692 | 28.252 | 1.00 | 72.44 | L |
| ATOM | 2346 | CB | PHE | L | 94 | 55.229 | 63.917 | 28.178 | 1.00 | 40.62 | L |
| ATOM | 2347 | CG | PHE | L | 94 | 55.075 | 62.842 | 29.222 | 1.00 | 40.62 | L |
| ATOM | 2348 | CD1 | PHE | L | 94 | 56.078 | 61.899 | 29.432 | 1.00 | 40.62 | L |
| ATOM | 2349 | CD2 | PHE | L | 94 | 53.898 | 62.745 | 29.966 | 1.00 | 40.62 | L |
| ATOM | 2350 | CE1 | PHE | L | 94 | 55.905 | 60.874 | 30.367 | 1.00 | 40.62 | L |
| ATOM | 2351 | CE2 | PHE | L | 94 | 53.716 | 61.731 | 30.899 | 1.00 | 40.62 | L |
| ATOM | 2352 | CZ | PHE | L | 94 | 54.716 | 60.795 | 31.101 | 1.00 | 40.62 | L |
| ATOM | 2353 | C | PHE | L | 94 | 56.622 | 65.590 | 27.029 | 1.00 | 72.44 | L |
| ATOM | 2354 | O | PHE | L | 94 | 56.099 | 66.701 | 27.035 | 1.00 | 72.44 | L |
| ATOM | 2355 | N | PRO | L | 95 | 57.284 | 65.124 | 25.962 | 1.00 | 66.58 | L |
| ATOM | 2356 | CD | PRO | L | 95 | 57.283 | 65.758 | 24.631 | 1.00 | 57.99 | L |
| ATOM | 2357 | CA | PRO | L | 95 | 57.941 | 63.821 | 25.905 | 1.00 | 66.58 | L |
| ATOM | 2358 | CB | PRO | L | 95 | 57.908 | 63.494 | 24.426 | 1.00 | 57.99 | L |
| ATOM | 2359 | CG | PRO | L | 95 | 58.188 | 64.834 | 23.825 | 1.00 | 57.99 | L |
| ATOM | 2360 | C | PRO | L | 95 | 59.361 | 63.955 | 26.406 | 1.00 | 66.58 | L |
| ATOM | 2361 | O | PRO | L | 95 | 60.013 | 64.979 | 26.195 | 1.00 | 66.58 | L |
| ATOM | 2362 | N | TYR | L | 96 | 59.835 | 62.929 | 27.088 | 1.00 | 40.29 | L |
| ATOM | 2363 | CA | TYR | L | 96 | 61.194 | 62.954 | 27.579 | 1.00 | 40.29 | L |
| ATOM | 2364 | CB | TYR | L | 96 | 61.515 | 61.618 | 28.208 | 1.00 | 38.78 | L |
| ATOM | 2365 | CG | TYR | L | 96 | 60.640 | 61.349 | 29.400 | 1.00 | 38.78 | L |
| ATOM | 2366 | CD1 | TYR | L | 96 | 60.035 | 60.109 | 29.573 | 1.00 | 38.78 | L |
| ATOM | 2367 | CE1 | TYR | L | 96 | 59.245 | 59.848 | 30.683 | 1.00 | 38.78 | L |
| ATOM | 2368 | CD2 | TYR | L | 96 | 60.433 | 62.333 | 30.370 | 1.00 | 38.78 | L |
| ATOM | 2369 | CE2 | TYR | L | 96 | 59.652 | 62.086 | 31.484 | 1.00 | 38.78 | L |
| ATOM | 2370 | CZ | TYR | L | 96 | 59.057 | 60.836 | 31.638 | 1.00 | 38.78 | L |
| ATOM | 2371 | OH | TYR | L | 96 | 58.276 | 60.560 | 32.742 | 1.00 | 38.78 | L |
| ATOM | 2372 | C | TYR | L | 96 | 62.020 | 63.202 | 26.339 | 1.00 | 40.29 | L |
| ATOM | 2373 | O | TYR | L | 96 | 61.702 | 62.671 | 25.270 | 1.00 | 40.29 | L |
| ATOM | 2374 | N | THR | L | 97 | 63.055 | 64.024 | 26.477 | 1.00 | 22.82 | L |
| ATOM | 2375 | CA | THR | L | 97 | 63.897 | 64.389 | 25.344 | 1.00 | 22.82 | L |
| ATOM | 2376 | CB | THR | L | 97 | 63.599 | 65.841 | 24.884 | 1.00 | 45.75 | L |
| ATOM | 2377 | OG1 | THR | L | 97 | 63.630 | 66.728 | 26.011 | 1.00 | 45.75 | L |
| ATOM | 2378 | CG2 | THR | L | 97 | 62.227 | 65.926 | 24.241 | 1.00 | 45.75 | L |
| ATOM | 2379 | C | THR | L | 97 | 65.372 | 64.275 | 25.666 | 1.00 | 22.82 | L |
| ATOM | 2380 | O | THR | L | 97 | 65.815 | 64.714 | 26.723 | 1.00 | 22.82 | L |
| ATOM | 2381 | N | PHE | L | 98 | 66.138 | 63.690 | 24.753 | 1.00 | 63.31 | L |
| ATOM | 2382 | CA | PHE | L | 98 | 67.568 | 63.526 | 24.986 | 1.00 | 63.31 | L |
| ATOM | 2383 | CB | PHE | L | 98 | 68.078 | 62.221 | 24.383 | 1.00 | 24.82 | L |
| ATOM | 2384 | CG | PHE | L | 98 | 67.511 | 61.002 | 25.011 | 1.00 | 24.82 | L |
| ATOM | 2385 | CD1 | PHE | L | 98 | 66.158 | 60.719 | 24.905 | 1.00 | 24.82 | L |
| ATOM | 2386 | CD2 | PHE | L | 98 | 68.333 | 60.130 | 25.713 | 1.00 | 24.82 | L |

TABLE 2-continued

Atomic coordinates of b2 adrenoreceptor

| ATOM | 2387 | CE1 | PHE | L | 98 | 65.635 | 59.581 | 25.493 | 1.00 | 24.82 | L |
|---|---|---|---|---|---|---|---|---|---|---|---|
| ATOM | 2388 | CE2 | PHE | L | 98 | 67.824 | 58.986 | 26.309 | 1.00 | 24.82 | L |
| ATOM | 2389 | CZ | PHE | L | 98 | 66.476 | 58.707 | 26.202 | 1.00 | 24.82 | L |
| ATOM | 2390 | C | PHE | L | 98 | 68.409 | 64.636 | 24.407 | 1.00 | 63.31 | L |
| ATOM | 2391 | O | PHE | L | 98 | 67.994 | 65.344 | 23.492 | 1.00 | 63.31 | L |
| ATOM | 2392 | N | GLY | L | 99 | 69.609 | 64.779 | 24.950 | 1.00 | 73.82 | L |
| ATOM | 2393 | CA | GLY | L | 99 | 70.523 | 65.764 | 24.424 | 1.00 | 73.82 | L |
| ATOM | 2394 | C | GLY | L | 99 | 71.040 | 65.096 | 23.165 | 1.00 | 73.82 | L |
| ATOM | 2395 | O | GLY | L | 99 | 70.387 | 64.206 | 22.612 | 1.00 | 73.82 | L |
| ATOM | 2396 | N | GLY | L | 100 | 72.214 | 65.500 | 22.707 | 1.00 | 36.84 | L |
| ATOM | 2397 | CA | GLY | L | 100 | 72.754 | 64.894 | 21.511 | 1.00 | 36.84 | L |
| ATOM | 2398 | C | GLY | L | 100 | 73.997 | 64.175 | 21.926 | 1.00 | 36.84 | L |
| ATOM | 2399 | O | GLY | L | 100 | 74.642 | 63.520 | 21.110 | 1.00 | 36.84 | L |
| ATOM | 2400 | N | GLY | L | 101 | 74.319 | 64.306 | 23.212 | 1.00 | 37.27 | L |
| ATOM | 2401 | CA | GLY | L | 101 | 75.511 | 63.685 | 23.767 | 1.00 | 37.27 | L |
| ATOM | 2402 | C | GLY | L | 101 | 76.848 | 64.147 | 23.186 | 1.00 | 37.27 | L |
| ATOM | 2403 | O | GLY | L | 101 | 77.044 | 64.213 | 21.974 | 1.00 | 37.27 | L |
| ATOM | 2404 | N | THR | L | 102 | 77.780 | 64.497 | 24.049 | 1.00 | 30.86 | L |
| ATOM | 2405 | CA | THR | L | 102 | 79.079 | 64.892 | 23.551 | 1.00 | 30.86 | L |
| ATOM | 2406 | CB | THR | L | 102 | 79.733 | 66.006 | 24.424 | 1.00 | 32.04 | L |
| ATOM | 2407 | OG1 | THR | L | 102 | 81.043 | 65.585 | 24.851 | 1.00 | 32.04 | L |
| ATOM | 2408 | CG2 | THR | L | 102 | 78.833 | 66.352 | 25.634 | 1.00 | 32.04 | L |
| ATOM | 2409 | C | THR | L | 102 | 79.877 | 63.597 | 23.641 | 1.00 | 30.86 | L |
| ATOM | 2410 | O | THR | L | 102 | 79.513 | 62.703 | 24.411 | 1.00 | 30.86 | L |
| ATOM | 2411 | N | LYS | L | 103 | 80.937 | 63.491 | 22.845 | 1.00 | 26.05 | L |
| ATOM | 2412 | CA | LYS | L | 103 | 81.778 | 62.301 | 22.807 | 1.00 | 26.05 | L |
| ATOM | 2413 | CB | LYS | L | 103 | 81.771 | 61.720 | 21.398 | 1.00 | 60.60 | L |
| ATOM | 2414 | CG | LYS | L | 103 | 82.757 | 60.608 | 21.119 | 1.00 | 60.60 | L |
| ATOM | 2415 | CD | LYS | L | 103 | 82.707 | 60.291 | 19.629 | 1.00 | 60.60 | L |
| ATOM | 2416 | CE | LYS | L | 103 | 83.816 | 59.365 | 19.201 | 1.00 | 60.60 | L |
| ATOM | 2417 | NZ | LYS | L | 103 | 85.125 | 60.006 | 19.460 | 1.00 | 60.60 | L |
| ATOM | 2418 | C | LYS | L | 103 | 83.173 | 62.726 | 23.207 | 1.00 | 26.05 | L |
| ATOM | 2419 | O | LYS | L | 103 | 83.697 | 63.723 | 22.715 | 1.00 | 26.05 | L |
| ATOM | 2420 | N | LEU | L | 104 | 83.781 | 61.942 | 24.084 | 1.00 | 32.51 | L |
| ATOM | 2421 | CA | LEU | L | 104 | 85.091 | 62.249 | 24.626 | 1.00 | 32.51 | L |
| ATOM | 2422 | CB | LEU | L | 104 | 84.933 | 62.368 | 26.132 | 1.00 | 33.88 | L |
| ATOM | 2423 | CG | LEU | L | 104 | 85.922 | 63.070 | 27.047 | 1.00 | 33.88 | L |
| ATOM | 2424 | CD1 | LEU | L | 104 | 85.330 | 62.978 | 28.441 | 1.00 | 33.88 | L |
| ATOM | 2425 | CD2 | LEU | L | 104 | 87.322 | 62.449 | 26.987 | 1.00 | 33.88 | L |
| ATOM | 2426 | C | LEU | L | 104 | 86.133 | 61.182 | 24.315 | 1.00 | 32.51 | L |
| ATOM | 2427 | O | LEU | L | 104 | 85.911 | 59.997 | 24.582 | 1.00 | 32.51 | L |
| ATOM | 2428 | N | GLU | L | 105 | 87.269 | 61.605 | 23.762 | 1.00 | 38.41 | L |
| ATOM | 2429 | CA | GLU | L | 105 | 88.374 | 60.702 | 23.441 | 1.00 | 38.41 | L |
| ATOM | 2430 | CB | GLU | L | 105 | 88.710 | 60.772 | 21.953 | 1.00 | 56.37 | L |
| ATOM | 2431 | CG | GLU | L | 105 | 87.822 | 59.915 | 21.071 | 1.00 | 56.37 | L |
| ATOM | 2432 | CD | GLU | L | 105 | 88.062 | 60.146 | 19.584 | 1.00 | 56.37 | L |
| ATOM | 2433 | OE1 | GLU | L | 105 | 87.827 | 61.281 | 19.131 | 1.00 | 56.37 | L |
| ATOM | 2434 | OE2 | GLU | L | 105 | 88.475 | 59.205 | 18.864 | 1.00 | 56.37 | L |
| ATOM | 2435 | C | GLU | L | 105 | 89.584 | 61.132 | 24.264 | 1.00 | 38.41 | L |
| ATOM | 2436 | O | GLU | L | 105 | 89.685 | 62.292 | 24.670 | 1.00 | 38.41 | L |
| ATOM | 2437 | N | ILE | L | 106 | 90.504 | 60.202 | 24.498 | 1.00 | 109.35 | L |
| ATOM | 2438 | CA | ILE | L | 106 | 91.705 | 60.470 | 25.288 | 1.00 | 109.35 | L |
| ATOM | 2439 | CB | ILE | L | 106 | 91.914 | 59.359 | 26.322 | 1.00 | 41.79 | L |
| ATOM | 2440 | CG2 | ILE | L | 106 | 93.370 | 59.289 | 26.739 | 1.00 | 41.79 | L |
| ATOM | 2441 | CG1 | ILE | L | 106 | 90.970 | 59.589 | 27.503 | 1.00 | 41.79 | L |
| ATOM | 2442 | CD1 | ILE | L | 106 | 90.885 | 58.424 | 28.456 | 1.00 | 41.79 | L |
| ATOM | 2443 | C | ILE | L | 106 | 92.979 | 60.584 | 24.465 | 1.00 | 109.35 | L |
| ATOM | 2444 | O | ILE | L | 106 | 93.353 | 59.635 | 23.777 | 1.00 | 109.35 | L |
| ATOM | 2445 | N | LYS | L | 107 | 93.660 | 61.728 | 24.544 | 1.00 | 68.12 | L |
| ATOM | 2446 | CA | LYS | L | 107 | 94.899 | 61.880 | 23.786 | 1.00 | 68.12 | L |
| ATOM | 2447 | CB | LYS | L | 107 | 95.356 | 63.346 | 23.689 | 1.00 | 113.16 | L |
| ATOM | 2448 | CG | LYS | L | 107 | 95.049 | 64.250 | 24.867 | 1.00 | 113.16 | L |
| ATOM | 2449 | CD | LYS | L | 107 | 95.346 | 65.697 | 24.464 | 1.00 | 113.16 | L |
| ATOM | 2450 | CE | LYS | L | 107 | 94.942 | 66.704 | 25.531 | 1.00 | 113.16 | L |
| ATOM | 2451 | NZ | LYS | L | 107 | 95.767 | 66.606 | 26.764 | 1.00 | 113.16 | L |
| ATOM | 2452 | C | LYS | L | 107 | 95.987 | 61.014 | 24.381 | 1.00 | 68.12 | L |
| ATOM | 2453 | O | LYS | L | 107 | 96.289 | 61.086 | 25.568 | 1.00 | 68.12 | L |
| ATOM | 2454 | N | ARG | L | 108 | 96.541 | 60.171 | 23.521 | 1.00 | 62.89 | L |
| ATOM | 2455 | CA | ARG | L | 108 | 97.581 | 59.223 | 23.872 | 1.00 | 62.89 | L |
| ATOM | 2456 | CB | ARG | L | 108 | 97.207 | 57.845 | 23.318 | 1.00 | 55.39 | L |
| ATOM | 2457 | CG | ARG | L | 108 | 98.194 | 56.764 | 23.664 | 1.00 | 55.39 | L |
| ATOM | 2458 | CD | ARG | L | 108 | 97.775 | 55.402 | 23.170 | 1.00 | 55.39 | L |
| ATOM | 2459 | NE | ARG | L | 108 | 98.728 | 54.412 | 23.650 | 1.00 | 55.39 | L |
| ATOM | 2460 | CZ | ARG | L | 108 | 100.029 | 54.455 | 23.381 | 1.00 | 55.39 | L |
| ATOM | 2461 | NH1 | ARG | L | 108 | 100.511 | 55.436 | 22.629 | 1.00 | 55.39 | L |
| ATOM | 2462 | NH2 | ARG | L | 108 | 100.852 | 53.537 | 23.882 | 1.00 | 55.39 | L |
| ATOM | 2463 | C | ARG | L | 108 | 98.882 | 59.688 | 23.248 | 1.00 | 62.89 | L |
| ATOM | 2464 | O | ARG | L | 108 | 98.949 | 60.791 | 22.715 | 1.00 | 62.89 | L |

TABLE 2-continued

Atomic coordinates of b2 adrenoreceptor

| ATOM | 2465 | N   | ALA | L | 109 | 99.910  | 58.848 | 23.313 | 1.00 | 57.13 | L |
|------|------|-----|-----|---|-----|---------|--------|--------|------|-------|---|
| ATOM | 2466 | CA  | ALA | L | 109 | 101.206 | 59.169 | 22.726 | 1.00 | 57.13 | L |
| ATOM | 2467 | CB  | ALA | L | 109 | 102.308 | 58.656 | 23.613 | 1.00 | 54.85 | L |
| ATOM | 2468 | C   | ALA | L | 109 | 101.300 | 58.520 | 21.347 | 1.00 | 57.13 | L |
| ATOM | 2469 | O   | ALA | L | 109 | 100.996 | 57.336 | 21.204 | 1.00 | 57.13 | L |
| ATOM | 2470 | N   | ASP | L | 110 | 101.711 | 59.297 | 20.341 | 1.00 | 64.05 | L |
| ATOM | 2471 | CA  | ASP | L | 110 | 101.842 | 58.808 | 18.961 | 1.00 | 64.05 | L |
| ATOM | 2472 | CB  | ASP | L | 110 | 102.788 | 59.718 | 18.166 | 1.00 | 60.33 | L |
| ATOM | 2473 | CG  | ASP | L | 110 | 102.117 | 60.993 | 17.688 | 1.00 | 60.33 | L |
| ATOM | 2474 | OD1 | ASP | L | 110 | 101.344 | 61.587 | 18.467 | 1.00 | 60.33 | L |
| ATOM | 2475 | OD2 | ASP | L | 110 | 102.374 | 61.411 | 16.536 | 1.00 | 60.33 | L |
| ATOM | 2476 | C   | ASP | L | 110 | 102.366 | 57.373 | 18.905 | 1.00 | 64.05 | L |
| ATOM | 2477 | O   | ASP | L | 110 | 103.386 | 57.053 | 19.509 | 1.00 | 64.05 | L |
| ATOM | 2478 | N   | ALA | L | 111 | 101.665 | 56.501 | 18.191 | 1.00 | 63.02 | L |
| ATOM | 2479 | CA  | ALA | L | 111 | 102.109 | 55.115 | 18.077 | 1.00 | 63.02 | L |
| ATOM | 2480 | CB  | ALA | L | 111 | 101.545 | 54.278 | 19.212 | 1.00 | 46.92 | L |
| ATOM | 2481 | C   | ALA | L | 111 | 101.693 | 54.528 | 16.738 | 1.00 | 63.02 | L |
| ATOM | 2482 | O   | ALA | L | 111 | 100.513 | 54.532 | 16.382 | 1.00 | 63.02 | L |
| ATOM | 2483 | N   | ALA | L | 112 | 102.680 | 54.028 | 16.001 | 1.00 | 68.66 | L |
| ATOM | 2484 | CA  | ALA | L | 112 | 102.446 | 53.442 | 14.693 | 1.00 | 68.66 | L |
| ATOM | 2485 | CB  | ALA | L | 112 | 103.746 | 53.250 | 13.984 | 1.00 | 37.92 | L |
| ATOM | 2486 | C   | ALA | L | 112 | 101.718 | 52.113 | 14.791 | 1.00 | 68.66 | L |
| ATOM | 2487 | O   | ALA | L | 112 | 101.674 | 51.481 | 15.851 | 1.00 | 68.66 | L |
| ATOM | 2488 | N   | PRO | L | 113 | 101.144 | 51.664 | 13.669 | 1.00 | 55.36 | L |
| ATOM | 2489 | CD  | PRO | L | 113 | 100.943 | 52.426 | 12.424 | 1.00 | 55.48 | L |
| ATOM | 2490 | CA  | PRO | L | 113 | 100.409 | 50.407 | 13.620 | 1.00 | 55.36 | L |
| ATOM | 2491 | CB  | PRO | L | 113 | 99.408  | 50.652 | 12.502 | 1.00 | 55.48 | L |
| ATOM | 2492 | CG  | PRO | L | 113 | 100.219 | 51.427 | 11.540 | 1.00 | 55.48 | L |
| ATOM | 2493 | C   | PRO | L | 113 | 101.263 | 49.188 | 13.349 | 1.00 | 55.36 | L |
| ATOM | 2494 | O   | PRO | L | 113 | 102.310 | 49.277 | 12.702 | 1.00 | 55.36 | L |
| ATOM | 2495 | N   | THR | L | 114 | 100.799 | 48.054 | 13.865 | 1.00 | 48.84 | L |
| ATOM | 2496 | CA  | THR | L | 114 | 101.458 | 46.774 | 13.662 | 1.00 | 48.84 | L |
| ATOM | 2497 | CB  | THR | L | 114 | 101.488 | 45.941 | 14.948 | 1.00 | 65.62 | L |
| ATOM | 2498 | OG1 | THR | L | 114 | 101.414 | 46.810 | 16.086 | 1.00 | 65.62 | L |
| ATOM | 2499 | CG2 | THR | L | 114 | 102.784 | 45.152 | 15.020 | 1.00 | 65.62 | L |
| ATOM | 2500 | C   | THR | L | 114 | 100.556 | 46.105 | 12.629 | 1.00 | 48.84 | L |
| ATOM | 2501 | O   | THR | L | 114 | 99.534  | 45.502 | 12.957 | 1.00 | 48.84 | L |
| ATOM | 2502 | N   | VAL | L | 115 | 100.945 | 46.253 | 11.370 | 1.00 | 53.39 | L |
| ATOM | 2503 | CA  | VAL | L | 115 | 100.197 | 45.733 | 10.240 | 1.00 | 53.39 | L |
| ATOM | 2504 | CB  | VAL | L | 115 | 100.449 | 46.652 | 9.029  | 1.00 | 30.85 | L |
| ATOM | 2505 | CG1 | VAL | L | 115 | 101.937 | 46.880 | 8.879  | 1.00 | 30.85 | L |
| ATOM | 2506 | CG2 | VAL | L | 115 | 99.848  | 46.052 | 7.757  | 1.00 | 30.85 | L |
| ATOM | 2507 | C   | VAL | L | 115 | 100.494 | 44.267 | 9.876  | 1.00 | 53.39 | L |
| ATOM | 2508 | O   | VAL | L | 115 | 101.641 | 43.814 | 9.941  | 1.00 | 53.39 | L |
| ATOM | 2509 | N   | SER | L | 116 | 99.447  | 43.539 | 9.486  | 1.00 | 55.00 | L |
| ATOM | 2510 | CA  | SER | L | 116 | 99.559  | 42.127 | 9.113  | 1.00 | 55.00 | L |
| ATOM | 2511 | CB  | SER | L | 116 | 99.383  | 41.268 | 10.357 | 1.00 | 49.15 | L |
| ATOM | 2512 | OG  | SER | L | 116 | 98.387  | 41.833 | 11.190 | 1.00 | 49.15 | L |
| ATOM | 2513 | C   | SER | L | 116 | 98.523  | 41.736 | 8.054  | 1.00 | 55.00 | L |
| ATOM | 2514 | O   | SER | L | 116 | 97.340  | 42.032 | 8.197  | 1.00 | 55.00 | L |
| ATOM | 2515 | N   | ILE | L | 117 | 98.971  | 41.063 | 6.997  | 1.00 | 48.62 | L |
| ATOM | 2516 | CA  | ILE | L | 117 | 98.086  | 40.663 | 5.901  | 1.00 | 48.62 | L |
| ATOM | 2517 | CB  | ILE | L | 117 | 98.585  | 41.244 | 4.570  | 1.00 | 58.98 | L |
| ATOM | 2518 | CG2 | ILE | L | 117 | 100.046 | 40.889 | 4.361  | 1.00 | 58.98 | L |
| ATOM | 2519 | CG1 | ILE | L | 117 | 97.728  | 40.731 | 3.419  | 1.00 | 58.98 | L |
| ATOM | 2520 | CD1 | ILE | L | 117 | 98.095  | 41.368 | 2.103  | 1.00 | 58.98 | L |
| ATOM | 2521 | C   | ILE | L | 117 | 97.968  | 39.153 | 5.764  | 1.00 | 48.62 | L |
| ATOM | 2522 | O   | ILE | L | 117 | 98.967  | 38.444 | 5.833  | 1.00 | 48.62 | L |
| ATOM | 2523 | N   | PHE | L | 118 | 96.747  | 38.668 | 5.547  | 1.00 | 37.82 | L |
| ATOM | 2524 | CA  | PHE | L | 118 | 96.486  | 37.232 | 5.439  | 1.00 | 37.82 | L |
| ATOM | 2525 | CB  | PHE | L | 118 | 95.494  | 36.789 | 6.531  | 1.00 | 30.45 | L |
| ATOM | 2526 | CG  | PHE | L | 118 | 95.856  | 37.250 | 7.921  | 1.00 | 30.45 | L |
| ATOM | 2527 | CD1 | PHE | L | 118 | 95.687  | 38.581 | 8.299  | 1.00 | 30.45 | L |
| ATOM | 2528 | CD2 | PHE | L | 118 | 96.394  | 36.362 | 8.846  | 1.00 | 30.45 | L |
| ATOM | 2529 | CE1 | PHE | L | 118 | 96.054  | 39.019 | 9.580  | 1.00 | 30.45 | L |
| ATOM | 2530 | CE2 | PHE | L | 118 | 96.763  | 36.793 | 10.131 | 1.00 | 30.45 | L |
| ATOM | 2531 | CZ  | PHE | L | 118 | 96.592  | 38.122 | 10.494 | 1.00 | 30.45 | L |
| ATOM | 2532 | C   | PHE | L | 118 | 95.912  | 36.832 | 4.085  | 1.00 | 37.82 | L |
| ATOM | 2533 | O   | PHE | L | 118 | 95.007  | 37.484 | 3.574  | 1.00 | 37.82 | L |
| ATOM | 2534 | N   | PRO | L | 119 | 96.432  | 35.754 | 3.478  | 1.00 | 39.85 | L |
| ATOM | 2535 | CD  | PRO | L | 119 | 97.682  | 35.015 | 3.705  | 1.00 | 26.66 | L |
| ATOM | 2536 | CA  | PRO | L | 119 | 95.851  | 35.392 | 2.184  | 1.00 | 39.85 | L |
| ATOM | 2537 | CB  | PRO | L | 119 | 96.929  | 34.519 | 1.542  | 1.00 | 26.66 | L |
| ATOM | 2538 | CG  | PRO | L | 119 | 98.194  | 34.883 | 2.299  | 1.00 | 26.66 | L |
| ATOM | 2539 | C   | PRO | L | 119 | 94.574  | 34.610 | 2.483  | 1.00 | 39.85 | L |
| ATOM | 2540 | O   | PRO | L | 119 | 94.332  | 34.213 | 3.629  | 1.00 | 39.85 | L |
| ATOM | 2541 | N   | PRO | L | 120 | 93.745  | 34.370 | 1.461  | 1.00 | 50.90 | L |
| ATOM | 2542 | CD  | PRO | L | 120 | 93.966  | 34.753 | 0.060  | 1.00 | 28.06 | L |

TABLE 2-continued

Atomic coordinates of b2 adrenoreceptor

| ATOM | 2543 | CA  | PRO | L | 120 | 92.484 | 33.635 | 1.606  | 1.00 | 50.90 | L |
| ---- | ---- | --- | --- | - | --- | ------ | ------ | ------ | ---- | ----- | - |
| ATOM | 2544 | CB  | PRO | L | 120 | 91.941 | 33.596 | 0.176  | 1.00 | 28.06 | L |
| ATOM | 2545 | CG  | PRO | L | 120 | 92.556 | 34.783 | −0.471 | 1.00 | 28.06 | L |
| ATOM | 2546 | C   | PRO | L | 120 | 92.695 | 32.231 | 2.158  | 1.00 | 50.90 | L |
| ATOM | 2547 | O   | PRO | L | 120 | 93.477 | 31.461 | 1.605  | 1.00 | 50.90 | L |
| ATOM | 2548 | N   | SER | L | 121 | 92.000 | 31.888 | 3.237  | 1.00 | 49.95 | L |
| ATOM | 2549 | CA  | SER | L | 121 | 92.147 | 30.552 | 3.808  | 1.00 | 49.95 | L |
| ATOM | 2550 | CB  | SER | L | 121 | 91.395 | 30.420 | 5.128  | 1.00 | 50.18 | L |
| ATOM | 2551 | OG  | SER | L | 121 | 90.007 | 30.319 | 4.884  | 1.00 | 50.18 | L |
| ATOM | 2552 | C   | SER | L | 121 | 91.571 | 29.543 | 2.831  | 1.00 | 49.95 | L |
| ATOM | 2553 | O   | SER | L | 121 | 90.455 | 29.708 | 2.335  | 1.00 | 49.95 | L |
| ATOM | 2554 | N   | SER | L | 122 | 92.350 | 28.503 | 2.560  | 1.00 | 56.37 | L |
| ATOM | 2555 | CA  | SER | L | 122 | 91.963 | 27.436 | 1.657  | 1.00 | 56.37 | L |
| ATOM | 2556 | CB  | SER | L | 122 | 92.717 | 26.173 | 2.044  | 1.00 | 81.31 | L |
| ATOM | 2557 | OG  | SER | L | 122 | 92.715 | 26.027 | 3.455  | 1.00 | 81.31 | L |
| ATOM | 2558 | C   | SER | L | 122 | 90.469 | 27.191 | 1.731  | 1.00 | 56.37 | L |
| ATOM | 2559 | O   | SER | L | 122 | 89.799 | 27.066 | 0.709  | 1.00 | 56.37 | L |
| ATOM | 2560 | N   | GLU | L | 123 | 89.955 | 27.148 | 2.956  | 1.00 | 48.72 | L |
| ATOM | 2561 | CA  | GLU | L | 123 | 88.534 | 26.900 | 3.214  | 1.00 | 48.72 | L |
| ATOM | 2562 | CB  | GLU | L | 123 | 88.241 | 27.121 | 4.696  | 1.00 | 63.47 | L |
| ATOM | 2563 | CG  | GLU | L | 123 | 86.853 | 26.724 | 5.123  | 1.00 | 63.47 | L |
| ATOM | 2564 | CD  | GLU | L | 123 | 86.568 | 27.113 | 6.563  | 1.00 | 63.47 | L |
| ATOM | 2565 | OE1 | GLU | L | 123 | 87.441 | 26.873 | 7.431  | 1.00 | 63.47 | L |
| ATOM | 2566 | OE2 | GLU | L | 123 | 85.468 | 27.656 | 6.830  | 1.00 | 63.47 | L |
| ATOM | 2567 | C   | GLU | L | 123 | 87.576 | 27.743 | 2.368  | 1.00 | 48.72 | L |
| ATOM | 2568 | O   | GLU | L | 123 | 86.694 | 27.209 | 1.704  | 1.00 | 48.72 | L |
| ATOM | 2569 | N   | GLN | L | 124 | 87.747 | 29.059 | 2.401  | 1.00 | 41.81 | L |
| ATOM | 2570 | CA  | GLN | L | 124 | 86.894 | 29.954 | 1.631  | 1.00 | 41.81 | L |
| ATOM | 2571 | CB  | GLN | L | 124 | 87.202 | 31.424 | 1.967  | 1.00 | 54.41 | L |
| ATOM | 2572 | CG  | GLN | L | 124 | 86.419 | 32.457 | 1.144  | 1.00 | 54.41 | L |
| ATOM | 2573 | CD  | GLN | L | 124 | 86.888 | 33.879 | 1.392  | 1.00 | 54.41 | L |
| ATOM | 2574 | OE1 | GLN | L | 124 | 88.032 | 34.100 | 1.785  | 1.00 | 54.41 | L |
| ATOM | 2575 | NE2 | GLN | L | 124 | 86.011 | 34.851 | 1.151  | 1.00 | 54.41 | L |
| ATOM | 2576 | C   | GLN | L | 124 | 87.163 | 29.701 | 0.167  | 1.00 | 41.81 | L |
| ATOM | 2577 | O   | GLN | L | 124 | 86.240 | 29.498 | −0.617 | 1.00 | 41.81 | L |
| ATOM | 2578 | N   | LEU | L | 125 | 88.436 | 29.713 | −0.193 | 1.00 | 45.64 | L |
| ATOM | 2579 | CA  | LEU | L | 125 | 88.822 | 29.491 | −1.572 | 1.00 | 45.64 | L |
| ATOM | 2580 | CB  | LEU | L | 125 | 90.313 | 29.161 | −1.647 | 1.00 | 17.27 | L |
| ATOM | 2581 | CG  | LEU | L | 125 | 91.267 | 30.354 | −1.567 | 1.00 | 17.27 | L |
| ATOM | 2582 | CD1 | LEU | L | 125 | 92.697 | 29.907 | −1.716 | 1.00 | 17.27 | L |
| ATOM | 2583 | CD2 | LEU | L | 125 | 90.932 | 31.313 | −2.675 | 1.00 | 17.27 | L |
| ATOM | 2584 | C   | LEU | L | 125 | 88.000 | 28.380 | −2.228 | 1.00 | 45.64 | L |
| ATOM | 2585 | O   | LEU | L | 125 | 87.419 | 28.567 | −3.309 | 1.00 | 45.64 | L |
| ATOM | 2586 | N   | THR | L | 126 | 87.956 | 27.226 | −1.568 | 1.00 | 35.95 | L |
| ATOM | 2587 | CA  | THR | L | 126 | 87.208 | 26.077 | −2.059 | 1.00 | 35.95 | L |
| ATOM | 2588 | CB  | THR | L | 126 | 87.273 | 24.923 | −1.072 | 1.00 | 43.55 | L |
| ATOM | 2589 | OG1 | THR | L | 126 | 88.611 | 24.422 | −1.014 | 1.00 | 43.55 | L |
| ATOM | 2590 | CG2 | THR | L | 126 | 86.311 | 23.828 | −1.483 | 1.00 | 43.55 | L |
| ATOM | 2591 | C   | THR | L | 126 | 85.751 | 26.449 | −2.203 | 1.00 | 35.95 | L |
| ATOM | 2592 | O   | THR | L | 126 | 85.112 | 26.124 | −3.201 | 1.00 | 35.95 | L |
| ATOM | 2593 | N   | SER | L | 127 | 85.235 | 27.129 | −1.182 | 1.00 | 32.23 | L |
| ATOM | 2594 | CA  | SER | L | 127 | 83.842 | 27.547 | −1.144 | 1.00 | 32.23 | L |
| ATOM | 2595 | CB  | SER | L | 127 | 83.597 | 28.471 | 0.050  | 1.00 | 81.42 | L |
| ATOM | 2596 | OG  | SER | L | 127 | 82.255 | 28.367 | 0.498  | 1.00 | 81.42 | L |
| ATOM | 2597 | C   | SER | L | 127 | 83.429 | 28.236 | −2.434 | 1.00 | 32.23 | L |
| ATOM | 2598 | O   | SER | L | 127 | 82.386 | 27.914 | −2.996 | 1.00 | 32.23 | L |
| ATOM | 2599 | N   | GLY | L | 128 | 84.245 | 29.173 | −2.907 | 1.00 | 41.15 | L |
| ATOM | 2600 | CA  | GLY | L | 128 | 83.909 | 29.857 | −4.142 | 1.00 | 41.15 | L |
| ATOM | 2601 | C   | GLY | L | 128 | 84.640 | 31.161 | −4.419 | 1.00 | 41.15 | L |
| ATOM | 2602 | O   | GLY | L | 128 | 84.554 | 31.722 | −5.511 | 1.00 | 41.15 | L |
| ATOM | 2603 | N   | GLY | L | 129 | 85.385 | 31.654 | −3.447 | 1.00 | 20.31 | L |
| ATOM | 2604 | CA  | GLY | L | 129 | 86.065 | 32.908 | −3.669 | 1.00 | 20.31 | L |
| ATOM | 2605 | C   | GLY | L | 129 | 87.104 | 33.185 | −2.617 | 1.00 | 20.31 | L |
| ATOM | 2606 | O   | GLY | L | 129 | 87.396 | 32.333 | −1.777 | 1.00 | 20.31 | L |
| ATOM | 2607 | N   | ALA | L | 130 | 87.655 | 34.389 | −2.645 | 1.00 | 35.31 | L |
| ATOM | 2608 | CA  | ALA | L | 130 | 88.692 | 34.727 | −1.697 | 1.00 | 35.31 | L |
| ATOM | 2609 | CB  | ALA | L | 130 | 90.043 | 34.329 | −2.275 | 1.00 | 0.01  | L |
| ATOM | 2610 | C   | ALA | L | 130 | 88.700 | 36.192 | −1.290 | 1.00 | 35.31 | L |
| ATOM | 2611 | O   | ALA | L | 130 | 88.653 | 37.099 | −2.126 | 1.00 | 35.31 | L |
| ATOM | 2612 | N   | SER | L | 131 | 88.765 | 36.404 | 0.016  | 1.00 | 40.49 | L |
| ATOM | 2613 | CA  | SER | L | 131 | 88.800 | 37.741 | 0.570  | 1.00 | 40.49 | L |
| ATOM | 2614 | CB  | SER | L | 131 | 87.649 | 37.920 | 1.570  | 1.00 | 49.30 | L |
| ATOM | 2615 | OG  | SER | L | 131 | 86.429 | 37.391 | 1.068  | 1.00 | 49.30 | L |
| ATOM | 2616 | C   | SER | L | 131 | 90.144 | 37.866 | 1.281  | 1.00 | 40.49 | L |
| ATOM | 2617 | O   | SER | L | 131 | 90.588 | 36.929 | 1.944  | 1.00 | 40.49 | L |
| ATOM | 2618 | N   | VAL | L | 132 | 90.808 | 39.004 | 1.131  | 1.00 | 50.86 | L |
| ATOM | 2619 | CA  | VAL | L | 132 | 92.082 | 39.187 | 1.804  | 1.00 | 50.86 | L |
| ATOM | 2620 | CB  | VAL | L | 132 | 93.184 | 39.576 | 0.845  | 1.00 | 22.80 | L |

TABLE 2-continued

Atomic coordinates of b2 adrenoreceptor

| ATOM | 2621 | CG1 | VAL | L | 132 | 94.505 | 39.707 | 1.609 | 1.00 | 22.80 | L |
|---|---|---|---|---|---|---|---|---|---|---|---|
| ATOM | 2622 | CG2 | VAL | L | 132 | 93.276 | 38.562 | −0.262 | 1.00 | 22.80 | L |
| ATOM | 2623 | C | VAL | L | 132 | 92.004 | 40.257 | 2.877 | 1.00 | 50.86 | L |
| ATOM | 2624 | O | VAL | L | 132 | 91.481 | 41.355 | 2.664 | 1.00 | 50.86 | L |
| ATOM | 2625 | N | VAL | L | 133 | 92.557 | 39.932 | 4.032 | 1.00 | 32.28 | L |
| ATOM | 2626 | CA | VAL | L | 133 | 92.534 | 40.839 | 5.147 | 1.00 | 32.28 | L |
| ATOM | 2627 | CB | VAL | L | 133 | 91.785 | 40.196 | 6.330 | 1.00 | 37.59 | L |
| ATOM | 2628 | CG1 | VAL | L | 133 | 92.035 | 40.973 | 7.609 | 1.00 | 37.59 | L |
| ATOM | 2629 | CG2 | VAL | L | 133 | 90.303 | 40.151 | 6.026 | 1.00 | 37.59 | L |
| ATOM | 2630 | C | VAL | L | 133 | 93.906 | 41.312 | 5.605 | 1.00 | 32.28 | L |
| ATOM | 2631 | O | VAL | L | 133 | 94.861 | 40.543 | 5.716 | 1.00 | 32.28 | L |
| ATOM | 2632 | N | CYS | L | 134 | 93.972 | 42.613 | 5.854 | 1.00 | 39.12 | L |
| ATOM | 2633 | CA | CYS | L | 134 | 95.157 | 43.284 | 6.343 | 1.00 | 39.12 | L |
| ATOM | 2634 | C | CYS | L | 134 | 94.641 | 43.971 | 7.606 | 1.00 | 39.12 | L |
| ATOM | 2635 | O | CYS | L | 134 | 93.492 | 44.426 | 7.645 | 1.00 | 39.12 | L |
| ATOM | 2636 | CB | CYS | L | 134 | 95.608 | 44.315 | 5.320 | 1.00 | 49.40 | L |
| ATOM | 2637 | SG | CYS | L | 134 | 97.024 | 45.337 | 5.824 | 1.00 | 49.40 | L |
| ATOM | 2638 | N | PHE | L | 135 | 95.456 | 44.013 | 8.651 | 1.00 | 33.04 | L |
| ATOM | 2639 | CA | PHE | L | 135 | 95.042 | 44.660 | 9.892 | 1.00 | 33.04 | L |
| ATOM | 2640 | CB | PHE | L | 135 | 95.012 | 43.693 | 11.078 | 1.00 | 25.88 | L |
| ATOM | 2641 | CG | PHE | L | 135 | 93.898 | 42.701 | 11.047 | 1.00 | 25.88 | L |
| ATOM | 2642 | CD1 | PHE | L | 135 | 92.580 | 43.112 | 11.045 | 1.00 | 25.88 | L |
| ATOM | 2643 | CD2 | PHE | L | 135 | 94.172 | 41.344 | 11.069 | 1.00 | 25.88 | L |
| ATOM | 2644 | CE1 | PHE | L | 135 | 91.539 | 42.174 | 11.071 | 1.00 | 25.88 | L |
| ATOM | 2645 | CE2 | PHE | L | 135 | 93.150 | 40.400 | 11.092 | 1.00 | 25.88 | L |
| ATOM | 2646 | CZ | PHE | L | 135 | 91.833 | 40.811 | 11.094 | 1.00 | 25.88 | L |
| ATOM | 2647 | C | PHE | L | 135 | 96.041 | 45.734 | 10.241 | 1.00 | 33.04 | L |
| ATOM | 2648 | O | PHE | L | 135 | 97.212 | 45.440 | 10.483 | 1.00 | 33.04 | L |
| ATOM | 2649 | N | LEU | L | 136 | 95.591 | 46.977 | 10.262 | 1.00 | 57.75 | L |
| ATOM | 2650 | CA | LEU | L | 136 | 96.470 | 48.063 | 10.646 | 1.00 | 57.75 | L |
| ATOM | 2651 | CB | LEU | L | 136 | 96.153 | 49.314 | 9.818 | 1.00 | 15.82 | L |
| ATOM | 2652 | CG | LEU | L | 136 | 96.470 | 49.214 | 8.312 | 1.00 | 15.82 | L |
| ATOM | 2653 | CD1 | LEU | L | 136 | 97.932 | 48.835 | 8.078 | 1.00 | 15.82 | L |
| ATOM | 2654 | CD2 | LEU | L | 136 | 95.573 | 48.163 | 7.681 | 1.00 | 15.82 | L |
| ATOM | 2655 | C | LEU | L | 136 | 96.043 | 48.189 | 12.097 | 1.00 | 57.75 | L |
| ATOM | 2656 | O | LEU | L | 136 | 94.894 | 48.535 | 12.374 | 1.00 | 57.75 | L |
| ATOM | 2657 | N | ASN | L | 137 | 96.941 | 47.873 | 13.024 | 1.00 | 78.24 | L |
| ATOM | 2658 | CA | ASN | L | 137 | 96.566 | 47.889 | 14.435 | 1.00 | 78.24 | L |
| ATOM | 2659 | CB | ASN | L | 137 | 96.866 | 46.525 | 15.058 | 1.00 | 43.24 | L |
| ATOM | 2660 | CG | ASN | L | 137 | 95.877 | 45.456 | 14.639 | 1.00 | 43.24 | L |
| ATOM | 2661 | OD1 | ASN | L | 137 | 96.204 | 44.270 | 14.651 | 1.00 | 43.24 | L |
| ATOM | 2662 | ND2 | ASN | L | 137 | 94.665 | 45.866 | 14.267 | 1.00 | 43.24 | L |
| ATOM | 2663 | C | ASN | L | 137 | 97.154 | 48.953 | 15.338 | 1.00 | 78.24 | L |
| ATOM | 2664 | O | ASN | L | 137 | 97.994 | 49.750 | 14.943 | 1.00 | 78.24 | L |
| ATOM | 2665 | N | ASN | L | 138 | 96.673 | 48.922 | 16.576 | 1.00 | 40.34 | L |
| ATOM | 2666 | CA | ASN | L | 138 | 97.066 | 49.805 | 17.659 | 1.00 | 40.34 | L |
| ATOM | 2667 | CB | ASN | L | 138 | 97.800 | 48.986 | 18.714 | 1.00 | 52.35 | L |
| ATOM | 2668 | CG | ASN | L | 138 | 96.953 | 47.843 | 19.248 | 1.00 | 52.35 | L |
| ATOM | 2669 | OD1 | ASN | L | 138 | 95.914 | 48.075 | 19.871 | 1.00 | 52.35 | L |
| ATOM | 2670 | ND2 | ASN | L | 138 | 97.384 | 46.604 | 19.001 | 1.00 | 52.35 | L |
| ATOM | 2671 | C | ASN | L | 138 | 97.911 | 50.982 | 17.244 | 1.00 | 40.34 | L |
| ATOM | 2672 | O | ASN | L | 138 | 99.129 | 50.950 | 17.402 | 1.00 | 40.34 | L |
| ATOM | 2673 | N | PHE | L | 139 | 97.268 | 52.021 | 16.719 | 1.00 | 36.68 | L |
| ATOM | 2674 | CA | PHE | L | 139 | 97.986 | 53.216 | 16.292 | 1.00 | 36.35 | L |
| ATOM | 2675 | CB | PHE | L | 139 | 98.121 | 53.202 | 14.774 | 1.00 | 11.88 | L |
| ATOM | 2676 | CG | PHE | L | 139 | 96.815 | 53.144 | 14.067 | 1.00 | 13.64 | L |
| ATOM | 2677 | CD1 | PHE | L | 139 | 96.052 | 54.298 | 13.891 | 1.00 | 14.98 | L |
| ATOM | 2678 | CD2 | PHE | L | 139 | 96.308 | 51.933 | 13.613 | 1.00 | 14.38 | L |
| ATOM | 2679 | CE1 | PHE | L | 139 | 94.791 | 54.251 | 13.269 | 1.00 | 12.94 | L |
| ATOM | 2680 | CE2 | PHE | L | 139 | 95.041 | 51.873 | 12.986 | 1.00 | 10.80 | L |
| ATOM | 2681 | CZ | PHE | L | 139 | 94.286 | 53.037 | 12.816 | 1.00 | 12.23 | L |
| ATOM | 2682 | C | PHE | L | 139 | 97.300 | 54.512 | 16.748 | 1.00 | 39.48 | L |
| ATOM | 2683 | O | PHE | L | 139 | 96.087 | 54.550 | 16.936 | 1.00 | 38.42 | L |
| ATOM | 2684 | N | TYR | L | 140 | 98.094 | 55.565 | 16.935 | 1.00 | 59.82 | L |
| ATOM | 2685 | CA | TYR | L | 140 | 97.601 | 56.884 | 17.349 | 1.00 | 63.21 | L |
| ATOM | 2686 | CB | TYR | L | 140 | 97.605 | 57.009 | 18.882 | 1.00 | 72.87 | L |
| ATOM | 2687 | CG | TYR | L | 140 | 97.094 | 58.343 | 19.410 | 1.00 | 77.70 | L |
| ATOM | 2688 | CD1 | TYR | L | 140 | 97.677 | 59.545 | 19.011 | 1.00 | 81.04 | L |
| ATOM | 2689 | CE1 | TYR | L | 140 | 97.195 | 60.769 | 19.456 | 1.00 | 81.67 | L |
| ATOM | 2690 | CD2 | TYR | L | 140 | 96.011 | 58.403 | 20.282 | 1.00 | 75.96 | L |
| ATOM | 2691 | CE2 | TYR | L | 140 | 95.520 | 59.626 | 20.737 | 1.00 | 76.76 | L |
| ATOM | 2692 | CZ | TYR | L | 140 | 96.117 | 60.806 | 20.317 | 1.00 | 78.86 | L |
| ATOM | 2693 | OH | TYR | L | 140 | 95.642 | 62.028 | 20.745 | 1.00 | 78.57 | L |
| ATOM | 2694 | C | TYR | L | 140 | 98.553 | 57.920 | 16.743 | 1.00 | 64.53 | L |
| ATOM | 2695 | O | TYR | L | 140 | 99.778 | 57.768 | 16.839 | 1.00 | 67.16 | L |
| ATOM | 2696 | N | PRO | L | 141 | 98.018 | 59.005 | 16.144 | 1.00 | 26.51 | L |
| ATOM | 2697 | CD | PRO | L | 141 | 98.991 | 59.996 | 15.656 | 1.00 | 34.01 | L |
| ATOM | 2698 | CA | PRO | L | 141 | 96.644 | 59.484 | 15.902 | 1.00 | 27.42 | L |

TABLE 2-continued

Atomic coordinates of b2 adrenoreceptor

| ATOM | 2699 | CB | PRO | L | 141 | 96.857 | 60.738 | 15.063 | 1.00 | 33.55 | L |
|---|---|---|---|---|---|---|---|---|---|---|---|
| ATOM | 2700 | CG | PRO | L | 141 | 98.153 | 61.248 | 15.587 | 1.00 | 31.31 | L |
| ATOM | 2701 | C | PRO | L | 141 | 95.663 | 58.552 | 15.220 | 1.00 | 30.03 | L |
| ATOM | 2702 | O | PRO | L | 141 | 96.045 | 57.586 | 14.562 | 1.00 | 30.55 | L |
| ATOM | 2703 | N | LYS | L | 142 | 94.384 | 58.884 | 15.357 | 1.00 | 33.86 | L |
| ATOM | 2704 | CA | LYS | L | 142 | 93.345 | 58.092 | 14.750 | 1.00 | 36.05 | L |
| ATOM | 2705 | CB | LYS | L | 142 | 91.958 | 58.617 | 15.134 | 1.00 | 58.99 | L |
| ATOM | 2706 | CG | LYS | L | 142 | 90.861 | 57.603 | 14.823 | 1.00 | 65.21 | L |
| ATOM | 2707 | CD | LYS | L | 142 | 89.434 | 58.063 | 15.129 | 1.00 | 70.82 | L |
| ATOM | 2708 | CE | LYS | L | 142 | 88.444 | 56.958 | 14.715 | 1.00 | 73.52 | L |
| ATOM | 2709 | NZ | LYS | L | 142 | 87.016 | 57.248 | 15.035 | 1.00 | 73.44 | L |
| ATOM | 2710 | C | LYS | L | 142 | 93.494 | 58.088 | 13.233 | 1.00 | 32.93 | L |
| ATOM | 2711 | O | LYS | L | 142 | 93.298 | 57.051 | 12.609 | 1.00 | 32.32 | L |
| ATOM | 2712 | N | ASP | L | 143 | 93.848 | 59.228 | 12.635 | 1.00 | 50.02 | L |
| ATOM | 2713 | CA | ASP | L | 143 | 93.996 | 59.302 | 11.175 | 1.00 | 50.02 | L |
| ATOM | 2714 | CB | ASP | L | 143 | 94.303 | 60.738 | 10.741 | 1.00 | 148.45 | L |
| ATOM | 2715 | CG | ASP | L | 143 | 94.330 | 60.896 | 9.231 | 1.00 | 148.45 | L |
| ATOM | 2716 | OD1 | ASP | L | 143 | 95.237 | 60.329 | 8.588 | 1.00 | 148.45 | L |
| ATOM | 2717 | OD2 | ASP | L | 143 | 93.443 | 61.584 | 8.685 | 1.00 | 148.45 | L |
| ATOM | 2718 | C | ASP | L | 143 | 95.081 | 58.349 | 10.649 | 1.00 | 50.02 | L |
| ATOM | 2719 | O | ASP | L | 143 | 96.283 | 58.550 | 10.872 | 1.00 | 50.02 | L |
| ATOM | 2720 | N | ILE | L | 144 | 94.626 | 57.314 | 9.941 | 1.00 | 61.97 | L |
| ATOM | 2721 | CA | ILE | L | 144 | 95.487 | 56.279 | 9.371 | 1.00 | 61.97 | L |
| ATOM | 2722 | CB | ILE | L | 144 | 95.160 | 54.916 | 10.037 | 1.00 | 49.19 | L |
| ATOM | 2723 | CG2 | ILE | L | 144 | 94.156 | 54.157 | 9.202 | 1.00 | 49.19 | L |
| ATOM | 2724 | CG1 | ILE | L | 144 | 96.449 | 54.134 | 10.336 | 1.00 | 49.19 | L |
| ATOM | 2725 | CD1 | ILE | L | 144 | 97.271 | 53.748 | 9.145 | 1.00 | 49.19 | L |
| ATOM | 2726 | C | ILE | L | 144 | 95.215 | 56.233 | 7.862 | 1.00 | 61.97 | L |
| ATOM | 2727 | O | ILE | L | 144 | 94.426 | 57.026 | 7.368 | 1.00 | 61.97 | L |
| ATOM | 2728 | N | ASN | L | 145 | 95.850 | 55.322 | 7.128 | 1.00 | 62.86 | L |
| ATOM | 2729 | CA | ASN | L | 145 | 95.632 | 55.249 | 5.678 | 1.00 | 62.86 | L |
| ATOM | 2730 | CB | ASN | L | 145 | 96.248 | 56.479 | 5.012 | 1.00 | 70.85 | L |
| ATOM | 2731 | CG | ASN | L | 145 | 95.681 | 56.742 | 3.640 | 1.00 | 70.85 | L |
| ATOM | 2732 | OD1 | ASN | L | 145 | 94.687 | 57.453 | 3.499 | 1.00 | 70.85 | L |
| ATOM | 2733 | ND2 | ASN | L | 145 | 96.300 | 56.163 | 2.617 | 1.00 | 70.85 | L |
| ATOM | 2734 | C | ASN | L | 145 | 96.214 | 53.987 | 5.021 | 1.00 | 62.86 | L |
| ATOM | 2735 | O | ASN | L | 145 | 97.338 | 53.576 | 5.338 | 1.00 | 62.86 | L |
| ATOM | 2736 | N | VAL | L | 146 | 95.456 | 53.388 | 4.098 | 1.00 | 55.65 | L |
| ATOM | 2737 | CA | VAL | L | 146 | 95.905 | 52.180 | 3.387 | 1.00 | 55.65 | L |
| ATOM | 2738 | CB | VAL | L | 146 | 95.230 | 50.909 | 3.884 | 1.00 | 19.22 | L |
| ATOM | 2739 | CG1 | VAL | L | 146 | 95.654 | 50.626 | 5.296 | 1.00 | 19.22 | L |
| ATOM | 2740 | CG2 | VAL | L | 146 | 93.729 | 51.052 | 3.795 | 1.00 | 19.22 | L |
| ATOM | 2741 | C | VAL | L | 146 | 95.618 | 52.197 | 1.908 | 1.00 | 55.65 | L |
| ATOM | 2742 | O | VAL | L | 146 | 94.674 | 52.842 | 1.456 | 1.00 | 55.65 | L |
| ATOM | 2743 | N | LYS | L | 147 | 96.435 | 51.466 | 1.161 | 1.00 | 57.30 | L |
| ATOM | 2744 | CA | LYS | L | 147 | 96.261 | 51.350 | −0.277 | 1.00 | 57.30 | L |
| ATOM | 2745 | CB | LYS | L | 147 | 97.065 | 52.419 | −1.030 | 1.00 | 110.48 | L |
| ATOM | 2746 | CG | LYS | L | 147 | 98.574 | 52.295 | −0.916 | 1.00 | 110.48 | L |
| ATOM | 2747 | CD | LYS | L | 147 | 99.276 | 53.390 | −1.726 | 1.00 | 110.48 | L |
| ATOM | 2748 | CE | LYS | L | 147 | 100.799 | 53.242 | −1.682 | 1.00 | 110.48 | L |
| ATOM | 2749 | NZ | LYS | L | 147 | 101.542 | 54.294 | −2.443 | 1.00 | 110.48 | L |
| ATOM | 2750 | C | LYS | L | 147 | 96.749 | 49.963 | −0.634 | 1.00 | 57.30 | L |
| ATOM | 2751 | O | LYS | L | 147 | 97.821 | 49.543 | −0.195 | 1.00 | 57.30 | L |
| ATOM | 2752 | N | TRP | L | 148 | 95.942 | 49.238 | −1.397 | 1.00 | 47.61 | L |
| ATOM | 2753 | CA | TRP | L | 148 | 96.303 | 47.892 | −1.806 | 1.00 | 47.61 | L |
| ATOM | 2754 | CB | TRP | L | 148 | 95.048 | 47.066 | −2.078 | 1.00 | 41.30 | L |
| ATOM | 2755 | CG | TRP | L | 148 | 94.356 | 46.591 | −0.847 | 1.00 | 41.30 | L |
| ATOM | 2756 | CD2 | TRP | L | 148 | 94.722 | 45.458 | −0.051 | 1.00 | 41.30 | L |
| ATOM | 2757 | CE2 | TRP | L | 148 | 93.813 | 45.394 | 1.022 | 1.00 | 41.30 | L |
| ATOM | 2758 | CE3 | TRP | L | 148 | 95.734 | 44.490 | −0.141 | 1.00 | 41.30 | L |
| ATOM | 2759 | CD1 | TRP | L | 148 | 93.268 | 47.152 | −0.244 | 1.00 | 41.30 | L |
| ATOM | 2760 | NE1 | TRP | L | 148 | 92.936 | 46.440 | 0.879 | 1.00 | 41.30 | L |
| ATOM | 2761 | CZ2 | TRP | L | 148 | 93.882 | 44.394 | 2.003 | 1.00 | 41.30 | L |
| ATOM | 2762 | CZ3 | TRP | L | 148 | 95.801 | 43.500 | 0.830 | 1.00 | 41.30 | L |
| ATOM | 2763 | CH2 | TRP | L | 148 | 94.882 | 43.460 | 1.888 | 1.00 | 41.30 | L |
| ATOM | 2764 | C | TRP | L | 148 | 97.154 | 47.911 | −3.065 | 1.00 | 47.61 | L |
| ATOM | 2765 | O | TRP | L | 148 | 96.920 | 48.708 | −3.969 | 1.00 | 47.61 | L |
| ATOM | 2766 | N | LYS | L | 149 | 98.156 | 47.045 | −3.121 | 1.00 | 74.10 | L |
| ATOM | 2767 | CA | LYS | L | 149 | 98.993 | 46.958 | −4.304 | 1.00 | 74.10 | L |
| ATOM | 2768 | CB | LYS | L | 149 | 100.414 | 47.429 | −4.022 | 1.00 | 63.89 | L |
| ATOM | 2769 | CG | LYS | L | 149 | 100.681 | 48.882 | −4.371 | 1.00 | 63.89 | L |
| ATOM | 2770 | CD | LYS | L | 149 | 102.184 | 49.118 | −4.450 | 1.00 | 63.89 | L |
| ATOM | 2771 | CE | LYS | L | 149 | 102.525 | 50.569 | −4.710 | 1.00 | 63.89 | L |
| ATOM | 2772 | NZ | LYS | L | 149 | 103.995 | 50.718 | −4.853 | 1.00 | 63.89 | L |
| ATOM | 2773 | C | LYS | L | 149 | 99.006 | 45.512 | −4.756 | 1.00 | 74.10 | L |
| ATOM | 2774 | O | LYS | L | 149 | 99.178 | 44.592 | −3.953 | 1.00 | 74.10 | L |
| ATOM | 2775 | N | ILE | L | 150 | 98.823 | 45.320 | −6.055 | 1.00 | 64.92 | L |
| ATOM | 2776 | CA | ILE | L | 150 | 98.778 | 43.988 | −6.627 | 1.00 | 64.92 | L |

TABLE 2-continued

Atomic coordinates of b2 adrenoreceptor

| ATOM | 2777 | CB  | ILE | L | 150 | 97.342  | 43.649 | -6.989  | 1.00 | 2.81   | L |
|------|------|-----|-----|---|-----|---------|--------|---------|------|--------|---|
| ATOM | 2778 | CG2 | ILE | L | 150 | 97.252  | 42.224 | -7.425  | 1.00 | 2.81   | L |
| ATOM | 2779 | CG1 | ILE | L | 150 | 96.440  | 43.895 | -5.779  | 1.00 | 2.81   | L |
| ATOM | 2780 | CD1 | ILE | L | 150 | 94.991  | 43.501 | -6.002  | 1.00 | 2.81   | L |
| ATOM | 2781 | C   | ILE | L | 150 | 99.653  | 43.866 | -7.871  | 1.00 | 64.92  | L |
| ATOM | 2782 | O   | ILE | L | 150 | 99.378  | 44.489 | -8.895  | 1.00 | 64.92  | L |
| ATOM | 2783 | N   | ASP | L | 151 | 100.693 | 43.044 | -7.784  | 1.00 | 83.03  | L |
| ATOM | 2784 | CA  | ASP | L | 151 | 101.620 | 42.866 | -8.897  | 1.00 | 83.03  | L |
| ATOM | 2785 | CB  | ASP | L | 151 | 100.922 | 42.265 | -10.116 | 1.00 | 72.92  | L |
| ATOM | 2786 | CG  | ASP | L | 151 | 100.590 | 40.807 | -9.938  | 1.00 | 72.92  | L |
| ATOM | 2787 | OD1 | ASP | L | 151 | 101.485 | 40.036 | -9.520  | 1.00 | 72.92  | L |
| ATOM | 2788 | OD2 | ASP | L | 151 | 99.437  | 40.430 | -10.233 | 1.00 | 72.92  | L |
| ATOM | 2789 | C   | ASP | L | 151 | 102.185 | 44.222 | -9.272  | 1.00 | 83.03  | L |
| ATOM | 2790 | O   | ASP | L | 151 | 102.226 | 44.587 | -10.447 | 1.00 | 83.03  | L |
| ATOM | 2791 | N   | GLY | L | 152 | 102.615 | 44.971 | -8.263  | 1.00 | 83.25  | L |
| ATOM | 2792 | CA  | GLY | L | 152 | 103.170 | 46.284 | -8.515  | 1.00 | 83.25  | L |
| ATOM | 2793 | C   | GLY | L | 152 | 102.062 | 47.280 | -8.771  | 1.00 | 83.25  | L |
| ATOM | 2794 | O   | GLY | L | 152 | 102.122 | 48.422 | -8.314  | 1.00 | 83.25  | L |
| ATOM | 2795 | N   | SER | L | 153 | 101.041 | 46.846 | -9.503  | 1.00 | 81.30  | L |
| ATOM | 2796 | CA  | SER | L | 153 | 99.916  | 47.714 | -9.811  | 1.00 | 81.30  | L |
| ATOM | 2797 | CB  | SER | L | 153 | 98.855  | 46.951 | -10.609 | 1.00 | 176.21 | L |
| ATOM | 2798 | OG  | SER | L | 153 | 97.826  | 47.819 | -11.047 | 1.00 | 176.21 | L |
| ATOM | 2799 | C   | SER | L | 153 | 99.323  | 48.234 | -8.506  | 1.00 | 81.30  | L |
| ATOM | 2800 | O   | SER | L | 153 | 99.902  | 48.051 | -7.435  | 1.00 | 81.30  | L |
| ATOM | 2801 | N   | GLU | L | 154 | 98.168  | 48.878 | -8.588  | 1.00 | 59.59  | L |
| ATOM | 2802 | CA  | GLU | L | 154 | 97.557  | 49.411 | -7.388  | 1.00 | 59.59  | L |
| ATOM | 2803 | CB  | GLU | L | 154 | 98.392  | 50.594 | -6.882  | 1.00 | 80.26  | L |
| ATOM | 2804 | CG  | GLU | L | 154 | 97.746  | 51.960 | -7.002  | 1.00 | 80.26  | L |
| ATOM | 2805 | CD  | GLU | L | 154 | 96.982  | 52.348 | -5.748  | 1.00 | 80.26  | L |
| ATOM | 2806 | OE1 | GLU | L | 154 | 96.155  | 51.531 | -5.291  | 1.00 | 80.26  | L |
| ATOM | 2807 | OE2 | GLU | L | 154 | 97.209  | 53.468 | -5.226  | 1.00 | 80.26  | L |
| ATOM | 2808 | C   | GLU | L | 154 | 96.131  | 49.831 | -7.676  | 1.00 | 59.59  | L |
| ATOM | 2809 | O   | GLU | L | 154 | 95.851  | 50.394 | -8.734  | 1.00 | 59.59  | L |
| ATOM | 2810 | N   | ARG | L | 155 | 95.235  | 49.542 | -6.732  | 1.00 | 80.57  | L |
| ATOM | 2811 | CA  | ARG | L | 155 | 93.822  | 49.882 | -6.875  | 1.00 | 80.57  | L |
| ATOM | 2812 | CB  | ARG | L | 155 | 93.170  | 49.008 | -7.948  | 1.00 | 124.08 | L |
| ATOM | 2813 | CG  | ARG | L | 155 | 91.791  | 49.472 | -8.357  | 1.00 | 124.08 | L |
| ATOM | 2814 | CD  | ARG | L | 155 | 91.183  | 48.491 | -9.312  | 1.00 | 124.08 | L |
| ATOM | 2815 | NE  | ARG | L | 155 | 89.959  | 49.002 | -9.909  | 1.00 | 124.08 | L |
| ATOM | 2816 | CZ  | ARG | L | 155 | 89.268  | 48.354 | -10.840 | 1.00 | 124.08 | L |
| ATOM | 2817 | NH1 | ARG | L | 155 | 89.688  | 47.170 | -11.271 | 1.00 | 124.08 | L |
| ATOM | 2818 | NH2 | ARG | L | 155 | 88.165  | 48.888 | -11.348 | 1.00 | 124.08 | L |
| ATOM | 2819 | C   | ARG | L | 155 | 93.016  | 49.766 | -5.580  | 1.00 | 80.57  | L |
| ATOM | 2820 | O   | ARG | L | 155 | 93.398  | 49.070 | -4.635  | 1.00 | 80.57  | L |
| ATOM | 2821 | N   | GLN | L | 156 | 91.883  | 50.459 | -5.577  | 1.00 | 122.22 | L |
| ATOM | 2822 | CA  | GLN | L | 156 | 90.971  | 50.515 | -4.445  | 1.00 | 122.22 | L |
| ATOM | 2823 | CB  | GLN | L | 156 | 91.072  | 51.901 | -3.798  | 1.00 | 109.36 | L |
| ATOM | 2824 | CG  | GLN | L | 156 | 91.043  | 53.050 | -4.809  | 1.00 | 109.36 | L |
| ATOM | 2825 | CD  | GLN | L | 156 | 91.955  | 54.207 | -4.425  | 1.00 | 109.36 | L |
| ATOM | 2826 | OE1 | GLN | L | 156 | 92.649  | 54.161 | -3.410  | 1.00 | 109.36 | L |
| ATOM | 2827 | NE2 | GLN | L | 156 | 91.960  | 55.248 | -5.244  | 1.00 | 109.36 | L |
| ATOM | 2828 | C   | GLN | L | 156 | 89.546  | 50.245 | -4.921  | 1.00 | 122.22 | L |
| ATOM | 2829 | O   | GLN | L | 156 | 88.658  | 51.089 | -4.802  | 1.00 | 122.22 | L |
| ATOM | 2830 | N   | ASN | L | 157 | 89.337  | 49.055 | -5.462  | 1.00 | 57.03  | L |
| ATOM | 2831 | CA  | ASN | L | 157 | 88.035  | 48.670 | -5.972  | 1.00 | 57.03  | L |
| ATOM | 2832 | CB  | ASN | L | 157 | 88.154  | 48.349 | -7.472  | 1.00 | 101.67 | L |
| ATOM | 2833 | CG  | ASN | L | 157 | 86.826  | 47.943 | -8.106  | 1.00 | 101.67 | L |
| ATOM | 2834 | OD1 | ASN | L | 157 | 86.700  | 47.906 | -9.331  | 1.00 | 101.67 | L |
| ATOM | 2835 | ND2 | ASN | L | 157 | 85.835  | 47.627 | -7.277  | 1.00 | 101.67 | L |
| ATOM | 2836 | C   | ASN | L | 157 | 87.486  | 47.466 | -5.207  | 1.00 | 57.03  | L |
| ATOM | 2837 | O   | ASN | L | 157 | 88.027  | 46.360 | -5.297  | 1.00 | 57.03  | L |
| ATOM | 2838 | N   | GLY | L | 158 | 86.415  | 47.690 | -4.449  | 1.00 | 76.23  | L |
| ATOM | 2839 | CA  | GLY | L | 158 | 85.797  | 46.608 | -3.701  | 1.00 | 76.23  | L |
| ATOM | 2840 | C   | GLY | L | 158 | 86.494  | 46.245 | -2.410  | 1.00 | 76.23  | L |
| ATOM | 2841 | O   | GLY | L | 158 | 86.525  | 45.079 | -2.013  | 1.00 | 76.23  | L |
| ATOM | 2842 | N   | VAL | L | 159 | 87.060  | 47.251 | -1.757  | 1.00 | 38.91  | L |
| ATOM | 2843 | CA  | VAL | L | 159 | 87.751  | 47.054 | -0.488  | 1.00 | 38.91  | L |
| ATOM | 2844 | CB  | VAL | L | 159 | 89.020  | 47.952 | -0.399  | 1.00 | 42.90  | L |
| ATOM | 2845 | CG1 | VAL | L | 159 | 89.746  | 47.713 | 0.908   | 1.00 | 42.90  | L |
| ATOM | 2846 | CG2 | VAL | L | 159 | 89.943  | 47.677 | -1.573  | 1.00 | 42.90  | L |
| ATOM | 2847 | C   | VAL | L | 159 | 86.770  | 47.442 | 0.620   | 1.00 | 38.91  | L |
| ATOM | 2848 | O   | VAL | L | 159 | 86.101  | 48.477 | 0.537   | 1.00 | 38.91  | L |
| ATOM | 2849 | N   | LEU | L | 160 | 86.660  | 46.602 | 1.640   | 1.00 | 32.50  | L |
| ATOM | 2850 | CA  | LEU | L | 160 | 85.752  | 46.878 | 2.751   | 1.00 | 32.50  | L |
| ATOM | 2851 | CB  | LEU | L | 160 | 84.906  | 45.641 | 3.080   | 1.00 | 45.15  | L |
| ATOM | 2852 | CG  | LEU | L | 160 | 83.922  | 45.766 | 4.251   | 1.00 | 45.15  | L |
| ATOM | 2853 | CD1 | LEU | L | 160 | 82.959  | 44.592 | 4.228   | 1.00 | 45.15  | L |
| ATOM | 2854 | CD2 | LEU | L | 160 | 84.671  | 45.816 | 5.580   | 1.00 | 45.15  | L |

TABLE 2-continued

Atomic coordinates of b2 adrenoreceptor

| ATOM | 2855 | C | LEU | L | 160 | 86.546 | 47.315 | 3.979 | 1.00 | 32.50 | L |
|---|---|---|---|---|---|---|---|---|---|---|---|
| ATOM | 2856 | O | LEU | L | 160 | 87.261 | 46.513 | 4.615 | 1.00 | 32.50 | L |
| ATOM | 2857 | N | ASN | L | 161 | 86.410 | 48.595 | 4.311 | 1.00 | 29.56 | L |
| ATOM | 2858 | CA | ASN | L | 161 | 87.121 | 49.144 | 5.448 | 1.00 | 29.56 | L |
| ATOM | 2859 | CB | ASN | L | 161 | 87.875 | 50.410 | 5.038 | 1.00 | 72.78 | L |
| ATOM | 2860 | CG | ASN | L | 161 | 89.004 | 50.119 | 4.066 | 1.00 | 72.78 | L |
| ATOM | 2861 | OD1 | ASN | L | 161 | 89.791 | 50.996 | 3.723 | 1.00 | 72.78 | L |
| ATOM | 2862 | ND2 | ASN | L | 161 | 89.085 | 48.873 | 3.618 | 1.00 | 72.78 | L |
| ATOM | 2863 | C | ASN | L | 161 | 86.252 | 49.413 | 6.666 | 1.00 | 29.56 | L |
| ATOM | 2864 | O | ASN | L | 161 | 85.029 | 49.550 | 6.578 | 1.00 | 29.56 | L |
| ATOM | 2865 | N | SER | L | 162 | 86.916 | 49.470 | 7.812 | 1.00 | 9.46 | L |
| ATOM | 2866 | CA | SER | L | 162 | 86.258 | 49.702 | 9.073 | 1.00 | 9.46 | L |
| ATOM | 2867 | CB | SER | L | 162 | 85.470 | 48.460 | 9.463 | 1.00 | 40.81 | L |
| ATOM | 2868 | OG | SER | L | 162 | 84.788 | 48.669 | 10.679 | 1.00 | 40.81 | L |
| ATOM | 2869 | C | SER | L | 162 | 87.345 | 50.005 | 10.107 | 1.00 | 9.46 | L |
| ATOM | 2870 | O | SER | L | 162 | 88.446 | 49.422 | 10.074 | 1.00 | 9.46 | L |
| ATOM | 2871 | N | TRP | L | 163 | 87.041 | 50.937 | 11.009 | 1.00 | 46.61 | L |
| ATOM | 2872 | CA | TRP | L | 163 | 87.967 | 51.339 | 12.064 | 1.00 | 46.61 | L |
| ATOM | 2873 | CB | TRP | L | 163 | 88.330 | 52.822 | 11.919 | 1.00 | 36.35 | L |
| ATOM | 2874 | CG | TRP | L | 163 | 88.636 | 53.236 | 10.543 | 1.00 | 36.35 | L |
| ATOM | 2875 | CD2 | TRP | L | 163 | 87.697 | 53.482 | 9.499 | 1.00 | 36.35 | L |
| ATOM | 2876 | CE2 | TRP | L | 163 | 88.435 | 53.736 | 8.317 | 1.00 | 36.35 | L |
| ATOM | 2877 | CE3 | TRP | L | 163 | 86.303 | 53.509 | 9.440 | 1.00 | 36.35 | L |
| ATOM | 2878 | CD1 | TRP | L | 163 | 89.870 | 53.355 | 9.984 | 1.00 | 36.35 | L |
| ATOM | 2879 | NE1 | TRP | L | 163 | 89.762 | 53.653 | 8.640 | 1.00 | 36.35 | L |
| ATOM | 2880 | CZ2 | TRP | L | 163 | 87.831 | 54.007 | 7.094 | 1.00 | 36.35 | L |
| ATOM | 2881 | CZ3 | TRP | L | 163 | 85.697 | 53.781 | 8.216 | 1.00 | 36.35 | L |
| ATOM | 2882 | CH2 | TRP | L | 163 | 86.467 | 54.025 | 7.060 | 1.00 | 36.35 | L |
| ATOM | 2883 | C | TRP | L | 163 | 87.238 | 51.152 | 13.390 | 1.00 | 46.61 | L |
| ATOM | 2884 | O | TRP | L | 163 | 86.007 | 51.117 | 13.430 | 1.00 | 46.61 | L |
| ATOM | 2885 | N | THR | L | 164 | 87.988 | 51.055 | 14.478 | 1.00 | 54.19 | L |
| ATOM | 2886 | CA | THR | L | 164 | 87.362 | 50.898 | 15.781 | 1.00 | 54.19 | L |
| ATOM | 2887 | CB | THR | L | 164 | 87.993 | 49.702 | 16.581 | 1.00 | 20.99 | L |
| ATOM | 2888 | OG1 | THR | L | 164 | 89.290 | 50.058 | 17.089 | 1.00 | 20.99 | L |
| ATOM | 2889 | CG2 | THR | L | 164 | 88.127 | 48.485 | 15.673 | 1.00 | 20.99 | L |
| ATOM | 2890 | C | THR | L | 164 | 87.493 | 52.190 | 16.591 | 1.00 | 54.19 | L |
| ATOM | 2891 | O | THR | L | 164 | 88.300 | 53.070 | 16.254 | 1.00 | 54.19 | L |
| ATOM | 2892 | N | ASP | L | 165 | 86.672 | 52.307 | 17.637 | 1.00 | 23.76 | L |
| ATOM | 2893 | CA | ASP | L | 165 | 86.707 | 53.461 | 18.525 | 1.00 | 23.76 | L |
| ATOM | 2894 | CB | ASP | L | 165 | 85.441 | 53.514 | 19.378 | 1.00 | 97.05 | L |
| ATOM | 2895 | CG | ASP | L | 165 | 84.215 | 53.902 | 18.568 | 1.00 | 97.05 | L |
| ATOM | 2896 | OD1 | ASP | L | 165 | 84.213 | 55.010 | 17.993 | 1.00 | 97.05 | L |
| ATOM | 2897 | OD2 | ASP | L | 165 | 83.256 | 53.104 | 18.500 | 1.00 | 97.05 | L |
| ATOM | 2898 | C | ASP | L | 165 | 87.947 | 53.271 | 19.383 | 1.00 | 23.76 | L |
| ATOM | 2899 | O | ASP | L | 165 | 88.653 | 52.281 | 19.231 | 1.00 | 23.76 | L |
| ATOM | 2900 | N | GLN | L | 166 | 88.232 | 54.207 | 20.273 | 1.00 | 47.09 | L |
| ATOM | 2901 | CA | GLN | L | 166 | 89.425 | 54.084 | 21.103 | 1.00 | 47.09 | L |
| ATOM | 2902 | CB | GLN | L | 166 | 89.587 | 55.344 | 21.956 | 1.00 | 66.70 | L |
| ATOM | 2903 | CG | GLN | L | 166 | 90.951 | 55.504 | 22.615 | 1.00 | 66.70 | L |
| ATOM | 2904 | CD | GLN | L | 166 | 91.402 | 56.949 | 22.617 | 1.00 | 66.70 | L |
| ATOM | 2905 | OE1 | GLN | L | 166 | 90.583 | 57.858 | 22.484 | 1.00 | 66.70 | L |
| ATOM | 2906 | NE2 | GLN | L | 166 | 92.705 | 57.170 | 22.769 | 1.00 | 66.70 | L |
| ATOM | 2907 | C | GLN | L | 166 | 89.418 | 52.836 | 21.990 | 1.00 | 47.09 | L |
| ATOM | 2908 | O | GLN | L | 166 | 88.506 | 52.637 | 22.793 | 1.00 | 47.09 | L |
| ATOM | 2909 | N | ASP | L | 167 | 90.440 | 51.999 | 21.824 | 1.00 | 63.51 | L |
| ATOM | 2910 | CA | ASP | L | 167 | 90.578 | 50.768 | 22.598 | 1.00 | 63.51 | L |
| ATOM | 2911 | CB | ASP | L | 167 | 91.833 | 50.005 | 22.172 | 1.00 | 99.28 | L |
| ATOM | 2912 | CG | ASP | L | 167 | 92.289 | 49.001 | 23.216 | 1.00 | 99.28 | L |
| ATOM | 2913 | OD1 | ASP | L | 167 | 91.494 | 48.107 | 23.576 | 1.00 | 99.28 | L |
| ATOM | 2914 | OD2 | ASP | L | 167 | 93.447 | 49.108 | 23.675 | 1.00 | 99.28 | L |
| ATOM | 2915 | C | ASP | L | 167 | 90.674 | 51.101 | 24.072 | 1.00 | 63.51 | L |
| ATOM | 2916 | O | ASP | L | 167 | 91.124 | 52.188 | 24.434 | 1.00 | 63.51 | L |
| ATOM | 2917 | N | SER | L | 168 | 90.260 | 50.158 | 24.915 | 1.00 | 76.46 | L |
| ATOM | 2918 | CA | SER | L | 168 | 90.284 | 50.354 | 26.359 | 1.00 | 76.46 | L |
| ATOM | 2919 | CB | SER | L | 168 | 89.557 | 49.211 | 27.069 | 1.00 | 49.67 | L |
| ATOM | 2920 | OG | SER | L | 168 | 88.171 | 49.220 | 26.770 | 1.00 | 49.67 | L |
| ATOM | 2921 | C | SER | L | 168 | 91.690 | 50.479 | 26.912 | 1.00 | 76.46 | L |
| ATOM | 2922 | O | SER | L | 168 | 92.123 | 51.573 | 27.257 | 1.00 | 76.46 | L |
| ATOM | 2923 | N | LYS | L | 169 | 92.412 | 49.368 | 26.995 | 1.00 | 48.60 | L |
| ATOM | 2924 | CA | LYS | L | 169 | 93.765 | 49.416 | 27.544 | 1.00 | 48.60 | L |
| ATOM | 2925 | CB | LYS | L | 169 | 94.454 | 48.038 | 27.487 | 1.00 | 75.61 | L |
| ATOM | 2926 | CG | LYS | L | 169 | 93.572 | 46.835 | 27.771 | 1.00 | 75.61 | L |
| ATOM | 2927 | CD | LYS | L | 169 | 92.656 | 46.553 | 26.592 | 1.00 | 75.61 | L |
| ATOM | 2928 | CE | LYS | L | 169 | 91.706 | 45.415 | 26.891 | 1.00 | 75.61 | L |
| ATOM | 2929 | NZ | LYS | L | 169 | 90.611 | 45.345 | 25.887 | 1.00 | 75.61 | L |
| ATOM | 2930 | C | LYS | L | 169 | 94.619 | 50.412 | 26.765 | 1.00 | 48.60 | L |
| ATOM | 2931 | O | LYS | L | 169 | 94.831 | 51.551 | 27.186 | 1.00 | 48.60 | L |
| ATOM | 2932 | N | ASP | L | 170 | 95.084 | 49.959 | 25.609 | 1.00 | 70.36 | L |

TABLE 2-continued

Atomic coordinates of b2 adrenoreceptor

| ATOM | 2933 | CA  | ASP | L | 170 | 95.949 | 50.735 | 24.746 | 1.00 | 70.36  | L |
| ---- | ---- | --- | --- | - | --- | ------ | ------ | ------ | ---- | ------ | - |
| ATOM | 2934 | CB  | ASP | L | 170 | 96.260 | 49.930 | 23.493 | 1.00 | 98.45  | L |
| ATOM | 2935 | CG  | ASP | L | 170 | 97.549 | 50.352 | 22.860 | 1.00 | 98.45  | L |
| ATOM | 2936 | OD1 | ASP | L | 170 | 98.573 | 50.353 | 23.574 | 1.00 | 98.45  | L |
| ATOM | 2937 | OD2 | ASP | L | 170 | 97.551 | 50.683 | 21.663 | 1.00 | 98.45  | L |
| ATOM | 2938 | C   | ASP | L | 170 | 95.484 | 52.123 | 24.335 | 1.00 | 70.36  | L |
| ATOM | 2939 | O   | ASP | L | 170 | 96.276 | 52.886 | 23.791 | 1.00 | 70.36  | L |
| ATOM | 2940 | N   | SER | L | 171 | 94.220 | 52.457 | 24.590 | 1.00 | 48.61  | L |
| ATOM | 2941 | CA  | SER | L | 171 | 93.688 | 53.770 | 24.208 | 1.00 | 48.61  | L |
| ATOM | 2942 | CB  | SER | L | 171 | 93.983 | 54.793 | 25.309 | 1.00 | 29.41  | L |
| ATOM | 2943 | OG  | SER | L | 171 | 95.320 | 54.677 | 25.767 | 1.00 | 29.41  | L |
| ATOM | 2944 | C   | SER | L | 171 | 94.295 | 54.211 | 22.862 | 1.00 | 48.61  | L |
| ATOM | 2945 | O   | SER | L | 171 | 94.706 | 55.368 | 22.669 | 1.00 | 48.61  | L |
| ATOM | 2946 | N   | THR | L | 172 | 94.334 | 53.252 | 21.939 | 1.00 | 48.07  | L |
| ATOM | 2947 | CA  | THR | L | 172 | 94.878 | 53.437 | 20.603 | 1.00 | 48.07  | L |
| ATOM | 2948 | CB  | THR | L | 172 | 96.006 | 52.453 | 20.371 | 1.00 | 42.56  | L |
| ATOM | 2949 | OG1 | THR | L | 172 | 96.732 | 52.820 | 19.195 | 1.00 | 42.56  | L |
| ATOM | 2950 | CG2 | THR | L | 172 | 95.434 | 51.054 | 20.194 | 1.00 | 42.56  | L |
| ATOM | 2951 | C   | THR | L | 172 | 93.791 | 53.156 | 19.558 | 1.00 | 48.07  | L |
| ATOM | 2952 | O   | THR | L | 172 | 92.658 | 52.842 | 19.909 | 1.00 | 48.07  | L |
| ATOM | 2953 | N   | TYR | L | 173 | 94.141 | 53.261 | 18.279 | 1.00 | 57.84  | L |
| ATOM | 2954 | CA  | TYR | L | 173 | 93.186 | 53.001 | 17.205 | 1.00 | 57.84  | L |
| ATOM | 2955 | CB  | TYR | L | 173 | 92.961 | 54.243 | 16.351 | 1.00 | 45.94  | L |
| ATOM | 2956 | CG  | TYR | L | 173 | 92.343 | 55.382 | 17.105 | 1.00 | 45.94  | L |
| ATOM | 2957 | CD1 | TYR | L | 173 | 91.036 | 55.302 | 17.587 | 1.00 | 45.94  | L |
| ATOM | 2958 | CE1 | TYR | L | 173 | 90.479 | 56.347 | 18.330 | 1.00 | 45.94  | L |
| ATOM | 2959 | CD2 | TYR | L | 173 | 93.080 | 56.530 | 17.376 | 1.00 | 45.94  | L |
| ATOM | 2960 | CE2 | TYR | L | 173 | 92.543 | 57.578 | 18.113 | 1.00 | 45.94  | L |
| ATOM | 2961 | CZ  | TYR | L | 173 | 91.244 | 57.486 | 18.592 | 1.00 | 45.94  | L |
| ATOM | 2962 | OH  | TYR | L | 173 | 90.739 | 58.530 | 19.338 | 1.00 | 45.94  | L |
| ATOM | 2963 | C   | TYR | L | 173 | 93.688 | 51.890 | 16.314 | 1.00 | 57.84  | L |
| ATOM | 2964 | O   | TYR | L | 173 | 94.888 | 51.788 | 16.056 | 1.00 | 57.84  | L |
| ATOM | 2965 | N   | SER | L | 174 | 92.759 | 51.068 | 15.837 | 1.00 | 44.80  | L |
| ATOM | 2966 | CA  | SER | L | 174 | 93.091 | 49.950 | 14.968 | 1.00 | 44.80  | L |
| ATOM | 2967 | CB  | SER | L | 174 | 92.992 | 48.631 | 15.740 | 1.00 | 120.14 | L |
| ATOM | 2968 | OG  | SER | L | 174 | 93.758 | 48.668 | 16.934 | 1.00 | 120.14 | L |
| ATOM | 2969 | C   | SER | L | 174 | 92.112 | 49.943 | 13.812 | 1.00 | 44.80  | L |
| ATOM | 2970 | O   | SER | L | 174 | 90.945 | 50.308 | 13.983 | 1.00 | 44.80  | L |
| ATOM | 2971 | N   | MET | L | 175 | 92.590 | 49.530 | 12.637 | 1.00 | 53.49  | L |
| ATOM | 2972 | CA  | MET | L | 175 | 91.756 | 49.468 | 11.434 | 1.00 | 53.49  | L |
| ATOM | 2973 | CB  | MET | L | 175 | 92.132 | 50.588 | 10.459 | 1.00 | 34.09  | L |
| ATOM | 2974 | CG  | MET | L | 175 | 91.374 | 50.503 | 9.129  | 1.00 | 34.09  | L |
| ATOM | 2975 | SD  | MET | L | 175 | 91.996 | 51.598 | 7.821  | 1.00 | 34.09  | L |
| ATOM | 2976 | CE  | MET | L | 175 | 93.793 | 51.208 | 7.889  | 1.00 | 34.09  | L |
| ATOM | 2977 | C   | MET | L | 175 | 91.851 | 48.137 | 10.691 | 1.00 | 53.49  | L |
| ATOM | 2978 | O   | MET | L | 175 | 92.880 | 47.453 | 10.734 | 1.00 | 53.49  | L |
| ATOM | 2979 | N   | SER | L | 176 | 90.764 | 47.789 | 10.004 | 1.00 | 39.48  | L |
| ATOM | 2980 | CA  | SER | L | 176 | 90.702 | 46.565 | 9.216  | 1.00 | 39.48  | L |
| ATOM | 2981 | CB  | SER | L | 176 | 89.745 | 45.558 | 9.844  | 1.00 | 50.12  | L |
| ATOM | 2982 | OG  | SER | L | 176 | 89.578 | 44.435 | 8.988  | 1.00 | 50.12  | L |
| ATOM | 2983 | C   | SER | L | 176 | 90.243 | 46.834 | 7.787  | 1.00 | 39.48  | L |
| ATOM | 2984 | O   | SER | L | 176 | 89.133 | 47.330 | 7.567  | 1.00 | 39.48  | L |
| ATOM | 2985 | N   | SER | L | 177 | 91.100 | 46.494 | 6.824  | 1.00 | 75.38  | L |
| ATOM | 2986 | CA  | SER | L | 177 | 90.790 | 46.669 | 5.405  | 1.00 | 75.38  | L |
| ATOM | 2987 | CB  | SER | L | 177 | 91.791 | 47.604 | 4.737  | 1.00 | 51.26  | L |
| ATOM | 2988 | OG  | SER | L | 177 | 91.485 | 47.741 | 3.359  | 1.00 | 51.26  | L |
| ATOM | 2989 | C   | SER | L | 177 | 90.806 | 45.333 | 4.675  | 1.00 | 75.38  | L |
| ATOM | 2990 | O   | SER | L | 177 | 91.790 | 44.592 | 4.712  | 1.00 | 75.38  | L |
| ATOM | 2991 | N   | THR | L | 178 | 89.709 | 45.040 | 3.994  | 1.00 | 46.59  | L |
| ATOM | 2992 | CA  | THR | L | 178 | 89.577 | 43.789 | 3.265  | 1.00 | 46.59  | L |
| ATOM | 2993 | CB  | THR | L | 178 | 88.391 | 42.962 | 3.827  | 1.00 | 43.59  | L |
| ATOM | 2994 | OG1 | THR | L | 178 | 88.643 | 42.632 | 5.195  | 1.00 | 43.59  | L |
| ATOM | 2995 | CG2 | THR | L | 178 | 88.175 | 41.687 | 3.011  | 1.00 | 43.59  | L |
| ATOM | 2996 | C   | THR | L | 178 | 89.290 | 44.047 | 1.793  | 1.00 | 46.59  | L |
| ATOM | 2997 | O   | THR | L | 178 | 88.466 | 44.908 | 1.464  | 1.00 | 46.59  | L |
| ATOM | 2998 | N   | LEU | L | 179 | 89.970 | 43.339 | 0.896  | 1.00 | 23.64  | L |
| ATOM | 2999 | CA  | LEU | L | 179 | 89.632 | 43.519 | −0.509 | 1.00 | 23.64  | L |
| ATOM | 3000 | CB  | LEU | L | 179 | 90.838 | 43.899 | −1.372 | 1.00 | 58.02  | L |
| ATOM | 3001 | CG  | LEU | L | 179 | 91.974 | 42.915 | −1.543 | 1.00 | 58.02  | L |
| ATOM | 3002 | CD1 | LEU | L | 179 | 93.083 | 43.557 | −2.364 | 1.00 | 58.02  | L |
| ATOM | 3003 | CD2 | LEU | L | 179 | 92.468 | 42.510 | −0.175 | 1.00 | 58.02  | L |
| ATOM | 3004 | C   | LEU | L | 179 | 89.012 | 42.220 | −0.978 | 1.00 | 23.64  | L |
| ATOM | 3005 | O   | LEU | L | 179 | 89.703 | 41.279 | −1.340 | 1.00 | 23.64  | L |
| ATOM | 3006 | N   | THR | L | 180 | 87.686 | 42.180 | −0.917 | 1.00 | 28.81  | L |
| ATOM | 3007 | CA  | THR | L | 180 | 86.913 | 41.027 | −1.321 | 1.00 | 28.81  | L |
| ATOM | 3008 | CB  | THR | L | 180 | 85.430 | 41.251 | −1.005 | 1.00 | 58.87  | L |
| ATOM | 3009 | OG1 | THR | L | 180 | 85.008 | 42.493 | −1.583 | 1.00 | 58.87  | L |
| ATOM | 3010 | CG2 | THR | L | 180 | 85.211 | 41.303 | 0.495  | 1.00 | 58.87  | L |

TABLE 2-continued

Atomic coordinates of b2 adrenoreceptor

| ATOM | 3011 | C | THR | L | 180 | 87.071 | 40.765 | −2.819 | 1.00 | 28.81 | L |
|---|---|---|---|---|---|---|---|---|---|---|---|
| ATOM | 3012 | O | THR | L | 180 | 86.792 | 41.637 | −3.645 | 1.00 | 28.81 | L |
| ATOM | 3013 | N | LEU | L | 181 | 87.506 | 39.552 | −3.154 | 1.00 | 49.56 | L |
| ATOM | 3014 | CA | LEU | L | 181 | 87.709 | 39.137 | −4.535 | 1.00 | 49.56 | L |
| ATOM | 3015 | CB | LEU | L | 181 | 89.184 | 38.929 | −4.780 | 1.00 | 4.89 | L |
| ATOM | 3016 | CG | LEU | L | 181 | 89.947 | 40.237 | −4.782 | 1.00 | 4.89 | L |
| ATOM | 3017 | CD1 | LEU | L | 181 | 91.453 | 40.004 | −5.114 | 1.00 | 4.89 | L |
| ATOM | 3018 | CD2 | LEU | L | 181 | 89.272 | 41.152 | −5.805 | 1.00 | 4.89 | L |
| ATOM | 3019 | C | LEU | L | 181 | 86.994 | 37.846 | −4.874 | 1.00 | 49.56 | L |
| ATOM | 3020 | O | LEU | L | 181 | 86.050 | 37.442 | −4.202 | 1.00 | 49.56 | L |
| ATOM | 3021 | N | THR | L | 182 | 87.452 | 37.197 | −5.934 | 1.00 | 69.58 | L |
| ATOM | 3022 | CA | THR | L | 182 | 86.876 | 35.923 | −6.321 | 1.00 | 69.58 | L |
| ATOM | 3023 | CB | THR | L | 182 | 86.199 | 35.986 | −7.671 | 1.00 | 30.09 | L |
| ATOM | 3024 | OG1 | THR | L | 182 | 85.417 | 37.176 | −7.747 | 1.00 | 30.09 | L |
| ATOM | 3025 | CG2 | THR | L | 182 | 85.284 | 34.772 | −7.850 | 1.00 | 30.09 | L |
| ATOM | 3026 | C | THR | L | 182 | 87.992 | 34.900 | −6.409 | 1.00 | 69.58 | L |
| ATOM | 3027 | O | THR | L | 182 | 89.175 | 35.250 | −6.405 | 1.00 | 69.58 | L |
| ATOM | 3028 | N | LYS | L | 183 | 87.617 | 33.630 | −6.471 | 1.00 | 34.56 | L |
| ATOM | 3029 | CA | LYS | L | 183 | 88.612 | 32.588 | −6.566 | 1.00 | 34.56 | L |
| ATOM | 3030 | CB | LYS | L | 183 | 87.927 | 31.229 | −6.762 | 1.00 | 102.95 | L |
| ATOM | 3031 | CG | LYS | L | 183 | 88.845 | 30.005 | −6.708 | 1.00 | 102.95 | L |
| ATOM | 3032 | CD | LYS | L | 183 | 88.045 | 28.720 | −6.922 | 1.00 | 102.95 | L |
| ATOM | 3033 | CE | LYS | L | 183 | 88.960 | 27.528 | −7.115 | 1.00 | 102.95 | L |
| ATOM | 3034 | NZ | LYS | L | 183 | 89.802 | 27.670 | −8.339 | 1.00 | 102.95 | L |
| ATOM | 3035 | C | LYS | L | 183 | 89.360 | 33.014 | −7.808 | 1.00 | 34.56 | L |
| ATOM | 3036 | O | LYS | L | 183 | 90.582 | 33.146 | −7.794 | 1.00 | 34.56 | L |
| ATOM | 3037 | N | ASP | L | 184 | 88.605 | 33.289 | −8.870 | 1.00 | 24.25 | L |
| ATOM | 3038 | CA | ASP | L | 184 | 89.204 | 33.704 | −10.134 | 1.00 | 24.25 | L |
| ATOM | 3039 | CB | ASP | L | 184 | 88.135 | 33.761 | −11.214 | 1.00 | 96.19 | L |
| ATOM | 3040 | CG | ASP | L | 184 | 87.433 | 32.437 | −11.385 | 1.00 | 96.19 | L |
| ATOM | 3041 | OD1 | ASP | L | 184 | 88.135 | 31.399 | −11.444 | 1.00 | 96.19 | L |
| ATOM | 3042 | OD2 | ASP | L | 184 | 86.184 | 32.439 | −11.459 | 1.00 | 96.19 | L |
| ATOM | 3043 | C | ASP | L | 184 | 89.927 | 35.048 | −10.008 | 1.00 | 24.25 | L |
| ATOM | 3044 | O | ASP | L | 184 | 91.155 | 35.122 | −10.188 | 1.00 | 24.25 | L |
| ATOM | 3045 | N | GLU | L | 185 | 89.170 | 36.102 | −9.699 | 1.00 | 39.01 | L |
| ATOM | 3046 | CA | GLU | L | 185 | 89.752 | 37.430 | −9.504 | 1.00 | 39.01 | L |
| ATOM | 3047 | CB | GLU | L | 185 | 88.884 | 38.252 | −8.549 | 1.00 | 143.23 | L |
| ATOM | 3048 | CG | GLU | L | 185 | 87.478 | 38.508 | −9.031 | 1.00 | 143.23 | L |
| ATOM | 3049 | CD | GLU | L | 185 | 87.404 | 39.646 | −10.013 | 1.00 | 143.23 | L |
| ATOM | 3050 | OE1 | GLU | L | 185 | 88.201 | 39.644 | −10.974 | 1.00 | 143.23 | L |
| ATOM | 3051 | OE2 | GLU | L | 185 | 86.547 | 40.537 | −9.826 | 1.00 | 143.23 | L |
| ATOM | 3052 | C | GLU | L | 185 | 91.124 | 37.232 | −8.861 | 1.00 | 39.01 | L |
| ATOM | 3053 | O | GLU | L | 185 | 92.151 | 37.550 | −9.443 | 1.00 | 39.01 | L |
| ATOM | 3054 | N | TYR | L | 186 | 91.120 | 36.668 | −7.660 | 1.00 | 27.38 | L |
| ATOM | 3055 | CA | TYR | L | 186 | 92.343 | 36.425 | −6.909 | 1.00 | 27.38 | L |
| ATOM | 3056 | CB | TYR | L | 186 | 92.007 | 35.726 | −5.591 | 1.00 | 35.39 | L |
| ATOM | 3057 | CG | TYR | L | 186 | 93.208 | 35.324 | −4.762 | 1.00 | 35.39 | L |
| ATOM | 3058 | CD1 | TYR | L | 186 | 94.353 | 36.102 | −4.736 | 1.00 | 35.39 | L |
| ATOM | 3059 | CE1 | TYR | L | 186 | 95.418 | 35.790 | −3.901 | 1.00 | 35.39 | L |
| ATOM | 3060 | CD2 | TYR | L | 186 | 93.157 | 34.214 | −3.940 | 1.00 | 35.39 | L |
| ATOM | 3061 | CE2 | TYR | L | 186 | 94.200 | 33.888 | −3.107 | 1.00 | 35.39 | L |
| ATOM | 3062 | CZ | TYR | L | 186 | 95.337 | 34.679 | −3.078 | 1.00 | 35.39 | L |
| ATOM | 3063 | OH | TYR | L | 186 | 96.374 | 34.379 | −2.202 | 1.00 | 35.39 | L |
| ATOM | 3064 | C | TYR | L | 186 | 93.411 | 35.623 | −7.640 | 1.00 | 27.38 | L |
| ATOM | 3065 | O | TYR | L | 186 | 94.607 | 35.937 | −7.552 | 1.00 | 27.38 | L |
| ATOM | 3066 | N | GLU | L | 187 | 92.978 | 34.591 | −8.356 | 1.00 | 89.19 | L |
| ATOM | 3067 | CA | GLU | L | 187 | 93.896 | 33.722 | −9.077 | 1.00 | 89.19 | L |
| ATOM | 3068 | CB | GLU | L | 187 | 93.155 | 32.475 | −9.560 | 1.00 | 118.17 | L |
| ATOM | 3069 | CG | GLU | L | 187 | 92.824 | 31.502 | −8.448 | 1.00 | 118.17 | L |
| ATOM | 3070 | CD | GLU | L | 187 | 94.061 | 31.048 | −7.690 | 1.00 | 118.17 | L |
| ATOM | 3071 | OE1 | GLU | L | 187 | 94.965 | 30.475 | −8.330 | 1.00 | 118.17 | L |
| ATOM | 3072 | OE2 | GLU | L | 187 | 94.135 | 31.262 | −6.458 | 1.00 | 118.17 | L |
| ATOM | 3073 | C | GLU | L | 187 | 94.641 | 34.357 | −10.245 | 1.00 | 89.19 | L |
| ATOM | 3074 | O | GLU | L | 187 | 95.604 | 33.775 | −10.756 | 1.00 | 89.19 | L |
| ATOM | 3075 | N | ARG | L | 188 | 94.222 | 35.548 | −10.663 | 1.00 | 43.52 | L |
| ATOM | 3076 | CA | ARG | L | 188 | 94.882 | 36.190 | −11.785 | 1.00 | 43.52 | L |
| ATOM | 3077 | CB | ARG | L | 188 | 93.866 | 36.995 | −12.596 | 1.00 | 86.22 | L |
| ATOM | 3078 | CG | ARG | L | 188 | 92.821 | 36.125 | −13.286 | 1.00 | 86.22 | L |
| ATOM | 3079 | CD | ARG | L | 188 | 91.953 | 36.939 | −14.230 | 1.00 | 86.22 | L |
| ATOM | 3080 | NE | ARG | L | 188 | 91.247 | 37.999 | −13.521 | 1.00 | 86.22 | L |
| ATOM | 3081 | CZ | ARG | L | 188 | 90.592 | 38.991 | −14.112 | 1.00 | 86.22 | L |
| ATOM | 3082 | NH1 | ARG | L | 188 | 90.547 | 39.063 | −15.435 | 1.00 | 86.22 | L |
| ATOM | 3083 | NH2 | ARG | L | 188 | 89.994 | 39.920 | −13.377 | 1.00 | 86.22 | L |
| ATOM | 3084 | C | ARG | L | 188 | 96.079 | 37.065 | −11.416 | 1.00 | 43.52 | L |
| ATOM | 3085 | O | ARG | L | 188 | 96.680 | 37.695 | −12.297 | 1.00 | 43.52 | L |
| ATOM | 3086 | N | HIS | L | 189 | 96.453 | 37.085 | −10.134 | 1.00 | 48.28 | L |
| ATOM | 3087 | CA | HIS | L | 189 | 97.583 | 37.911 | −9.692 | 1.00 | 48.28 | L |
| ATOM | 3088 | CB | HIS | L | 189 | 97.069 | 39.240 | −9.156 | 1.00 | 67.31 | L |

TABLE 2-continued

Atomic coordinates of b2 adrenoreceptor

| ATOM | 3089 | CG | HIS | L | 189 | 96.425 | 40.083 | −10.206 | 1.00 | 67.31 | L |
|---|---|---|---|---|---|---|---|---|---|---|---|
| ATOM | 3090 | CD2 | HIS | L | 189 | 95.129 | 40.411 | −10.413 | 1.00 | 67.31 | L |
| ATOM | 3091 | ND1 | HIS | L | 189 | 97.131 | 40.605 | −11.270 | 1.00 | 67.31 | L |
| ATOM | 3092 | CE1 | HIS | L | 189 | 96.295 | 41.212 | −12.091 | 1.00 | 67.31 | L |
| ATOM | 3093 | NE2 | HIS | L | 189 | 95.074 | 41.108 | −11.595 | 1.00 | 67.31 | L |
| ATOM | 3094 | C | HIS | L | 189 | 98.472 | 37.255 | −8.665 | 1.00 | 48.28 | L |
| ATOM | 3095 | O | HIS | L | 189 | 97.995 | 36.527 | −7.802 | 1.00 | 48.28 | L |
| ATOM | 3096 | N | ASN | L | 190 | 99.766 | 37.539 | −8.740 | 1.00 | 39.02 | L |
| ATOM | 3097 | CA | ASN | L | 190 | 100.717 | 36.918 | −7.832 | 1.00 | 39.02 | L |
| ATOM | 3098 | CB | ASN | L | 190 | 101.961 | 36.530 | −8.617 | 1.00 | 71.11 | L |
| ATOM | 3099 | CG | ASN | L | 190 | 101.673 | 35.447 | −9.634 | 1.00 | 71.11 | L |
| ATOM | 3100 | OD1 | ASN | L | 190 | 102.413 | 34.473 | −9.738 | 1.00 | 71.11 | L |
| ATOM | 3101 | ND2 | ASN | L | 190 | 100.588 | 35.609 | −10.390 | 1.00 | 71.11 | L |
| ATOM | 3102 | C | ASN | L | 190 | 101.103 | 37.667 | −6.554 | 1.00 | 39.02 | L |
| ATOM | 3103 | O | ASN | L | 190 | 101.044 | 37.107 | −5.452 | 1.00 | 39.02 | L |
| ATOM | 3104 | N | SER | L | 191 | 101.499 | 38.924 | −6.688 | 1.00 | 52.85 | L |
| ATOM | 3105 | CA | SER | L | 191 | 101.879 | 39.714 | −5.529 | 1.00 | 52.85 | L |
| ATOM | 3106 | CB | SER | L | 191 | 102.909 | 40.755 | −5.954 | 1.00 | 74.26 | L |
| ATOM | 3107 | OG | SER | L | 191 | 103.200 | 41.629 | −4.887 | 1.00 | 74.26 | L |
| ATOM | 3108 | C | SER | L | 191 | 100.672 | 40.401 | −4.868 | 1.00 | 52.85 | L |
| ATOM | 3109 | O | SER | L | 191 | 99.685 | 40.739 | −5.526 | 1.00 | 52.85 | L |
| ATOM | 3110 | N | TYR | L | 192 | 100.742 | 40.599 | −3.560 | 1.00 | 56.19 | L |
| ATOM | 3111 | CA | TYR | L | 192 | 99.662 | 41.267 | −2.846 | 1.00 | 56.19 | L |
| ATOM | 3112 | CB | TYR | L | 192 | 98.630 | 40.256 | −2.382 | 1.00 | 12.26 | L |
| ATOM | 3113 | CG | TYR | L | 192 | 97.649 | 39.906 | −3.460 | 1.00 | 12.26 | L |
| ATOM | 3114 | CD1 | TYR | L | 192 | 96.529 | 40.687 | −3.680 | 1.00 | 12.26 | L |
| ATOM | 3115 | CE1 | TYR | L | 192 | 95.603 | 40.371 | −4.683 | 1.00 | 12.26 | L |
| ATOM | 3116 | CD2 | TYR | L | 192 | 97.840 | 38.794 | −4.270 | 1.00 | 12.26 | L |
| ATOM | 3117 | CE2 | TYR | L | 192 | 96.931 | 38.467 | −5.281 | 1.00 | 12.26 | L |
| ATOM | 3118 | CZ | TYR | L | 192 | 95.809 | 39.261 | −5.484 | 1.00 | 12.26 | L |
| ATOM | 3119 | OH | TYR | L | 192 | 94.905 | 38.952 | −6.490 | 1.00 | 12.26 | L |
| ATOM | 3120 | C | TYR | L | 192 | 100.222 | 42.023 | −1.663 | 1.00 | 56.19 | L |
| ATOM | 3121 | O | TYR | L | 192 | 100.647 | 41.422 | −0.674 | 1.00 | 56.19 | L |
| ATOM | 3122 | N | THR | L | 193 | 100.217 | 43.348 | −1.770 | 1.00 | 54.51 | L |
| ATOM | 3123 | CA | THR | L | 193 | 100.758 | 44.193 | −0.717 | 1.00 | 54.51 | L |
| ATOM | 3124 | CB | THR | L | 193 | 101.872 | 45.095 | −1.267 | 1.00 | 62.71 | L |
| ATOM | 3125 | OG1 | THR | L | 193 | 102.327 | 44.582 | −2.524 | 1.00 | 62.71 | L |
| ATOM | 3126 | CG2 | THR | L | 193 | 103.036 | 45.139 | −0.306 | 1.00 | 62.71 | L |
| ATOM | 3127 | C | THR | L | 193 | 99.723 | 45.085 | −0.046 | 1.00 | 54.51 | L |
| ATOM | 3128 | O | THR | L | 193 | 98.707 | 45.461 | −0.640 | 1.00 | 54.51 | L |
| ATOM | 3129 | N | CYS | L | 194 | 100.002 | 45.418 | 1.208 | 1.00 | 55.93 | L |
| ATOM | 3130 | CA | CYS | L | 194 | 99.144 | 46.288 | 1.995 | 1.00 | 55.93 | L |
| ATOM | 3131 | C | CYS | L | 194 | 100.056 | 47.391 | 2.517 | 1.00 | 55.93 | L |
| ATOM | 3132 | O | CYS | L | 194 | 100.931 | 47.136 | 3.343 | 1.00 | 55.93 | L |
| ATOM | 3133 | CB | CYS | L | 194 | 98.526 | 45.511 | 3.162 | 1.00 | 67.78 | L |
| ATOM | 3134 | SG | CYS | L | 194 | 97.361 | 46.478 | 4.177 | 1.00 | 67.78 | L |
| ATOM | 3135 | N | GLU | L | 195 | 99.872 | 48.608 | 2.015 | 1.00 | 103.93 | L |
| ATOM | 3136 | CA | GLU | L | 195 | 100.698 | 49.729 | 2.448 | 1.00 | 103.93 | L |
| ATOM | 3137 | CB | GLU | L | 195 | 101.271 | 50.469 | 1.242 | 1.00 | 107.92 | L |
| ATOM | 3138 | CG | GLU | L | 195 | 102.337 | 49.683 | 0.514 | 1.00 | 107.92 | L |
| ATOM | 3139 | CD | GLU | L | 195 | 103.059 | 50.516 | −0.514 | 1.00 | 107.92 | L |
| ATOM | 3140 | OE1 | GLU | L | 195 | 104.033 | 50.018 | −1.116 | 1.00 | 107.92 | L |
| ATOM | 3141 | OE2 | GLU | L | 195 | 102.653 | 51.674 | −0.719 | 1.00 | 107.92 | L |
| ATOM | 3142 | C | GLU | L | 195 | 99.962 | 50.708 | 3.348 | 1.00 | 103.93 | L |
| ATOM | 3143 | O | GLU | L | 195 | 98.995 | 51.355 | 2.942 | 1.00 | 103.93 | L |
| ATOM | 3144 | N | ALA | L | 196 | 100.443 | 50.805 | 4.580 | 1.00 | 45.56 | L |
| ATOM | 3145 | CA | ALA | L | 196 | 99.863 | 51.685 | 5.576 | 1.00 | 45.56 | L |
| ATOM | 3146 | CB | ALA | L | 196 | 99.815 | 50.992 | 6.918 | 1.00 | 21.18 | L |
| ATOM | 3147 | C | ALA | L | 196 | 100.738 | 52.905 | 5.680 | 1.00 | 45.56 | L |
| ATOM | 3148 | O | ALA | L | 196 | 101.954 | 52.778 | 5.845 | 1.00 | 45.56 | L |
| ATOM | 3149 | N | THR | L | 197 | 100.117 | 54.078 | 5.577 | 1.00 | 80.14 | L |
| ATOM | 3150 | CA | THR | L | 197 | 100.816 | 55.354 | 5.687 | 1.00 | 80.14 | L |
| ATOM | 3151 | CB | THR | L | 197 | 100.650 | 56.195 | 4.408 | 1.00 | 70.88 | L |
| ATOM | 3152 | OG1 | THR | L | 197 | 99.270 | 56.212 | 4.023 | 1.00 | 70.88 | L |
| ATOM | 3153 | CG2 | THR | L | 197 | 101.468 | 55.608 | 3.274 | 1.00 | 70.88 | L |
| ATOM | 3154 | C | THR | L | 197 | 100.209 | 56.095 | 6.879 | 1.00 | 80.14 | L |
| ATOM | 3155 | O | THR | L | 197 | 99.058 | 56.525 | 6.831 | 1.00 | 80.14 | L |
| ATOM | 3156 | N | HIS | L | 198 | 100.988 | 56.226 | 7.951 | 1.00 | 91.98 | L |
| ATOM | 3157 | CA | HIS | L | 198 | 100.530 | 56.881 | 9.171 | 1.00 | 91.98 | L |
| ATOM | 3158 | CB | HIS | L | 198 | 100.313 | 55.836 | 10.253 | 1.00 | 49.42 | L |
| ATOM | 3159 | CG | HIS | L | 198 | 99.926 | 56.413 | 11.576 | 1.00 | 49.42 | L |
| ATOM | 3160 | CD2 | HIS | L | 198 | 100.486 | 56.287 | 12.802 | 1.00 | 49.42 | L |
| ATOM | 3161 | ND1 | HIS | L | 198 | 98.810 | 57.204 | 11.743 | 1.00 | 49.42 | L |
| ATOM | 3162 | CE1 | HIS | L | 198 | 98.698 | 57.539 | 13.017 | 1.00 | 49.42 | L |
| ATOM | 3163 | NE2 | HIS | L | 198 | 99.702 | 56.995 | 13.681 | 1.00 | 49.42 | L |
| ATOM | 3164 | C | HIS | L | 198 | 101.496 | 57.933 | 9.696 | 1.00 | 91.98 | L |
| ATOM | 3165 | O | HIS | L | 198 | 102.704 | 57.726 | 9.686 | 1.00 | 91.98 | L |
| ATOM | 3166 | N | LYS | L | 199 | 100.949 | 59.050 | 10.170 | 1.00 | 46.82 | L |

TABLE 2-continued

Atomic coordinates of b2 adrenoreceptor

| ATOM | 3167 | CA | LYS | L | 199 | 101.739 | 60.158 | 10.716 | 1.00 | 46.82 | L |
| --- | --- | --- | --- | --- | --- | --- | --- | --- | --- | --- | --- |
| ATOM | 3168 | CB | LYS | L | 199 | 100.912 | 60.942 | 11.753 | 1.00 | 49.34 | L |
| ATOM | 3169 | CG | LYS | L | 199 | 101.677 | 62.084 | 12.430 | 1.00 | 49.34 | L |
| ATOM | 3170 | CD | LYS | L | 199 | 101.009 | 62.550 | 13.714 | 1.00 | 49.34 | L |
| ATOM | 3171 | CE | LYS | L | 199 | 101.913 | 63.489 | 14.508 | 1.00 | 49.34 | L |
| ATOM | 3172 | NZ | LYS | L | 199 | 101.345 | 63.823 | 15.852 | 1.00 | 49.34 | L |
| ATOM | 3173 | C | LYS | L | 199 | 103.014 | 59.635 | 11.372 | 1.00 | 46.82 | L |
| ATOM | 3174 | O | LYS | L | 199 | 104.100 | 60.172 | 11.174 | 1.00 | 46.82 | L |
| ATOM | 3175 | N | THR | L | 200 | 102.862 | 58.577 | 12.156 | 1.00 | 66.71 | L |
| ATOM | 3176 | CA | THR | L | 200 | 103.978 | 57.957 | 12.846 | 1.00 | 66.71 | L |
| ATOM | 3177 | CB | THR | L | 200 | 103.636 | 56.481 | 13.154 | 1.00 | 117.18 | L |
| ATOM | 3178 | OG1 | THR | L | 200 | 104.700 | 55.885 | 13.899 | 1.00 | 117.18 | L |
| ATOM | 3179 | CG2 | THR | L | 200 | 103.402 | 55.701 | 11.864 | 1.00 | 117.18 | L |
| ATOM | 3180 | C | THR | L | 200 | 105.290 | 58.059 | 12.037 | 1.00 | 66.71 | L |
| ATOM | 3181 | O | THR | L | 200 | 106.314 | 58.512 | 12.551 | 1.00 | 66.71 | L |
| ATOM | 3182 | N | SER | L | 201 | 105.256 | 57.651 | 10.771 | 1.00 | 147.01 | L |
| ATOM | 3183 | CA | SER | L | 201 | 106.444 | 57.721 | 9.923 | 1.00 | 147.01 | L |
| ATOM | 3184 | CB | SER | L | 201 | 107.049 | 56.330 | 9.711 | 1.00 | 51.54 | L |
| ATOM | 3185 | OG | SER | L | 201 | 108.196 | 56.398 | 8.865 | 1.00 | 51.54 | L |
| ATOM | 3186 | C | SER | L | 201 | 106.128 | 58.329 | 8.565 | 1.00 | 147.01 | L |
| ATOM | 3187 | O | SER | L | 201 | 104.984 | 58.680 | 8.277 | 1.00 | 147.01 | L |
| ATOM | 3188 | N | THR | L | 202 | 107.156 | 58.450 | 7.732 | 1.00 | 92.86 | L |
| ATOM | 3189 | CA | THR | L | 202 | 106.996 | 59.006 | 6.398 | 1.00 | 92.86 | L |
| ATOM | 3190 | CB | THR | L | 202 | 108.086 | 60.049 | 6.100 | 1.00 | 80.19 | L |
| ATOM | 3191 | OG1 | THR | L | 202 | 107.796 | 60.705 | 4.859 | 1.00 | 80.19 | L |
| ATOM | 3192 | CG2 | THR | L | 202 | 109.454 | 59.384 | 6.028 | 1.00 | 80.19 | L |
| ATOM | 3193 | C | THR | L | 202 | 107.095 | 57.862 | 5.399 | 1.00 | 92.86 | L |
| ATOM | 3194 | O | THR | L | 202 | 106.604 | 57.954 | 4.273 | 1.00 | 92.86 | L |
| ATOM | 3195 | N | SER | L | 203 | 107.738 | 56.782 | 5.829 | 1.00 | 77.33 | L |
| ATOM | 3196 | CA | SER | L | 203 | 107.895 | 55.593 | 5.003 | 1.00 | 77.33 | L |
| ATOM | 3197 | CB | SER | L | 203 | 109.171 | 54.844 | 5.398 | 1.00 | 116.81 | L |
| ATOM | 3198 | OG | SER | L | 203 | 110.267 | 55.731 | 5.541 | 1.00 | 116.81 | L |
| ATOM | 3199 | C | SER | L | 203 | 106.680 | 54.710 | 5.286 | 1.00 | 77.33 | L |
| ATOM | 3200 | O | SER | L | 203 | 106.462 | 54.304 | 6.429 | 1.00 | 77.33 | L |
| ATOM | 3201 | N | PRO | L | 204 | 105.868 | 54.405 | 4.258 | 1.00 | 37.02 | L |
| ATOM | 3202 | CD | PRO | L | 204 | 106.038 | 54.715 | 2.826 | 1.00 | 43.67 | L |
| ATOM | 3203 | CA | PRO | L | 204 | 104.685 | 53.558 | 4.480 | 1.00 | 37.02 | L |
| ATOM | 3204 | CB | PRO | L | 204 | 104.141 | 53.336 | 3.061 | 1.00 | 43.67 | L |
| ATOM | 3205 | CG | PRO | L | 204 | 104.637 | 54.537 | 2.290 | 1.00 | 43.67 | L |
| ATOM | 3206 | C | PRO | L | 204 | 105.066 | 52.228 | 5.139 | 1.00 | 37.02 | L |
| ATOM | 3207 | O | PRO | L | 204 | 106.090 | 51.638 | 4.798 | 1.00 | 37.02 | L |
| ATOM | 3208 | N | ILE | L | 205 | 104.287 | 51.753 | 6.102 | 1.00 | 58.46 | L |
| ATOM | 3209 | CA | ILE | L | 205 | 104.634 | 50.459 | 6.658 | 1.00 | 58.46 | L |
| ATOM | 3210 | CB | ILE | L | 205 | 103.948 | 50.173 | 7.990 | 1.00 | 66.50 | L |
| ATOM | 3211 | CG2 | ILE | L | 205 | 104.381 | 48.809 | 8.485 | 1.00 | 66.50 | L |
| ATOM | 3212 | CG1 | ILE | L | 205 | 104.338 | 51.232 | 9.020 | 1.00 | 66.50 | L |
| ATOM | 3213 | CD1 | ILE | L | 205 | 103.894 | 50.910 | 10.448 | 1.00 | 66.50 | L |
| ATOM | 3214 | C | ILE | L | 205 | 104.073 | 49.541 | 5.582 | 1.00 | 58.46 | L |
| ATOM | 3215 | O | ILE | L | 205 | 103.025 | 49.842 | 4.991 | 1.00 | 58.46 | L |
| ATOM | 3216 | N | VAL | L | 206 | 104.763 | 48.438 | 5.306 | 1.00 | 95.97 | L |
| ATOM | 3217 | CA | VAL | L | 206 | 104.308 | 47.542 | 4.251 | 1.00 | 95.97 | L |
| ATOM | 3218 | CB | VAL | L | 206 | 105.119 | 47.757 | 2.967 | 1.00 | 45.68 | L |
| ATOM | 3219 | CG1 | VAL | L | 206 | 104.393 | 47.162 | 1.801 | 1.00 | 45.68 | L |
| ATOM | 3220 | CG2 | VAL | L | 206 | 105.359 | 49.219 | 2.738 | 1.00 | 45.68 | L |
| ATOM | 3221 | C | VAL | L | 206 | 104.376 | 46.057 | 4.556 | 1.00 | 95.97 | L |
| ATOM | 3222 | O | VAL | L | 206 | 105.234 | 45.602 | 5.308 | 1.00 | 95.97 | L |
| ATOM | 3223 | N | LYS | L | 207 | 103.462 | 45.315 | 3.939 | 1.00 | 43.17 | L |
| ATOM | 3224 | CA | LYS | L | 207 | 103.386 | 43.867 | 4.069 | 1.00 | 43.17 | L |
| ATOM | 3225 | CB | LYS | L | 207 | 102.460 | 43.461 | 5.228 | 1.00 | 42.15 | L |
| ATOM | 3226 | CG | LYS | L | 207 | 102.932 | 43.918 | 6.605 | 1.00 | 42.15 | L |
| ATOM | 3227 | CD | LYS | L | 207 | 104.391 | 43.535 | 6.829 | 1.00 | 42.15 | L |
| ATOM | 3228 | CE | LYS | L | 207 | 104.961 | 44.041 | 8.159 | 1.00 | 42.15 | L |
| ATOM | 3229 | NZ | LYS | L | 207 | 104.453 | 43.269 | 9.327 | 1.00 | 42.15 | L |
| ATOM | 3230 | C | LYS | L | 207 | 102.850 | 43.318 | 2.744 | 1.00 | 43.17 | L |
| ATOM | 3231 | O | LYS | L | 207 | 101.826 | 43.774 | 2.228 | 1.00 | 43.17 | L |
| ATOM | 3232 | N | SER | L | 208 | 103.561 | 42.345 | 2.189 | 1.00 | 57.80 | L |
| ATOM | 3233 | CA | SER | L | 208 | 103.170 | 41.735 | 0.926 | 1.00 | 57.80 | L |
| ATOM | 3234 | CB | SER | L | 208 | 104.120 | 42.193 | −0.181 | 1.00 | 125.41 | L |
| ATOM | 3235 | OG | SER | L | 208 | 103.857 | 41.513 | −1.394 | 1.00 | 125.41 | L |
| ATOM | 3236 | C | SER | L | 208 | 103.195 | 40.211 | 1.014 | 1.00 | 57.80 | L |
| ATOM | 3237 | O | SER | L | 208 | 103.507 | 39.646 | 2.059 | 1.00 | 57.80 | L |
| ATOM | 3238 | N | PHE | L | 209 | 102.855 | 39.553 | −0.087 | 1.00 | 61.46 | L |
| ATOM | 3239 | CA | PHE | L | 209 | 102.877 | 38.100 | −0.142 | 1.00 | 61.46 | L |
| ATOM | 3240 | CB | PHE | L | 209 | 101.854 | 37.496 | 0.840 | 1.00 | 36.64 | L |
| ATOM | 3241 | CG | PHE | L | 209 | 100.409 | 37.530 | 0.375 | 1.00 | 36.64 | L |
| ATOM | 3242 | CD1 | PHE | L | 209 | 100.017 | 36.949 | −0.823 | 1.00 | 36.64 | L |
| ATOM | 3243 | CD2 | PHE | L | 209 | 99.426 | 38.075 | 1.190 | 1.00 | 36.64 | L |
| ATOM | 3244 | CE1 | PHE | L | 209 | 98.670 | 36.906 | −1.206 | 1.00 | 36.64 | L |

TABLE 2-continued

Atomic coordinates of b2 adrenoreceptor

| ATOM | 3245 | CE2 | PHE | L | 209 | 98.073 | 38.036 | 0.816 | 1.00 | 36.64 | L |
|---|---|---|---|---|---|---|---|---|---|---|---|
| ATOM | 3246 | CZ | PHE | L | 209 | 97.697 | 37.449 | −0.387 | 1.00 | 36.64 | L |
| ATOM | 3247 | C | PHE | L | 209 | 102.621 | 37.603 | −1.554 | 1.00 | 61.46 | L |
| ATOM | 3248 | O | PHE | L | 209 | 101.918 | 38.259 | −2.327 | 1.00 | 61.46 | L |
| ATOM | 3249 | N | ASN | L | 210 | 103.198 | 36.460 | −1.910 | 1.00 | 48.29 | L |
| ATOM | 3250 | CA | ASN | L | 210 | 102.942 | 35.936 | −3.240 | 1.00 | 48.29 | L |
| ATOM | 3251 | CB | ASN | L | 210 | 104.242 | 35.616 | −3.967 | 1.00 | 60.33 | L |
| ATOM | 3252 | CG | ASN | L | 210 | 104.034 | 35.458 | −5.467 | 1.00 | 60.33 | L |
| ATOM | 3253 | OD1 | ASN | L | 210 | 103.325 | 34.554 | −5.917 | 1.00 | 60.33 | L |
| ATOM | 3254 | ND2 | ASN | L | 210 | 104.639 | 36.348 | −6.244 | 1.00 | 60.33 | L |
| ATOM | 3255 | C | ASN | L | 210 | 102.026 | 34.703 | −3.200 | 1.00 | 48.29 | L |
| ATOM | 3256 | O | ASN | L | 210 | 102.034 | 33.926 | −2.241 | 1.00 | 48.29 | L |
| ATOM | 3257 | N | ARG | L | 211 | 101.231 | 34.537 | −4.249 | 1.00 | 67.02 | L |
| ATOM | 3258 | CA | ARG | L | 211 | 100.293 | 33.437 | −4.309 | 1.00 | 67.02 | L |
| ATOM | 3259 | CB | ARG | L | 211 | 99.108 | 33.830 | −5.205 | 1.00 | 62.33 | L |
| ATOM | 3260 | CG | ARG | L | 211 | 97.992 | 32.780 | −5.263 | 1.00 | 62.33 | L |
| ATOM | 3261 | CD | ARG | L | 211 | 96.837 | 33.224 | −6.146 | 1.00 | 62.33 | L |
| ATOM | 3262 | NE | ARG | L | 211 | 96.701 | 32.427 | −7.363 | 1.00 | 62.33 | L |
| ATOM | 3263 | CZ | ARG | L | 211 | 97.622 | 32.341 | −8.319 | 1.00 | 62.33 | L |
| ATOM | 3264 | NH1 | ARG | L | 211 | 98.767 | 33.003 | −8.201 | 1.00 | 62.33 | L |
| ATOM | 3265 | NH2 | ARG | L | 211 | 97.391 | 31.606 | −9.403 | 1.00 | 62.33 | L |
| ATOM | 3266 | C | ARG | L | 211 | 100.897 | 32.116 | −4.786 | 1.00 | 67.02 | L |
| ATOM | 3267 | O | ARG | L | 211 | 100.190 | 31.106 | −4.894 | 1.00 | 67.02 | L |
| ATOM | 3268 | N | ASN | L | 212 | 102.197 | 32.091 | −5.048 | 1.00 | 185.93 | L |
| ATOM | 3269 | CA | ASN | L | 212 | 102.798 | 30.857 | −5.532 | 1.00 | 185.93 | L |
| ATOM | 3270 | CB | ASN | L | 212 | 103.748 | 31.170 | −6.679 | 1.00 | 93.51 | L |
| ATOM | 3271 | CG | ASN | L | 212 | 103.025 | 31.766 | −7.871 | 1.00 | 93.51 | L |
| ATOM | 3272 | OD1 | ASN | L | 212 | 102.098 | 31.164 | −8.418 | 1.00 | 93.51 | L |
| ATOM | 3273 | ND2 | ASN | L | 212 | 103.442 | 32.957 | −8.278 | 1.00 | 93.51 | L |
| ATOM | 3274 | C | ASN | L | 212 | 103.483 | 29.983 | −4.493 | 1.00 | 185.93 | L |
| ATOM | 3275 | O | ASN | L | 212 | 102.979 | 28.909 | −4.168 | 1.00 | 185.93 | L |
| ATOM | 3276 | N | GLU | L | 213 | 104.625 | 30.421 | −3.972 | 1.00 | 128.18 | L |
| ATOM | 3277 | CA | GLU | L | 213 | 105.319 | 29.617 | −2.972 | 1.00 | 128.18 | L |
| ATOM | 3278 | CB | GLU | L | 213 | 106.521 | 30.375 | −2.405 | 1.00 | 162.15 | L |
| ATOM | 3279 | CG | GLU | L | 213 | 107.445 | 29.518 | −1.542 | 1.00 | 162.15 | L |
| ATOM | 3280 | CD | GLU | L | 213 | 108.136 | 28.414 | −2.329 | 1.00 | 162.15 | L |
| ATOM | 3281 | OE1 | GLU | L | 213 | 108.823 | 28.732 | −3.322 | 1.00 | 162.15 | L |
| ATOM | 3282 | OE2 | GLU | L | 213 | 107.996 | 27.230 | −1.953 | 1.00 | 162.15 | L |
| ATOM | 3283 | C | GLU | L | 213 | 104.330 | 29.296 | −1.857 | 1.00 | 128.18 | L |
| ATOM | 3284 | O | GLU | L | 213 | 104.505 | 28.335 | −1.107 | 1.00 | 128.18 | L |
| ATOM | 3285 | N | CYS | L | 214 | 103.284 | 30.113 | −1.774 | 1.00 | 149.65 | L |
| ATOM | 3286 | CA | CYS | L | 214 | 102.230 | 29.959 | −0.778 | 1.00 | 149.65 | L |
| ATOM | 3287 | CB | CYS | L | 214 | 101.839 | 31.335 | −0.225 | 1.00 | 223.22 | L |
| ATOM | 3288 | SG | CYS | L | 214 | 100.465 | 31.340 | 0.973 | 1.00 | 223.22 | L |
| ATOM | 3289 | C | CYS | L | 214 | 101.017 | 29.289 | −1.420 | 1.00 | 149.65 | L |
| ATOM | 3290 | O | CYS | L | 214 | 99.907 | 29.848 | −1.321 | 1.00 | 149.65 | L |
| ATOM | 3291 | OXT | CYS | L | 214 | 101.193 | 28.208 | −2.019 | 1.00 | 117.83 | L |
| ATOM | 3292 | CB | GLU | H | 1 | 71.663 | 39.128 | 40.318 | 1.00 | 98.18 | H |
| ATOM | 3293 | CG | GLU | H | 1 | 72.870 | 38.291 | 40.669 | 1.00 | 98.18 | H |
| ATOM | 3294 | CD | GLU | H | 1 | 72.507 | 36.844 | 40.950 | 1.00 | 98.18 | H |
| ATOM | 3295 | OE1 | GLU | H | 1 | 71.504 | 36.611 | 41.665 | 1.00 | 98.18 | H |
| ATOM | 3296 | OE2 | GLU | H | 1 | 73.227 | 35.943 | 40.458 | 1.00 | 98.18 | H |
| ATOM | 3297 | C | GLU | H | 1 | 70.700 | 41.200 | 39.317 | 1.00 | 38.60 | H |
| ATOM | 3298 | O | GLU | H | 1 | 69.640 | 40.849 | 39.841 | 1.00 | 38.60 | H |
| ATOM | 3299 | N | GLU | H | 1 | 72.989 | 41.198 | 40.312 | 1.00 | 38.60 | H |
| ATOM | 3300 | CA | GLU | H | 1 | 71.991 | 40.414 | 39.564 | 1.00 | 38.60 | H |
| ATOM | 3301 | N | VAL | H | 2 | 70.789 | 42.268 | 38.527 | 1.00 | 69.61 | H |
| ATOM | 3302 | CA | VAL | H | 2 | 69.620 | 43.085 | 38.161 | 1.00 | 69.61 | H |
| ATOM | 3303 | CB | VAL | H | 2 | 69.778 | 44.568 | 38.568 | 1.00 | 8.92 | H |
| ATOM | 3304 | CG1 | VAL | H | 2 | 68.457 | 45.325 | 38.320 | 1.00 | 8.92 | H |
| ATOM | 3305 | CG2 | VAL | H | 2 | 70.288 | 44.661 | 40.035 | 1.00 | 8.92 | H |
| ATOM | 3306 | C | VAL | H | 2 | 69.608 | 43.038 | 36.647 | 1.00 | 69.61 | H |
| ATOM | 3307 | O | VAL | H | 2 | 70.659 | 43.164 | 36.017 | 1.00 | 69.61 | H |
| ATOM | 3308 | N | GLN | H | 3 | 68.446 | 42.859 | 36.041 | 1.00 | 36.68 | H |
| ATOM | 3309 | CA | GLN | H | 3 | 68.446 | 42.798 | 34.585 | 1.00 | 36.68 | H |
| ATOM | 3310 | CB | GLN | H | 3 | 69.358 | 41.641 | 34.138 | 1.00 | 96.49 | H |
| ATOM | 3311 | CG | GLN | H | 3 | 69.226 | 40.370 | 34.985 | 1.00 | 96.49 | H |
| ATOM | 3312 | CD | GLN | H | 3 | 70.182 | 39.260 | 34.562 | 1.00 | 96.49 | H |
| ATOM | 3313 | OE1 | GLN | H | 3 | 70.862 | 39.361 | 33.543 | 1.00 | 96.49 | H |
| ATOM | 3314 | NE2 | GLN | H | 3 | 70.227 | 38.189 | 35.348 | 1.00 | 96.49 | H |
| ATOM | 3315 | C | GLN | H | 3 | 67.106 | 42.715 | 33.841 | 1.00 | 36.68 | H |
| ATOM | 3316 | O | GLN | H | 3 | 66.131 | 42.109 | 34.305 | 1.00 | 36.68 | H |
| ATOM | 3317 | N | LEU | H | 4 | 67.062 | 43.355 | 32.680 | 1.00 | 62.09 | H |
| ATOM | 3318 | CA | LEU | H | 4 | 65.871 | 43.308 | 31.852 | 1.00 | 62.09 | H |
| ATOM | 3319 | CB | LEU | H | 4 | 65.375 | 44.721 | 31.514 | 1.00 | 41.57 | H |
| ATOM | 3320 | CG | LEU | H | 4 | 65.067 | 45.645 | 32.695 | 1.00 | 41.57 | H |
| ATOM | 3321 | CD1 | LEU | H | 4 | 66.356 | 46.257 | 33.158 | 1.00 | 41.57 | H |
| ATOM | 3322 | CD2 | LEU | H | 4 | 64.105 | 46.752 | 32.297 | 1.00 | 41.57 | H |

TABLE 2-continued

Atomic coordinates of b2 adrenoreceptor

| ATOM | 3323 | C | LEU | H | 4 | 66.334 | 42.581 | 30.593 | 1.00 | 62.09 | H |
|---|---|---|---|---|---|---|---|---|---|---|---|
| ATOM | 3324 | O | LEU | H | 4 | 67.124 | 43.120 | 29.819 | 1.00 | 62.09 | H |
| ATOM | 3325 | N | GLN | H | 5 | 65.874 | 41.348 | 30.405 | 1.00 | 43.98 | H |
| ATOM | 3326 | CA | GLN | H | 5 | 66.282 | 40.587 | 29.240 | 1.00 | 43.98 | H |
| ATOM | 3327 | CB | GLN | H | 5 | 66.042 | 39.097 | 29.451 | 1.00 | 95.37 | H |
| ATOM | 3328 | CG | GLN | H | 5 | 67.036 | 38.418 | 30.363 | 1.00 | 95.37 | H |
| ATOM | 3329 | CD | GLN | H | 5 | 67.094 | 36.919 | 30.119 | 1.00 | 95.37 | H |
| ATOM | 3330 | OE1 | GLN | H | 5 | 66.254 | 36.356 | 29.407 | 1.00 | 95.37 | H |
| ATOM | 3331 | NE2 | GLN | H | 5 | 68.087 | 36.264 | 30.709 | 1.00 | 95.37 | H |
| ATOM | 3332 | C | GLN | H | 5 | 65.567 | 41.027 | 27.975 | 1.00 | 43.98 | H |
| ATOM | 3333 | O | GLN | H | 5 | 64.382 | 41.383 | 27.997 | 1.00 | 43.98 | H |
| ATOM | 3334 | N | GLN | H | 6 | 66.302 | 40.992 | 26.867 | 1.00 | 61.05 | H |
| ATOM | 3335 | CA | GLN | H | 6 | 65.755 | 41.370 | 25.579 | 1.00 | 61.05 | H |
| ATOM | 3336 | CB | GLN | H | 6 | 66.095 | 42.827 | 25.274 | 1.00 | 39.09 | H |
| ATOM | 3337 | CG | GLN | H | 6 | 64.849 | 43.681 | 25.167 | 1.00 | 39.09 | H |
| ATOM | 3338 | CD | GLN | H | 6 | 65.051 | 45.096 | 25.653 | 1.00 | 39.09 | H |
| ATOM | 3339 | OE1 | GLN | H | 6 | 66.012 | 45.398 | 26.366 | 1.00 | 39.09 | H |
| ATOM | 3340 | NE2 | GLN | H | 6 | 64.132 | 45.975 | 25.282 | 1.00 | 39.09 | H |
| ATOM | 3341 | C | GLN | H | 6 | 66.237 | 40.456 | 24.459 | 1.00 | 61.05 | H |
| ATOM | 3342 | O | GLN | H | 6 | 67.233 | 39.750 | 24.603 | 1.00 | 61.05 | H |
| ATOM | 3343 | N | SER | H | 7 | 65.511 | 40.482 | 23.347 | 1.00 | 76.52 | H |
| ATOM | 3344 | CA | SER | H | 7 | 65.798 | 39.646 | 22.195 | 1.00 | 76.52 | H |
| ATOM | 3345 | CB | SER | H | 7 | 64.655 | 39.760 | 21.186 | 1.00 | 208.98 | H |
| ATOM | 3346 | OG | SER | H | 7 | 63.427 | 39.355 | 21.768 | 1.00 | 208.98 | H |
| ATOM | 3347 | C | SER | H | 7 | 67.124 | 39.901 | 21.495 | 1.00 | 76.52 | H |
| ATOM | 3348 | O | SER | H | 7 | 67.739 | 38.970 | 20.980 | 1.00 | 76.52 | H |
| ATOM | 3349 | N | GLY | H | 8 | 67.576 | 41.144 | 21.448 | 1.00 | 81.81 | H |
| ATOM | 3350 | CA | GLY | H | 8 | 68.848 | 41.393 | 20.788 | 1.00 | 81.81 | H |
| ATOM | 3351 | C | GLY | H | 8 | 68.818 | 41.443 | 19.265 | 1.00 | 81.81 | H |
| ATOM | 3352 | O | GLY | H | 8 | 69.545 | 42.236 | 18.669 | 1.00 | 81.81 | H |
| ATOM | 3353 | N | ALA | H | 9 | 67.999 | 40.605 | 18.631 | 1.00 | 57.67 | H |
| ATOM | 3354 | CA | ALA | H | 9 | 67.889 | 40.590 | 17.170 | 1.00 | 57.67 | H |
| ATOM | 3355 | CB | ALA | H | 9 | 68.847 | 39.558 | 16.593 | 1.00 | 122.53 | H |
| ATOM | 3356 | C | ALA | H | 9 | 66.461 | 40.292 | 16.708 | 1.00 | 57.67 | H |
| ATOM | 3357 | O | ALA | H | 9 | 65.907 | 39.242 | 17.032 | 1.00 | 57.67 | H |
| ATOM | 3358 | N | GLU | H | 10 | 65.867 | 41.203 | 15.944 | 1.00 | 42.12 | H |
| ATOM | 3359 | CA | GLU | H | 10 | 64.496 | 40.986 | 15.466 | 1.00 | 42.12 | H |
| ATOM | 3360 | CB | GLU | H | 10 | 63.516 | 41.752 | 16.359 | 1.00 | 93.88 | H |
| ATOM | 3361 | CG | GLU | H | 10 | 62.045 | 41.571 | 15.998 | 1.00 | 93.88 | H |
| ATOM | 3362 | CD | GLU | H | 10 | 61.578 | 40.136 | 16.145 | 1.00 | 93.88 | H |
| ATOM | 3363 | OE1 | GLU | H | 10 | 61.881 | 39.514 | 17.190 | 1.00 | 93.88 | H |
| ATOM | 3364 | OE2 | GLU | H | 10 | 60.901 | 39.636 | 15.220 | 1.00 | 93.88 | H |
| ATOM | 3365 | C | GLU | H | 10 | 64.255 | 41.373 | 13.999 | 1.00 | 42.12 | H |
| ATOM | 3366 | O | GLU | H | 10 | 64.262 | 42.551 | 13.658 | 1.00 | 42.12 | H |
| ATOM | 3367 | N | LEU | H | 11 | 64.014 | 40.383 | 13.143 | 1.00 | 70.80 | H |
| ATOM | 3368 | CA | LEU | H | 11 | 63.791 | 40.631 | 11.716 | 1.00 | 70.80 | H |
| ATOM | 3369 | CB | LEU | H | 11 | 64.412 | 39.505 | 10.892 | 1.00 | 68.97 | H |
| ATOM | 3370 | CG | LEU | H | 11 | 64.684 | 39.707 | 9.401 | 1.00 | 68.97 | H |
| ATOM | 3371 | CD1 | LEU | H | 11 | 63.442 | 40.173 | 8.675 | 1.00 | 68.97 | H |
| ATOM | 3372 | CD2 | LEU | H | 11 | 65.792 | 40.721 | 9.247 | 1.00 | 68.97 | H |
| ATOM | 3373 | C | LEU | H | 11 | 62.309 | 40.705 | 11.392 | 1.00 | 70.80 | H |
| ATOM | 3374 | O | LEU | H | 11 | 61.525 | 39.909 | 11.910 | 1.00 | 70.80 | H |
| ATOM | 3375 | N | ALA | H | 12 | 61.925 | 41.638 | 10.521 | 1.00 | 33.40 | H |
| ATOM | 3376 | CA | ALA | H | 12 | 60.515 | 41.771 | 10.151 | 1.00 | 33.40 | H |
| ATOM | 3377 | CB | ALA | H | 12 | 59.794 | 42.633 | 11.164 | 1.00 | 47.12 | H |
| ATOM | 3378 | C | ALA | H | 12 | 60.313 | 42.342 | 8.755 | 1.00 | 33.40 | H |
| ATOM | 3379 | O | ALA | H | 12 | 61.026 | 43.267 | 8.343 | 1.00 | 33.40 | H |
| ATOM | 3380 | N | ARG | H | 13 | 59.342 | 41.785 | 8.027 | 1.00 | 52.20 | H |
| ATOM | 3381 | CA | ARG | H | 13 | 59.048 | 42.249 | 6.676 | 1.00 | 52.20 | H |
| ATOM | 3382 | CB | ARG | H | 13 | 58.187 | 41.237 | 5.908 | 1.00 | 140.51 | H |
| ATOM | 3383 | CG | ARG | H | 13 | 58.990 | 40.162 | 5.170 | 1.00 | 140.51 | H |
| ATOM | 3384 | CD | ARG | H | 13 | 58.114 | 39.303 | 4.244 | 1.00 | 140.51 | H |
| ATOM | 3385 | NE | ARG | H | 13 | 57.721 | 39.981 | 3.004 | 1.00 | 140.51 | H |
| ATOM | 3386 | CZ | ARG | H | 13 | 58.519 | 40.161 | 1.954 | 1.00 | 140.51 | H |
| ATOM | 3387 | NH1 | ARG | H | 13 | 59.767 | 39.715 | 1.975 | 1.00 | 140.51 | H |
| ATOM | 3388 | NH2 | ARG | H | 13 | 58.064 | 40.786 | 0.878 | 1.00 | 140.51 | H |
| ATOM | 3389 | C | ARG | H | 13 | 58.338 | 43.585 | 6.722 | 1.00 | 52.20 | H |
| ATOM | 3390 | O | ARG | H | 13 | 57.567 | 43.867 | 7.642 | 1.00 | 52.20 | H |
| ATOM | 3391 | N | PRO | H | 14 | 58.598 | 44.436 | 5.725 | 1.00 | 49.48 | H |
| ATOM | 3392 | CD | PRO | H | 14 | 59.350 | 44.155 | 4.493 | 1.00 | 50.37 | H |
| ATOM | 3393 | CA | PRO | H | 14 | 57.974 | 45.755 | 5.658 | 1.00 | 49.48 | H |
| ATOM | 3394 | CB | PRO | H | 14 | 58.479 | 46.304 | 4.330 | 1.00 | 50.37 | H |
| ATOM | 3395 | CG | PRO | H | 14 | 58.671 | 45.069 | 3.511 | 1.00 | 50.37 | H |
| ATOM | 3396 | C | PRO | H | 14 | 56.462 | 45.652 | 5.707 | 1.00 | 49.48 | H |
| ATOM | 3397 | O | PRO | H | 14 | 55.864 | 44.812 | 5.028 | 1.00 | 49.48 | H |
| ATOM | 3398 | N | GLY | H | 15 | 55.853 | 46.509 | 6.520 | 1.00 | 42.49 | H |
| ATOM | 3399 | CA | GLY | H | 15 | 54.409 | 46.515 | 6.651 | 1.00 | 42.49 | H |
| ATOM | 3400 | C | GLY | H | 15 | 53.886 | 45.598 | 7.740 | 1.00 | 42.49 | H |

TABLE 2-continued

Atomic coordinates of b2 adrenoreceptor

| ATOM | 3401 | O | GLY | H | 15 | 52.728 | 45.704 | 8.155 | 1.00 | 42.49 | H |
| --- | --- | --- | --- | --- | --- | --- | --- | --- | --- | --- | --- |
| ATOM | 3402 | N | ALA | H | 16 | 54.729 | 44.693 | 8.217 | 1.00 | 64.95 | H |
| ATOM | 3403 | CA | ALA | H | 16 | 54.309 | 43.777 | 9.269 | 1.00 | 64.95 | H |
| ATOM | 3404 | CB | ALA | H | 16 | 55.248 | 42.572 | 9.296 | 1.00 | 132.99 | H |
| ATOM | 3405 | C | ALA | H | 16 | 54.230 | 44.430 | 10.657 | 1.00 | 64.95 | H |
| ATOM | 3406 | O | ALA | H | 16 | 54.022 | 45.639 | 10.803 | 1.00 | 64.95 | H |
| ATOM | 3407 | N | SER | H | 17 | 54.404 | 43.619 | 11.687 | 1.00 | 81.17 | H |
| ATOM | 3408 | CA | SER | H | 17 | 54.348 | 44.135 | 13.041 | 1.00 | 81.17 | H |
| ATOM | 3409 | CB | SER | H | 17 | 52.891 | 44.257 | 13.466 | 1.00 | 44.08 | H |
| ATOM | 3410 | OG | SER | H | 17 | 52.798 | 44.172 | 14.873 | 1.00 | 44.08 | H |
| ATOM | 3411 | C | SER | H | 17 | 55.105 | 43.220 | 13.995 | 1.00 | 81.17 | H |
| ATOM | 3412 | O | SER | H | 17 | 54.842 | 42.016 | 14.051 | 1.00 | 81.17 | H |
| ATOM | 3413 | N | VAL | H | 18 | 56.061 | 43.797 | 14.720 | 1.00 | 36.97 | H |
| ATOM | 3414 | CA | VAL | H | 18 | 56.884 | 43.065 | 15.682 | 1.00 | 36.97 | H |
| ATOM | 3415 | CB | VAL | H | 18 | 58.330 | 43.553 | 15.672 | 1.00 | 57.61 | H |
| ATOM | 3416 | CG1 | VAL | H | 18 | 59.071 | 43.021 | 14.467 | 1.00 | 57.61 | H |
| ATOM | 3417 | CG2 | VAL | H | 18 | 58.355 | 45.074 | 15.678 | 1.00 | 57.61 | H |
| ATOM | 3418 | C | VAL | H | 18 | 56.349 | 43.359 | 17.066 | 1.00 | 36.97 | H |
| ATOM | 3419 | O | VAL | H | 18 | 55.568 | 44.319 | 17.232 | 1.00 | 36.97 | H |
| ATOM | 3420 | N | LYS | H | 19 | 56.741 | 42.531 | 18.044 | 1.00 | 60.94 | H |
| ATOM | 3421 | CA | LYS | H | 19 | 56.323 | 42.731 | 19.438 | 1.00 | 60.94 | H |
| ATOM | 3422 | CB | LYS | H | 19 | 55.072 | 41.917 | 19.777 | 1.00 | 56.98 | H |
| ATOM | 3423 | CG | LYS | H | 19 | 54.615 | 42.125 | 21.198 | 1.00 | 56.98 | H |
| ATOM | 3424 | CD | LYS | H | 19 | 53.293 | 41.437 | 21.452 | 1.00 | 56.98 | H |
| ATOM | 3425 | CE | LYS | H | 19 | 52.728 | 41.893 | 22.787 | 1.00 | 56.98 | H |
| ATOM | 3426 | NZ | LYS | H | 19 | 51.436 | 41.241 | 23.114 | 1.00 | 56.98 | H |
| ATOM | 3427 | C | LYS | H | 19 | 57.424 | 42.402 | 20.443 | 1.00 | 60.94 | H |
| ATOM | 3428 | O | LYS | H | 19 | 57.414 | 41.353 | 21.078 | 1.00 | 60.94 | H |
| ATOM | 3429 | N | LEU | H | 20 | 58.365 | 43.325 | 20.590 | 1.00 | 53.48 | H |
| ATOM | 3430 | CA | LEU | H | 20 | 59.491 | 43.158 | 21.505 | 1.00 | 53.48 | H |
| ATOM | 3431 | CB | LEU | H | 20 | 60.442 | 44.374 | 21.376 | 1.00 | 43.77 | H |
| ATOM | 3432 | CG | LEU | H | 20 | 61.237 | 44.645 | 20.081 | 1.00 | 43.77 | H |
| ATOM | 3433 | CD1 | LEU | H | 20 | 60.738 | 43.827 | 18.899 | 1.00 | 43.77 | H |
| ATOM | 3434 | CD2 | LEU | H | 20 | 61.124 | 46.122 | 19.788 | 1.00 | 43.77 | H |
| ATOM | 3435 | C | LEU | H | 20 | 59.088 | 42.944 | 22.982 | 1.00 | 53.48 | H |
| ATOM | 3436 | O | LEU | H | 20 | 58.135 | 43.558 | 23.475 | 1.00 | 53.48 | H |
| ATOM | 3437 | N | SER | H | 21 | 59.824 | 42.067 | 23.671 | 1.00 | 63.77 | H |
| ATOM | 3438 | CA | SER | H | 21 | 59.580 | 41.772 | 25.086 | 1.00 | 63.77 | H |
| ATOM | 3439 | CB | SER | H | 21 | 59.357 | 40.280 | 25.316 | 1.00 | 63.90 | H |
| ATOM | 3440 | OG | SER | H | 21 | 60.599 | 39.606 | 25.457 | 1.00 | 63.90 | H |
| ATOM | 3441 | C | SER | H | 21 | 60.798 | 42.201 | 25.893 | 1.00 | 63.77 | H |
| ATOM | 3442 | O | SER | H | 21 | 61.858 | 42.469 | 25.332 | 1.00 | 63.77 | H |
| ATOM | 3443 | N | CYS | H | 22 | 60.658 | 42.233 | 27.211 | 1.00 | 45.75 | H |
| ATOM | 3444 | CA | CYS | H | 22 | 61.745 | 42.663 | 28.081 | 1.00 | 45.75 | H |
| ATOM | 3445 | C | CYS | H | 22 | 61.511 | 42.056 | 29.446 | 1.00 | 45.75 | H |
| ATOM | 3446 | O | CYS | H | 22 | 60.761 | 42.620 | 30.246 | 1.00 | 45.75 | H |
| ATOM | 3447 | CB | CYS | H | 22 | 61.711 | 44.179 | 28.194 | 1.00 | 56.10 | H |
| ATOM | 3448 | SG | CYS | H | 22 | 62.993 | 44.968 | 29.213 | 1.00 | 56.10 | H |
| ATOM | 3449 | N | LYS | H | 23 | 62.155 | 40.920 | 29.712 | 1.00 | 41.98 | H |
| ATOM | 3450 | CA | LYS | H | 23 | 61.981 | 40.221 | 30.984 | 1.00 | 41.98 | H |
| ATOM | 3451 | CB | LYS | H | 23 | 62.149 | 38.715 | 30.779 | 1.00 | 101.59 | H |
| ATOM | 3452 | CG | LYS | H | 23 | 61.772 | 37.892 | 31.998 | 1.00 | 101.59 | H |
| ATOM | 3453 | CD | LYS | H | 23 | 61.447 | 36.455 | 31.608 | 1.00 | 101.59 | H |
| ATOM | 3454 | CE | LYS | H | 23 | 60.916 | 35.651 | 32.792 | 1.00 | 101.59 | H |
| ATOM | 3455 | NZ | LYS | H | 23 | 60.408 | 34.313 | 32.370 | 1.00 | 101.59 | H |
| ATOM | 3456 | C | LYS | H | 23 | 62.905 | 40.702 | 32.093 | 1.00 | 41.98 | H |
| ATOM | 3457 | O | LYS | H | 23 | 64.032 | 40.226 | 32.243 | 1.00 | 41.98 | H |
| ATOM | 3458 | N | ALA | H | 24 | 62.405 | 41.661 | 32.865 | 1.00 | 56.25 | H |
| ATOM | 3459 | CA | ALA | H | 24 | 63.144 | 42.225 | 33.983 | 1.00 | 56.25 | H |
| ATOM | 3460 | CB | ALA | H | 24 | 62.462 | 43.486 | 34.487 | 1.00 | 27.18 | H |
| ATOM | 3461 | C | ALA | H | 24 | 63.121 | 41.165 | 35.059 | 1.00 | 56.25 | H |
| ATOM | 3462 | O | ALA | H | 24 | 62.120 | 40.460 | 35.211 | 1.00 | 56.25 | H |
| ATOM | 3463 | N | SER | H | 25 | 64.214 | 41.056 | 35.804 | 1.00 | 55.78 | H |
| ATOM | 3464 | CA | SER | H | 25 | 64.317 | 40.060 | 36.854 | 1.00 | 55.78 | H |
| ATOM | 3465 | CB | SER | H | 25 | 64.483 | 38.670 | 36.231 | 1.00 | 56.85 | H |
| ATOM | 3466 | OG | SER | H | 25 | 65.400 | 38.687 | 35.144 | 1.00 | 56.85 | H |
| ATOM | 3467 | C | SER | H | 25 | 65.486 | 40.358 | 37.777 | 1.00 | 55.78 | H |
| ATOM | 3468 | O | SER | H | 25 | 66.627 | 39.977 | 37.498 | 1.00 | 55.78 | H |
| ATOM | 3469 | N | GLY | H | 26 | 65.202 | 41.036 | 38.883 | 1.00 | 65.06 | H |
| ATOM | 3470 | CA | GLY | H | 26 | 66.251 | 41.371 | 39.828 | 1.00 | 65.06 | H |
| ATOM | 3471 | C | GLY | H | 26 | 65.785 | 42.472 | 40.753 | 1.00 | 65.06 | H |
| ATOM | 3472 | O | GLY | H | 26 | 66.564 | 43.048 | 41.512 | 1.00 | 65.06 | H |
| ATOM | 3473 | N | TYR | H | 27 | 64.498 | 42.774 | 40.674 | 1.00 | 86.79 | H |
| ATOM | 3474 | CA | TYR | H | 27 | 63.906 | 43.808 | 41.503 | 1.00 | 86.79 | H |
| ATOM | 3475 | CB | TYR | H | 27 | 64.338 | 45.206 | 41.021 | 1.00 | 59.22 | H |
| ATOM | 3476 | CG | TYR | H | 27 | 63.736 | 45.663 | 39.705 | 1.00 | 59.22 | H |
| ATOM | 3477 | CD1 | TYR | H | 27 | 64.042 | 45.023 | 38.506 | 1.00 | 59.22 | H |
| ATOM | 3478 | CE1 | TYR | H | 27 | 63.475 | 45.430 | 37.310 | 1.00 | 59.22 | H |

TABLE 2-continued

Atomic coordinates of b2 adrenoreceptor

| ATOM | 3479 | CD2 | TYR | H | 27 | 62.846 | 46.731 | 39.667 | 1.00 | 59.22 | H |
|---|---|---|---|---|---|---|---|---|---|---|---|
| ATOM | 3480 | CE2 | TYR | H | 27 | 62.273 | 47.143 | 38.479 | 1.00 | 59.22 | H |
| ATOM | 3481 | CZ | TYR | H | 27 | 62.588 | 46.489 | 37.302 | 1.00 | 59.22 | H |
| ATOM | 3482 | OH | TYR | H | 27 | 61.990 | 46.897 | 36.126 | 1.00 | 59.22 | H |
| ATOM | 3483 | C | TYR | H | 27 | 62.400 | 43.638 | 41.414 | 1.00 | 86.79 | H |
| ATOM | 3484 | O | TYR | H | 27 | 61.918 | 42.677 | 40.812 | 1.00 | 86.79 | H |
| ATOM | 3485 | N | ILE | H | 28 | 61.651 | 44.555 | 42.009 | 1.00 | 46.51 | H |
| ATOM | 3486 | CA | ILE | H | 28 | 60.204 | 44.447 | 41.973 | 1.00 | 46.51 | H |
| ATOM | 3487 | CB | ILE | H | 28 | 59.599 | 44.951 | 43.290 | 1.00 | 50.56 | H |
| ATOM | 3488 | CG2 | ILE | H | 28 | 58.116 | 44.583 | 43.353 | 1.00 | 50.56 | H |
| ATOM | 3489 | CG1 | ILE | H | 28 | 60.349 | 44.329 | 44.471 | 1.00 | 50.56 | H |
| ATOM | 3490 | CD1 | ILE | H | 28 | 59.926 | 44.874 | 45.811 | 1.00 | 50.56 | H |
| ATOM | 3491 | C | ILE | H | 28 | 59.609 | 45.216 | 40.788 | 1.00 | 46.51 | H |
| ATOM | 3492 | O | ILE | H | 28 | 59.420 | 46.433 | 40.848 | 1.00 | 46.51 | H |
| ATOM | 3493 | N | PHE | H | 29 | 59.327 | 44.481 | 39.714 | 1.00 | 84.49 | H |
| ATOM | 3494 | CA | PHE | H | 29 | 58.759 | 45.030 | 38.485 | 1.00 | 84.49 | H |
| ATOM | 3495 | CB | PHE | H | 29 | 57.859 | 43.984 | 37.813 | 1.00 | 30.79 | H |
| ATOM | 3496 | CG | PHE | H | 29 | 57.598 | 44.231 | 36.340 | 1.00 | 30.79 | H |
| ATOM | 3497 | CD1 | PHE | H | 29 | 58.647 | 44.527 | 35.464 | 1.00 | 30.79 | H |
| ATOM | 3498 | CD2 | PHE | H | 29 | 56.313 | 44.095 | 35.815 | 1.00 | 30.79 | H |
| ATOM | 3499 | CE1 | PHE | H | 29 | 58.412 | 44.679 | 34.082 | 1.00 | 30.79 | H |
| ATOM | 3500 | CE2 | PHE | H | 29 | 56.074 | 44.245 | 34.439 | 1.00 | 30.79 | H |
| ATOM | 3501 | CZ | PHE | H | 29 | 57.125 | 44.536 | 33.572 | 1.00 | 30.79 | H |
| ATOM | 3502 | C | PHE | H | 29 | 57.942 | 46.272 | 38.775 | 1.00 | 84.49 | H |
| ATOM | 3503 | O | PHE | H | 29 | 58.252 | 47.360 | 38.284 | 1.00 | 84.49 | H |
| ATOM | 3504 | N | THR | H | 30 | 56.912 | 46.101 | 39.598 | 1.00 | 37.84 | H |
| ATOM | 3505 | CA | THR | H | 30 | 56.011 | 47.197 | 39.943 | 1.00 | 37.84 | H |
| ATOM | 3506 | CB | THR | H | 30 | 54.618 | 46.647 | 40.300 | 1.00 | 74.17 | H |
| ATOM | 3507 | OG1 | THR | H | 30 | 53.799 | 47.714 | 40.786 | 1.00 | 74.17 | H |
| ATOM | 3508 | CG2 | THR | H | 30 | 54.727 | 45.552 | 41.349 | 1.00 | 74.17 | H |
| ATOM | 3509 | C | THR | H | 30 | 56.488 | 48.130 | 41.060 | 1.00 | 37.84 | H |
| ATOM | 3510 | O | THR | H | 30 | 55.873 | 48.212 | 42.126 | 1.00 | 37.84 | H |
| ATOM | 3511 | N | ASP | H | 31 | 57.584 | 48.833 | 40.791 | 1.00 | 76.32 | H |
| ATOM | 3512 | CA | ASP | H | 31 | 58.185 | 49.784 | 41.725 | 1.00 | 76.32 | H |
| ATOM | 3513 | CB | ASP | H | 31 | 59.174 | 49.078 | 42.657 | 1.00 | 89.77 | H |
| ATOM | 3514 | CG | ASP | H | 31 | 58.507 | 48.483 | 43.883 | 1.00 | 89.77 | H |
| ATOM | 3515 | OD1 | ASP | H | 31 | 57.533 | 47.719 | 43.731 | 1.00 | 89.77 | H |
| ATOM | 3516 | OD2 | ASP | H | 31 | 58.966 | 48.776 | 45.008 | 1.00 | 89.77 | H |
| ATOM | 3517 | C | ASP | H | 31 | 58.932 | 50.826 | 40.900 | 1.00 | 76.32 | H |
| ATOM | 3518 | O | ASP | H | 31 | 59.498 | 51.781 | 41.441 | 1.00 | 76.32 | H |
| ATOM | 3519 | N | TYR | H | 32 | 58.919 | 50.621 | 39.582 | 1.00 | 51.88 | H |
| ATOM | 3520 | CA | TYR | H | 32 | 59.589 | 51.490 | 38.617 | 1.00 | 51.88 | H |
| ATOM | 3521 | CB | TYR | H | 32 | 60.988 | 50.987 | 38.321 | 1.00 | 46.31 | H |
| ATOM | 3522 | CG | TYR | H | 32 | 61.977 | 51.067 | 39.442 | 1.00 | 46.31 | H |
| ATOM | 3523 | CD1 | TYR | H | 32 | 62.612 | 52.264 | 39.733 | 1.00 | 46.31 | H |
| ATOM | 3524 | CE1 | TYR | H | 32 | 63.559 | 52.341 | 40.727 | 1.00 | 46.31 | H |
| ATOM | 3525 | CD2 | TYR | H | 32 | 62.313 | 49.934 | 40.185 | 1.00 | 46.31 | H |
| ATOM | 3526 | CE2 | TYR | H | 32 | 63.256 | 49.997 | 41.185 | 1.00 | 46.31 | H |
| ATOM | 3527 | CZ | TYR | H | 32 | 63.882 | 51.210 | 41.454 | 1.00 | 46.31 | H |
| ATOM | 3528 | OH | TYR | H | 32 | 64.837 | 51.312 | 42.449 | 1.00 | 46.31 | H |
| ATOM | 3529 | C | TYR | H | 32 | 58.857 | 51.384 | 37.308 | 1.00 | 51.88 | H |
| ATOM | 3530 | O | TYR | H | 32 | 58.510 | 50.278 | 36.901 | 1.00 | 51.88 | H |
| ATOM | 3531 | N | TYR | H | 33 | 58.629 | 52.500 | 36.625 | 1.00 | 31.30 | H |
| ATOM | 3532 | CA | TYR | H | 33 | 57.990 | 52.376 | 35.321 | 1.00 | 31.30 | H |
| ATOM | 3533 | CB | TYR | H | 33 | 57.511 | 53.699 | 34.719 | 1.00 | 76.06 | H |
| ATOM | 3534 | CG | TYR | H | 33 | 57.214 | 54.847 | 35.640 | 1.00 | 76.06 | H |
| ATOM | 3535 | CD1 | TYR | H | 33 | 58.231 | 55.489 | 36.343 | 1.00 | 76.06 | H |
| ATOM | 3536 | CE1 | TYR | H | 33 | 57.971 | 56.647 | 37.069 | 1.00 | 76.06 | H |
| ATOM | 3537 | CD2 | TYR | H | 33 | 55.929 | 55.381 | 35.700 | 1.00 | 76.06 | H |
| ATOM | 3538 | CE2 | TYR | H | 33 | 55.657 | 56.533 | 36.420 | 1.00 | 76.06 | H |
| ATOM | 3539 | CZ | TYR | H | 33 | 56.677 | 57.168 | 37.095 | 1.00 | 76.06 | H |
| ATOM | 3540 | OH | TYR | H | 33 | 56.400 | 58.352 | 37.740 | 1.00 | 76.06 | H |
| ATOM | 3541 | C | TYR | H | 33 | 59.135 | 51.914 | 34.444 | 1.00 | 31.30 | H |
| ATOM | 3542 | O | TYR | H | 33 | 60.286 | 51.832 | 34.890 | 1.00 | 31.30 | H |
| ATOM | 3543 | N | ILE | H | 34 | 58.835 | 51.624 | 33.189 | 1.00 | 63.77 | H |
| ATOM | 3544 | CA | ILE | H | 34 | 59.887 | 51.219 | 32.282 | 1.00 | 63.77 | H |
| ATOM | 3545 | CB | ILE | H | 34 | 59.989 | 49.673 | 32.174 | 1.00 | 64.88 | H |
| ATOM | 3546 | CG2 | ILE | H | 34 | 59.699 | 49.031 | 33.533 | 1.00 | 64.88 | H |
| ATOM | 3547 | CG1 | ILE | H | 34 | 58.998 | 49.131 | 31.160 | 1.00 | 64.88 | H |
| ATOM | 3548 | CD1 | ILE | H | 34 | 59.302 | 47.718 | 30.796 | 1.00 | 64.88 | H |
| ATOM | 3549 | C | ILE | H | 34 | 59.571 | 51.841 | 30.938 | 1.00 | 63.77 | H |
| ATOM | 3550 | O | ILE | H | 34 | 58.498 | 51.621 | 30.384 | 1.00 | 63.77 | H |
| ATOM | 3551 | N | ASN | H | 35 | 60.489 | 52.653 | 30.431 | 1.00 | 49.38 | H |
| ATOM | 3552 | CA | ASN | H | 35 | 60.259 | 53.297 | 29.149 | 1.00 | 49.38 | H |
| ATOM | 3553 | CB | ASN | H | 35 | 60.894 | 54.687 | 29.085 | 1.00 | 36.13 | H |
| ATOM | 3554 | CG | ASN | H | 35 | 60.864 | 55.407 | 30.398 | 1.00 | 36.13 | H |
| ATOM | 3555 | OD1 | ASN | H | 35 | 60.517 | 56.587 | 30.457 | 1.00 | 36.13 | H |
| ATOM | 3556 | ND2 | ASN | H | 35 | 61.255 | 54.715 | 31.463 | 1.00 | 36.13 | H |

TABLE 2-continued

Atomic coordinates of b2 adrenoreceptor

| ATOM | 3557 | C | ASN | H | 35 | 60.882 | 52.469 | 28.055 | 1.00 | 49.38 | H |
|---|---|---|---|---|---|---|---|---|---|---|---|
| ATOM | 3558 | O | ASN | H | 35 | 61.666 | 51.564 | 28.323 | 1.00 | 49.38 | H |
| ATOM | 3559 | N | TRP | H | 36 | 60.528 | 52.787 | 26.819 | 1.00 | 37.85 | H |
| ATOM | 3560 | CA | TRP | H | 36 | 61.088 | 52.114 | 25.667 | 1.00 | 37.85 | H |
| ATOM | 3561 | CB | TRP | H | 36 | 60.012 | 51.344 | 24.914 | 1.00 | 53.49 | H |
| ATOM | 3562 | CG | TRP | H | 36 | 59.576 | 50.106 | 25.605 | 1.00 | 53.49 | H |
| ATOM | 3563 | CD2 | TRP | H | 36 | 60.053 | 48.779 | 25.360 | 1.00 | 53.49 | H |
| ATOM | 3564 | CE2 | TRP | H | 36 | 59.387 | 47.923 | 26.258 | 1.00 | 53.49 | H |
| ATOM | 3565 | CE3 | TRP | H | 36 | 60.983 | 48.230 | 24.465 | 1.00 | 53.49 | H |
| ATOM | 3566 | CD1 | TRP | H | 36 | 58.662 | 50.004 | 26.615 | 1.00 | 53.49 | H |
| ATOM | 3567 | NE1 | TRP | H | 36 | 58.541 | 48.695 | 27.011 | 1.00 | 53.49 | H |
| ATOM | 3568 | CZ2 | TRP | H | 36 | 59.621 | 46.541 | 26.289 | 1.00 | 53.49 | H |
| ATOM | 3569 | CZ3 | TRP | H | 36 | 61.213 | 46.850 | 24.496 | 1.00 | 53.49 | H |
| ATOM | 3570 | CH2 | TRP | H | 36 | 60.534 | 46.027 | 25.402 | 1.00 | 53.49 | H |
| ATOM | 3571 | C | TRP | H | 36 | 61.648 | 53.217 | 24.782 | 1.00 | 37.85 | H |
| ATOM | 3572 | O | TRP | H | 36 | 60.890 | 53.989 | 24.199 | 1.00 | 37.85 | H |
| ATOM | 3573 | N | VAL | H | 37 | 62.971 | 53.310 | 24.689 | 1.00 | 32.16 | H |
| ATOM | 3574 | CA | VAL | H | 37 | 63.597 | 54.346 | 23.866 | 1.00 | 32.16 | H |
| ATOM | 3575 | CB | VAL | H | 37 | 64.694 | 55.113 | 24.645 | 1.00 | 56.01 | H |
| ATOM | 3576 | CG1 | VAL | H | 37 | 65.358 | 56.149 | 23.740 | 1.00 | 56.01 | H |
| ATOM | 3577 | CG2 | VAL | H | 37 | 64.090 | 55.779 | 25.868 | 1.00 | 56.01 | H |
| ATOM | 3578 | C | VAL | H | 37 | 64.252 | 53.727 | 22.658 | 1.00 | 32.16 | H |
| ATOM | 3579 | O | VAL | H | 37 | 65.044 | 52.800 | 22.786 | 1.00 | 32.16 | H |
| ATOM | 3580 | N | ARG | H | 38 | 63.925 | 54.242 | 21.485 | 1.00 | 43.47 | H |
| ATOM | 3581 | CA | ARG | H | 38 | 64.513 | 53.738 | 20.250 | 1.00 | 43.47 | H |
| ATOM | 3582 | CB | ARG | H | 38 | 63.524 | 53.949 | 19.097 | 1.00 | 55.23 | H |
| ATOM | 3583 | CG | ARG | H | 38 | 64.137 | 53.866 | 17.723 | 1.00 | 55.23 | H |
| ATOM | 3584 | CD | ARG | H | 38 | 63.394 | 54.744 | 16.729 | 1.00 | 55.23 | H |
| ATOM | 3585 | NE | ARG | H | 38 | 62.076 | 54.230 | 16.369 | 1.00 | 55.23 | H |
| ATOM | 3586 | CZ | ARG | H | 38 | 61.351 | 54.709 | 15.360 | 1.00 | 55.23 | H |
| ATOM | 3587 | NH1 | ARG | H | 38 | 61.816 | 55.711 | 14.623 | 1.00 | 55.23 | H |
| ATOM | 3588 | NH2 | ARG | H | 38 | 60.169 | 54.179 | 15.073 | 1.00 | 55.23 | H |
| ATOM | 3589 | C | ARG | H | 38 | 65.808 | 54.507 | 19.976 | 1.00 | 43.47 | H |
| ATOM | 3590 | O | ARG | H | 38 | 65.863 | 55.722 | 20.184 | 1.00 | 43.47 | H |
| ATOM | 3591 | N | GLN | H | 39 | 66.854 | 53.808 | 19.542 | 1.00 | 31.48 | H |
| ATOM | 3592 | CA | GLN | H | 39 | 68.123 | 54.473 | 19.211 | 1.00 | 31.48 | H |
| ATOM | 3593 | CB | GLN | H | 39 | 69.198 | 54.228 | 20.268 | 1.00 | 57.04 | H |
| ATOM | 3594 | CG | GLN | H | 39 | 70.544 | 54.815 | 19.866 | 1.00 | 57.04 | H |
| ATOM | 3595 | CD | GLN | H | 39 | 71.709 | 54.128 | 20.538 | 1.00 | 57.04 | H |
| ATOM | 3596 | OE1 | GLN | H | 39 | 71.671 | 52.919 | 20.759 | 1.00 | 57.04 | H |
| ATOM | 3597 | NE2 | GLN | H | 39 | 72.758 | 54.891 | 20.860 | 1.00 | 57.04 | H |
| ATOM | 3598 | C | GLN | H | 39 | 68.623 | 53.929 | 17.881 | 1.00 | 31.48 | H |
| ATOM | 3599 | O | GLN | H | 39 | 69.280 | 52.881 | 17.841 | 1.00 | 31.48 | H |
| ATOM | 3600 | N | ARG | H | 40 | 68.313 | 54.655 | 16.803 | 1.00 | 58.17 | H |
| ATOM | 3601 | CA | ARG | H | 40 | 68.692 | 54.252 | 15.447 | 1.00 | 58.17 | H |
| ATOM | 3602 | CB | ARG | H | 40 | 68.263 | 55.299 | 14.421 | 1.00 | 31.14 | H |
| ATOM | 3603 | CG | ARG | H | 40 | 68.350 | 54.791 | 12.982 | 1.00 | 31.14 | H |
| ATOM | 3604 | CD | ARG | H | 40 | 68.006 | 55.868 | 11.955 | 1.00 | 31.14 | H |
| ATOM | 3605 | NE | ARG | H | 40 | 66.597 | 55.968 | 11.536 | 1.00 | 31.14 | H |
| ATOM | 3606 | CZ | ARG | H | 40 | 65.577 | 56.330 | 12.316 | 1.00 | 31.14 | H |
| ATOM | 3607 | NH1 | ARG | H | 40 | 65.761 | 56.625 | 13.597 | 1.00 | 31.14 | H |
| ATOM | 3608 | NH2 | ARG | H | 40 | 64.364 | 56.448 | 11.797 | 1.00 | 31.14 | H |
| ATOM | 3609 | C | ARG | H | 40 | 70.176 | 54.032 | 15.314 | 1.00 | 58.17 | H |
| ATOM | 3610 | O | ARG | H | 40 | 70.933 | 54.394 | 16.203 | 1.00 | 58.17 | H |
| ATOM | 3611 | N | THR | H | 41 | 70.599 | 53.437 | 14.205 | 1.00 | 46.68 | H |
| ATOM | 3612 | CA | THR | H | 41 | 72.022 | 53.204 | 14.005 | 1.00 | 46.68 | H |
| ATOM | 3613 | CB | THR | H | 41 | 72.314 | 52.619 | 12.617 | 1.00 | 89.67 | H |
| ATOM | 3614 | OG1 | THR | H | 41 | 73.727 | 52.423 | 12.471 | 1.00 | 89.67 | H |
| ATOM | 3615 | CG2 | THR | H | 41 | 71.799 | 53.555 | 11.521 | 1.00 | 89.67 | H |
| ATOM | 3616 | C | THR | H | 41 | 72.676 | 54.569 | 14.126 | 1.00 | 46.68 | H |
| ATOM | 3617 | O | THR | H | 41 | 72.013 | 55.540 | 14.503 | 1.00 | 46.68 | H |
| ATOM | 3618 | N | GLY | H | 42 | 73.955 | 54.678 | 13.793 | 1.00 | 52.93 | H |
| ATOM | 3619 | CA | GLY | H | 42 | 74.582 | 55.975 | 13.933 | 1.00 | 52.93 | H |
| ATOM | 3620 | C | GLY | H | 42 | 74.340 | 56.336 | 15.383 | 1.00 | 52.93 | H |
| ATOM | 3621 | O | GLY | H | 42 | 74.520 | 55.489 | 16.252 | 1.00 | 52.93 | H |
| ATOM | 3622 | N | GLN | H | 43 | 73.902 | 57.551 | 15.675 | 1.00 | 144.64 | H |
| ATOM | 3623 | CA | GLN | H | 43 | 73.679 | 57.902 | 17.070 | 1.00 | 144.64 | H |
| ATOM | 3624 | CB | GLN | H | 43 | 74.903 | 58.658 | 17.605 | 1.00 | 106.82 | H |
| ATOM | 3625 | CG | GLN | H | 43 | 76.162 | 57.795 | 17.716 | 1.00 | 106.82 | H |
| ATOM | 3626 | CD | GLN | H | 43 | 77.421 | 58.519 | 17.265 | 1.00 | 106.82 | H |
| ATOM | 3627 | OE1 | GLN | H | 43 | 77.399 | 59.722 | 16.999 | 1.00 | 106.82 | H |
| ATOM | 3628 | NE2 | GLN | H | 43 | 78.526 | 57.785 | 17.177 | 1.00 | 106.82 | H |
| ATOM | 3629 | C | GLN | H | 43 | 72.409 | 58.713 | 17.288 | 1.00 | 144.64 | H |
| ATOM | 3630 | O | GLN | H | 43 | 71.901 | 59.347 | 16.364 | 1.00 | 144.64 | H |
| ATOM | 3631 | N | GLY | H | 44 | 71.890 | 58.671 | 18.511 | 1.00 | 61.88 | H |
| ATOM | 3632 | CA | GLY | H | 44 | 70.689 | 59.420 | 18.828 | 1.00 | 61.88 | H |
| ATOM | 3633 | C | GLY | H | 44 | 69.670 | 58.609 | 19.595 | 1.00 | 61.88 | H |
| ATOM | 3634 | O | GLY | H | 44 | 69.460 | 57.430 | 19.314 | 1.00 | 61.88 | H |

TABLE 2-continued

Atomic coordinates of b2 adrenoreceptor

| ATOM | 3635 | N | PHE | H | 45 | 69.028 | 59.240 | 20.568 | 1.00 | 48.67 | H |
|---|---|---|---|---|---|---|---|---|---|---|---|
| ATOM | 3636 | CA | PHE | H | 45 | 68.018 | 58.558 | 21.364 | 1.00 | 48.67 | H |
| ATOM | 3637 | CB | PHE | H | 45 | 68.436 | 58.547 | 22.825 | 1.00 | 19.29 | H |
| ATOM | 3638 | CG | PHE | H | 45 | 69.498 | 57.549 | 23.138 | 1.00 | 19.29 | H |
| ATOM | 3639 | CD1 | PHE | H | 45 | 69.162 | 56.230 | 23.426 | 1.00 | 19.29 | H |
| ATOM | 3640 | CD2 | PHE | H | 45 | 70.837 | 57.926 | 23.154 | 1.00 | 19.29 | H |
| ATOM | 3641 | CE1 | PHE | H | 45 | 70.143 | 55.297 | 23.730 | 1.00 | 19.29 | H |
| ATOM | 3642 | CE2 | PHE | H | 45 | 71.835 | 57.004 | 23.456 | 1.00 | 19.29 | H |
| ATOM | 3643 | CZ | PHE | H | 45 | 71.487 | 55.683 | 23.747 | 1.00 | 19.29 | H |
| ATOM | 3644 | C | PHE | H | 45 | 66.650 | 59.215 | 21.246 | 1.00 | 48.67 | H |
| ATOM | 3645 | O | PHE | H | 45 | 66.527 | 60.432 | 21.364 | 1.00 | 48.67 | H |
| ATOM | 3646 | N | GLU | H | 46 | 65.614 | 58.428 | 21.005 | 1.00 | 27.05 | H |
| ATOM | 3647 | CA | GLU | H | 46 | 64.297 | 59.022 | 20.912 | 1.00 | 27.05 | H |
| ATOM | 3648 | CB | GLU | H | 46 | 63.862 | 59.193 | 19.453 | 1.00 | 111.12 | H |
| ATOM | 3649 | CG | GLU | H | 46 | 63.820 | 57.922 | 18.634 | 1.00 | 111.12 | H |
| ATOM | 3650 | CD | GLU | H | 46 | 63.364 | 58.176 | 17.209 | 1.00 | 111.12 | H |
| ATOM | 3651 | OE1 | GLU | H | 46 | 62.238 | 58.689 | 17.029 | 1.00 | 111.12 | H |
| ATOM | 3652 | OE2 | GLU | H | 46 | 64.132 | 57.863 | 16.272 | 1.00 | 111.12 | H |
| ATOM | 3653 | C | GLU | H | 46 | 63.300 | 58.184 | 21.678 | 1.00 | 27.05 | H |
| ATOM | 3654 | O | GLU | H | 46 | 62.972 | 57.056 | 21.286 | 1.00 | 27.05 | H |
| ATOM | 3655 | N | TRP | H | 47 | 62.840 | 58.749 | 22.794 | 1.00 | 29.49 | H |
| ATOM | 3656 | CA | TRP | H | 47 | 61.867 | 58.116 | 23.683 | 1.00 | 29.49 | H |
| ATOM | 3657 | CB | TRP | H | 47 | 61.572 | 59.095 | 24.804 | 1.00 | 42.14 | H |
| ATOM | 3658 | CG | TRP | H | 47 | 60.560 | 58.638 | 25.755 | 1.00 | 42.14 | H |
| ATOM | 3659 | CD2 | TRP | H | 47 | 59.254 | 59.175 | 25.915 | 1.00 | 42.14 | H |
| ATOM | 3660 | CE2 | TRP | H | 47 | 58.646 | 58.477 | 26.974 | 1.00 | 42.14 | H |
| ATOM | 3661 | CE3 | TRP | H | 47 | 58.536 | 60.179 | 25.264 | 1.00 | 42.14 | H |
| ATOM | 3662 | CD1 | TRP | H | 47 | 60.694 | 57.659 | 26.687 | 1.00 | 42.14 | H |
| ATOM | 3663 | NE1 | TRP | H | 47 | 59.549 | 57.555 | 27.430 | 1.00 | 42.14 | H |
| ATOM | 3664 | CZ2 | TRP | H | 47 | 57.348 | 58.751 | 27.400 | 1.00 | 42.14 | H |
| ATOM | 3665 | CZ3 | TRP | H | 47 | 57.247 | 60.451 | 25.681 | 1.00 | 42.14 | H |
| ATOM | 3666 | CH2 | TRP | H | 47 | 56.665 | 59.739 | 26.742 | 1.00 | 42.14 | H |
| ATOM | 3667 | C | TRP | H | 47 | 60.556 | 57.685 | 22.980 | 1.00 | 29.49 | H |
| ATOM | 3668 | O | TRP | H | 47 | 59.879 | 58.489 | 22.344 | 1.00 | 29.49 | H |
| ATOM | 3669 | N | ILE | H | 48 | 60.192 | 56.415 | 23.093 | 1.00 | 36.85 | H |
| ATOM | 3670 | CA | ILE | H | 48 | 58.975 | 55.936 | 22.439 | 1.00 | 36.85 | H |
| ATOM | 3671 | CB | ILE | H | 48 | 59.150 | 54.512 | 21.880 | 1.00 | 20.87 | H |
| ATOM | 3672 | CG2 | ILE | H | 48 | 57.887 | 54.063 | 21.183 | 1.00 | 20.87 | H |
| ATOM | 3673 | CG1 | ILE | H | 48 | 60.336 | 54.491 | 20.907 | 1.00 | 20.87 | H |
| ATOM | 3674 | CD1 | ILE | H | 48 | 60.621 | 53.126 | 20.272 | 1.00 | 20.87 | H |
| ATOM | 3675 | C | ILE | H | 48 | 57.784 | 55.929 | 23.371 | 1.00 | 36.85 | H |
| ATOM | 3676 | O | ILE | H | 48 | 56.650 | 55.894 | 22.920 | 1.00 | 36.85 | H |
| ATOM | 3677 | N | GLY | H | 49 | 58.037 | 55.967 | 24.673 | 1.00 | 59.85 | H |
| ATOM | 3678 | CA | GLY | H | 49 | 56.939 | 55.956 | 25.626 | 1.00 | 59.85 | H |
| ATOM | 3679 | C | GLY | H | 49 | 57.348 | 55.360 | 26.957 | 1.00 | 59.85 | H |
| ATOM | 3680 | O | GLY | H | 49 | 58.416 | 54.754 | 27.076 | 1.00 | 59.85 | H |
| ATOM | 3681 | N | GLU | H | 50 | 56.493 | 55.529 | 27.959 | 1.00 | 62.23 | H |
| ATOM | 3682 | CA | GLU | H | 50 | 56.760 | 55.014 | 29.298 | 1.00 | 62.23 | H |
| ATOM | 3683 | CB | GLU | H | 50 | 57.281 | 56.149 | 30.167 | 1.00 | 43.77 | H |
| ATOM | 3684 | CG | GLU | H | 50 | 57.563 | 55.798 | 31.592 | 1.00 | 43.77 | H |
| ATOM | 3685 | CD | GLU | H | 50 | 57.945 | 57.038 | 32.383 | 1.00 | 43.77 | H |
| ATOM | 3686 | OE1 | GLU | H | 50 | 57.144 | 58.006 | 32.409 | 1.00 | 43.77 | H |
| ATOM | 3687 | OE2 | GLU | H | 50 | 59.047 | 57.055 | 32.973 | 1.00 | 43.77 | H |
| ATOM | 3688 | C | GLU | H | 50 | 55.490 | 54.404 | 29.900 | 1.00 | 62.23 | H |
| ATOM | 3689 | O | GLU | H | 50 | 54.436 | 55.032 | 29.937 | 1.00 | 62.23 | H |
| ATOM | 3690 | N | ILE | H | 51 | 55.592 | 53.167 | 30.357 | 1.00 | 38.08 | H |
| ATOM | 3691 | CA | ILE | H | 51 | 54.448 | 52.488 | 30.930 | 1.00 | 38.08 | H |
| ATOM | 3692 | CB | ILE | H | 51 | 54.090 | 51.224 | 30.082 | 1.00 | 25.52 | H |
| ATOM | 3693 | CG2 | ILE | H | 51 | 55.332 | 50.358 | 29.906 | 1.00 | 25.52 | H |
| ATOM | 3694 | CG1 | ILE | H | 51 | 52.941 | 50.422 | 30.714 | 1.00 | 25.52 | H |
| ATOM | 3695 | CD1 | ILE | H | 51 | 53.356 | 49.514 | 31.835 | 1.00 | 25.52 | H |
| ATOM | 3696 | C | ILE | H | 51 | 54.810 | 52.112 | 32.355 | 1.00 | 38.08 | H |
| ATOM | 3697 | O | ILE | H | 51 | 55.895 | 51.572 | 32.603 | 1.00 | 38.08 | H |
| ATOM | 3698 | N | TYR | H | 52 | 53.909 | 52.429 | 33.286 | 1.00 | 34.23 | H |
| ATOM | 3699 | CA | TYR | H | 52 | 54.108 | 52.130 | 34.702 | 1.00 | 34.23 | H |
| ATOM | 3700 | CB | TYR | H | 52 | 53.487 | 53.219 | 35.574 | 1.00 | 69.03 | H |
| ATOM | 3701 | CG | TYR | H | 52 | 53.736 | 53.015 | 37.046 | 1.00 | 69.03 | H |
| ATOM | 3702 | CD1 | TYR | H | 52 | 55.027 | 53.073 | 37.568 | 1.00 | 69.03 | H |
| ATOM | 3703 | CE1 | TYR | H | 52 | 55.267 | 52.864 | 38.923 | 1.00 | 69.03 | H |
| ATOM | 3704 | CD2 | TYR | H | 52 | 52.685 | 52.744 | 37.917 | 1.00 | 69.03 | H |
| ATOM | 3705 | CE2 | TYR | H | 52 | 52.915 | 52.532 | 39.278 | 1.00 | 69.03 | H |
| ATOM | 3706 | CZ | TYR | H | 52 | 54.207 | 52.594 | 39.771 | 1.00 | 69.03 | H |
| ATOM | 3707 | OH | TYR | H | 52 | 54.437 | 52.389 | 41.108 | 1.00 | 69.03 | H |
| ATOM | 3708 | C | TYR | H | 52 | 53.443 | 50.793 | 34.996 | 1.00 | 34.23 | H |
| ATOM | 3709 | O | TYR | H | 52 | 52.222 | 50.718 | 35.159 | 1.00 | 34.23 | H |
| ATOM | 3710 | N | PRO | H | 53 | 54.249 | 49.719 | 35.090 | 1.00 | 53.10 | H |
| ATOM | 3711 | CD | PRO | H | 53 | 55.704 | 49.788 | 35.320 | 1.00 | 59.00 | H |
| ATOM | 3712 | CA | PRO | H | 53 | 53.760 | 48.364 | 35.354 | 1.00 | 53.10 | H |

TABLE 2-continued

Atomic coordinates of b2 adrenoreceptor

| ATOM | 3713 | CB | PRO | H | 53 | 55.047 | 47.580 | 35.600 | 1.00 | 59.00 | H |
|---|---|---|---|---|---|---|---|---|---|---|---|
| ATOM | 3714 | CG | PRO | H | 53 | 55.935 | 48.607 | 36.222 | 1.00 | 59.00 | H |
| ATOM | 3715 | C | PRO | H | 53 | 52.782 | 48.275 | 36.513 | 1.00 | 53.10 | H |
| ATOM | 3716 | O | PRO | H | 53 | 51.747 | 47.614 | 36.402 | 1.00 | 53.10 | H |
| ATOM | 3717 | N | GLY | H | 54 | 53.110 | 48.956 | 37.610 | 1.00 | 56.61 | H |
| ATOM | 3718 | CA | GLY | H | 54 | 52.257 | 48.935 | 38.788 | 1.00 | 56.61 | H |
| ATOM | 3719 | C | GLY | H | 54 | 50.804 | 49.372 | 38.618 | 1.00 | 56.61 | H |
| ATOM | 3720 | O | GLY | H | 54 | 49.885 | 48.696 | 39.092 | 1.00 | 56.61 | H |
| ATOM | 3721 | N | SER | H | 55 | 50.591 | 50.505 | 37.950 | 1.00 | 55.72 | H |
| ATOM | 3722 | CA | SER | H | 55 | 49.251 | 51.039 | 37.737 | 1.00 | 55.72 | H |
| ATOM | 3723 | CB | SER | H | 55 | 49.283 | 52.564 | 37.748 | 1.00 | 90.27 | H |
| ATOM | 3724 | OG | SER | H | 55 | 48.144 | 53.090 | 37.088 | 1.00 | 90.27 | H |
| ATOM | 3725 | C | SER | H | 55 | 48.655 | 50.583 | 36.430 | 1.00 | 55.72 | H |
| ATOM | 3726 | O | SER | H | 55 | 47.844 | 49.665 | 36.394 | 1.00 | 55.72 | H |
| ATOM | 3727 | N | GLY | H | 56 | 49.068 | 51.255 | 35.361 | 1.00 | 76.95 | H |
| ATOM | 3728 | CA | GLY | H | 56 | 48.588 | 50.957 | 34.028 | 1.00 | 76.95 | H |
| ATOM | 3729 | C | GLY | H | 56 | 48.873 | 52.132 | 33.110 | 1.00 | 76.95 | H |
| ATOM | 3730 | O | GLY | H | 56 | 48.865 | 51.983 | 31.890 | 1.00 | 76.95 | H |
| ATOM | 3731 | N | ASN | H | 57 | 49.128 | 53.300 | 33.702 | 1.00 | 70.43 | H |
| ATOM | 3732 | CA | ASN | H | 57 | 49.422 | 54.525 | 32.951 | 1.00 | 70.43 | H |
| ATOM | 3733 | CB | ASN | H | 57 | 49.926 | 55.626 | 33.889 | 1.00 | 112.76 | H |
| ATOM | 3734 | CG | ASN | H | 57 | 48.801 | 56.377 | 34.566 | 1.00 | 112.76 | H |
| ATOM | 3735 | OD1 | ASN | H | 57 | 47.980 | 55.790 | 35.275 | 1.00 | 112.76 | H |
| ATOM | 3736 | ND2 | ASN | H | 57 | 48.756 | 57.687 | 34.352 | 1.00 | 112.76 | H |
| ATOM | 3737 | C | ASN | H | 57 | 50.460 | 54.303 | 31.872 | 1.00 | 70.43 | H |
| ATOM | 3738 | O | ASN | H | 57 | 51.560 | 53.840 | 32.159 | 1.00 | 70.43 | H |
| ATOM | 3739 | N | ILE | H | 58 | 50.113 | 54.638 | 30.632 | 1.00 | 64.38 | H |
| ATOM | 3740 | CA | ILE | H | 58 | 51.044 | 54.477 | 29.518 | 1.00 | 64.38 | H |
| ATOM | 3741 | CB | ILE | H | 58 | 50.591 | 53.402 | 28.522 | 1.00 | 44.70 | H |
| ATOM | 3742 | CG2 | ILE | H | 58 | 51.709 | 53.131 | 27.521 | 1.00 | 44.70 | H |
| ATOM | 3743 | CG1 | ILE | H | 58 | 50.203 | 52.124 | 29.259 | 1.00 | 44.70 | H |
| ATOM | 3744 | CD1 | ILE | H | 58 | 49.639 | 51.073 | 28.353 | 1.00 | 44.70 | H |
| ATOM | 3745 | C | ILE | H | 58 | 51.122 | 55.766 | 28.734 | 1.00 | 64.38 | H |
| ATOM | 3746 | O | ILE | H | 58 | 50.371 | 55.955 | 27.791 | 1.00 | 64.38 | H |
| ATOM | 3747 | N | ASP | H | 59 | 52.025 | 56.656 | 29.108 | 1.00 | 54.85 | H |
| ATOM | 3748 | CA | ASP | H | 59 | 52.140 | 57.910 | 28.387 | 1.00 | 54.85 | H |
| ATOM | 3749 | CB | ASP | H | 59 | 52.725 | 58.975 | 29.300 | 1.00 | 83.63 | H |
| ATOM | 3750 | CG | ASP | H | 59 | 51.927 | 59.139 | 30.565 | 1.00 | 83.63 | H |
| ATOM | 3751 | OD1 | ASP | H | 59 | 50.713 | 59.403 | 30.459 | 1.00 | 83.63 | H |
| ATOM | 3752 | OD2 | ASP | H | 59 | 52.506 | 59.000 | 31.661 | 1.00 | 83.63 | H |
| ATOM | 3753 | C | ASP | H | 59 | 53.007 | 57.748 | 27.142 | 1.00 | 54.85 | H |
| ATOM | 3754 | O | ASP | H | 59 | 54.237 | 57.636 | 27.231 | 1.00 | 54.85 | H |
| ATOM | 3755 | N | TYR | H | 60 | 52.367 | 57.730 | 25.977 | 1.00 | 36.48 | H |
| ATOM | 3756 | CA | TYR | H | 60 | 53.110 | 57.578 | 24.741 | 1.00 | 36.48 | H |
| ATOM | 3757 | CB | TYR | H | 60 | 52.227 | 57.021 | 23.625 | 1.00 | 38.45 | H |
| ATOM | 3758 | CG | TYR | H | 60 | 51.734 | 55.626 | 23.856 | 1.00 | 38.45 | H |
| ATOM | 3759 | CD1 | TYR | H | 60 | 50.524 | 55.397 | 24.490 | 1.00 | 38.45 | H |
| ATOM | 3760 | CE1 | TYR | H | 60 | 50.048 | 54.105 | 24.693 | 1.00 | 38.45 | H |
| ATOM | 3761 | CD2 | TYR | H | 60 | 52.474 | 54.526 | 23.427 | 1.00 | 38.45 | H |
| ATOM | 3762 | CE2 | TYR | H | 60 | 52.011 | 53.221 | 23.624 | 1.00 | 38.45 | H |
| ATOM | 3763 | CZ | TYR | H | 60 | 50.792 | 53.020 | 24.258 | 1.00 | 38.45 | H |
| ATOM | 3764 | OH | TYR | H | 60 | 50.312 | 51.742 | 24.455 | 1.00 | 38.45 | H |
| ATOM | 3765 | C | TYR | H | 60 | 53.667 | 58.900 | 24.274 | 1.00 | 36.48 | H |
| ATOM | 3766 | O | TYR | H | 60 | 53.251 | 59.964 | 24.707 | 1.00 | 36.48 | H |
| ATOM | 3767 | N | ASN | H | 61 | 54.632 | 58.804 | 23.381 | 1.00 | 57.07 | H |
| ATOM | 3768 | CA | ASN | H | 61 | 55.227 | 59.964 | 22.770 | 1.00 | 57.07 | H |
| ATOM | 3769 | CB | ASN | H | 61 | 56.658 | 59.646 | 22.362 | 1.00 | 72.58 | H |
| ATOM | 3770 | CG | ASN | H | 61 | 57.186 | 60.601 | 21.327 | 1.00 | 72.58 | H |
| ATOM | 3771 | OD1 | ASN | H | 61 | 56.617 | 60.737 | 20.243 | 1.00 | 72.58 | H |
| ATOM | 3772 | ND2 | ASN | H | 61 | 58.282 | 61.274 | 21.648 | 1.00 | 72.58 | H |
| ATOM | 3773 | C | ASN | H | 61 | 54.354 | 60.154 | 21.524 | 1.00 | 57.07 | H |
| ATOM | 3774 | O | ASN | H | 61 | 54.140 | 59.192 | 20.772 | 1.00 | 57.07 | H |
| ATOM | 3775 | N | GLU | H | 62 | 53.830 | 61.366 | 21.319 | 1.00 | 53.78 | H |
| ATOM | 3776 | CA | GLU | H | 62 | 52.991 | 61.656 | 20.152 | 1.00 | 53.78 | H |
| ATOM | 3777 | CB | GLU | H | 62 | 53.098 | 63.125 | 19.743 | 1.00 | 160.58 | H |
| ATOM | 3778 | CG | GLU | H | 62 | 52.239 | 64.091 | 20.515 | 1.00 | 160.58 | H |
| ATOM | 3779 | CD | GLU | H | 62 | 52.216 | 65.458 | 19.860 | 1.00 | 160.58 | H |
| ATOM | 3780 | OE1 | GLU | H | 62 | 53.298 | 66.067 | 19.709 | 1.00 | 160.58 | H |
| ATOM | 3781 | OE2 | GLU | H | 62 | 51.117 | 65.920 | 19.487 | 1.00 | 160.58 | H |
| ATOM | 3782 | C | GLU | H | 62 | 53.424 | 60.814 | 18.963 | 1.00 | 53.78 | H |
| ATOM | 3783 | O | GLU | H | 62 | 52.701 | 59.923 | 18.527 | 1.00 | 53.78 | H |
| ATOM | 3784 | N | ARG | H | 63 | 54.619 | 61.104 | 18.452 | 1.00 | 55.64 | H |
| ATOM | 3785 | CA | ARG | H | 63 | 55.164 | 60.401 | 17.300 | 1.00 | 55.64 | H |
| ATOM | 3786 | CB | ARG | H | 63 | 56.683 | 60.550 | 17.277 | 1.00 | 99.57 | H |
| ATOM | 3787 | CG | ARG | H | 63 | 57.133 | 62.009 | 17.272 | 1.00 | 99.57 | H |
| ATOM | 3788 | CD | ARG | H | 63 | 58.640 | 62.121 | 17.440 | 1.00 | 99.57 | H |
| ATOM | 3789 | NE | ARG | H | 63 | 59.032 | 63.312 | 18.195 | 1.00 | 99.57 | H |
| ATOM | 3790 | CZ | ARG | H | 63 | 60.076 | 63.363 | 19.023 | 1.00 | 99.57 | H |

TABLE 2-continued

Atomic coordinates of b2 adrenoreceptor

| ATOM | 3791 | NH1 | ARG | H | 63 | 60.844 | 62.290 | 19.207 | 1.00 | 99.57 | H |
|---|---|---|---|---|---|---|---|---|---|---|---|
| ATOM | 3792 | NH2 | ARG | H | 63 | 60.348 | 64.486 | 19.680 | 1.00 | 99.57 | H |
| ATOM | 3793 | C | ARG | H | 63 | 54.751 | 58.929 | 17.251 | 1.00 | 55.64 | H |
| ATOM | 3794 | O | ARG | H | 63 | 54.039 | 58.523 | 16.332 | 1.00 | 55.64 | H |
| ATOM | 3795 | N | PHE | H | 64 | 55.155 | 58.125 | 18.232 | 1.00 | 46.91 | H |
| ATOM | 3796 | CA | PHE | H | 64 | 54.778 | 56.707 | 18.211 | 1.00 | 46.91 | H |
| ATOM | 3797 | CB | PHE | H | 64 | 55.798 | 55.839 | 18.968 | 1.00 | 41.50 | H |
| ATOM | 3798 | CG | PHE | H | 64 | 57.235 | 56.132 | 18.624 | 1.00 | 41.50 | H |
| ATOM | 3799 | CD1 | PHE | H | 64 | 57.913 | 57.183 | 19.234 | 1.00 | 41.50 | H |
| ATOM | 3800 | CD2 | PHE | H | 64 | 57.912 | 55.359 | 17.696 | 1.00 | 41.50 | H |
| ATOM | 3801 | CE1 | PHE | H | 64 | 59.244 | 57.452 | 18.924 | 1.00 | 41.50 | H |
| ATOM | 3802 | CE2 | PHE | H | 64 | 59.243 | 55.625 | 17.382 | 1.00 | 41.50 | H |
| ATOM | 3803 | CZ | PHE | H | 64 | 59.908 | 56.671 | 17.997 | 1.00 | 41.50 | H |
| ATOM | 3804 | C | PHE | H | 64 | 53.394 | 56.467 | 18.805 | 1.00 | 46.91 | H |
| ATOM | 3805 | O | PHE | H | 64 | 53.022 | 55.329 | 19.066 | 1.00 | 46.91 | H |
| ATOM | 3806 | N | LYS | H | 65 | 52.636 | 57.536 | 19.015 | 1.00 | 78.11 | H |
| ATOM | 3807 | CA | LYS | H | 65 | 51.298 | 57.421 | 19.580 | 1.00 | 78.11 | H |
| ATOM | 3808 | CB | LYS | H | 65 | 50.512 | 58.710 | 19.331 | 1.00 | 116.99 | H |
| ATOM | 3809 | CG | LYS | H | 65 | 49.081 | 58.710 | 19.834 | 1.00 | 116.99 | H |
| ATOM | 3810 | CD | LYS | H | 65 | 48.453 | 60.063 | 19.564 | 1.00 | 116.99 | H |
| ATOM | 3811 | CE | LYS | H | 65 | 47.015 | 60.131 | 20.029 | 1.00 | 116.99 | H |
| ATOM | 3812 | NZ | LYS | H | 65 | 46.447 | 61.494 | 19.803 | 1.00 | 116.99 | H |
| ATOM | 3813 | C | LYS | H | 65 | 50.524 | 56.236 | 19.009 | 1.00 | 78.11 | H |
| ATOM | 3814 | O | LYS | H | 65 | 50.241 | 55.270 | 19.715 | 1.00 | 78.11 | H |
| ATOM | 3815 | N | ASP | H | 66 | 50.183 | 56.304 | 17.731 | 1.00 | 87.31 | H |
| ATOM | 3816 | CA | ASP | H | 66 | 49.429 | 55.231 | 17.104 | 1.00 | 87.31 | H |
| ATOM | 3817 | CB | ASP | H | 66 | 48.638 | 55.785 | 15.922 | 1.00 | 122.24 | H |
| ATOM | 3818 | CG | ASP | H | 66 | 49.527 | 56.436 | 14.884 | 1.00 | 122.24 | H |
| ATOM | 3819 | OD1 | ASP | H | 66 | 48.986 | 57.007 | 13.914 | 1.00 | 122.24 | H |
| ATOM | 3820 | OD2 | ASP | H | 66 | 50.767 | 56.373 | 15.035 | 1.00 | 122.24 | H |
| ATOM | 3821 | C | ASP | H | 66 | 50.301 | 54.067 | 16.638 | 1.00 | 87.31 | H |
| ATOM | 3822 | O | ASP | H | 66 | 49.808 | 52.955 | 16.455 | 1.00 | 87.31 | H |
| ATOM | 3823 | N | LYS | H | 67 | 51.594 | 54.320 | 16.457 | 1.00 | 63.37 | H |
| ATOM | 3824 | CA | LYS | H | 67 | 52.532 | 53.292 | 15.994 | 1.00 | 63.37 | H |
| ATOM | 3825 | CB | LYS | H | 67 | 53.859 | 53.954 | 15.617 | 1.00 | 82.94 | H |
| ATOM | 3826 | CG | LYS | H | 67 | 54.915 | 52.995 | 15.075 | 1.00 | 82.94 | H |
| ATOM | 3827 | CD | LYS | H | 67 | 54.600 | 52.545 | 13.660 | 1.00 | 82.94 | H |
| ATOM | 3828 | CE | LYS | H | 67 | 55.797 | 51.871 | 13.028 | 1.00 | 82.94 | H |
| ATOM | 3829 | NZ | LYS | H | 67 | 55.556 | 51.665 | 11.583 | 1.00 | 82.94 | H |
| ATOM | 3830 | C | LYS | H | 67 | 52.808 | 52.150 | 16.985 | 1.00 | 63.37 | H |
| ATOM | 3831 | O | LYS | H | 67 | 52.772 | 50.970 | 16.629 | 1.00 | 63.37 | H |
| ATOM | 3832 | N | ALA | H | 68 | 53.094 | 52.505 | 18.229 | 1.00 | 75.36 | H |
| ATOM | 3833 | CA | ALA | H | 68 | 53.402 | 51.505 | 19.232 | 1.00 | 75.36 | H |
| ATOM | 3834 | CB | ALA | H | 68 | 54.837 | 51.694 | 19.721 | 1.00 | 41.23 | H |
| ATOM | 3835 | C | ALA | H | 68 | 52.450 | 51.537 | 20.410 | 1.00 | 75.36 | H |
| ATOM | 3836 | O | ALA | H | 68 | 51.886 | 52.576 | 20.741 | 1.00 | 75.36 | H |
| ATOM | 3837 | N | THR | H | 69 | 52.274 | 50.381 | 21.040 | 1.00 | 38.75 | H |
| ATOM | 3838 | CA | THR | H | 69 | 51.414 | 50.279 | 22.205 | 1.00 | 38.75 | H |
| ATOM | 3839 | CB | THR | H | 69 | 50.055 | 49.707 | 21.822 | 1.00 | 52.74 | H |
| ATOM | 3840 | OG1 | THR | H | 69 | 50.234 | 48.496 | 21.088 | 1.00 | 52.74 | H |
| ATOM | 3841 | CG2 | THR | H | 69 | 49.300 | 50.705 | 20.957 | 1.00 | 52.74 | H |
| ATOM | 3842 | C | THR | H | 69 | 52.070 | 49.436 | 23.303 | 1.00 | 38.75 | H |
| ATOM | 3843 | O | THR | H | 69 | 52.239 | 48.218 | 23.175 | 1.00 | 38.75 | H |
| ATOM | 3844 | N | LEU | H | 70 | 52.454 | 50.116 | 24.381 | 1.00 | 48.22 | H |
| ATOM | 3845 | CA | LEU | H | 70 | 53.109 | 49.483 | 25.510 | 1.00 | 48.22 | H |
| ATOM | 3846 | CB | LEU | H | 70 | 53.704 | 50.547 | 26.425 | 1.00 | 39.33 | H |
| ATOM | 3847 | CG | LEU | H | 70 | 54.639 | 51.563 | 25.760 | 1.00 | 39.33 | H |
| ATOM | 3848 | CD1 | LEU | H | 70 | 55.471 | 52.258 | 26.827 | 1.00 | 39.33 | H |
| ATOM | 3849 | CD2 | LEU | H | 70 | 55.566 | 50.866 | 24.784 | 1.00 | 39.33 | H |
| ATOM | 3850 | C | LEU | H | 70 | 52.162 | 48.600 | 26.302 | 1.00 | 48.22 | H |
| ATOM | 3851 | O | LEU | H | 70 | 50.942 | 48.753 | 26.234 | 1.00 | 48.22 | H |
| ATOM | 3852 | N | THR | H | 71 | 52.732 | 47.679 | 27.068 | 1.00 | 62.14 | H |
| ATOM | 3853 | CA | THR | H | 71 | 51.939 | 46.754 | 27.857 | 1.00 | 62.14 | H |
| ATOM | 3854 | CB | THR | H | 71 | 51.186 | 45.770 | 26.918 | 1.00 | 56.58 | H |
| ATOM | 3855 | OG1 | THR | H | 71 | 50.753 | 44.629 | 27.656 | 1.00 | 56.58 | H |
| ATOM | 3856 | CG2 | THR | H | 71 | 52.080 | 45.312 | 25.777 | 1.00 | 56.58 | H |
| ATOM | 3857 | C | THR | H | 71 | 52.845 | 46.000 | 28.830 | 1.00 | 62.14 | H |
| ATOM | 3858 | O | THR | H | 71 | 53.994 | 45.690 | 28.505 | 1.00 | 62.14 | H |
| ATOM | 3859 | N | ALA | H | 72 | 52.331 | 45.721 | 30.027 | 1.00 | 62.46 | H |
| ATOM | 3860 | CA | ALA | H | 72 | 53.104 | 45.018 | 31.054 | 1.00 | 62.46 | H |
| ATOM | 3861 | CB | ALA | H | 72 | 53.274 | 45.913 | 32.271 | 1.00 | 37.18 | H |
| ATOM | 3862 | C | ALA | H | 72 | 52.483 | 43.698 | 31.490 | 1.00 | 62.46 | H |
| ATOM | 3863 | O | ALA | H | 72 | 51.295 | 43.457 | 31.273 | 1.00 | 62.46 | H |
| ATOM | 3864 | N | ASP | H | 73 | 53.292 | 42.849 | 32.122 | 1.00 | 73.88 | H |
| ATOM | 3865 | CA | ASP | H | 73 | 52.809 | 41.561 | 32.614 | 1.00 | 73.88 | H |
| ATOM | 3866 | CB | ASP | H | 73 | 53.324 | 40.421 | 31.743 | 1.00 | 117.13 | H |
| ATOM | 3867 | CG | ASP | H | 73 | 52.385 | 39.241 | 31.738 | 1.00 | 117.13 | H |
| ATOM | 3868 | OD1 | ASP | H | 73 | 51.240 | 39.406 | 31.265 | 1.00 | 117.13 | H |

TABLE 2-continued

Atomic coordinates of b2 adrenoreceptor

| ATOM | 3869 | OD2 | ASP | H | 73 | 52.782 | 38.158 | 32.212 | 1.00 | 117.13 | H |
|---|---|---|---|---|---|---|---|---|---|---|---|
| ATOM | 3870 | C | ASP | H | 73 | 53.246 | 41.336 | 34.060 | 1.00 | 73.88 | H |
| ATOM | 3871 | O | ASP | H | 73 | 54.317 | 40.786 | 34.322 | 1.00 | 73.88 | H |
| ATOM | 3872 | N | LYS | H | 74 | 52.391 | 41.769 | 34.984 | 1.00 | 114.12 | H |
| ATOM | 3873 | CA | LYS | H | 74 | 52.624 | 41.676 | 36.422 | 1.00 | 114.12 | H |
| ATOM | 3874 | CB | LYS | H | 74 | 51.326 | 42.022 | 37.159 | 1.00 | 145.15 | H |
| ATOM | 3875 | CG | LYS | H | 74 | 50.764 | 43.387 | 36.756 | 1.00 | 145.15 | H |
| ATOM | 3876 | CD | LYS | H | 74 | 49.408 | 43.686 | 37.386 | 1.00 | 145.15 | H |
| ATOM | 3877 | CE | LYS | H | 74 | 48.846 | 45.005 | 36.862 | 1.00 | 145.15 | H |
| ATOM | 3878 | NZ | LYS | H | 74 | 47.497 | 45.320 | 37.414 | 1.00 | 145.15 | H |
| ATOM | 3879 | C | LYS | H | 74 | 53.163 | 40.327 | 36.889 | 1.00 | 114.12 | H |
| ATOM | 3880 | O | LYS | H | 74 | 54.053 | 40.262 | 37.736 | 1.00 | 114.12 | H |
| ATOM | 3881 | N | SER | H | 75 | 52.622 | 39.250 | 36.339 | 1.00 | 70.86 | H |
| ATOM | 3882 | CA | SER | H | 75 | 53.076 | 37.918 | 36.703 | 1.00 | 70.86 | H |
| ATOM | 3883 | CB | SER | H | 75 | 52.123 | 36.862 | 36.136 | 1.00 | 101.83 | H |
| ATOM | 3884 | OG | SER | H | 75 | 52.658 | 35.556 | 36.293 | 1.00 | 101.83 | H |
| ATOM | 3885 | C | SER | H | 75 | 54.475 | 37.684 | 36.147 | 1.00 | 70.86 | H |
| ATOM | 3886 | O | SER | H | 75 | 55.466 | 37.720 | 36.888 | 1.00 | 70.86 | H |
| ATOM | 3887 | N | SER | H | 76 | 54.529 | 37.449 | 34.833 | 1.00 | 83.87 | H |
| ATOM | 3888 | CA | SER | H | 76 | 55.765 | 37.186 | 34.092 | 1.00 | 83.87 | H |
| ATOM | 3889 | CB | SER | H | 76 | 55.510 | 37.272 | 32.587 | 1.00 | 127.59 | H |
| ATOM | 3890 | OG | SER | H | 76 | 54.547 | 36.321 | 32.174 | 1.00 | 127.59 | H |
| ATOM | 3891 | C | SER | H | 76 | 56.860 | 38.158 | 34.455 | 1.00 | 83.87 | H |
| ATOM | 3892 | O | SER | H | 76 | 58.038 | 37.866 | 34.280 | 1.00 | 83.87 | H |
| ATOM | 3893 | N | SER | H | 77 | 56.456 | 39.318 | 34.960 | 1.00 | 48.82 | H |
| ATOM | 3894 | CA | SER | H | 77 | 57.390 | 40.355 | 35.354 | 1.00 | 48.82 | H |
| ATOM | 3895 | CB | SER | H | 77 | 58.264 | 39.865 | 36.513 | 1.00 | 66.70 | H |
| ATOM | 3896 | OG | SER | H | 77 | 58.763 | 40.947 | 37.277 | 1.00 | 66.70 | H |
| ATOM | 3897 | C | SER | H | 77 | 58.226 | 40.671 | 34.122 | 1.00 | 48.82 | H |
| ATOM | 3898 | O | SER | H | 77 | 59.461 | 40.756 | 34.169 | 1.00 | 48.82 | H |
| ATOM | 3899 | N | THR | H | 78 | 57.520 | 40.803 | 33.004 | 1.00 | 56.07 | H |
| ATOM | 3900 | CA | THR | H | 78 | 58.128 | 41.140 | 31.726 | 1.00 | 56.07 | H |
| ATOM | 3901 | CB | THR | H | 78 | 58.219 | 39.936 | 30.781 | 1.00 | 80.98 | H |
| ATOM | 3902 | OG1 | THR | H | 78 | 57.030 | 39.865 | 29.987 | 1.00 | 80.98 | H |
| ATOM | 3903 | CG2 | THR | H | 78 | 58.369 | 38.651 | 31.572 | 1.00 | 80.98 | H |
| ATOM | 3904 | C | THR | H | 78 | 57.180 | 42.157 | 31.110 | 1.00 | 56.07 | H |
| ATOM | 3905 | O | THR | H | 78 | 55.990 | 42.170 | 31.428 | 1.00 | 56.07 | H |
| ATOM | 3906 | N | ALA | H | 79 | 57.705 | 43.008 | 30.237 | 1.00 | 65.73 | H |
| ATOM | 3907 | CA | ALA | H | 79 | 56.888 | 44.032 | 29.607 | 1.00 | 65.73 | H |
| ATOM | 3908 | CB | ALA | H | 79 | 57.351 | 45.381 | 30.065 | 1.00 | 0.49 | H |
| ATOM | 3909 | C | ALA | H | 79 | 56.978 | 43.914 | 28.095 | 1.00 | 65.73 | H |
| ATOM | 3910 | O | ALA | H | 79 | 57.852 | 43.221 | 27.589 | 1.00 | 65.73 | H |
| ATOM | 3911 | N | TYR | H | 80 | 56.080 | 44.579 | 27.374 | 1.00 | 85.35 | H |
| ATOM | 3912 | CA | TYR | H | 80 | 56.082 | 44.490 | 25.914 | 1.00 | 85.35 | H |
| ATOM | 3913 | CB | TYR | H | 80 | 55.003 | 43.514 | 25.440 | 1.00 | 67.80 | H |
| ATOM | 3914 | CG | TYR | H | 80 | 55.076 | 42.151 | 26.065 | 1.00 | 67.80 | H |
| ATOM | 3915 | CD1 | TYR | H | 80 | 54.719 | 41.952 | 27.393 | 1.00 | 67.80 | H |
| ATOM | 3916 | CE1 | TYR | H | 80 | 54.831 | 40.705 | 27.984 | 1.00 | 67.80 | H |
| ATOM | 3917 | CD2 | TYR | H | 80 | 55.541 | 41.065 | 25.339 | 1.00 | 67.80 | H |
| ATOM | 3918 | CE2 | TYR | H | 80 | 55.658 | 39.816 | 25.917 | 1.00 | 67.80 | H |
| ATOM | 3919 | CZ | TYR | H | 80 | 55.305 | 39.639 | 27.240 | 1.00 | 67.80 | H |
| ATOM | 3920 | OH | TYR | H | 80 | 55.458 | 38.397 | 27.819 | 1.00 | 67.80 | H |
| ATOM | 3921 | C | TYR | H | 80 | 55.853 | 45.807 | 25.189 | 1.00 | 85.35 | H |
| ATOM | 3922 | O | TYR | H | 80 | 55.495 | 46.816 | 25.798 | 1.00 | 85.35 | H |
| ATOM | 3923 | N | MET | H | 81 | 56.063 | 45.771 | 23.875 | 1.00 | 77.93 | H |
| ATOM | 3924 | CA | MET | H | 81 | 55.845 | 46.925 | 23.009 | 1.00 | 77.93 | H |
| ATOM | 3925 | CB | MET | H | 81 | 57.118 | 47.741 | 22.822 | 1.00 | 95.85 | H |
| ATOM | 3926 | CG | MET | H | 81 | 56.924 | 48.842 | 21.792 | 1.00 | 95.85 | H |
| ATOM | 3927 | SD | MET | H | 81 | 58.301 | 49.953 | 21.692 | 1.00 | 95.85 | H |
| ATOM | 3928 | CE | MET | H | 81 | 59.554 | 48.839 | 21.058 | 1.00 | 95.85 | H |
| ATOM | 3929 | C | MET | H | 81 | 55.342 | 46.482 | 21.639 | 1.00 | 77.93 | H |
| ATOM | 3930 | O | MET | H | 81 | 55.991 | 45.698 | 20.953 | 1.00 | 77.93 | H |
| ATOM | 3931 | N | GLN | H | 82 | 54.188 | 47.005 | 21.239 | 1.00 | 109.95 | H |
| ATOM | 3932 | CA | GLN | H | 82 | 53.586 | 46.646 | 19.962 | 1.00 | 109.95 | H |
| ATOM | 3933 | CB | GLN | H | 82 | 52.069 | 46.544 | 20.121 | 1.00 | 122.83 | H |
| ATOM | 3934 | CG | GLN | H | 82 | 51.349 | 46.008 | 18.904 | 1.00 | 122.83 | H |
| ATOM | 3935 | CD | GLN | H | 82 | 51.670 | 44.557 | 18.652 | 1.00 | 122.83 | H |
| ATOM | 3936 | OE1 | GLN | H | 82 | 52.451 | 43.945 | 19.382 | 1.00 | 122.83 | H |
| ATOM | 3937 | NE2 | GLN | H | 82 | 51.067 | 43.992 | 17.617 | 1.00 | 122.83 | H |
| ATOM | 3938 | C | GLN | H | 82 | 53.909 | 47.658 | 18.874 | 1.00 | 109.95 | H |
| ATOM | 3939 | O | GLN | H | 82 | 53.428 | 48.791 | 18.912 | 1.00 | 109.95 | H |
| ATOM | 3940 | N | LEU | H | 83 | 54.709 | 47.239 | 17.896 | 1.00 | 46.55 | H |
| ATOM | 3941 | CA | LEU | H | 83 | 55.090 | 48.121 | 16.800 | 1.00 | 46.55 | H |
| ATOM | 3942 | CB | LEU | H | 83 | 56.606 | 48.132 | 16.673 | 1.00 | 45.63 | H |
| ATOM | 3943 | CG | LEU | H | 83 | 57.197 | 49.511 | 16.375 | 1.00 | 45.63 | H |
| ATOM | 3944 | CD1 | LEU | H | 83 | 56.191 | 50.615 | 16.735 | 1.00 | 45.63 | H |
| ATOM | 3945 | CD2 | LEU | H | 83 | 58.512 | 49.671 | 17.148 | 1.00 | 45.63 | H |
| ATOM | 3946 | C | LEU | H | 83 | 54.439 | 47.688 | 15.488 | 1.00 | 46.55 | H |

TABLE 2-continued

Atomic coordinates of b2 adrenoreceptor

| ATOM | 3947 | O | LEU | H | 83 | 54.906 | 46.756 | 14.839 | 1.00 | 46.55 | H |
|---|---|---|---|---|---|---|---|---|---|---|---|
| ATOM | 3948 | N | SER | H | 84 | 53.366 | 48.379 | 15.101 | 1.00 | 51.98 | H |
| ATOM | 3949 | CA | SER | H | 84 | 52.611 | 48.037 | 13.894 | 1.00 | 51.98 | H |
| ATOM | 3950 | CB | SER | H | 84 | 51.121 | 48.315 | 14.122 | 1.00 | 109.90 | H |
| ATOM | 3951 | OG | SER | H | 84 | 50.628 | 47.591 | 15.238 | 1.00 | 109.90 | H |
| ATOM | 3952 | C | SER | H | 84 | 53.053 | 48.720 | 12.605 | 1.00 | 51.98 | H |
| ATOM | 3953 | O | SER | H | 84 | 53.684 | 49.779 | 12.630 | 1.00 | 51.98 | H |
| ATOM | 3954 | N | SER | H | 85 | 52.699 | 48.090 | 11.482 | 1.00 | 47.98 | H |
| ATOM | 3955 | CA | SER | H | 85 | 53.020 | 48.576 | 10.136 | 1.00 | 47.98 | H |
| ATOM | 3956 | CB | SER | H | 85 | 52.045 | 49.679 | 9.720 | 1.00 | 69.55 | H |
| ATOM | 3957 | OG | SER | H | 85 | 52.148 | 50.789 | 10.590 | 1.00 | 69.55 | H |
| ATOM | 3958 | C | SER | H | 85 | 54.442 | 49.099 | 10.031 | 1.00 | 47.98 | H |
| ATOM | 3959 | O | SER | H | 85 | 54.658 | 50.255 | 9.678 | 1.00 | 47.98 | H |
| ATOM | 3960 | N | LEU | H | 86 | 55.403 | 48.229 | 10.325 | 1.00 | 52.75 | H |
| ATOM | 3961 | CA | LEU | H | 86 | 56.821 | 48.574 | 10.295 | 1.00 | 52.75 | H |
| ATOM | 3962 | CB | LEU | H | 86 | 57.649 | 47.368 | 10.724 | 1.00 | 28.77 | H |
| ATOM | 3963 | CG | LEU | H | 86 | 57.118 | 46.718 | 12.000 | 1.00 | 28.77 | H |
| ATOM | 3964 | CD1 | LEU | H | 86 | 58.016 | 45.574 | 12.418 | 1.00 | 28.77 | H |
| ATOM | 3965 | CD2 | LEU | H | 86 | 57.058 | 47.761 | 13.091 | 1.00 | 28.77 | H |
| ATOM | 3966 | C | LEU | H | 86 | 57.311 | 49.071 | 8.945 | 1.00 | 52.75 | H |
| ATOM | 3967 | O | LEU | H | 86 | 56.846 | 48.636 | 7.895 | 1.00 | 52.75 | H |
| ATOM | 3968 | N | THR | H | 87 | 58.272 | 49.980 | 8.984 | 1.00 | 62.72 | H |
| ATOM | 3969 | CA | THR | H | 87 | 58.817 | 50.551 | 7.771 | 1.00 | 62.72 | H |
| ATOM | 3970 | CB | THR | H | 87 | 58.313 | 51.977 | 7.601 | 1.00 | 58.38 | H |
| ATOM | 3971 | OG1 | THR | H | 87 | 58.696 | 52.469 | 6.318 | 1.00 | 58.38 | H |
| ATOM | 3972 | CG2 | THR | H | 87 | 58.913 | 52.865 | 8.658 | 1.00 | 58.38 | H |
| ATOM | 3973 | C | THR | H | 87 | 60.344 | 50.547 | 7.831 | 1.00 | 62.72 | H |
| ATOM | 3974 | O | THR | H | 87 | 60.927 | 50.345 | 8.899 | 1.00 | 62.72 | H |
| ATOM | 3975 | N | SER | H | 88 | 60.984 | 50.771 | 6.685 | 1.00 | 50.99 | H |
| ATOM | 3976 | CA | SER | H | 88 | 62.445 | 50.776 | 6.583 | 1.00 | 50.99 | H |
| ATOM | 3977 | CB | SER | H | 88 | 62.870 | 51.239 | 5.189 | 1.00 | 101.97 | H |
| ATOM | 3978 | OG | SER | H | 88 | 62.303 | 50.417 | 4.187 | 1.00 | 101.97 | H |
| ATOM | 3979 | C | SER | H | 88 | 63.128 | 51.652 | 7.630 | 1.00 | 50.99 | H |
| ATOM | 3980 | O | SER | H | 88 | 64.275 | 51.400 | 8.016 | 1.00 | 50.99 | H |
| ATOM | 3981 | N | GLU | H | 89 | 62.416 | 52.680 | 8.086 | 1.00 | 63.32 | H |
| ATOM | 3982 | CA | GLU | H | 89 | 62.956 | 53.599 | 9.076 | 1.00 | 63.32 | H |
| ATOM | 3983 | CB | GLU | H | 89 | 62.531 | 55.027 | 8.736 | 1.00 | 141.16 | H |
| ATOM | 3984 | CG | GLU | H | 89 | 61.164 | 55.129 | 8.100 | 1.00 | 141.16 | H |
| ATOM | 3985 | CD | GLU | H | 89 | 60.875 | 56.518 | 7.578 | 1.00 | 141.16 | H |
| ATOM | 3986 | OE1 | GLU | H | 89 | 60.819 | 57.461 | 8.394 | 1.00 | 141.16 | H |
| ATOM | 3987 | OE2 | GLU | H | 89 | 60.710 | 56.666 | 6.349 | 1.00 | 141.16 | H |
| ATOM | 3988 | C | GLU | H | 89 | 62.592 | 53.261 | 10.518 | 1.00 | 63.32 | H |
| ATOM | 3989 | O | GLU | H | 89 | 62.966 | 53.975 | 11.442 | 1.00 | 63.32 | H |
| ATOM | 3990 | N | ASP | H | 90 | 61.849 | 52.181 | 10.717 | 1.00 | 41.42 | H |
| ATOM | 3991 | CA | ASP | H | 90 | 61.501 | 51.771 | 12.068 | 1.00 | 41.42 | H |
| ATOM | 3992 | CB | ASP | H | 90 | 60.179 | 51.007 | 12.077 | 1.00 | 83.99 | H |
| ATOM | 3993 | CG | ASP | H | 90 | 58.987 | 51.923 | 12.209 | 1.00 | 83.99 | H |
| ATOM | 3994 | OD1 | ASP | H | 90 | 58.863 | 52.588 | 13.258 | 1.00 | 83.99 | H |
| ATOM | 3995 | OD2 | ASP | H | 90 | 58.174 | 51.982 | 11.270 | 1.00 | 83.99 | H |
| ATOM | 3996 | C | ASP | H | 90 | 62.627 | 50.878 | 12.578 | 1.00 | 41.42 | H |
| ATOM | 3997 | O | ASP | H | 90 | 62.695 | 50.556 | 13.764 | 1.00 | 41.42 | H |
| ATOM | 3998 | N | SER | H | 91 | 63.519 | 50.492 | 11.665 | 1.00 | 45.92 | H |
| ATOM | 3999 | CA | SER | H | 91 | 64.648 | 49.633 | 12.002 | 1.00 | 45.92 | H |
| ATOM | 4000 | CB | SER | H | 91 | 65.379 | 49.200 | 10.731 | 1.00 | 75.80 | H |
| ATOM | 4001 | OG | SER | H | 91 | 64.484 | 48.619 | 9.798 | 1.00 | 75.80 | H |
| ATOM | 4002 | C | SER | H | 91 | 65.603 | 50.391 | 12.904 | 1.00 | 45.92 | H |
| ATOM | 4003 | O | SER | H | 91 | 65.879 | 51.561 | 12.667 | 1.00 | 45.92 | H |
| ATOM | 4004 | N | ALA | H | 92 | 66.101 | 49.719 | 13.937 | 1.00 | 51.91 | H |
| ATOM | 4005 | CA | ALA | H | 92 | 67.036 | 50.312 | 14.895 | 1.00 | 51.91 | H |
| ATOM | 4006 | CB | ALA | H | 92 | 66.612 | 51.722 | 15.239 | 1.00 | 8.17 | H |
| ATOM | 4007 | C | ALA | H | 92 | 67.068 | 49.481 | 16.162 | 1.00 | 51.91 | H |
| ATOM | 4008 | O | ALA | H | 92 | 66.384 | 48.467 | 16.277 | 1.00 | 51.91 | H |
| ATOM | 4009 | N | VAL | H | 93 | 67.866 | 49.911 | 17.123 | 1.00 | 34.85 | H |
| ATOM | 4010 | CA | VAL | H | 93 | 67.925 | 49.192 | 18.378 | 1.00 | 34.85 | H |
| ATOM | 4011 | CB | VAL | H | 93 | 69.307 | 49.270 | 19.026 | 1.00 | 24.29 | H |
| ATOM | 4012 | CG1 | VAL | H | 93 | 69.239 | 48.679 | 20.420 | 1.00 | 24.29 | H |
| ATOM | 4013 | CG2 | VAL | H | 93 | 70.329 | 48.519 | 18.178 | 1.00 | 24.29 | H |
| ATOM | 4014 | C | VAL | H | 93 | 66.896 | 49.798 | 19.329 | 1.00 | 34.85 | H |
| ATOM | 4015 | O | VAL | H | 93 | 66.810 | 51.026 | 19.500 | 1.00 | 34.85 | H |
| ATOM | 4016 | N | TYR | H | 94 | 66.102 | 48.922 | 19.934 | 1.00 | 51.97 | H |
| ATOM | 4017 | CA | TYR | H | 94 | 65.072 | 49.356 | 20.852 | 1.00 | 51.97 | H |
| ATOM | 4018 | CB | TYR | H | 94 | 63.731 | 48.737 | 20.457 | 1.00 | 58.28 | H |
| ATOM | 4019 | CG | TYR | H | 94 | 63.147 | 49.346 | 19.194 | 1.00 | 58.28 | H |
| ATOM | 4020 | CD1 | TYR | H | 94 | 63.753 | 49.155 | 17.948 | 1.00 | 58.28 | H |
| ATOM | 4021 | CE1 | TYR | H | 94 | 63.236 | 49.749 | 16.797 | 1.00 | 58.28 | H |
| ATOM | 4022 | CD2 | TYR | H | 94 | 62.006 | 50.147 | 19.254 | 1.00 | 58.28 | H |
| ATOM | 4023 | CE2 | TYR | H | 94 | 61.480 | 50.746 | 18.115 | 1.00 | 58.28 | H |
| ATOM | 4024 | CZ | TYR | H | 94 | 62.096 | 50.547 | 16.890 | 1.00 | 58.28 | H |

TABLE 2-continued

Atomic coordinates of b2 adrenoreceptor

| ATOM | 4025 | OH | TYR | H | 94 | 61.568 | 51.164 | 15.774 | 1.00 | 58.28 | H |
| ATOM | 4026 | C | TYR | H | 94 | 65.459 | 48.989 | 22.266 | 1.00 | 51.97 | H |
| ATOM | 4027 | O | TYR | H | 94 | 65.670 | 47.822 | 22.587 | 1.00 | 51.97 | H |
| ATOM | 4028 | N | PHE | H | 95 | 65.568 | 50.014 | 23.101 | 1.00 | 41.38 | H |
| ATOM | 4029 | CA | PHE | H | 95 | 65.958 | 49.841 | 24.487 | 1.00 | 41.38 | H |
| ATOM | 4030 | CB | PHE | H | 95 | 66.960 | 50.919 | 24.906 | 1.00 | 37.97 | H |
| ATOM | 4031 | CG | PHE | H | 95 | 68.321 | 50.741 | 24.309 | 1.00 | 37.97 | H |
| ATOM | 4032 | CD1 | PHE | H | 95 | 68.688 | 51.438 | 23.162 | 1.00 | 37.97 | H |
| ATOM | 4033 | CD2 | PHE | H | 95 | 69.221 | 49.843 | 24.868 | 1.00 | 37.97 | H |
| ATOM | 4034 | CE1 | PHE | H | 95 | 69.930 | 51.247 | 22.575 | 1.00 | 37.97 | H |
| ATOM | 4035 | CE2 | PHE | H | 95 | 70.457 | 49.644 | 24.294 | 1.00 | 37.97 | H |
| ATOM | 4036 | CZ | PHE | H | 95 | 70.817 | 50.350 | 23.137 | 1.00 | 37.97 | H |
| ATOM | 4037 | C | PHE | H | 95 | 64.804 | 49.850 | 25.453 | 1.00 | 41.38 | H |
| ATOM | 4038 | O | PHE | H | 95 | 63.859 | 50.637 | 25.327 | 1.00 | 41.38 | H |
| ATOM | 4039 | N | CYS | H | 96 | 64.914 | 48.965 | 26.435 | 1.00 | 24.19 | H |
| ATOM | 4040 | CA | CYS | H | 96 | 63.904 | 48.821 | 27.458 | 1.00 | 24.19 | H |
| ATOM | 4041 | C | CYS | H | 96 | 64.568 | 49.171 | 28.750 | 1.00 | 24.19 | H |
| ATOM | 4042 | O | CYS | H | 96 | 65.275 | 48.357 | 29.327 | 1.00 | 24.19 | H |
| ATOM | 4043 | CB | CYS | H | 96 | 63.406 | 47.391 | 27.487 | 1.00 | 68.43 | H |
| ATOM | 4044 | SG | CYS | H | 96 | 62.520 | 46.936 | 28.993 | 1.00 | 68.43 | H |
| ATOM | 4045 | N | VAL | H | 97 | 64.356 | 50.402 | 29.191 | 1.00 | 38.97 | H |
| ATOM | 4046 | CA | VAL | H | 97 | 64.957 | 50.887 | 30.422 | 1.00 | 38.97 | H |
| ATOM | 4047 | CB | VAL | H | 97 | 65.364 | 52.364 | 30.311 | 1.00 | 26.35 | H |
| ATOM | 4048 | CG1 | VAL | H | 97 | 66.815 | 52.480 | 29.949 | 1.00 | 26.35 | H |
| ATOM | 4049 | CG2 | VAL | H | 97 | 64.496 | 53.051 | 29.267 | 1.00 | 26.35 | H |
| ATOM | 4050 | C | VAL | H | 97 | 64.030 | 50.791 | 31.608 | 1.00 | 38.97 | H |
| ATOM | 4051 | O | VAL | H | 97 | 62.826 | 50.580 | 31.468 | 1.00 | 38.97 | H |
| ATOM | 4052 | N | ARG | H | 98 | 64.627 | 50.956 | 32.783 | 1.00 | 62.10 | H |
| ATOM | 4053 | CA | ARG | H | 98 | 63.899 | 50.953 | 34.034 | 1.00 | 62.10 | H |
| ATOM | 4054 | CB | ARG | H | 98 | 64.586 | 50.087 | 35.080 | 1.00 | 50.45 | H |
| ATOM | 4055 | CG | ARG | H | 98 | 63.842 | 50.081 | 36.391 | 1.00 | 50.45 | H |
| ATOM | 4056 | CD | ARG | H | 98 | 64.435 | 49.119 | 37.401 | 1.00 | 50.45 | H |
| ATOM | 4057 | NE | ARG | H | 98 | 65.561 | 49.669 | 38.146 | 1.00 | 50.45 | H |
| ATOM | 4058 | CZ | ARG | H | 98 | 66.074 | 49.095 | 39.233 | 1.00 | 50.45 | H |
| ATOM | 4059 | NH1 | ARG | H | 98 | 65.549 | 47.965 | 39.688 | 1.00 | 50.45 | H |
| ATOM | 4060 | NH2 | ARG | H | 98 | 67.112 | 49.633 | 39.862 | 1.00 | 50.45 | H |
| ATOM | 4061 | C | ARG | H | 98 | 63.952 | 52.398 | 34.475 | 1.00 | 62.10 | H |
| ATOM | 4062 | O | ARG | H | 98 | 64.689 | 52.739 | 35.405 | 1.00 | 62.10 | H |
| ATOM | 4063 | N | GLY | H | 99 | 63.193 | 53.240 | 33.771 | 1.00 | 44.07 | H |
| ATOM | 4064 | CA | GLY | H | 99 | 63.143 | 54.656 | 34.092 | 1.00 | 44.07 | H |
| ATOM | 4065 | C | GLY | H | 99 | 64.470 | 55.378 | 33.996 | 1.00 | 44.07 | H |
| ATOM | 4066 | O | GLY | H | 99 | 64.796 | 56.221 | 34.832 | 1.00 | 44.07 | H |
| ATOM | 4067 | N | PHE | H | 100 | 65.252 | 55.031 | 32.986 | 1.00 | 44.45 | H |
| ATOM | 4068 | CA | PHE | H | 100 | 66.546 | 55.677 | 32.762 | 1.00 | 44.45 | H |
| ATOM | 4069 | CB | PHE | H | 100 | 66.368 | 57.197 | 32.705 | 1.00 | 44.79 | H |
| ATOM | 4070 | CG | PHE | H | 100 | 65.261 | 57.643 | 31.778 | 1.00 | 44.79 | H |
| ATOM | 4071 | CD1 | PHE | H | 100 | 64.827 | 56.822 | 30.735 | 1.00 | 44.79 | H |
| ATOM | 4072 | CD2 | PHE | H | 100 | 64.656 | 58.884 | 31.941 | 1.00 | 44.79 | H |
| ATOM | 4073 | CE1 | PHE | H | 100 | 63.808 | 57.230 | 29.874 | 1.00 | 44.79 | H |
| ATOM | 4074 | CE2 | PHE | H | 100 | 63.638 | 59.304 | 31.087 | 1.00 | 44.79 | H |
| ATOM | 4075 | CZ | PHE | H | 100 | 63.211 | 58.475 | 30.051 | 1.00 | 44.79 | H |
| ATOM | 4076 | C | PHE | H | 100 | 67.637 | 55.325 | 33.766 | 1.00 | 44.45 | H |
| ATOM | 4077 | O | PHE | H | 100 | 68.776 | 55.774 | 33.639 | 1.00 | 44.45 | H |
| ATOM | 4078 | N | GLY | H | 101 | 67.296 | 54.523 | 34.762 | 1.00 | 65.42 | H |
| ATOM | 4079 | CA | GLY | H | 101 | 68.302 | 54.132 | 35.729 | 1.00 | 65.42 | H |
| ATOM | 4080 | C | GLY | H | 101 | 69.200 | 53.059 | 35.135 | 1.00 | 65.42 | H |
| ATOM | 4081 | O | GLY | H | 101 | 70.348 | 53.301 | 34.768 | 1.00 | 65.42 | H |
| ATOM | 4082 | N | TYR | H | 102 | 68.652 | 51.853 | 35.061 | 1.00 | 22.98 | H |
| ATOM | 4083 | CA | TYR | H | 102 | 69.339 | 50.696 | 34.514 | 1.00 | 22.98 | H |
| ATOM | 4084 | CB | TYR | H | 102 | 69.064 | 49.479 | 35.392 | 1.00 | 29.09 | H |
| ATOM | 4085 | CG | TYR | H | 102 | 69.731 | 48.218 | 34.928 | 1.00 | 29.09 | H |
| ATOM | 4086 | CD1 | TYR | H | 102 | 71.042 | 47.943 | 35.269 | 1.00 | 29.09 | H |
| ATOM | 4087 | CE1 | TYR | H | 102 | 71.667 | 46.768 | 34.831 | 1.00 | 29.09 | H |
| ATOM | 4088 | CD2 | TYR | H | 102 | 69.048 | 47.296 | 34.134 | 1.00 | 29.09 | H |
| ATOM | 4089 | CE2 | TYR | H | 102 | 69.657 | 46.116 | 33.686 | 1.00 | 29.09 | H |
| ATOM | 4090 | CZ | TYR | H | 102 | 70.970 | 45.858 | 34.041 | 1.00 | 29.09 | H |
| ATOM | 4091 | OH | TYR | H | 102 | 71.597 | 44.696 | 33.638 | 1.00 | 29.09 | H |
| ATOM | 4092 | C | TYR | H | 102 | 68.739 | 50.477 | 33.125 | 1.00 | 22.98 | H |
| ATOM | 4093 | O | TYR | H | 102 | 67.508 | 50.466 | 32.961 | 1.00 | 22.98 | H |
| ATOM | 4094 | N | TRP | H | 103 | 69.602 | 50.338 | 32.122 | 1.00 | 45.19 | H |
| ATOM | 4095 | CA | TRP | H | 103 | 69.138 | 50.130 | 30.757 | 1.00 | 45.19 | H |
| ATOM | 4096 | CB | TRP | H | 103 | 70.109 | 50.738 | 29.738 | 1.00 | 47.72 | H |
| ATOM | 4097 | CG | TRP | H | 103 | 70.109 | 52.233 | 29.694 | 1.00 | 47.72 | H |
| ATOM | 4098 | CD2 | TRP | H | 103 | 69.539 | 53.057 | 28.678 | 1.00 | 47.72 | H |
| ATOM | 4099 | CE2 | TRP | H | 103 | 69.789 | 54.397 | 29.038 | 1.00 | 47.72 | H |
| ATOM | 4100 | CE3 | TRP | H | 103 | 68.844 | 52.794 | 27.495 | 1.00 | 47.72 | H |
| ATOM | 4101 | CD1 | TRP | H | 103 | 70.661 | 53.079 | 30.606 | 1.00 | 47.72 | H |
| ATOM | 4102 | NE1 | TRP | H | 103 | 70.475 | 54.380 | 30.221 | 1.00 | 47.72 | H |

TABLE 2-continued

Atomic coordinates of b2 adrenoreceptor

| ATOM | 4103 | CZ2 | TRP | H | 103 | 69.373 | 55.472 | 28.263 | 1.00 | 47.72 | H |
|------|------|-----|-----|---|-----|--------|--------|--------|------|-------|---|
| ATOM | 4104 | CZ3 | TRP | H | 103 | 68.425 | 53.862 | 26.720 | 1.00 | 47.72 | H |
| ATOM | 4105 | CH2 | TRP | H | 103 | 68.693 | 55.188 | 27.108 | 1.00 | 47.72 | H |
| ATOM | 4106 | C | TRP | H | 103 | 69.019 | 48.658 | 30.485 | 1.00 | 45.19 | H |
| ATOM | 4107 | O | TRP | H | 103 | 69.571 | 47.848 | 31.212 | 1.00 | 45.19 | H |
| ATOM | 4108 | N | GLY | H | 104 | 68.295 | 48.314 | 29.430 | 1.00 | 23.43 | H |
| ATOM | 4109 | CA | GLY | H | 104 | 68.139 | 46.921 | 29.061 | 1.00 | 23.43 | H |
| ATOM | 4110 | C | GLY | H | 104 | 69.332 | 46.424 | 28.253 | 1.00 | 23.43 | H |
| ATOM | 4111 | O | GLY | H | 104 | 70.423 | 47.017 | 28.292 | 1.00 | 23.43 | H |
| ATOM | 4112 | N | GLN | H | 105 | 69.136 | 45.319 | 27.536 | 1.00 | 47.29 | H |
| ATOM | 4113 | CA | GLN | H | 105 | 70.189 | 44.756 | 26.697 | 1.00 | 47.29 | H |
| ATOM | 4114 | CB | GLN | H | 105 | 69.998 | 43.247 | 26.504 | 1.00 | 98.69 | H |
| ATOM | 4115 | CG | GLN | H | 105 | 70.514 | 42.407 | 27.666 | 1.00 | 98.69 | H |
| ATOM | 4116 | CD | GLN | H | 105 | 70.023 | 40.973 | 27.617 | 1.00 | 98.69 | H |
| ATOM | 4117 | OE1 | GLN | H | 105 | 68.935 | 40.698 | 27.110 | 1.00 | 98.69 | H |
| ATOM | 4118 | NE2 | GLN | H | 105 | 70.816 | 40.051 | 28.162 | 1.00 | 98.69 | H |
| ATOM | 4119 | C | GLN | H | 105 | 70.067 | 45.458 | 25.368 | 1.00 | 47.29 | H |
| ATOM | 4120 | O | GLN | H | 105 | 70.918 | 46.265 | 25.000 | 1.00 | 99.26 | H |
| ATOM | 4121 | N | GLY | H | 106 | 68.979 | 45.163 | 24.670 | 1.00 | 70.03 | H |
| ATOM | 4122 | CA | GLY | H | 106 | 68.734 | 45.771 | 23.381 | 1.00 | 70.03 | H |
| ATOM | 4123 | C | GLY | H | 106 | 68.123 | 44.759 | 22.443 | 1.00 | 70.03 | H |
| ATOM | 4124 | O | GLY | H | 106 | 68.256 | 43.551 | 22.647 | 1.00 | 70.03 | H |
| ATOM | 4125 | N | THR | H | 107 | 67.423 | 45.252 | 21.430 | 1.00 | 25.82 | H |
| ATOM | 4126 | CA | THR | H | 107 | 66.810 | 44.379 | 20.440 | 1.00 | 25.82 | H |
| ATOM | 4127 | CB | THR | H | 107 | 65.339 | 44.164 | 20.732 | 1.00 | 32.22 | H |
| ATOM | 4128 | OG1 | THR | H | 107 | 65.156 | 43.997 | 22.144 | 1.00 | 32.22 | H |
| ATOM | 4129 | CG2 | THR | H | 107 | 64.865 | 42.906 | 20.020 | 1.00 | 32.22 | H |
| ATOM | 4130 | C | THR | H | 107 | 67.000 | 45.032 | 19.078 | 1.00 | 25.82 | H |
| ATOM | 4131 | O | THR | H | 107 | 66.330 | 46.013 | 18.739 | 1.00 | 25.82 | H |
| ATOM | 4132 | N | THR | H | 108 | 67.944 | 44.470 | 18.323 | 1.00 | 24.18 | H |
| ATOM | 4133 | CA | THR | H | 108 | 68.339 | 44.967 | 17.009 | 1.00 | 24.18 | H |
| ATOM | 4134 | CB | THR | H | 108 | 69.719 | 44.364 | 16.604 | 1.00 | 29.19 | H |
| ATOM | 4135 | OG1 | THR | H | 108 | 70.571 | 44.327 | 17.756 | 1.00 | 29.19 | H |
| ATOM | 4136 | CG2 | THR | H | 108 | 70.400 | 45.209 | 15.549 | 1.00 | 29.19 | H |
| ATOM | 4137 | C | THR | H | 108 | 67.312 | 44.713 | 15.913 | 1.00 | 24.18 | H |
| ATOM | 4138 | O | THR | H | 108 | 67.594 | 44.052 | 14.915 | 1.00 | 24.18 | H |
| ATOM | 4139 | N | LEU | H | 109 | 66.122 | 45.266 | 16.113 | 1.00 | 21.19 | H |
| ATOM | 4140 | CA | LEU | H | 109 | 65.029 | 45.141 | 15.163 | 1.00 | 21.19 | H |
| ATOM | 4141 | CB | LEU | H | 109 | 63.814 | 45.907 | 15.654 | 1.00 | 12.05 | H |
| ATOM | 4142 | CG | LEU | H | 109 | 62.684 | 46.173 | 14.666 | 1.00 | 12.05 | H |
| ATOM | 4143 | CD1 | LEU | H | 109 | 62.374 | 44.919 | 13.880 | 1.00 | 12.05 | H |
| ATOM | 4144 | CD2 | LEU | H | 109 | 61.447 | 46.640 | 15.439 | 1.00 | 12.05 | H |
| ATOM | 4145 | C | LEU | H | 109 | 65.412 | 45.680 | 13.813 | 1.00 | 21.19 | H |
| ATOM | 4146 | O | LEU | H | 109 | 66.027 | 46.732 | 13.706 | 1.00 | 21.19 | H |
| ATOM | 4147 | N | THR | H | 110 | 65.047 | 44.952 | 12.774 | 1.00 | 45.20 | H |
| ATOM | 4148 | CA | THR | H | 110 | 65.340 | 45.381 | 11.423 | 1.00 | 45.20 | H |
| ATOM | 4149 | CB | THR | H | 110 | 66.656 | 44.764 | 10.903 | 1.00 | 58.04 | H |
| ATOM | 4150 | OG1 | THR | H | 110 | 66.518 | 44.443 | 9.515 | 1.00 | 58.04 | H |
| ATOM | 4151 | CG2 | THR | H | 110 | 67.025 | 43.526 | 11.700 | 1.00 | 58.04 | H |
| ATOM | 4152 | C | THR | H | 110 | 64.176 | 45.011 | 10.521 | 1.00 | 45.20 | H |
| ATOM | 4153 | O | THR | H | 110 | 63.783 | 43.844 | 10.414 | 1.00 | 45.20 | H |
| ATOM | 4154 | N | VAL | H | 111 | 63.605 | 46.039 | 9.907 | 1.00 | 39.44 | H |
| ATOM | 4155 | CA | VAL | H | 111 | 62.477 | 45.879 | 9.012 | 1.00 | 39.44 | H |
| ATOM | 4156 | CB | VAL | H | 111 | 61.582 | 47.145 | 9.019 | 1.00 | 43.40 | H |
| ATOM | 4157 | CG1 | VAL | H | 111 | 60.361 | 46.920 | 8.155 | 1.00 | 43.40 | H |
| ATOM | 4158 | CG2 | VAL | H | 111 | 61.153 | 47.482 | 10.440 | 1.00 | 43.40 | H |
| ATOM | 4159 | C | VAL | H | 111 | 63.079 | 45.693 | 7.637 | 1.00 | 39.44 | H |
| ATOM | 4160 | O | VAL | H | 111 | 63.694 | 46.613 | 7.113 | 1.00 | 39.44 | H |
| ATOM | 4161 | N | SER | H | 112 | 62.933 | 44.504 | 7.061 | 1.00 | 47.22 | H |
| ATOM | 4162 | CA | SER | H | 112 | 63.500 | 44.268 | 5.743 | 1.00 | 47.22 | H |
| ATOM | 4163 | CB | SER | H | 112 | 64.964 | 43.861 | 5.849 | 1.00 | 45.03 | H |
| ATOM | 4164 | OG | SER | H | 112 | 65.540 | 43.812 | 4.555 | 1.00 | 45.03 | H |
| ATOM | 4165 | C | SER | H | 112 | 62.779 | 43.230 | 4.913 | 1.00 | 47.22 | H |
| ATOM | 4166 | O | SER | H | 112 | 62.042 | 42.399 | 5.444 | 1.00 | 47.22 | H |
| ATOM | 4167 | N | SER | H | 113 | 63.007 | 43.302 | 3.599 | 1.00 | 47.10 | H |
| ATOM | 4168 | CA | SER | H | 113 | 62.418 | 42.384 | 2.632 | 1.00 | 47.10 | H |
| ATOM | 4169 | CB | SER | H | 113 | 62.307 | 43.051 | 1.262 | 1.00 | 88.90 | H |
| ATOM | 4170 | OG | SER | H | 113 | 61.407 | 44.141 | 1.287 | 1.00 | 88.90 | H |
| ATOM | 4171 | C | SER | H | 113 | 63.365 | 41.208 | 2.536 | 1.00 | 47.10 | H |
| ATOM | 4172 | O | SER | H | 113 | 62.981 | 40.115 | 2.123 | 1.00 | 47.10 | H |
| ATOM | 4173 | N | ALA | H | 114 | 64.608 | 41.453 | 2.943 | 1.00 | 53.13 | H |
| ATOM | 4174 | CA | ALA | H | 114 | 65.665 | 40.447 | 2.918 | 1.00 | 53.13 | H |
| ATOM | 4175 | CB | ALA | H | 114 | 66.967 | 41.033 | 3.464 | 1.00 | 43.88 | H |
| ATOM | 4176 | C | ALA | H | 114 | 65.366 | 39.149 | 3.649 | 1.00 | 53.13 | H |
| ATOM | 4177 | O | ALA | H | 114 | 64.561 | 39.087 | 4.590 | 1.00 | 53.13 | H |
| ATOM | 4178 | N | LYS | H | 115 | 66.058 | 38.117 | 3.183 | 1.00 | 46.43 | H |
| ATOM | 4179 | CA | LYS | H | 115 | 65.973 | 36.770 | 3.717 | 1.00 | 46.43 | H |
| ATOM | 4180 | CB | LYS | H | 115 | 65.971 | 35.774 | 2.553 | 1.00 | 114.32 | H |

TABLE 2-continued

Atomic coordinates of b2 adrenoreceptor

| ATOM | 4181 | CG | LYS | H | 115 | 66.940 | 36.162 | 1.429 | 1.00 | 114.32 | H |
| ATOM | 4182 | CD | LYS | H | 115 | 66.996 | 35.116 | 0.322 | 1.00 | 114.32 | H |
| ATOM | 4183 | CE | LYS | H | 115 | 68.006 | 35.495 | −0.755 | 1.00 | 114.32 | H |
| ATOM | 4184 | NZ | LYS | H | 115 | 68.116 | 34.435 | −1.795 | 1.00 | 114.32 | H |
| ATOM | 4185 | C | LYS | H | 115 | 67.210 | 36.575 | 4.593 | 1.00 | 46.43 | H |
| ATOM | 4186 | O | LYS | H | 115 | 68.309 | 37.005 | 4.234 | 1.00 | 77.01 | H |
| ATOM | 4187 | N | THR | H | 116 | 67.048 | 35.944 | 5.743 | 1.00 | 88.23 | H |
| ATOM | 4188 | CA | THR | H | 116 | 68.197 | 35.742 | 6.603 | 1.00 | 88.23 | H |
| ATOM | 4189 | CB | THR | H | 116 | 67.774 | 35.228 | 7.972 | 1.00 | 43.53 | H |
| ATOM | 4190 | OG1 | THR | H | 116 | 66.949 | 36.210 | 8.609 | 1.00 | 43.53 | H |
| ATOM | 4191 | CG2 | THR | H | 116 | 69.000 | 34.962 | 8.836 | 1.00 | 43.53 | H |
| ATOM | 4192 | C | THR | H | 116 | 69.215 | 34.769 | 6.011 | 1.00 | 88.23 | H |
| ATOM | 4193 | O | THR | H | 116 | 68.858 | 33.801 | 5.339 | 1.00 | 88.23 | H |
| ATOM | 4194 | N | THR | H | 117 | 70.488 | 35.043 | 6.267 | 1.00 | 34.92 | H |
| ATOM | 4195 | CA | THR | H | 117 | 71.577 | 34.206 | 5.792 | 1.00 | 34.92 | H |
| ATOM | 4196 | CB | THR | H | 117 | 72.104 | 34.694 | 4.431 | 1.00 | 112.71 | H |
| ATOM | 4197 | OG1 | THR | H | 117 | 72.309 | 36.109 | 4.482 | 1.00 | 112.71 | H |
| ATOM | 4198 | CG2 | THR | H | 117 | 71.115 | 34.366 | 3.321 | 1.00 | 112.71 | H |
| ATOM | 4199 | C | THR | H | 117 | 72.692 | 34.302 | 6.817 | 1.00 | 34.92 | H |
| ATOM | 4200 | O | THR | H | 117 | 73.245 | 35.373 | 7.023 | 1.00 | 34.92 | H |
| ATOM | 4201 | N | PRO | H | 118 | 73.028 | 33.185 | 7.488 | 1.00 | 38.76 | H |
| ATOM | 4202 | CD | PRO | H | 118 | 72.357 | 31.878 | 7.396 | 1.00 | 103.68 | H |
| ATOM | 4203 | CA | PRO | H | 118 | 74.093 | 33.159 | 8.508 | 1.00 | 38.76 | H |
| ATOM | 4204 | CB | PRO | H | 118 | 73.928 | 31.778 | 9.140 | 1.00 | 103.68 | H |
| ATOM | 4205 | CG | PRO | H | 118 | 73.373 | 30.962 | 8.017 | 1.00 | 103.68 | H |
| ATOM | 4206 | C | PRO | H | 118 | 75.517 | 33.421 | 8.002 | 1.00 | 38.76 | H |
| ATOM | 4207 | O | PRO | H | 118 | 75.816 | 33.238 | 6.833 | 1.00 | 38.76 | H |
| ATOM | 4208 | N | PRO | H | 119 | 76.418 | 33.838 | 8.894 | 1.00 | 24.51 | H |
| ATOM | 4209 | CD | PRO | H | 119 | 76.261 | 33.862 | 10.358 | 1.00 | 83.88 | H |
| ATOM | 4210 | CA | PRO | H | 119 | 77.809 | 34.129 | 8.521 | 1.00 | 24.51 | H |
| ATOM | 4211 | CB | PRO | H | 119 | 78.424 | 34.594 | 9.839 | 1.00 | 83.88 | H |
| ATOM | 4212 | CG | PRO | H | 119 | 77.695 | 33.756 | 10.833 | 1.00 | 83.88 | H |
| ATOM | 4213 | C | PRO | H | 119 | 78.629 | 33.004 | 7.882 | 1.00 | 24.51 | H |
| ATOM | 4214 | O | PRO | H | 119 | 78.089 | 32.002 | 7.411 | 1.00 | 24.51 | H |
| ATOM | 4215 | N | SER | H | 120 | 79.945 | 33.207 | 7.866 | 1.00 | 8.76 | H |
| ATOM | 4216 | CA | SER | H | 120 | 80.890 | 32.240 | 7.318 | 1.00 | 8.76 | H |
| ATOM | 4217 | CB | SER | H | 120 | 81.028 | 32.386 | 5.801 | 1.00 | 17.51 | H |
| ATOM | 4218 | OG | SER | H | 120 | 79.890 | 31.881 | 5.142 | 1.00 | 17.51 | H |
| ATOM | 4219 | C | SER | H | 120 | 82.236 | 32.498 | 7.957 | 1.00 | 8.76 | H |
| ATOM | 4220 | O | SER | H | 120 | 83.115 | 33.119 | 7.375 | 1.00 | 8.76 | H |
| ATOM | 4221 | N | VAL | H | 121 | 82.407 | 32.021 | 9.171 | 1.00 | 29.67 | H |
| ATOM | 4222 | CA | VAL | H | 121 | 83.670 | 32.256 | 9.826 | 1.00 | 29.67 | H |
| ATOM | 4223 | CB | VAL | H | 121 | 83.631 | 31.737 | 11.294 | 1.00 | 25.81 | H |
| ATOM | 4224 | CG1 | VAL | H | 121 | 84.698 | 32.443 | 12.134 | 1.00 | 25.81 | H |
| ATOM | 4225 | CG2 | VAL | H | 121 | 82.235 | 31.959 | 11.891 | 1.00 | 25.81 | H |
| ATOM | 4226 | C | VAL | H | 121 | 84.808 | 31.588 | 9.046 | 1.00 | 29.67 | H |
| ATOM | 4227 | O | VAL | H | 121 | 84.806 | 30.384 | 8.804 | 1.00 | 29.67 | H |
| ATOM | 4228 | N | TYR | H | 122 | 85.749 | 32.396 | 8.591 | 1.00 | 42.62 | H |
| ATOM | 4229 | CA | TYR | H | 122 | 86.910 | 31.863 | 7.905 | 1.00 | 42.62 | H |
| ATOM | 4230 | CB | TYR | H | 122 | 87.104 | 32.477 | 6.510 | 1.00 | 42.49 | H |
| ATOM | 4231 | CG | TYR | H | 122 | 86.032 | 32.139 | 5.497 | 1.00 | 42.49 | H |
| ATOM | 4232 | CD1 | TYR | H | 122 | 85.792 | 30.825 | 5.101 | 1.00 | 42.49 | H |
| ATOM | 4233 | CE1 | TYR | H | 122 | 84.761 | 30.520 | 4.198 | 1.00 | 42.49 | H |
| ATOM | 4234 | CD2 | TYR | H | 122 | 85.228 | 33.140 | 4.963 | 1.00 | 42.49 | H |
| ATOM | 4235 | CE2 | TYR | H | 122 | 84.197 | 32.847 | 4.066 | 1.00 | 42.49 | H |
| ATOM | 4236 | CZ | TYR | H | 122 | 83.964 | 31.542 | 3.695 | 1.00 | 42.49 | H |
| ATOM | 4237 | OH | TYR | H | 122 | 82.887 | 31.279 | 2.880 | 1.00 | 42.49 | H |
| ATOM | 4238 | C | TYR | H | 122 | 88.017 | 32.343 | 8.825 | 1.00 | 42.62 | H |
| ATOM | 4239 | O | TYR | H | 122 | 87.909 | 33.418 | 9.417 | 1.00 | 42.62 | H |
| ATOM | 4240 | N | PRO | H | 123 | 89.075 | 31.541 | 8.993 | 1.00 | 39.85 | H |
| ATOM | 4241 | CD | PRO | H | 123 | 89.065 | 30.076 | 8.822 | 1.00 | 42.06 | H |
| ATOM | 4242 | CA | PRO | H | 123 | 90.176 | 31.949 | 9.867 | 1.00 | 39.85 | H |
| ATOM | 4243 | CB | PRO | H | 123 | 90.488 | 30.669 | 10.619 | 1.00 | 42.06 | H |
| ATOM | 4244 | CG | PRO | H | 123 | 90.342 | 29.657 | 9.531 | 1.00 | 42.06 | H |
| ATOM | 4245 | C | PRO | H | 123 | 91.392 | 32.476 | 9.112 | 1.00 | 39.85 | H |
| ATOM | 4246 | O | PRO | H | 123 | 91.771 | 31.941 | 8.074 | 1.00 | 39.85 | H |
| ATOM | 4247 | N | LEU | H | 124 | 92.004 | 33.521 | 9.657 | 1.00 | 43.43 | H |
| ATOM | 4248 | CA | LEU | H | 124 | 93.186 | 34.113 | 9.055 | 1.00 | 43.43 | H |
| ATOM | 4249 | CB | LEU | H | 124 | 93.027 | 35.626 | 8.943 | 1.00 | 66.00 | H |
| ATOM | 4250 | CG | LEU | H | 124 | 91.723 | 36.140 | 8.335 | 1.00 | 66.00 | H |
| ATOM | 4251 | CD1 | LEU | H | 124 | 91.274 | 35.229 | 7.201 | 1.00 | 66.00 | H |
| ATOM | 4252 | CD2 | LEU | H | 124 | 90.658 | 36.197 | 9.404 | 1.00 | 66.00 | H |
| ATOM | 4253 | C | LEU | H | 124 | 94.409 | 33.808 | 9.905 | 1.00 | 43.43 | H |
| ATOM | 4254 | O | LEU | H | 124 | 94.489 | 34.253 | 11.047 | 1.00 | 43.43 | H |
| ATOM | 4255 | N | ALA | H | 125 | 95.348 | 33.046 | 9.345 | 1.00 | 18.92 | H |
| ATOM | 4256 | CA | ALA | H | 125 | 96.588 | 32.682 | 10.040 | 1.00 | 18.92 | H |
| ATOM | 4257 | CB | ALA | H | 125 | 96.736 | 31.180 | 10.076 | 1.00 | 51.83 | H |
| ATOM | 4258 | C | ALA | H | 125 | 97.766 | 33.300 | 9.297 | 1.00 | 18.92 | H |

TABLE 2-continued

Atomic coordinates of b2 adrenoreceptor

| ATOM | 4259 | O   | ALA | H | 125 | 97.678  | 33.546 | 8.093  | 1.00 | 18.92  | H |
|------|------|-----|-----|---|-----|---------|--------|--------|------|--------|---|
| ATOM | 4260 | N   | PRO | H | 126 | 98.891  | 33.546 | 9.992  | 1.00 | 49.67  | H |
| ATOM | 4261 | CD  | PRO | H | 126 | 99.155  | 33.108 | 11.372 | 1.00 | 48.50  | H |
| ATOM | 4262 | CA  | PRO | H | 126 | 100.098 | 34.147 | 9.390  | 1.00 | 49.67  | H |
| ATOM | 4263 | CB  | PRO | H | 126 | 101.141 | 34.033 | 10.509 | 1.00 | 48.50  | H |
| ATOM | 4264 | CG  | PRO | H | 126 | 100.645 | 32.871 | 11.340 | 1.00 | 48.50  | H |
| ATOM | 4265 | C   | PRO | H | 126 | 100.583 | 33.542 | 8.063  | 1.00 | 49.67  | H |
| ATOM | 4266 | O   | PRO | H | 126 | 100.703 | 32.326 | 7.926  | 1.00 | 49.67  | H |
| ATOM | 4267 | N   | GLY | H | 127 | 100.875 | 34.413 | 7.101  | 1.00 | 97.25  | H |
| ATOM | 4268 | CA  | GLY | H | 127 | 101.323 | 33.988 | 5.782  | 1.00 | 97.25  | H |
| ATOM | 4269 | C   | GLY | H | 127 | 102.498 | 33.026 | 5.625  | 1.00 | 97.25  | H |
| ATOM | 4270 | O   | GLY | H | 127 | 102.305 | 31.810 | 5.548  | 1.00 | 97.25  | H |
| ATOM | 4271 | N   | SER | H | 128 | 103.715 | 33.568 | 5.564  | 1.00 | 142.50 | H |
| ATOM | 4272 | CA  | SER | H | 128 | 104.923 | 32.761 | 5.371  | 1.00 | 142.50 | H |
| ATOM | 4273 | CB  | SER | H | 128 | 105.781 | 33.376 | 4.264  | 1.00 | 137.80 | H |
| ATOM | 4274 | OG  | SER | H | 128 | 106.236 | 34.669 | 4.634  | 1.00 | 137.80 | H |
| ATOM | 4275 | C   | SER | H | 128 | 105.800 | 32.564 | 6.603  | 1.00 | 142.50 | H |
| ATOM | 4276 | O   | SER | H | 128 | 106.912 | 33.087 | 6.657  | 1.00 | 142.50 | H |
| ATOM | 4277 | N   | ALA | H | 129 | 105.308 | 31.798 | 7.573  | 1.00 | 200.24 | H |
| ATOM | 4278 | CA  | ALA | H | 129 | 106.046 | 31.517 | 8.807  | 1.00 | 200.24 | H |
| ATOM | 4279 | CB  | ALA | H | 129 | 106.880 | 30.252 | 8.639  | 1.00 | 66.32  | H |
| ATOM | 4280 | C   | ALA | H | 129 | 106.946 | 32.668 | 9.242  | 1.00 | 200.24 | H |
| ATOM | 4281 | O   | ALA | H | 129 | 108.056 | 32.446 | 9.732  | 1.00 | 200.24 | H |
| ATOM | 4282 | N   | ALA | H | 130 | 106.466 | 33.895 | 9.065  | 1.00 | 154.98 | H |
| ATOM | 4283 | CA  | ALA | H | 130 | 107.238 | 35.072 | 9.434  | 1.00 | 154.98 | H |
| ATOM | 4284 | CB  | ALA | H | 130 | 106.646 | 36.309 | 8.780  | 1.00 | 84.07  | H |
| ATOM | 4285 | C   | ALA | H | 130 | 107.298 | 35.259 | 10.943 | 1.00 | 154.98 | H |
| ATOM | 4286 | O   | ALA | H | 130 | 106.442 | 35.918 | 11.532 | 1.00 | 154.98 | H |
| ATOM | 4287 | N   | GLN | H | 131 | 108.308 | 34.663 | 11.566 | 1.00 | 171.38 | H |
| ATOM | 4288 | CA  | GLN | H | 131 | 108.498 | 34.786 | 13.004 | 1.00 | 171.38 | H |
| ATOM | 4289 | CB  | GLN | H | 131 | 109.442 | 33.688 | 13.506 | 1.00 | 197.34 | H |
| ATOM | 4290 | CG  | GLN | H | 131 | 109.793 | 33.775 | 14.987 | 1.00 | 197.34 | H |
| ATOM | 4291 | CD  | GLN | H | 131 | 111.270 | 34.051 | 15.224 | 1.00 | 197.34 | H |
| ATOM | 4292 | OE1 | GLN | H | 131 | 112.054 | 34.161 | 14.281 | 1.00 | 197.34 | H |
| ATOM | 4293 | NE2 | GLN | H | 131 | 111.655 | 34.163 | 16.489 | 1.00 | 197.34 | H |
| ATOM | 4294 | C   | GLN | H | 131 | 109.118 | 36.159 | 13.228 | 1.00 | 171.38 | H |
| ATOM | 4295 | O   | GLN | H | 131 | 110.303 | 36.277 | 13.537 | 1.00 | 171.38 | H |
| ATOM | 4296 | N   | THR | H | 132 | 108.309 | 37.199 | 13.062 | 1.00 | 227.61 | H |
| ATOM | 4297 | CA  | THR | H | 132 | 108.788 | 38.566 | 13.217 | 1.00 | 227.61 | H |
| ATOM | 4298 | CB  | THR | H | 132 | 108.466 | 39.406 | 11.965 | 1.00 | 159.16 | H |
| ATOM | 4299 | OG1 | THR | H | 132 | 107.052 | 39.640 | 11.899 | 1.00 | 159.16 | H |
| ATOM | 4300 | CG2 | THR | H | 132 | 108.912 | 38.675 | 10.703 | 1.00 | 159.16 | H |
| ATOM | 4301 | C   | THR | H | 132 | 108.196 | 39.286 | 14.419 | 1.00 | 227.61 | H |
| ATOM | 4302 | O   | THR | H | 132 | 107.693 | 40.403 | 14.283 | 1.00 | 227.61 | H |
| ATOM | 4303 | N   | ASN | H | 133 | 108.255 | 38.666 | 15.594 | 1.00 | 127.00 | H |
| ATOM | 4304 | CA  | ASN | H | 133 | 107.706 | 39.312 | 16.781 | 1.00 | 127.00 | H |
| ATOM | 4305 | CB  | ASN | H | 133 | 106.244 | 39.714 | 16.531 | 1.00 | 146.46 | H |
| ATOM | 4306 | CG  | ASN | H | 133 | 105.809 | 40.906 | 17.366 | 1.00 | 146.46 | H |
| ATOM | 4307 | OD1 | ASN | H | 133 | 104.622 | 41.230 | 17.435 | 1.00 | 146.46 | H |
| ATOM | 4308 | ND2 | ASN | H | 133 | 106.772 | 41.575 | 17.991 | 1.00 | 146.46 | H |
| ATOM | 4309 | C   | ASN | H | 133 | 107.772 | 38.452 | 18.039 | 1.00 | 127.00 | H |
| ATOM | 4310 | O   | ASN | H | 133 | 108.006 | 37.241 | 17.985 | 1.00 | 127.00 | H |
| ATOM | 4311 | N   | SER | H | 134 | 107.570 | 39.116 | 19.171 | 1.00 | 86.25  | H |
| ATOM | 4312 | CA  | SER | H | 134 | 107.547 | 38.481 | 20.477 | 1.00 | 86.25  | H |
| ATOM | 4313 | CB  | SER | H | 134 | 107.889 | 39.513 | 21.558 | 1.00 | 102.68 | H |
| ATOM | 4314 | OG  | SER | H | 134 | 107.638 | 39.016 | 22.861 | 1.00 | 102.68 | H |
| ATOM | 4315 | C   | SER | H | 134 | 106.102 | 38.031 | 20.621 | 1.00 | 86.25  | H |
| ATOM | 4316 | O   | SER | H | 134 | 105.739 | 37.307 | 21.550 | 1.00 | 86.25  | H |
| ATOM | 4317 | N   | ALA | H | 135 | 105.289 | 38.471 | 19.664 | 1.00 | 81.02  | H |
| ATOM | 4318 | CA  | ALA | H | 135 | 103.866 | 38.170 | 19.637 | 1.00 | 81.02  | H |
| ATOM | 4319 | CB  | ALA | H | 135 | 103.085 | 39.405 | 20.116 | 1.00 | 29.85  | H |
| ATOM | 4320 | C   | ALA | H | 135 | 103.384 | 37.739 | 18.242 | 1.00 | 81.02  | H |
| ATOM | 4321 | O   | ALA | H | 135 | 104.184 | 37.583 | 17.315 | 1.00 | 81.02  | H |
| ATOM | 4322 | N   | VAL | H | 136 | 102.072 | 37.529 | 18.117 | 1.00 | 65.37  | H |
| ATOM | 4323 | CA  | VAL | H | 136 | 101.435 | 37.137 | 16.856 | 1.00 | 65.37  | H |
| ATOM | 4324 | CB  | VAL | H | 136 | 101.327 | 35.617 | 16.688 | 1.00 | 34.49  | H |
| ATOM | 4325 | CG1 | VAL | H | 136 | 100.712 | 35.305 | 15.339 | 1.00 | 34.49  | H |
| ATOM | 4326 | CG2 | VAL | H | 136 | 102.686 | 34.983 | 16.789 | 1.00 | 34.49  | H |
| ATOM | 4327 | C   | VAL | H | 136 | 100.015 | 37.668 | 16.794 | 1.00 | 65.37  | H |
| ATOM | 4328 | O   | VAL | H | 136 | 99.348  | 37.797 | 17.819 | 1.00 | 65.37  | H |
| ATOM | 4329 | N   | THR | H | 137 | 99.540  | 37.973 | 15.596 | 1.00 | 46.12  | H |
| ATOM | 4330 | CA  | THR | H | 137 | 98.185  | 38.465 | 15.482 | 1.00 | 46.12  | H |
| ATOM | 4331 | CB  | THR | H | 137 | 98.140  | 39.998 | 15.233 | 1.00 | 76.70  | H |
| ATOM | 4332 | OG1 | THR | H | 137 | 98.713  | 40.305 | 13.962 | 1.00 | 76.70  | H |
| ATOM | 4333 | CG2 | THR | H | 137 | 98.925  | 40.734 | 16.299 | 1.00 | 76.70  | H |
| ATOM | 4334 | C   | THR | H | 137 | 97.426  | 37.735 | 14.387 | 1.00 | 46.12  | H |
| ATOM | 4335 | O   | THR | H | 137 | 97.655  | 37.934 | 13.200 | 1.00 | 46.12  | H |
| ATOM | 4336 | N   | LEU | H | 138 | 96.539  | 36.850 | 14.803 | 1.00 | 49.28  | H |

TABLE 2-continued

Atomic coordinates of b2 adrenoreceptor

| ATOM | 4337 | CA | LEU | H | 138 | 95.719 | 36.104 | 13.869 | 1.00 | 49.28 | H |
| ATOM | 4338 | CB | LEU | H | 138 | 95.725 | 34.617 | 14.215 | 1.00 | 32.73 | H |
| ATOM | 4339 | CG | LEU | H | 138 | 96.254 | 34.312 | 15.610 | 1.00 | 32.73 | H |
| ATOM | 4340 | CD1 | LEU | H | 138 | 95.638 | 33.034 | 16.165 | 1.00 | 32.73 | H |
| ATOM | 4341 | CD2 | LEU | H | 138 | 97.760 | 34.233 | 15.524 | 1.00 | 32.73 | H |
| ATOM | 4342 | C | LEU | H | 138 | 94.319 | 36.663 | 14.035 | 1.00 | 49.28 | H |
| ATOM | 4343 | O | LEU | H | 138 | 94.070 | 37.452 | 14.947 | 1.00 | 49.28 | H |
| ATOM | 4344 | N | GLY | H | 139 | 93.405 | 36.258 | 13.163 | 1.00 | 16.20 | H |
| ATOM | 4345 | CA | GLY | H | 139 | 92.049 | 36.757 | 13.267 | 1.00 | 16.20 | H |
| ATOM | 4346 | C | GLY | H | 139 | 91.079 | 35.871 | 12.527 | 1.00 | 16.20 | H |
| ATOM | 4347 | O | GLY | H | 139 | 91.493 | 34.946 | 11.824 | 1.00 | 16.20 | H |
| ATOM | 4348 | N | CYS | H | 140 | 89.789 | 36.138 | 12.698 | 1.00 | 36.59 | H |
| ATOM | 4349 | CA | CYS | H | 140 | 88.782 | 35.357 | 12.009 | 1.00 | 36.59 | H |
| ATOM | 4350 | C | CYS | H | 140 | 87.650 | 36.229 | 11.495 | 1.00 | 36.59 | H |
| ATOM | 4351 | O | CYS | H | 140 | 86.812 | 36.722 | 12.246 | 1.00 | 36.59 | H |
| ATOM | 4352 | CB | CYS | H | 140 | 88.250 | 34.219 | 12.899 | 1.00 | 52.48 | H |
| ATOM | 4353 | SG | CYS | H | 140 | 86.818 | 34.522 | 13.988 | 1.00 | 52.48 | H |
| ATOM | 4354 | N | LEU | H | 141 | 87.659 | 36.413 | 10.183 | 1.00 | 5.16 | H |
| ATOM | 4355 | CA | LEU | H | 141 | 86.670 | 37.203 | 9.482 | 1.00 | 5.16 | H |
| ATOM | 4356 | CB | LEU | H | 141 | 87.301 | 37.666 | 8.146 | 1.00 | 17.92 | H |
| ATOM | 4357 | CG | LEU | H | 141 | 86.655 | 37.653 | 6.748 | 1.00 | 17.92 | H |
| ATOM | 4358 | CD1 | LEU | H | 141 | 86.487 | 36.204 | 6.321 | 1.00 | 17.92 | H |
| ATOM | 4359 | CD2 | LEU | H | 141 | 85.331 | 38.430 | 6.719 | 1.00 | 17.92 | H |
| ATOM | 4360 | C | LEU | H | 141 | 85.349 | 36.432 | 9.272 | 1.00 | 5.16 | H |
| ATOM | 4361 | O | LEU | H | 141 | 85.342 | 35.315 | 8.742 | 1.00 | 5.16 | H |
| ATOM | 4362 | N | VAL | H | 142 | 84.245 | 37.020 | 9.722 | 1.00 | 27.04 | H |
| ATOM | 4363 | CA | VAL | H | 142 | 82.938 | 36.407 | 9.548 | 1.00 | 27.04 | H |
| ATOM | 4364 | CB | VAL | H | 142 | 82.034 | 36.588 | 10.813 | 1.00 | 11.21 | H |
| ATOM | 4365 | CG1 | VAL | H | 142 | 82.845 | 37.191 | 11.949 | 1.00 | 11.21 | H |
| ATOM | 4366 | CG2 | VAL | H | 142 | 80.782 | 37.424 | 10.490 | 1.00 | 11.21 | H |
| ATOM | 4367 | C | VAL | H | 142 | 82.323 | 37.115 | 8.351 | 1.00 | 27.04 | H |
| ATOM | 4368 | O | VAL | H | 142 | 81.980 | 38.296 | 8.427 | 1.00 | 27.04 | H |
| ATOM | 4369 | N | LYS | H | 143 | 82.198 | 36.404 | 7.235 | 1.00 | 41.64 | H |
| ATOM | 4370 | CA | LYS | H | 143 | 81.655 | 37.017 | 6.030 | 1.00 | 41.64 | H |
| ATOM | 4371 | CB | LYS | H | 143 | 82.519 | 36.690 | 4.817 | 1.00 | 53.22 | H |
| ATOM | 4372 | CG | LYS | H | 143 | 81.957 | 37.263 | 3.541 | 1.00 | 53.22 | H |
| ATOM | 4373 | CD | LYS | H | 143 | 82.839 | 37.003 | 2.336 | 1.00 | 53.22 | H |
| ATOM | 4374 | CE | LYS | H | 143 | 82.121 | 37.415 | 1.045 | 1.00 | 53.22 | H |
| ATOM | 4375 | NZ | LYS | H | 143 | 82.947 | 37.137 | −0.166 | 1.00 | 53.22 | H |
| ATOM | 4376 | C | LYS | H | 143 | 80.221 | 36.662 | 5.712 | 1.00 | 41.64 | H |
| ATOM | 4377 | O | LYS | H | 143 | 79.750 | 35.567 | 6.011 | 1.00 | 41.64 | H |
| ATOM | 4378 | N | GLY | H | 144 | 79.544 | 37.633 | 5.106 | 1.00 | 30.13 | H |
| ATOM | 4379 | CA | GLY | H | 144 | 78.158 | 37.514 | 4.681 | 1.00 | 30.13 | H |
| ATOM | 4380 | C | GLY | H | 144 | 77.093 | 36.930 | 5.583 | 1.00 | 30.13 | H |
| ATOM | 4381 | O | GLY | H | 144 | 76.888 | 35.719 | 5.567 | 1.00 | 30.13 | H |
| ATOM | 4382 | N | TYR | H | 145 | 76.410 | 37.780 | 6.351 | 1.00 | 43.65 | H |
| ATOM | 4383 | CA | TYR | H | 145 | 75.322 | 37.337 | 7.234 | 1.00 | 43.65 | H |
| ATOM | 4384 | CB | TYR | H | 145 | 75.840 | 36.990 | 8.624 | 1.00 | 9.74 | H |
| ATOM | 4385 | CG | TYR | H | 145 | 76.376 | 38.180 | 9.364 | 1.00 | 9.74 | H |
| ATOM | 4386 | CD1 | TYR | H | 145 | 75.509 | 39.113 | 9.925 | 1.00 | 9.74 | H |
| ATOM | 4387 | CE1 | TYR | H | 145 | 75.988 | 40.220 | 10.615 | 1.00 | 9.74 | H |
| ATOM | 4388 | CD2 | TYR | H | 145 | 77.756 | 38.379 | 9.503 | 1.00 | 9.74 | H |
| ATOM | 4389 | CE2 | TYR | H | 145 | 78.254 | 39.480 | 10.191 | 1.00 | 9.74 | H |
| ATOM | 4390 | CZ | TYR | H | 145 | 77.359 | 40.402 | 10.752 | 1.00 | 9.74 | H |
| ATOM | 4391 | OH | TYR | H | 145 | 77.823 | 41.487 | 11.476 | 1.00 | 9.74 | H |
| ATOM | 4392 | C | TYR | H | 145 | 74.279 | 38.447 | 7.327 | 1.00 | 43.65 | H |
| ATOM | 4393 | O | TYR | H | 145 | 74.501 | 39.540 | 6.797 | 1.00 | 43.65 | H |
| ATOM | 4394 | N | PHE | H | 146 | 73.161 | 38.180 | 8.008 | 1.00 | 32.66 | H |
| ATOM | 4395 | CA | PHE | H | 146 | 72.073 | 39.163 | 8.119 | 1.00 | 32.66 | H |
| ATOM | 4396 | CB | PHE | H | 146 | 71.724 | 39.650 | 6.699 | 1.00 | 19.31 | H |
| ATOM | 4397 | CG | PHE | H | 146 | 70.490 | 40.514 | 6.601 | 1.00 | 19.31 | H |
| ATOM | 4398 | CD1 | PHE | H | 146 | 69.225 | 40.008 | 6.898 | 1.00 | 19.31 | H |
| ATOM | 4399 | CD2 | PHE | H | 146 | 70.589 | 41.818 | 6.134 | 1.00 | 19.31 | H |
| ATOM | 4400 | CE1 | PHE | H | 146 | 68.085 | 40.783 | 6.728 | 1.00 | 19.31 | H |
| ATOM | 4401 | CE2 | PHE | H | 146 | 69.449 | 42.605 | 5.956 | 1.00 | 19.31 | H |
| ATOM | 4402 | CZ | PHE | H | 146 | 68.197 | 42.085 | 6.255 | 1.00 | 19.31 | H |
| ATOM | 4403 | C | PHE | H | 146 | 70.819 | 38.596 | 8.819 | 1.00 | 32.66 | H |
| ATOM | 4404 | O | PHE | H | 146 | 70.512 | 37.407 | 8.721 | 1.00 | 32.66 | H |
| ATOM | 4405 | N | PRO | H | 147 | 70.099 | 39.444 | 9.567 | 1.00 | 20.21 | H |
| ATOM | 4406 | CD | PRO | H | 147 | 68.787 | 39.099 | 10.132 | 1.00 | 17.10 | H |
| ATOM | 4407 | CA | PRO | H | 147 | 70.393 | 40.864 | 9.788 | 1.00 | 20.21 | H |
| ATOM | 4408 | CB | PRO | H | 147 | 69.073 | 41.406 | 10.309 | 1.00 | 17.10 | H |
| ATOM | 4409 | CG | PRO | H | 147 | 68.551 | 40.253 | 11.078 | 1.00 | 17.10 | H |
| ATOM | 4410 | C | PRO | H | 147 | 71.503 | 40.992 | 10.816 | 1.00 | 20.21 | H |
| ATOM | 4411 | O | PRO | H | 147 | 72.273 | 40.057 | 11.016 | 1.00 | 20.21 | H |
| ATOM | 4412 | N | GLU | H | 148 | 71.611 | 42.153 | 11.447 | 1.00 | 42.67 | H |
| ATOM | 4413 | CA | GLU | H | 148 | 72.623 | 42.324 | 12.480 | 1.00 | 42.67 | H |
| ATOM | 4414 | CB | GLU | H | 148 | 72.964 | 43.811 | 12.663 | 1.00 | 67.88 | H |

TABLE 2-continued

Atomic coordinates of b2 adrenoreceptor

| ATOM | 4415 | CG | GLU | H | 148 | 74.180 | 44.283 | 11.869 | 1.00 | 67.88 | H |
| ATOM | 4416 | CD | GLU | H | 148 | 75.495 | 43.718 | 12.414 | 1.00 | 67.88 | H |
| ATOM | 4417 | OE1 | GLU | H | 148 | 75.611 | 42.480 | 12.567 | 1.00 | 67.88 | H |
| ATOM | 4418 | OE2 | GLU | H | 148 | 76.418 | 44.515 | 12.693 | 1.00 | 67.88 | H |
| ATOM | 4419 | C | GLU | H | 148 | 71.896 | 41.784 | 13.698 | 1.00 | 42.67 | H |
| ATOM | 4420 | O | GLU | H | 148 | 70.684 | 41.596 | 13.645 | 1.00 | 42.67 | H |
| ATOM | 4421 | N | PRO | H | 149 | 72.609 | 41.494 | 14.792 | 1.00 | 35.73 | H |
| ATOM | 4422 | CD | PRO | H | 149 | 71.850 | 41.429 | 16.055 | 1.00 | 42.41 | H |
| ATOM | 4423 | CA | PRO | H | 149 | 74.037 | 41.624 | 15.082 | 1.00 | 35.73 | H |
| ATOM | 4424 | CB | PRO | H | 149 | 74.027 | 42.261 | 16.450 | 1.00 | 42.41 | H |
| ATOM | 4425 | CG | PRO | H | 149 | 72.933 | 41.490 | 17.107 | 1.00 | 42.41 | H |
| ATOM | 4426 | C | PRO | H | 149 | 74.724 | 40.264 | 15.117 | 1.00 | 35.73 | H |
| ATOM | 4427 | O | PRO | H | 149 | 74.110 | 39.261 | 14.761 | 1.00 | 35.73 | H |
| ATOM | 4428 | N | VAL | H | 150 | 75.989 | 40.240 | 15.547 | 1.00 | 15.30 | H |
| ATOM | 4429 | CA | VAL | H | 150 | 76.730 | 38.983 | 15.667 | 1.00 | 15.30 | H |
| ATOM | 4430 | CB | VAL | H | 150 | 77.471 | 38.574 | 14.346 | 1.00 | 27.90 | H |
| ATOM | 4431 | CG1 | VAL | H | 150 | 76.484 | 38.379 | 13.217 | 1.00 | 27.90 | H |
| ATOM | 4432 | CG2 | VAL | H | 150 | 78.484 | 39.602 | 13.961 | 1.00 | 27.90 | H |
| ATOM | 4433 | C | VAL | H | 150 | 77.760 | 39.015 | 16.792 | 1.00 | 15.30 | H |
| ATOM | 4434 | O | VAL | H | 150 | 78.786 | 39.691 | 16.700 | 1.00 | 15.30 | H |
| ATOM | 4435 | N | THR | H | 151 | 77.491 | 38.286 | 17.869 | 1.00 | 47.40 | H |
| ATOM | 4436 | CA | THR | H | 151 | 78.425 | 38.246 | 18.989 | 1.00 | 47.40 | H |
| ATOM | 4437 | CB | THR | H | 151 | 77.826 | 37.481 | 20.180 | 1.00 | 59.44 | H |
| ATOM | 4438 | OG1 | THR | H | 151 | 76.520 | 37.994 | 20.474 | 1.00 | 59.44 | H |
| ATOM | 4439 | CG2 | THR | H | 151 | 78.703 | 37.647 | 21.403 | 1.00 | 59.44 | H |
| ATOM | 4440 | C | THR | H | 151 | 79.696 | 37.540 | 18.514 | 1.00 | 47.40 | H |
| ATOM | 4441 | O | THR | H | 151 | 79.633 | 36.514 | 17.832 | 1.00 | 47.40 | H |
| ATOM | 4442 | N | VAL | H | 152 | 80.852 | 38.086 | 18.862 | 1.00 | 25.72 | H |
| ATOM | 4443 | CA | VAL | H | 152 | 82.104 | 37.477 | 18.424 | 1.00 | 25.72 | H |
| ATOM | 4444 | CB | VAL | H | 152 | 82.708 | 38.221 | 17.212 | 1.00 | 50.45 | H |
| ATOM | 4445 | CG1 | VAL | H | 152 | 84.027 | 37.559 | 16.801 | 1.00 | 50.45 | H |
| ATOM | 4446 | CG2 | VAL | H | 152 | 81.704 | 38.243 | 16.055 | 1.00 | 50.45 | H |
| ATOM | 4447 | C | VAL | H | 152 | 83.169 | 37.439 | 19.496 | 1.00 | 25.72 | H |
| ATOM | 4448 | O | VAL | H | 152 | 83.916 | 38.403 | 19.675 | 1.00 | 25.72 | H |
| ATOM | 4449 | N | THR | H | 153 | 83.246 | 36.311 | 20.192 | 1.00 | 69.48 | H |
| ATOM | 4450 | CA | THR | H | 153 | 84.231 | 36.134 | 21.247 | 1.00 | 69.48 | H |
| ATOM | 4451 | CB | THR | H | 153 | 83.585 | 35.543 | 22.496 | 1.00 | 57.75 | H |
| ATOM | 4452 | OG1 | THR | H | 153 | 84.592 | 34.892 | 23.274 | 1.00 | 57.75 | H |
| ATOM | 4453 | CG2 | THR | H | 153 | 82.493 | 34.553 | 22.122 | 1.00 | 57.75 | H |
| ATOM | 4454 | C | THR | H | 153 | 85.402 | 35.242 | 20.822 | 1.00 | 69.48 | H |
| ATOM | 4455 | O | THR | H | 153 | 85.338 | 34.555 | 19.803 | 1.00 | 69.48 | H |
| ATOM | 4456 | N | TRP | H | 154 | 86.481 | 35.272 | 21.598 | 1.00 | 74.35 | H |
| ATOM | 4457 | CA | TRP | H | 154 | 87.654 | 34.461 | 21.296 | 1.00 | 74.35 | H |
| ATOM | 4458 | CB | TRP | H | 154 | 88.863 | 35.343 | 20.956 | 1.00 | 69.11 | H |
| ATOM | 4459 | CG | TRP | H | 154 | 88.878 | 35.820 | 19.538 | 1.00 | 69.11 | H |
| ATOM | 4460 | CD2 | TRP | H | 154 | 89.778 | 35.408 | 18.500 | 1.00 | 69.11 | H |
| ATOM | 4461 | CE2 | TRP | H | 154 | 89.381 | 36.067 | 17.318 | 1.00 | 69.11 | H |
| ATOM | 4462 | CE3 | TRP | H | 154 | 90.880 | 34.543 | 18.453 | 1.00 | 69.11 | H |
| ATOM | 4463 | CD1 | TRP | H | 154 | 88.004 | 36.688 | 18.960 | 1.00 | 69.11 | H |
| ATOM | 4464 | NE1 | TRP | H | 154 | 88.296 | 36.841 | 17.628 | 1.00 | 69.11 | H |
| ATOM | 4465 | CZ2 | TRP | H | 154 | 90.045 | 35.888 | 16.097 | 1.00 | 69.11 | H |
| ATOM | 4466 | CZ3 | TRP | H | 154 | 91.543 | 34.365 | 17.233 | 1.00 | 69.11 | H |
| ATOM | 4467 | CH2 | TRP | H | 154 | 91.119 | 35.037 | 16.075 | 1.00 | 69.11 | H |
| ATOM | 4468 | C | TRP | H | 154 | 87.992 | 33.554 | 22.470 | 1.00 | 74.35 | H |
| ATOM | 4469 | O | TRP | H | 154 | 87.979 | 33.993 | 23.624 | 1.00 | 74.35 | H |
| ATOM | 4470 | N | ASN | H | 155 | 88.296 | 32.293 | 22.156 | 1.00 | 78.10 | H |
| ATOM | 4471 | CA | ASN | H | 155 | 88.630 | 31.277 | 23.151 | 1.00 | 78.10 | H |
| ATOM | 4472 | CB | ASN | H | 155 | 89.848 | 31.724 | 23.963 | 1.00 | 125.67 | H |
| ATOM | 4473 | CG | ASN | H | 155 | 91.028 | 30.791 | 23.794 | 1.00 | 125.67 | H |
| ATOM | 4474 | OD1 | ASN | H | 155 | 91.253 | 30.247 | 22.711 | 1.00 | 125.67 | H |
| ATOM | 4475 | ND2 | ASN | H | 155 | 91.799 | 30.609 | 24.862 | 1.00 | 125.67 | H |
| ATOM | 4476 | C | ASN | H | 155 | 87.427 | 31.048 | 24.066 | 1.00 | 78.10 | H |
| ATOM | 4477 | O | ASN | H | 155 | 87.579 | 30.782 | 25.257 | 1.00 | 78.10 | H |
| ATOM | 4478 | N | SER | H | 156 | 86.231 | 31.143 | 23.486 | 1.00 | 75.77 | H |
| ATOM | 4479 | CA | SER | H | 156 | 84.981 | 30.979 | 24.225 | 1.00 | 75.77 | H |
| ATOM | 4480 | CB | SER | H | 156 | 84.834 | 29.537 | 24.728 | 1.00 | 97.47 | H |
| ATOM | 4481 | OG | SER | H | 156 | 84.627 | 28.635 | 23.655 | 1.00 | 97.47 | H |
| ATOM | 4482 | C | SER | H | 156 | 84.930 | 31.963 | 25.396 | 1.00 | 75.77 | H |
| ATOM | 4483 | O | SER | H | 156 | 84.647 | 31.595 | 26.532 | 1.00 | 75.77 | H |
| ATOM | 4484 | N | GLY | H | 157 | 85.212 | 33.225 | 25.105 | 1.00 | 93.40 | H |
| ATOM | 4485 | CA | GLY | H | 157 | 85.189 | 34.233 | 26.142 | 1.00 | 93.40 | H |
| ATOM | 4486 | C | GLY | H | 157 | 86.487 | 34.279 | 26.916 | 1.00 | 93.40 | H |
| ATOM | 4487 | O | GLY | H | 157 | 86.835 | 35.318 | 27.477 | 1.00 | 93.40 | H |
| ATOM | 4488 | N | SER | H | 158 | 87.205 | 33.158 | 26.947 | 1.00 | 70.14 | H |
| ATOM | 4489 | CA | SER | H | 158 | 88.477 | 33.079 | 27.666 | 1.00 | 70.14 | H |
| ATOM | 4490 | CB | SER | H | 158 | 89.201 | 31.768 | 27.345 | 1.00 | 73.43 | H |
| ATOM | 4491 | OG | SER | H | 158 | 88.553 | 30.659 | 27.939 | 1.00 | 73.43 | H |
| ATOM | 4492 | C | SER | H | 158 | 89.425 | 34.248 | 27.389 | 1.00 | 70.14 | H |

TABLE 2-continued

Atomic coordinates of b2 adrenoreceptor

| ATOM | 4493 | O   | SER | H | 158 | 89.664 | 35.070 | 28.272 | 1.00 | 70.14  | H |
|------|------|-----|-----|---|-----|--------|--------|--------|------|--------|---|
| ATOM | 4494 | N   | LEU | H | 159 | 89.965 | 34.317 | 26.171 | 1.00 | 91.03  | H |
| ATOM | 4495 | CA  | LEU | H | 159 | 90.896 | 35.383 | 25.793 | 1.00 | 91.03  | H |
| ATOM | 4496 | CB  | LEU | H | 159 | 91.562 | 35.049 | 24.459 | 1.00 | 91.24  | H |
| ATOM | 4497 | CG  | LEU | H | 159 | 93.030 | 34.640 | 24.567 | 1.00 | 91.24  | H |
| ATOM | 4498 | CD1 | LEU | H | 159 | 93.133 | 33.310 | 25.311 | 1.00 | 91.24  | H |
| ATOM | 4499 | CD2 | LEU | H | 159 | 93.645 | 34.557 | 23.172 | 1.00 | 91.24  | H |
| ATOM | 4500 | C   | LEU | H | 159 | 90.259 | 36.769 | 25.698 | 1.00 | 91.03  | H |
| ATOM | 4501 | O   | LEU | H | 159 | 89.158 | 36.916 | 25.167 | 1.00 | 91.03  | H |
| ATOM | 4502 | N   | SER | H | 160 | 90.965 | 37.784 | 26.198 | 1.00 | 93.80  | H |
| ATOM | 4503 | CA  | SER | H | 160 | 90.453 | 39.152 | 26.173 | 1.00 | 93.80  | H |
| ATOM | 4504 | CB  | SER | H | 160 | 89.766 | 39.490 | 27.510 | 1.00 | 71.60  | H |
| ATOM | 4505 | OG  | SER | H | 160 | 90.674 | 39.500 | 28.606 | 1.00 | 71.60  | H |
| ATOM | 4506 | C   | SER | H | 160 | 91.499 | 40.225 | 25.864 | 1.00 | 93.80  | H |
| ATOM | 4507 | O   | SER | H | 160 | 91.323 | 41.029 | 24.950 | 1.00 | 93.80  | H |
| ATOM | 4508 | N   | SER | H | 161 | 92.587 | 40.233 | 26.626 | 1.00 | 101.74 | H |
| ATOM | 4509 | CA  | SER | H | 161 | 93.637 | 41.231 | 26.454 | 1.00 | 101.74 | H |
| ATOM | 4510 | CB  | SER | H | 161 | 94.694 | 41.066 | 27.546 | 1.00 | 238.64 | H |
| ATOM | 4511 | OG  | SER | H | 161 | 95.647 | 42.112 | 27.486 | 1.00 | 238.64 | H |
| ATOM | 4512 | C   | SER | H | 161 | 94.315 | 41.222 | 25.088 | 1.00 | 101.74 | H |
| ATOM | 4513 | O   | SER | H | 161 | 95.149 | 40.359 | 24.804 | 1.00 | 101.74 | H |
| ATOM | 4514 | N   | GLY | H | 162 | 93.954 | 42.193 | 24.252 | 1.00 | 100.06 | H |
| ATOM | 4515 | CA  | GLY | H | 162 | 94.549 | 42.301 | 22.932 | 1.00 | 100.06 | H |
| ATOM | 4516 | C   | GLY | H | 162 | 93.724 | 41.761 | 21.777 | 1.00 | 100.06 | H |
| ATOM | 4517 | O   | GLY | H | 162 | 94.275 | 41.349 | 20.752 | 1.00 | 100.06 | H |
| ATOM | 4518 | N   | VAL | H | 163 | 92.405 | 41.757 | 21.923 | 1.00 | 46.36  | H |
| ATOM | 4519 | CA  | VAL | H | 163 | 91.557 | 41.258 | 20.849 | 1.00 | 46.36  | H |
| ATOM | 4520 | CB  | VAL | H | 163 | 90.687 | 40.065 | 21.311 | 1.00 | 63.75  | H |
| ATOM | 4521 | CG1 | VAL | H | 163 | 89.675 | 40.519 | 22.357 | 1.00 | 63.75  | H |
| ATOM | 4522 | CG2 | VAL | H | 163 | 89.978 | 39.446 | 20.116 | 1.00 | 63.75  | H |
| ATOM | 4523 | C   | VAL | H | 163 | 90.640 | 42.351 | 20.331 | 1.00 | 46.36  | H |
| ATOM | 4524 | O   | VAL | H | 163 | 89.873 | 42.936 | 21.092 | 1.00 | 46.36  | H |
| ATOM | 4525 | N   | HIS | H | 164 | 90.725 | 42.631 | 19.036 | 1.00 | 60.71  | H |
| ATOM | 4526 | CA  | HIS | H | 164 | 89.879 | 43.650 | 18.438 | 1.00 | 60.71  | H |
| ATOM | 4527 | CB  | HIS | H | 164 | 90.715 | 44.643 | 17.645 | 1.00 | 74.49  | H |
| ATOM | 4528 | CG  | HIS | H | 164 | 91.896 | 45.168 | 18.391 | 1.00 | 74.49  | H |
| ATOM | 4529 | CD2 | HIS | H | 164 | 92.070 | 46.311 | 19.095 | 1.00 | 74.49  | H |
| ATOM | 4530 | ND1 | HIS | H | 164 | 93.097 | 44.495 | 18.450 | 1.00 | 74.49  | H |
| ATOM | 4531 | CE1 | HIS | H | 164 | 93.962 | 45.204 | 19.153 | 1.00 | 74.49  | H |
| ATOM | 4532 | NE2 | HIS | H | 164 | 93.364 | 46.311 | 19.555 | 1.00 | 74.49  | H |
| ATOM | 4533 | C   | HIS | H | 164 | 88.847 | 43.012 | 17.514 | 1.00 | 60.71  | H |
| ATOM | 4534 | O   | HIS | H | 164 | 89.112 | 41.980 | 16.897 | 1.00 | 60.71  | H |
| ATOM | 4535 | N   | THR | H | 165 | 87.669 | 43.629 | 17.441 | 1.00 | 30.81  | H |
| ATOM | 4536 | CA  | THR | H | 165 | 86.581 | 43.162 | 16.590 | 1.00 | 30.81  | H |
| ATOM | 4537 | CB  | THR | H | 165 | 85.428 | 42.511 | 17.395 | 1.00 | 40.15  | H |
| ATOM | 4538 | OG1 | THR | H | 165 | 85.930 | 41.410 | 18.157 | 1.00 | 40.15  | H |
| ATOM | 4539 | CG2 | THR | H | 165 | 84.343 | 41.995 | 16.459 | 1.00 | 40.15  | H |
| ATOM | 4540 | C   | THR | H | 165 | 86.027 | 44.401 | 15.929 | 1.00 | 30.81  | H |
| ATOM | 4541 | O   | THR | H | 165 | 85.598 | 45.331 | 16.614 | 1.00 | 30.81  | H |
| ATOM | 4542 | N   | PHE | H | 166 | 86.017 | 44.414 | 14.602 | 1.00 | 23.54  | H |
| ATOM | 4543 | CA  | PHE | H | 166 | 85.510 | 45.571 | 13.870 | 1.00 | 23.54  | H |
| ATOM | 4544 | CB  | PHE | H | 166 | 86.352 | 45.790 | 12.624 | 1.00 | 32.21  | H |
| ATOM | 4545 | CG  | PHE | H | 166 | 87.802 | 45.872 | 12.913 | 1.00 | 32.21  | H |
| ATOM | 4546 | CD1 | PHE | H | 166 | 88.464 | 44.783 | 13.479 | 1.00 | 32.21  | H |
| ATOM | 4547 | CD2 | PHE | H | 166 | 88.501 | 47.043 | 12.668 | 1.00 | 32.21  | H |
| ATOM | 4548 | CE1 | PHE | H | 166 | 89.800 | 44.856 | 13.803 | 1.00 | 32.21  | H |
| ATOM | 4549 | CE2 | PHE | H | 166 | 89.840 | 47.133 | 12.986 | 1.00 | 32.21  | H |
| ATOM | 4550 | CZ  | PHE | H | 166 | 90.499 | 46.032 | 13.560 | 1.00 | 32.21  | H |
| ATOM | 4551 | C   | PHE | H | 166 | 84.033 | 45.523 | 13.495 | 1.00 | 23.54  | H |
| ATOM | 4552 | O   | PHE | H | 166 | 83.482 | 44.456 | 13.197 | 1.00 | 23.54  | H |
| ATOM | 4553 | N   | PRO | H | 167 | 83.381 | 46.700 | 13.507 | 1.00 | 21.61  | H |
| ATOM | 4554 | CD  | PRO | H | 167 | 84.000 | 47.994 | 13.824 | 1.00 | 28.67  | H |
| ATOM | 4555 | CA  | PRO | H | 167 | 81.966 | 46.885 | 13.184 | 1.00 | 21.61  | H |
| ATOM | 4556 | CB  | PRO | H | 167 | 81.760 | 48.393 | 13.370 | 1.00 | 28.67  | H |
| ATOM | 4557 | CG  | PRO | H | 167 | 83.099 | 48.953 | 13.096 | 1.00 | 28.67  | H |
| ATOM | 4558 | C   | PRO | H | 167 | 81.575 | 46.380 | 11.798 | 1.00 | 21.61  | H |
| ATOM | 4559 | O   | PRO | H | 167 | 82.192 | 46.713 | 10.787 | 1.00 | 21.61  | H |
| ATOM | 4560 | N   | ALA | H | 168 | 80.536 | 45.556 | 11.785 | 1.00 | 44.49  | H |
| ATOM | 4561 | CA  | ALA | H | 168 | 80.052 | 44.967 | 10.561 | 1.00 | 44.49  | H |
| ATOM | 4562 | CB  | ALA | H | 168 | 78.777 | 44.191 | 10.826 | 1.00 | 187.21 | H |
| ATOM | 4563 | C   | ALA | H | 168 | 79.801 | 46.044 | 9.540  | 1.00 | 44.49  | H |
| ATOM | 4564 | O   | ALA | H | 168 | 79.015 | 46.953 | 9.772  | 1.00 | 44.49  | H |
| ATOM | 4565 | N   | VAL | H | 169 | 80.506 | 45.953 | 8.421  | 1.00 | 46.83  | H |
| ATOM | 4566 | CA  | VAL | H | 169 | 80.331 | 46.898 | 7.329  | 1.00 | 46.83  | H |
| ATOM | 4567 | CB  | VAL | H | 169 | 81.632 | 47.188 | 6.590  | 1.00 | 28.19  | H |
| ATOM | 4568 | CG1 | VAL | H | 169 | 81.322 | 47.904 | 5.289  | 1.00 | 28.19  | H |
| ATOM | 4569 | CG2 | VAL | H | 169 | 82.562 | 48.016 | 7.470  | 1.00 | 28.19  | H |
| ATOM | 4570 | C   | VAL | H | 169 | 79.447 | 46.147 | 6.378  | 1.00 | 46.83  | H |

TABLE 2-continued

Atomic coordinates of b2 adrenoreceptor

| ATOM | 4571 | O | VAL | H | 169 | 79.496 | 44.921 | 6.332 | 1.00 | 46.83 | H |
|---|---|---|---|---|---|---|---|---|---|---|---|
| ATOM | 4572 | N | LEU | H | 170 | 78.631 | 46.859 | 5.625 | 1.00 | 36.37 | H |
| ATOM | 4573 | CA | LEU | H | 170 | 77.777 | 46.160 | 4.696 | 1.00 | 36.37 | H |
| ATOM | 4574 | CB | LEU | H | 170 | 76.484 | 46.941 | 4.486 | 1.00 | 33.30 | H |
| ATOM | 4575 | CG | LEU | H | 170 | 75.318 | 46.107 | 3.960 | 1.00 | 33.30 | H |
| ATOM | 4576 | CD1 | LEU | H | 170 | 75.321 | 44.762 | 4.627 | 1.00 | 33.30 | H |
| ATOM | 4577 | CD2 | LEU | H | 170 | 74.012 | 46.813 | 4.239 | 1.00 | 33.30 | H |
| ATOM | 4578 | C | LEU | H | 170 | 78.559 | 45.987 | 3.398 | 1.00 | 36.37 | H |
| ATOM | 4579 | O | LEU | H | 170 | 79.701 | 46.439 | 3.306 | 1.00 | 36.37 | H |
| ATOM | 4580 | N | GLN | H | 171 | 77.965 | 45.318 | 2.413 | 1.00 | 45.68 | H |
| ATOM | 4581 | CA | GLN | H | 171 | 78.617 | 45.077 | 1.126 | 1.00 | 45.68 | H |
| ATOM | 4582 | CB | GLN | H | 171 | 79.972 | 44.382 | 1.344 | 1.00 | 45.83 | H |
| ATOM | 4583 | CG | GLN | H | 171 | 80.881 | 44.191 | 0.132 | 1.00 | 45.83 | H |
| ATOM | 4584 | CD | GLN | H | 171 | 82.335 | 43.872 | 0.540 | 1.00 | 45.83 | H |
| ATOM | 4585 | OE1 | GLN | H | 171 | 82.573 | 43.050 | 1.427 | 1.00 | 45.83 | H |
| ATOM | 4586 | NE2 | GLN | H | 171 | 83.307 | 44.534 | −0.103 | 1.00 | 45.83 | H |
| ATOM | 4587 | C | GLN | H | 171 | 77.664 | 44.169 | 0.370 | 1.00 | 45.68 | H |
| ATOM | 4588 | O | GLN | H | 171 | 77.480 | 43.015 | 0.734 | 1.00 | 45.68 | H |
| ATOM | 4589 | N | SER | H | 172 | 77.022 | 44.714 | −0.655 | 1.00 | 59.17 | H |
| ATOM | 4590 | CA | SER | H | 172 | 76.085 | 43.953 | −1.478 | 1.00 | 59.17 | H |
| ATOM | 4591 | CB | SER | H | 172 | 76.851 | 42.891 | −2.272 | 1.00 | 61.36 | H |
| ATOM | 4592 | OG | SER | H | 172 | 77.875 | 43.481 | −3.059 | 1.00 | 61.36 | H |
| ATOM | 4593 | C | SER | H | 172 | 74.949 | 43.298 | −0.685 | 1.00 | 59.17 | H |
| ATOM | 4594 | O | SER | H | 172 | 74.795 | 42.080 | −0.694 | 1.00 | 59.17 | H |
| ATOM | 4595 | N | ASP | H | 173 | 74.152 | 44.123 | −0.015 | 1.00 | 64.29 | H |
| ATOM | 4596 | CA | ASP | H | 173 | 73.025 | 43.658 | 0.789 | 1.00 | 64.29 | H |
| ATOM | 4597 | CB | ASP | H | 173 | 71.851 | 43.286 | −0.123 | 1.00 | 250.90 | H |
| ATOM | 4598 | CG | ASP | H | 173 | 70.535 | 43.179 | 0.630 | 1.00 | 250.90 | H |
| ATOM | 4599 | OD1 | ASP | H | 173 | 69.529 | 42.767 | 0.015 | 1.00 | 250.90 | H |
| ATOM | 4600 | OD2 | ASP | H | 173 | 70.503 | 43.513 | 1.834 | 1.00 | 250.90 | H |
| ATOM | 4601 | C | ASP | H | 173 | 73.379 | 42.465 | 1.693 | 1.00 | 64.29 | H |
| ATOM | 4602 | O | ASP | H | 173 | 72.587 | 41.526 | 1.832 | 1.00 | 64.29 | H |
| ATOM | 4603 | N | LEU | H | 174 | 74.553 | 42.520 | 2.323 | 1.00 | 17.81 | H |
| ATOM | 4604 | CA | LEU | H | 174 | 75.011 | 41.443 | 3.198 | 1.00 | 17.81 | H |
| ATOM | 4605 | CB | LEU | H | 174 | 75.521 | 40.293 | 2.327 | 1.00 | 23.42 | H |
| ATOM | 4606 | CG | LEU | H | 174 | 74.861 | 38.945 | 2.549 | 1.00 | 23.42 | H |
| ATOM | 4607 | CD1 | LEU | H | 174 | 75.182 | 38.484 | 3.950 | 1.00 | 23.42 | H |
| ATOM | 4608 | CD2 | LEU | H | 174 | 73.354 | 39.068 | 2.357 | 1.00 | 23.42 | H |
| ATOM | 4609 | C | LEU | H | 174 | 76.126 | 41.899 | 4.161 | 1.00 | 17.81 | H |
| ATOM | 4610 | O | LEU | H | 174 | 77.092 | 42.548 | 3.743 | 1.00 | 17.81 | H |
| ATOM | 4611 | N | TYR | H | 175 | 76.008 | 41.549 | 5.441 | 1.00 | 28.90 | H |
| ATOM | 4612 | CA | TYR | H | 175 | 77.025 | 41.958 | 6.408 | 1.00 | 28.90 | H |
| ATOM | 4613 | CB | TYR | H | 175 | 76.438 | 42.016 | 7.810 | 1.00 | 36.04 | H |
| ATOM | 4614 | CG | TYR | H | 175 | 75.639 | 43.261 | 7.980 | 1.00 | 36.04 | H |
| ATOM | 4615 | CD1 | TYR | H | 175 | 76.264 | 44.503 | 7.978 | 1.00 | 36.04 | H |
| ATOM | 4616 | CE1 | TYR | H | 175 | 75.527 | 45.673 | 7.995 | 1.00 | 36.04 | H |
| ATOM | 4617 | CD2 | TYR | H | 175 | 74.252 | 43.219 | 8.017 | 1.00 | 36.04 | H |
| ATOM | 4618 | CE2 | TYR | H | 175 | 73.503 | 44.383 | 8.037 | 1.00 | 36.04 | H |
| ATOM | 4619 | CZ | TYR | H | 175 | 74.148 | 45.603 | 8.020 | 1.00 | 36.04 | H |
| ATOM | 4620 | OH | TYR | H | 175 | 73.407 | 46.756 | 7.983 | 1.00 | 36.04 | H |
| ATOM | 4621 | C | TYR | H | 175 | 78.292 | 41.141 | 6.438 | 1.00 | 28.90 | H |
| ATOM | 4622 | O | TYR | H | 175 | 78.268 | 39.930 | 6.230 | 1.00 | 28.90 | H |
| ATOM | 4623 | N | THR | H | 176 | 79.400 | 41.828 | 6.705 | 1.00 | 35.05 | H |
| ATOM | 4624 | CA | THR | H | 176 | 80.724 | 41.212 | 6.780 | 1.00 | 35.05 | H |
| ATOM | 4625 | CB | THR | H | 176 | 81.529 | 41.383 | 5.443 | 1.00 | 32.24 | H |
| ATOM | 4626 | OG1 | THR | H | 176 | 80.782 | 40.848 | 4.346 | 1.00 | 32.24 | H |
| ATOM | 4627 | CG2 | THR | H | 176 | 82.852 | 40.660 | 5.512 | 1.00 | 32.24 | H |
| ATOM | 4628 | C | THR | H | 176 | 81.495 | 41.921 | 7.892 | 1.00 | 35.05 | H |
| ATOM | 4629 | O | THR | H | 176 | 81.403 | 43.140 | 8.050 | 1.00 | 35.05 | H |
| ATOM | 4630 | N | LEU | H | 177 | 82.240 | 41.155 | 8.674 | 1.00 | 34.70 | H |
| ATOM | 4631 | CA | LEU | H | 177 | 83.033 | 41.742 | 9.738 | 1.00 | 34.70 | H |
| ATOM | 4632 | CB | LEU | H | 177 | 82.161 | 42.077 | 10.949 | 1.00 | 31.79 | H |
| ATOM | 4633 | CG | LEU | H | 177 | 81.667 | 41.032 | 11.937 | 1.00 | 31.79 | H |
| ATOM | 4634 | CD1 | LEU | H | 177 | 82.826 | 40.461 | 12.736 | 1.00 | 31.79 | H |
| ATOM | 4635 | CD2 | LEU | H | 177 | 80.689 | 41.715 | 12.869 | 1.00 | 31.79 | H |
| ATOM | 4636 | C | LEU | H | 177 | 84.154 | 40.794 | 10.114 | 1.00 | 34.70 | H |
| ATOM | 4637 | O | LEU | H | 177 | 84.196 | 39.658 | 9.641 | 1.00 | 34.70 | H |
| ATOM | 4638 | N | SER | H | 178 | 85.054 | 41.252 | 10.974 | 1.00 | 27.67 | H |
| ATOM | 4639 | CA | SER | H | 178 | 86.192 | 40.432 | 11.342 | 1.00 | 27.67 | H |
| ATOM | 4640 | CB | SER | H | 178 | 87.221 | 40.493 | 10.223 | 1.00 | 48.49 | H |
| ATOM | 4641 | OG | SER | H | 178 | 87.518 | 41.844 | 9.904 | 1.00 | 48.49 | H |
| ATOM | 4642 | C | SER | H | 178 | 86.859 | 40.840 | 12.635 | 1.00 | 27.67 | H |
| ATOM | 4643 | O | SER | H | 178 | 86.922 | 42.019 | 12.968 | 1.00 | 27.67 | H |
| ATOM | 4644 | N | SER | H | 179 | 87.384 | 39.853 | 13.345 | 1.00 | 44.35 | H |
| ATOM | 4645 | CA | SER | H | 179 | 88.059 | 40.104 | 14.597 | 1.00 | 44.35 | H |
| ATOM | 4646 | CB | SER | H | 179 | 87.276 | 39.481 | 15.736 | 1.00 | 42.33 | H |
| ATOM | 4647 | OG | SER | H | 179 | 87.969 | 39.686 | 16.951 | 1.00 | 42.33 | H |
| ATOM | 4648 | C | SER | H | 179 | 89.477 | 39.539 | 14.577 | 1.00 | 44.35 | H |

TABLE 2-continued

Atomic coordinates of b2 adrenoreceptor

| ATOM | 4649 | O   | SER | H | 179 | 89.674  | 38.361 | 14.286 | 1.00 | 44.35  | H |
|------|------|-----|-----|---|-----|---------|--------|--------|------|--------|---|
| ATOM | 4650 | N   | SER | H | 180 | 90.459  | 40.384 | 14.882 | 1.00 | 42.50  | H |
| ATOM | 4651 | CA  | SER | H | 180 | 91.863  | 39.981 | 14.895 | 1.00 | 42.50  | H |
| ATOM | 4652 | CB  | SER | H | 180 | 92.731  | 41.024 | 14.182 | 1.00 | 55.81  | H |
| ATOM | 4653 | OG  | SER | H | 180 | 92.644  | 42.298 | 14.800 | 1.00 | 55.81  | H |
| ATOM | 4654 | C   | SER | H | 180 | 92.307  | 39.855 | 16.335 | 1.00 | 42.50  | H |
| ATOM | 4655 | O   | SER | H | 180 | 91.654  | 40.392 | 17.227 | 1.00 | 42.50  | H |
| ATOM | 4656 | N   | VAL | H | 181 | 93.426  | 39.172 | 16.563 | 1.00 | 64.38  | H |
| ATOM | 4657 | CA  | VAL | H | 181 | 93.915  | 38.979 | 17.920 | 1.00 | 64.38  | H |
| ATOM | 4658 | CB  | VAL | H | 181 | 93.285  | 37.738 | 18.548 | 1.00 | 33.59  | H |
| ATOM | 4659 | CG1 | VAL | H | 181 | 93.932  | 36.481 | 17.958 | 1.00 | 33.59  | H |
| ATOM | 4660 | CG2 | VAL | H | 181 | 93.439  | 37.795 | 20.064 | 1.00 | 33.59  | H |
| ATOM | 4661 | C   | VAL | H | 181 | 95.420  | 38.813 | 18.044 | 1.00 | 64.38  | H |
| ATOM | 4662 | O   | VAL | H | 181 | 96.065  | 38.167 | 17.224 | 1.00 | 64.38  | H |
| ATOM | 4663 | N   | THR | H | 182 | 95.964  | 39.382 | 19.108 | 1.00 | 70.13  | H |
| ATOM | 4664 | CA  | THR | H | 182 | 97.386  | 39.295 | 19.372 | 1.00 | 70.13  | H |
| ATOM | 4665 | CB  | THR | H | 182 | 97.986  | 40.704 | 19.624 | 1.00 | 87.86  | H |
| ATOM | 4666 | OG1 | THR | H | 182 | 97.541  | 41.609 | 18.605 | 1.00 | 87.86  | H |
| ATOM | 4667 | CG2 | THR | H | 182 | 99.505  | 40.653 | 19.607 | 1.00 | 87.86  | H |
| ATOM | 4668 | C   | THR | H | 182 | 97.590  | 38.422 | 20.616 | 1.00 | 70.13  | H |
| ATOM | 4669 | O   | THR | H | 182 | 96.794  | 38.469 | 21.563 | 1.00 | 70.13  | H |
| ATOM | 4670 | N   | VAL | H | 183 | 98.647  | 37.612 | 20.594 | 1.00 | 45.47  | H |
| ATOM | 4671 | CA  | VAL | H | 183 | 99.005  | 36.724 | 21.707 | 1.00 | 45.47  | H |
| ATOM | 4672 | CB  | VAL | H | 183 | 98.342  | 35.315 | 21.580 | 1.00 | 35.68  | H |
| ATOM | 4673 | CG1 | VAL | H | 183 | 96.816  | 35.431 | 21.703 | 1.00 | 35.68  | H |
| ATOM | 4674 | CG2 | VAL | H | 183 | 98.742  | 34.662 | 20.258 | 1.00 | 35.68  | H |
| ATOM | 4675 | C   | VAL | H | 183 | 100.518 | 36.563 | 21.640 | 1.00 | 45.47  | H |
| ATOM | 4676 | O   | VAL | H | 183 | 101.138 | 37.033 | 20.697 | 1.00 | 45.47  | H |
| ATOM | 4677 | N   | PRO | H | 184 | 101.138 | 35.916 | 22.641 | 1.00 | 65.62  | H |
| ATOM | 4678 | CD  | PRO | H | 184 | 100.661 | 35.535 | 23.979 | 1.00 | 66.51  | H |
| ATOM | 4679 | CA  | PRO | H | 184 | 102.595 | 35.770 | 22.554 | 1.00 | 65.62  | H |
| ATOM | 4680 | CB  | PRO | H | 184 | 102.996 | 35.363 | 23.969 | 1.00 | 66.51  | H |
| ATOM | 4681 | CG  | PRO | H | 184 | 101.859 | 35.854 | 24.820 | 1.00 | 66.51  | H |
| ATOM | 4682 | C   | PRO | H | 184 | 102.915 | 34.677 | 21.556 | 1.00 | 65.62  | H |
| ATOM | 4683 | O   | PRO | H | 184 | 102.312 | 33.606 | 21.600 | 1.00 | 65.62  | H |
| ATOM | 4684 | N   | SER | H | 185 | 103.844 | 34.943 | 20.646 | 1.00 | 70.62  | H |
| ATOM | 4685 | CA  | SER | H | 185 | 104.213 | 33.933 | 19.670 | 1.00 | 70.62  | H |
| ATOM | 4686 | CB  | SER | H | 185 | 105.397 | 34.416 | 18.826 | 1.00 | 65.78  | H |
| ATOM | 4687 | OG  | SER | H | 185 | 106.153 | 35.394 | 19.514 | 1.00 | 65.78  | H |
| ATOM | 4688 | C   | SER | H | 185 | 104.582 | 32.692 | 20.472 | 1.00 | 70.62  | H |
| ATOM | 4689 | O   | SER | H | 185 | 104.509 | 31.560 | 19.981 | 1.00 | 70.62  | H |
| ATOM | 4690 | N   | SER | H | 186 | 104.943 | 32.935 | 21.732 | 1.00 | 70.16  | H |
| ATOM | 4691 | CA  | SER | H | 186 | 105.337 | 31.897 | 22.676 | 1.00 | 70.16  | H |
| ATOM | 4692 | CB  | SER | H | 186 | 105.971 | 32.529 | 23.922 | 1.00 | 146.67 | H |
| ATOM | 4693 | OG  | SER | H | 186 | 106.676 | 33.716 | 23.608 | 1.00 | 146.67 | H |
| ATOM | 4694 | C   | SER | H | 186 | 104.122 | 31.101 | 23.116 | 1.00 | 70.16  | H |
| ATOM | 4695 | O   | SER | H | 186 | 104.194 | 30.350 | 24.081 | 1.00 | 70.16  | H |
| ATOM | 4696 | N   | THR | H | 187 | 103.006 | 31.256 | 22.416 | 1.00 | 137.54 | H |
| ATOM | 4697 | CA  | THR | H | 187 | 101.810 | 30.547 | 22.826 | 1.00 | 137.54 | H |
| ATOM | 4698 | CB  | THR | H | 187 | 100.902 | 31.469 | 23.677 | 1.00 | 67.50  | H |
| ATOM | 4699 | OG1 | THR | H | 187 | 100.766 | 32.742 | 23.032 | 1.00 | 67.50  | H |
| ATOM | 4700 | CG2 | THR | H | 187 | 101.488 | 31.663 | 25.066 | 1.00 | 67.50  | H |
| ATOM | 4701 | C   | THR | H | 187 | 100.943 | 29.884 | 21.764 | 1.00 | 137.54 | H |
| ATOM | 4702 | O   | THR | H | 187 | 100.755 | 28.673 | 21.800 | 1.00 | 137.54 | H |
| ATOM | 4703 | N   | TRP | H | 188 | 100.424 | 30.660 | 20.820 | 1.00 | 159.42 | H |
| ATOM | 4704 | CA  | TRP | H | 188 | 99.516  | 30.122 | 19.807 | 1.00 | 159.42 | H |
| ATOM | 4705 | CB  | TRP | H | 188 | 99.321  | 31.115 | 18.668 | 1.00 | 46.85  | H |
| ATOM | 4706 | CG  | TRP | H | 188 | 98.559  | 30.510 | 17.528 | 1.00 | 46.85  | H |
| ATOM | 4707 | CD2 | TRP | H | 188 | 98.938  | 30.520 | 16.157 | 1.00 | 46.85  | H |
| ATOM | 4708 | CE2 | TRP | H | 188 | 97.928  | 29.840 | 15.438 | 1.00 | 46.85  | H |
| ATOM | 4709 | CE3 | TRP | H | 188 | 100.031 | 31.043 | 15.463 | 1.00 | 46.85  | H |
| ATOM | 4710 | CD1 | TRP | H | 188 | 97.362  | 29.838 | 17.593 | 1.00 | 46.85  | H |
| ATOM | 4711 | NE1 | TRP | H | 188 | 96.979  | 29.431 | 16.337 | 1.00 | 46.85  | H |
| ATOM | 4712 | CZ2 | TRP | H | 188 | 97.981  | 29.673 | 14.065 | 1.00 | 46.85  | H |
| ATOM | 4713 | CZ3 | TRP | H | 188 | 100.085 | 30.880 | 14.104 | 1.00 | 46.85  | H |
| ATOM | 4714 | CH2 | TRP | H | 188 | 99.066  | 30.200 | 13.413 | 1.00 | 46.85  | H |
| ATOM | 4715 | C   | TRP | H | 188 | 99.719  | 28.740 | 19.188 | 1.00 | 159.42 | H |
| ATOM | 4716 | O   | TRP | H | 188 | 99.103  | 27.772 | 19.623 | 1.00 | 159.42 | H |
| ATOM | 4717 | N   | PRO | H | 189 | 100.566 | 28.629 | 18.155 | 1.00 | 105.90 | H |
| ATOM | 4718 | CD  | PRO | H | 189 | 101.725 | 29.486 | 17.849 | 1.00 | 42.42  | H |
| ATOM | 4719 | CA  | PRO | H | 189 | 100.736 | 27.295 | 17.565 | 1.00 | 105.90 | H |
| ATOM | 4720 | CB  | PRO | H | 189 | 101.927 | 27.483 | 16.642 | 1.00 | 42.42  | H |
| ATOM | 4721 | CG  | PRO | H | 189 | 102.752 | 28.474 | 17.403 | 1.00 | 42.42  | H |
| ATOM | 4722 | C   | PRO | H | 189 | 100.972 | 26.222 | 18.627 | 1.00 | 105.90 | H |
| ATOM | 4723 | O   | PRO | H | 189 | 100.754 | 25.029 | 18.387 | 1.00 | 105.90 | H |
| ATOM | 4724 | N   | SER | H | 190 | 101.411 | 26.669 | 19.803 | 1.00 | 86.71  | H |
| ATOM | 4725 | CA  | SER | H | 190 | 101.668 | 25.789 | 20.934 | 1.00 | 86.71  | H |
| ATOM | 4726 | CB  | SER | H | 190 | 102.506 | 26.514 | 21.987 | 1.00 | 68.02  | H |

TABLE 2-continued

Atomic coordinates of b2 adrenoreceptor

| ATOM | 4727 | OG | SER | H | 190 | 103.545 | 27.269 | 21.390 | 1.00 | 68.02 | H |
|---|---|---|---|---|---|---|---|---|---|---|---|
| ATOM | 4728 | C | SER | H | 190 | 100.327 | 25.395 | 21.544 | 1.00 | 86.71 | H |
| ATOM | 4729 | O | SER | H | 190 | 99.947 | 24.226 | 21.531 | 1.00 | 86.71 | H |
| ATOM | 4730 | N | GLU | H | 191 | 99.613 | 26.389 | 22.068 | 1.00 | 45.45 | H |
| ATOM | 4731 | CA | GLU | H | 191 | 98.308 | 26.179 | 22.698 | 1.00 | 45.45 | H |
| ATOM | 4732 | CB | GLU | H | 191 | 98.229 | 26.995 | 23.999 | 1.00 | 175.16 | H |
| ATOM | 4733 | CG | GLU | H | 191 | 97.028 | 26.688 | 24.888 | 1.00 | 175.16 | H |
| ATOM | 4734 | CD | GLU | H | 191 | 97.151 | 27.319 | 26.269 | 1.00 | 175.16 | H |
| ATOM | 4735 | OE1 | GLU | H | 191 | 98.086 | 26.951 | 27.011 | 1.00 | 175.16 | H |
| ATOM | 4736 | OE2 | GLU | H | 191 | 96.317 | 28.183 | 26.614 | 1.00 | 175.16 | H |
| ATOM | 4737 | C | GLU | H | 191 | 97.137 | 26.540 | 21.763 | 1.00 | 45.45 | H |
| ATOM | 4738 | O | GLU | H | 191 | 97.191 | 27.512 | 21.006 | 1.00 | 45.45 | H |
| ATOM | 4739 | N | THR | H | 192 | 96.075 | 25.743 | 21.826 | 1.00 | 95.12 | H |
| ATOM | 4740 | CA | THR | H | 192 | 94.899 | 25.948 | 20.989 | 1.00 | 95.12 | H |
| ATOM | 4741 | CB | THR | H | 192 | 93.795 | 24.939 | 21.364 | 1.00 | 153.58 | H |
| ATOM | 4742 | OG1 | THR | H | 192 | 92.635 | 25.168 | 20.558 | 1.00 | 153.58 | H |
| ATOM | 4743 | CG2 | THR | H | 192 | 93.429 | 25.075 | 22.831 | 1.00 | 153.58 | H |
| ATOM | 4744 | C | THR | H | 192 | 94.333 | 27.367 | 21.075 | 1.00 | 95.12 | H |
| ATOM | 4745 | O | THR | H | 192 | 94.436 | 28.030 | 22.113 | 1.00 | 95.12 | H |
| ATOM | 4746 | N | VAL | H | 193 | 93.748 | 27.826 | 19.969 | 1.00 | 46.11 | H |
| ATOM | 4747 | CA | VAL | H | 193 | 93.135 | 29.157 | 19.887 | 1.00 | 46.11 | H |
| ATOM | 4748 | CB | VAL | H | 193 | 94.136 | 30.214 | 19.364 | 1.00 | 60.42 | H |
| ATOM | 4749 | CG1 | VAL | H | 193 | 93.457 | 31.580 | 19.283 | 1.00 | 60.42 | H |
| ATOM | 4750 | CG2 | VAL | H | 193 | 95.349 | 30.279 | 20.286 | 1.00 | 60.42 | H |
| ATOM | 4751 | C | VAL | H | 193 | 91.924 | 29.139 | 18.952 | 1.00 | 46.11 | H |
| ATOM | 4752 | O | VAL | H | 193 | 92.066 | 28.997 | 17.738 | 1.00 | 46.11 | H |
| ATOM | 4753 | N | THR | H | 194 | 90.730 | 29.275 | 19.512 | 1.00 | 76.31 | H |
| ATOM | 4754 | CA | THR | H | 194 | 89.530 | 29.264 | 18.686 | 1.00 | 76.31 | H |
| ATOM | 4755 | CB | THR | H | 194 | 88.511 | 28.206 | 19.184 | 1.00 | 96.27 | H |
| ATOM | 4756 | OG1 | THR | H | 194 | 87.306 | 28.294 | 18.410 | 1.00 | 96.27 | H |
| ATOM | 4757 | CG2 | THR | H | 194 | 88.190 | 28.417 | 20.658 | 1.00 | 96.27 | H |
| ATOM | 4758 | C | THR | H | 194 | 88.867 | 30.637 | 18.669 | 1.00 | 76.31 | H |
| ATOM | 4759 | O | THR | H | 194 | 89.184 | 31.494 | 19.497 | 1.00 | 76.31 | H |
| ATOM | 4760 | N | CYS | H | 195 | 87.963 | 30.844 | 17.713 | 1.00 | 40.67 | H |
| ATOM | 4761 | CA | CYS | H | 195 | 87.244 | 32.104 | 17.587 | 1.00 | 40.67 | H |
| ATOM | 4762 | C | CYS | H | 195 | 85.779 | 31.733 | 17.471 | 1.00 | 40.67 | H |
| ATOM | 4763 | O | CYS | H | 195 | 85.383 | 30.990 | 16.571 | 1.00 | 40.67 | H |
| ATOM | 4764 | CB | CYS | H | 195 | 87.701 | 32.861 | 16.340 | 1.00 | 61.25 | H |
| ATOM | 4765 | SG | CYS | H | 195 | 86.595 | 32.725 | 14.901 | 1.00 | 61.25 | H |
| ATOM | 4766 | N | ASN | H | 196 | 84.982 | 32.240 | 18.401 | 1.00 | 80.82 | H |
| ATOM | 4767 | CA | ASN | H | 196 | 83.559 | 31.949 | 18.434 | 1.00 | 80.82 | H |
| ATOM | 4768 | CB | ASN | H | 196 | 83.085 | 31.853 | 19.887 | 1.00 | 72.91 | H |
| ATOM | 4769 | CG | ASN | H | 196 | 84.145 | 31.258 | 20.814 | 1.00 | 72.91 | H |
| ATOM | 4770 | OD1 | ASN | H | 196 | 85.203 | 31.852 | 21.030 | 1.00 | 72.91 | H |
| ATOM | 4771 | ND2 | ASN | H | 196 | 83.863 | 30.083 | 21.362 | 1.00 | 72.91 | H |
| ATOM | 4772 | C | ASN | H | 196 | 82.789 | 33.041 | 17.710 | 1.00 | 80.82 | H |
| ATOM | 4773 | O | ASN | H | 196 | 83.265 | 34.167 | 17.581 | 1.00 | 80.82 | H |
| ATOM | 4774 | N | VAL | H | 197 | 81.598 | 32.700 | 17.237 | 1.00 | 48.09 | H |
| ATOM | 4775 | CA | VAL | H | 197 | 80.745 | 33.646 | 16.521 | 1.00 | 48.09 | H |
| ATOM | 4776 | CB | VAL | H | 197 | 81.012 | 33.617 | 15.006 | 1.00 | 26.02 | H |
| ATOM | 4777 | CG1 | VAL | H | 197 | 80.162 | 34.673 | 14.325 | 1.00 | 26.02 | H |
| ATOM | 4778 | CG2 | VAL | H | 197 | 82.505 | 33.818 | 14.720 | 1.00 | 26.02 | H |
| ATOM | 4779 | C | VAL | H | 197 | 79.282 | 33.290 | 16.736 | 1.00 | 48.09 | H |
| ATOM | 4780 | O | VAL | H | 197 | 78.916 | 32.117 | 16.771 | 1.00 | 48.09 | H |
| ATOM | 4781 | N | ALA | H | 198 | 78.442 | 34.303 | 16.865 | 1.00 | 50.07 | H |
| ATOM | 4782 | CA | ALA | H | 198 | 77.027 | 34.057 | 17.091 | 1.00 | 50.07 | H |
| ATOM | 4783 | CB | ALA | H | 198 | 76.707 | 34.247 | 18.571 | 1.00 | 0.01 | H |
| ATOM | 4784 | C | ALA | H | 198 | 76.132 | 34.952 | 16.240 | 1.00 | 50.07 | H |
| ATOM | 4785 | O | ALA | H | 198 | 76.349 | 36.155 | 16.140 | 1.00 | 50.07 | H |
| ATOM | 4786 | N | HIS | H | 199 | 75.128 | 34.357 | 15.616 | 1.00 | 30.80 | H |
| ATOM | 4787 | CA | HIS | H | 199 | 74.209 | 35.121 | 14.802 | 1.00 | 30.80 | H |
| ATOM | 4788 | CB | HIS | H | 199 | 74.406 | 34.824 | 13.319 | 1.00 | 73.63 | H |
| ATOM | 4789 | CG | HIS | H | 199 | 73.540 | 35.658 | 12.429 | 1.00 | 73.63 | H |
| ATOM | 4790 | CD2 | HIS | H | 199 | 72.851 | 36.797 | 12.673 | 1.00 | 73.63 | H |
| ATOM | 4791 | ND1 | HIS | H | 199 | 73.292 | 35.333 | 11.113 | 1.00 | 73.63 | H |
| ATOM | 4792 | CE1 | HIS | H | 199 | 72.484 | 36.235 | 10.584 | 1.00 | 73.63 | H |
| ATOM | 4793 | NE2 | HIS | H | 199 | 72.201 | 37.134 | 11.510 | 1.00 | 73.63 | H |
| ATOM | 4794 | C | HIS | H | 199 | 72.779 | 34.774 | 15.222 | 1.00 | 30.80 | H |
| ATOM | 4795 | O | HIS | H | 199 | 72.096 | 33.949 | 14.594 | 1.00 | 30.80 | H |
| ATOM | 4796 | N | PRO | H | 200 | 72.310 | 35.408 | 16.304 | 1.00 | 45.45 | H |
| ATOM | 4797 | CD | PRO | H | 200 | 73.079 | 36.405 | 17.065 | 1.00 | 42.33 | H |
| ATOM | 4798 | CA | PRO | H | 200 | 70.983 | 35.237 | 16.888 | 1.00 | 45.45 | H |
| ATOM | 4799 | CB | PRO | H | 200 | 70.900 | 36.402 | 17.854 | 1.00 | 42.33 | H |
| ATOM | 4800 | CG | PRO | H | 200 | 72.295 | 36.501 | 18.337 | 1.00 | 42.33 | H |
| ATOM | 4801 | C | PRO | H | 200 | 69.860 | 35.261 | 15.867 | 1.00 | 45.45 | H |
| ATOM | 4802 | O | PRO | H | 200 | 68.996 | 34.381 | 15.855 | 1.00 | 45.45 | H |
| ATOM | 4803 | N | ALA | H | 201 | 69.872 | 36.278 | 15.018 | 1.00 | 57.12 | H |
| ATOM | 4804 | CA | ALA | H | 201 | 68.835 | 36.417 | 14.010 | 1.00 | 57.12 | H |

TABLE 2-continued

Atomic coordinates of b2 adrenoreceptor

| ATOM | 4805 | CB  | ALA | H | 201 | 69.223 | 37.510 | 13.023 | 1.00 | 33.25  | H |
|------|------|-----|-----|---|-----|--------|--------|--------|------|--------|---|
| ATOM | 4806 | C   | ALA | H | 201 | 68.564 | 35.097 | 13.278 | 1.00 | 57.12  | H |
| ATOM | 4807 | O   | ALA | H | 201 | 67.520 | 34.931 | 12.635 | 1.00 | 57.12  | H |
| ATOM | 4808 | N   | SER | H | 202 | 69.504 | 34.161 | 13.384 | 1.00 | 37.07  | H |
| ATOM | 4809 | CA  | SER | H | 202 | 69.374 | 32.859 | 12.738 | 1.00 | 37.07  | H |
| ATOM | 4810 | CB  | SER | H | 202 | 70.392 | 32.726 | 11.604 | 1.00 | 38.14  | H |
| ATOM | 4811 | OG  | SER | H | 202 | 71.721 | 32.756 | 12.101 | 1.00 | 38.14  | H |
| ATOM | 4812 | C   | SER | H | 202 | 69.639 | 31.786 | 13.779 | 1.00 | 37.07  | H |
| ATOM | 4813 | O   | SER | H | 202 | 69.636 | 30.591 | 13.476 | 1.00 | 37.07  | H |
| ATOM | 4814 | N   | SER | H | 203 | 69.847 | 32.228 | 15.016 | 1.00 | 102.65 | H |
| ATOM | 4815 | CA  | SER | H | 203 | 70.141 | 31.315 | 16.105 | 1.00 | 102.65 | H |
| ATOM | 4816 | CB  | SER | H | 203 | 68.918 | 30.461 | 16.438 | 1.00 | 60.74  | H |
| ATOM | 4817 | OG  | SER | H | 203 | 67.825 | 31.267 | 16.838 | 1.00 | 60.74  | H |
| ATOM | 4818 | C   | SER | H | 203 | 71.253 | 30.455 | 15.547 | 1.00 | 102.65 | H |
| ATOM | 4819 | O   | SER | H | 203 | 71.071 | 29.271 | 15.280 | 1.00 | 102.65 | H |
| ATOM | 4820 | N   | THR | H | 204 | 72.402 | 31.081 | 15.343 | 1.00 | 44.16  | H |
| ATOM | 4821 | CA  | THR | H | 204 | 73.561 | 30.402 | 14.785 | 1.00 | 44.16  | H |
| ATOM | 4822 | CB  | THR | H | 204 | 73.780 | 30.862 | 13.334 | 1.00 | 53.40  | H |
| ATOM | 4823 | OG1 | THR | H | 204 | 72.769 | 30.288 | 12.501 | 1.00 | 53.40  | H |
| ATOM | 4824 | CG2 | THR | H | 204 | 75.173 | 30.471 | 12.839 | 1.00 | 53.40  | H |
| ATOM | 4825 | C   | THR | H | 204 | 74.840 | 30.669 | 15.573 | 1.00 | 44.16  | H |
| ATOM | 4826 | O   | THR | H | 204 | 75.359 | 31.780 | 15.542 | 1.00 | 44.16  | H |
| ATOM | 4827 | N   | LYS | H | 205 | 75.346 | 29.671 | 16.290 | 1.00 | 89.97  | H |
| ATOM | 4828 | CA  | LYS | H | 205 | 76.587 | 29.865 | 17.030 | 1.00 | 89.97  | H |
| ATOM | 4829 | CB  | LYS | H | 205 | 76.453 | 29.405 | 18.483 | 1.00 | 86.89  | H |
| ATOM | 4830 | CG  | LYS | H | 205 | 77.661 | 29.764 | 19.335 | 1.00 | 86.89  | H |
| ATOM | 4831 | CD  | LYS | H | 205 | 77.416 | 29.501 | 20.812 | 1.00 | 86.89  | H |
| ATOM | 4832 | CE  | LYS | H | 205 | 78.593 | 29.973 | 21.668 | 1.00 | 86.89  | H |
| ATOM | 4833 | NZ  | LYS | H | 205 | 78.311 | 29.844 | 23.133 | 1.00 | 86.89  | H |
| ATOM | 4834 | C   | LYS | H | 205 | 77.651 | 29.057 | 16.296 | 1.00 | 89.97  | H |
| ATOM | 4835 | O   | LYS | H | 205 | 77.362 | 27.986 | 15.753 | 1.00 | 89.97  | H |
| ATOM | 4836 | N   | VAL | H | 206 | 78.877 | 29.574 | 16.261 | 1.00 | 61.99  | H |
| ATOM | 4837 | CA  | VAL | H | 206 | 79.940 | 28.896 | 15.541 | 1.00 | 61.99  | H |
| ATOM | 4838 | CB  | VAL | H | 206 | 80.008 | 29.380 | 14.104 | 1.00 | 21.89  | H |
| ATOM | 4839 | CG1 | VAL | H | 206 | 80.043 | 28.178 | 13.174 | 1.00 | 21.89  | H |
| ATOM | 4840 | CG2 | VAL | H | 206 | 78.820 | 30.303 | 13.800 | 1.00 | 21.89  | H |
| ATOM | 4841 | C   | VAL | H | 206 | 81.321 | 29.072 | 16.131 | 1.00 | 61.99  | H |
| ATOM | 4842 | O   | VAL | H | 206 | 81.678 | 30.153 | 16.599 | 1.00 | 61.99  | H |
| ATOM | 4843 | N   | ASP | H | 207 | 82.102 | 27.998 | 16.077 | 1.00 | 117.78 | H |
| ATOM | 4844 | CA  | ASP | H | 207 | 83.462 | 27.990 | 16.600 | 1.00 | 117.78 | H |
| ATOM | 4845 | CB  | ASP | H | 207 | 83.599 | 26.870 | 17.630 | 1.00 | 74.02  | H |
| ATOM | 4846 | CG  | ASP | H | 207 | 82.534 | 26.943 | 18.718 | 1.00 | 74.02  | H |
| ATOM | 4847 | OD1 | ASP | H | 207 | 82.629 | 27.826 | 19.600 | 1.00 | 74.02  | H |
| ATOM | 4848 | OD2 | ASP | H | 207 | 81.591 | 26.121 | 18.682 | 1.00 | 74.02  | H |
| ATOM | 4849 | C   | ASP | H | 207 | 84.409 | 27.745 | 15.432 | 1.00 | 117.78 | H |
| ATOM | 4850 | O   | ASP | H | 207 | 84.037 | 27.064 | 14.476 | 1.00 | 117.78 | H |
| ATOM | 4851 | N   | LYS | H | 208 | 85.621 | 28.295 | 15.489 | 1.00 | 35.46  | H |
| ATOM | 4852 | CA  | LYS | H | 208 | 86.567 | 28.082 | 14.391 | 1.00 | 35.46  | H |
| ATOM | 4853 | CB  | LYS | H | 208 | 86.334 | 29.113 | 13.286 | 1.00 | 58.27  | H |
| ATOM | 4854 | CG  | LYS | H | 208 | 86.530 | 28.576 | 11.869 | 1.00 | 58.27  | H |
| ATOM | 4855 | CD  | LYS | H | 208 | 85.329 | 27.753 | 11.408 | 1.00 | 58.27  | H |
| ATOM | 4856 | CE  | LYS | H | 208 | 85.479 | 27.310 | 9.953  | 1.00 | 58.27  | H |
| ATOM | 4857 | NZ  | LYS | H | 208 | 84.287 | 26.567 | 9.459  | 1.00 | 58.27  | H |
| ATOM | 4858 | C   | LYS | H | 208 | 88.026 | 28.125 | 14.836 | 1.00 | 35.46  | H |
| ATOM | 4859 | O   | LYS | H | 208 | 88.645 | 29.180 | 14.880 | 1.00 | 35.46  | H |
| ATOM | 4860 | N   | LYS | H | 209 | 88.559 | 26.956 | 15.164 | 1.00 | 40.45  | H |
| ATOM | 4861 | CA  | LYS | H | 209 | 89.934 | 26.781 | 15.619 | 1.00 | 40.45  | H |
| ATOM | 4862 | CB  | LYS | H | 209 | 90.199 | 25.280 | 15.777 | 1.00 | 149.29 | H |
| ATOM | 4863 | CG  | LYS | H | 209 | 91.231 | 24.861 | 16.813 | 1.00 | 149.29 | H |
| ATOM | 4864 | CD  | LYS | H | 209 | 91.220 | 23.333 | 16.957 | 1.00 | 149.29 | H |
| ATOM | 4865 | CE  | LYS | H | 209 | 92.094 | 22.837 | 18.102 | 1.00 | 149.29 | H |
| ATOM | 4866 | NZ  | LYS | H | 209 | 92.009 | 21.354 | 18.242 | 1.00 | 149.29 | H |
| ATOM | 4867 | C   | LYS | H | 209 | 90.846 | 27.361 | 14.546 | 1.00 | 40.45  | H |
| ATOM | 4868 | O   | LYS | H | 209 | 90.436 | 27.488 | 13.387 | 1.00 | 40.45  | H |
| ATOM | 4869 | N   | ILE | H | 210 | 92.075 | 27.700 | 14.927 | 1.00 | 83.94  | H |
| ATOM | 4870 | CA  | ILE | H | 210 | 93.047 | 28.258 | 13.989 | 1.00 | 83.94  | H |
| ATOM | 4871 | CB  | ILE | H | 210 | 93.568 | 29.643 | 14.443 | 1.00 | 45.76  | H |
| ATOM | 4872 | CG2 | ILE | H | 210 | 94.726 | 30.098 | 13.545 | 1.00 | 45.76  | H |
| ATOM | 4873 | CG1 | ILE | H | 210 | 92.448 | 30.672 | 14.389 | 1.00 | 45.76  | H |
| ATOM | 4874 | CD1 | ILE | H | 210 | 92.912 | 32.076 | 14.757 | 1.00 | 45.76  | H |
| ATOM | 4875 | C   | ILE | H | 210 | 94.266 | 27.368 | 13.811 | 1.00 | 83.94  | H |
| ATOM | 4876 | O   | ILE | H | 210 | 95.246 | 27.493 | 14.552 | 1.00 | 83.94  | H |
| ATOM | 4877 | N   | VAL | H | 211 | 94.210 | 26.472 | 12.834 | 1.00 | 73.42  | H |
| ATOM | 4878 | CA  | VAL | H | 211 | 95.350 | 25.606 | 12.556 | 1.00 | 73.42  | H |
| ATOM | 4879 | CB  | VAL | H | 211 | 94.991 | 24.528 | 11.507 | 1.00 | 73.75  | H |
| ATOM | 4880 | CG1 | VAL | H | 211 | 96.221 | 23.723 | 11.149 | 1.00 | 73.75  | H |
| ATOM | 4881 | CG2 | VAL | H | 211 | 93.904 | 23.614 | 12.046 | 1.00 | 73.75  | H |
| ATOM | 4882 | C   | VAL | H | 211 | 96.445 | 26.524 | 11.993 | 1.00 | 73.42  | H |

TABLE 2-continued

Atomic coordinates of b2 adrenoreceptor

| ATOM | 4883 | O | VAL | H | 211 | 96.157 | 27.396 | 11.177 | 1.00 | 73.42 | H |
|---|---|---|---|---|---|---|---|---|---|---|---|
| ATOM | 4884 | N | PRO | H | 212 | 97.706 | 26.339 | 12.420 | 1.00 | 63.25 | H |
| ATOM | 4885 | CD | PRO | H | 212 | 98.245 | 25.177 | 13.139 | 1.00 | 87.71 | H |
| ATOM | 4886 | CA | PRO | H | 212 | 98.800 | 27.182 | 11.931 | 1.00 | 63.25 | H |
| ATOM | 4887 | CB | PRO | H | 212 | 100.051 | 26.362 | 12.256 | 1.00 | 87.71 | H |
| ATOM | 4888 | CG | PRO | H | 212 | 99.532 | 24.960 | 12.412 | 1.00 | 87.71 | H |
| ATOM | 4889 | C | PRO | H | 212 | 98.685 | 27.558 | 10.463 | 1.00 | 63.25 | H |
| ATOM | 4890 | O | PRO | H | 212 | 98.083 | 28.575 | 10.140 | 1.00 | 63.25 | H |
| ATOM | 4891 | N | ARG | H | 213 | 99.258 | 26.770 | 9.567 | 1.00 | 137.96 | H |
| ATOM | 4892 | CA | ARG | H | 213 | 99.155 | 27.091 | 8.150 | 1.00 | 137.96 | H |
| ATOM | 4893 | CB | ARG | H | 213 | 100.086 | 28.261 | 7.788 | 1.00 | 76.29 | H |
| ATOM | 4894 | CG | ARG | H | 213 | 99.333 | 29.557 | 7.417 | 1.00 | 76.29 | H |
| ATOM | 4895 | CD | ARG | H | 213 | 98.625 | 29.438 | 6.055 | 1.00 | 76.29 | H |
| ATOM | 4896 | NE | ARG | H | 213 | 97.516 | 30.380 | 5.859 | 1.00 | 76.29 | H |
| ATOM | 4897 | CZ | ARG | H | 213 | 97.629 | 31.709 | 5.810 | 1.00 | 76.29 | H |
| ATOM | 4898 | NH1 | ARG | H | 213 | 98.815 | 32.287 | 5.944 | 1.00 | 76.29 | H |
| ATOM | 4899 | NH2 | ARG | H | 213 | 96.551 | 32.468 | 5.620 | 1.00 | 76.29 | H |
| ATOM | 4900 | C | ARG | H | 213 | 99.469 | 25.873 | 7.305 | 1.00 | 137.96 | H |
| ATOM | 4901 | O | ARG | H | 213 | 99.765 | 24.806 | 7.840 | 1.00 | 137.96 | H |
| ATOM | 4902 | N | ASP | H | 214 | 99.389 | 26.032 | 5.988 | 1.00 | 220.47 | H |
| ATOM | 4903 | CA | ASP | H | 214 | 99.655 | 24.940 | 5.057 | 1.00 | 220.47 | H |
| ATOM | 4904 | CB | ASP | H | 214 | 99.315 | 25.369 | 3.624 | 1.00 | 87.14 | H |
| ATOM | 4905 | CG | ASP | H | 214 | 97.819 | 25.533 | 3.396 | 1.00 | 87.14 | H |
| ATOM | 4906 | OD1 | ASP | H | 214 | 97.186 | 26.346 | 4.097 | 1.00 | 87.14 | H |
| ATOM | 4907 | OD2 | ASP | H | 214 | 97.274 | 24.848 | 2.507 | 1.00 | 87.14 | H |
| ATOM | 4908 | C | ASP | H | 214 | 101.105 | 24.466 | 5.115 | 1.00 | 220.47 | H |
| ATOM | 4909 | O | ASP | H | 214 | 101.551 | 23.716 | 4.246 | 1.00 | 220.47 | H |
| ATOM | 4910 | N | CYS | H | 215 | 101.832 | 24.900 | 6.141 | 1.00 | 174.03 | H |
| ATOM | 4911 | CA | CYS | H | 215 | 103.234 | 24.529 | 6.313 | 1.00 | 174.03 | H |
| ATOM | 4912 | CB | CYS | H | 215 | 103.386 | 23.006 | 6.447 | 1.00 | 161.96 | H |
| ATOM | 4913 | SG | CYS | H | 215 | 102.925 | 22.305 | 8.060 | 1.00 | 161.96 | H |
| ATOM | 4914 | C | CYS | H | 215 | 104.078 | 25.022 | 5.143 | 1.00 | 174.03 | H |
| ATOM | 4915 | O | CYS | H | 215 | 105.282 | 25.237 | 5.285 | 1.00 | 174.03 | H |
| ATOM | 4916 | N | GLY | H | 216 | 103.440 | 25.200 | 3.991 | 1.00 | 198.46 | H |
| ATOM | 4917 | CA | GLY | H | 216 | 104.148 | 25.662 | 2.813 | 1.00 | 198.46 | H |
| ATOM | 4918 | C | GLY | H | 216 | 104.236 | 27.172 | 2.747 | 1.00 | 198.46 | H |
| ATOM | 4919 | O | GLY | H | 216 | 105.289 | 27.724 | 2.426 | 1.00 | 198.46 | H |
| ATOM | 4920 | N | CYS | H | 217 | 103.132 | 27.846 | 3.056 | 1.00 | 167.59 | H |
| ATOM | 4921 | CA | CYS | H | 217 | 103.097 | 29.303 | 3.018 | 1.00 | 167.59 | H |
| ATOM | 4922 | CB | CYS | H | 217 | 101.677 | 29.803 | 3.295 | 1.00 | 150.46 | H |
| ATOM | 4923 | SG | CYS | H | 217 | 101.375 | 31.524 | 2.779 | 1.00 | 150.46 | H |
| ATOM | 4924 | C | CYS | H | 217 | 104.061 | 29.901 | 4.040 | 1.00 | 167.59 | H |
| ATOM | 4925 | O | CYS | H | 217 | 105.059 | 30.517 | 3.612 | 1.00 | 167.59 | H |
| ATOM | 4926 | OXT | CYS | H | 217 | 103.813 | 29.740 | 5.254 | 1.00 | 150.46 | H |
| END | | | | | | | | | | | |

UTILITY

Compounds identified using the methods described above are useful, for example, in the treatment of a condition requiring relaxation of smooth muscle of the uterus or vascular system. They are thus useful for the prevention or alleviation of premature labour pains in pregnancy. They are also useful in the treatment of chronic or acute asthma, urticaria, psoriasis, rhinitis, allergic conjunctivitis, actinitis, hay fever, and mastocytosis.

In certain cases, a compound identified by the methods described above may be employed as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Such anti-inflammatory drugs include steroids, in particular glucocorticosteroids such as budesonide, beclamethasone, fluticasone, ciclesonide or mometasone or steroids described in WO 0200679 especially those of Examples 3, 11, 14, 17, 19, 26, 34, 37, 39, 51, 60, 67, 72, 73, 90, 99 and 101, LTB4 antagonists such as those described in U.S. Pat. No. 5,451,700, LTD4 antagonists such as montelukast and zafirlukast, and PDE4 inhibitors such as Ariflo® (GlaxoSmith Kline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene) and KW-4490 (Kyowa Hakko Kogyo) and A2a agonists such as those described in EP 1052264, EP 1241176, WO 0023457, WO0077018, WO 0123399, WO 0160835, WO 0194368, WO 0200676, WO 0222630, WO 0296462, WO 0127130, WO 0127131, WO 9602543, WO 9602553, WO 9828319, WO 9924449, WO 9924450, WO 9924451, WO 9938877, WO 9941267, WO 9967263, WO 9967264, WO 9967265, WO 9967266, WO 9417090, EP 409595A2 and WO 0078774 and A2b antagonists such as those described in WO 02/42298. Such bronchodilatory drugs include anticholinergic or antimuscarinic agents, in particular ipratropium bromide, oxitropium bromide and tiotropium bromide, but also those described in EP 424021, U.S. Pat. No. 5,171,744 (Pfizer) and WO 01/04118 (Almirall Prodesfarma).

In order to further illustrate the present invention, the following specific examples are given with the understanding that they are being offered to illustrate the present invention and should not be construed in any way as limiting its scope. All amino acid positions recited in the following Examples section are with reference to SEQ ID NO:1.

EXAMPLE 1

Summary of Methods $\beta_2AR$ was expressed in Sf9 cells using recombinant baculovirus. Sf9 cell membranes were solubilized in dodecylmaltoside and purified by sequential antibody and ligand affinity chromatography. Fab 5 was generated by papain digestion of Mab5 and purified by ion-exchange chromatography. The $\beta_2AR$-Fab5 complex was formed by mixing purified $\beta_2AR$ with a stoichiometric excess of Fab5, and then isolated by size exclusion chromatography. The Fab5 antibody is described in U.S. provisional patent application Ser. No. 60.960,300, filed on Oct. 15, 2007, which description is incorporated by reference. The purified $\beta_2AR$-Fab5 complex was mixed with bicelles composed of the lipid DMPC and the detergent CHAPSO. The final $\beta_2AR$-Fab concentration ranged between 8 and 12 mg/ml. Crystals were grown by hanging-drop vapor diffusion in a mixture of ammonium sulfate, sodium acetate, and EDTA over a pH range of 6.5 to 7.5. Crystals grew within 7 to 10 days. They were cryoprotected in 20% glycerol before freezing in liquid nitrogen. Due to the size and radiation sensitivity of the crystals, diffraction images were obtained by microcrystallography. The structure of the $\beta_2AR365$-Fab5 complex was solved by molecular replacement, using the separate constant and variable domain structures as search models.

EXAMPLE 2

Generation of $\beta_2AR365$ Encoded Baculovirus

The plasmid used for $\beta_2AR$ expression and mutagenesis is described in Gether et al, EMBO J. 1997 16: 6737-47. Briefly, the wild-type coding sequence of the human $\beta_2AR$ (starting at Gly2) was cloned into the pFastbac1 Sf-9 expression vector (Invitrogen) with the HA signal sequence followed by the Flag epitope tag at the amino terminus. The mutation N187E was made to remove the third glycosylation site. A sequence encoding ENLYFQGP was introduced between the FLAG tag and the start of the receptor, in order to install a TEV protease site and a Phe residue to inhibit aminopeptidase activity. Finally, a TAA stop codon was placed between G365 and Y366, terminating translation without the 48 C-terminal residues of the wild-type $\beta_2AR$. The resulting construct is referred to as $\beta_2AR365$. The mutations and insertions described above were made using the Quickchange Multi protocol (Stratagene), and the resulting construct was confirmed by sequencing. Recombinant baculovirus was made using the Bac-to-Bac system (Invitrogen).

EXAMPLE 3

Preparation of Fab Fragments

Monoclonal mouse immunoglobulins against the $\beta_2AR$ reconstituted in liposomes were raised. Mab5 IgGs from mouse hybridoma cell culture supernatant were purified using a Protein G column (Pierce). Fab5 fragments were generated by papain proteolysis (Worthington) and purified by Mono Q chromatography. The fragments were concentrated to ~100 mg ml$^{-1}$ with a Millipore concentrator (5 kDa molecular weight cut off) in a solution of 10 mM HEPES pH 7.5 and 100 mM NaCl.

EXAMPLE 4

Preparation of $\beta_2AR365$-Fab5 Complexes

The $\beta_2AR365$ was expressed in Sf-9 insect cells infected with $\beta_2AR365$ baculovirus, and solubilized according to previously described methods. Functional protein was obtained by M1 FLAG affinity chromatography (Sigma) prior to and following alprenolol-Sepharose chromatography. Receptor bound alprenolol was exchanged for carazolol on the second M1 resin. N-linked glycolsylations were removed by treatment with PNGaseF (NEB), and the FLAG epitope was removed by treatment with AcTEV protease (Invitrogen). Protein was concentrated to ~50 mg/ml with a 100 kDa molecular weight cut off Vivaspin concentrator (Vivascience) and mixed in stoichiometric excess of Fab5. The complex was purified on a Superdex-200 (10/300 GL) column in a solution of 10 mM HEPES pH 7.5, 100 mM NaCl, 0.1% dodecylmaltoside, and 10 µM carazolol. The purified $\beta_2AR365$-Fab5 complexes were concentrated to ~60 mg ml$^{-1}$ using a Vivaspin concentrator.

EXAMPLE 5

Crystallization

The $\beta_2AR365$-Fab5 complexes were mixed with bicelles (10% w/v 3:1 DMPC:CHAPSO in 10 mM HEPES pH 7.5, 100 mM NaCl) at a 1:5 (protein:bicelle) ratio, and crystals were grown in sitting- and hanging-drop formats at 22° C. using equal volumes of protein mixture and reservoir solutions. Initial crystallization leads were identified using multiple 96-well sitting-drop screens from Nextal (Qiagen). After extensive optimization, crystals for data collection were grown in hanging-drop format over a reservoir solution of 1.85-2.0 M ammonium sulfate, 180 mM sodium acetate, 5 mM EDTA, 100 mM MES or HEPES pH 6.5-7.5. Crystals grew to full size within 7 to 10 days. Crystals were flash frozen and stored in liquid nitrogen, with reservoir solution plus 20% glycerol as cryoprotectant.

EXAMPLE 6

Microcrystallography Data Collection and Processing

Microbeams were employed for data collection. The shape of the crystals permitted complete data to be measured from a single crystal. A small wedge of data, typically 5-10°, (1° per frame) could be measured before significant radiation damage was observed. The crystal was then translated to a new, undamaged position to collect the next wedge of data. A total of 182° of data collected in this manner, measured at beamline ID23-2 of the ESRF, were used for the final $\beta_2AR365$-Fab5 data set (Table 1). The $\beta_2AR24/365$-Fab5 data set was obtained from 225° of data measured on beamline 23ID-B of the APS (Table 1).

TABLE 1

X-ray data collection and refinement statistics

|  | $\beta_2$AR365-Fab5 | $\beta_2$AR24/365-Fab5 |
|---|---|---|
| Data collection | | |
| Space group | C2 | C2 |
| Cell dimensions | | |
| a, b, c (Å) | 338.4, 48.5, 89.4 | 338.4, 48.5, 89.4 |
| $\alpha, \beta, \gamma$ (°) | 90., 104.6, 90. | 90., 104.6, 90. |
| Resolution (Å) | 86.4.-3.4 (3.49-3.40)* | 50-3.4 (3.52-3.40)* |
| $R_{merge}$ | 0.117 (0.407) | 0.120 (0.456) |
| I/$\sigma$I | 9.9 (2.3) | 7.8 (2.6) |
| Completeness (%) | 98.9 (94.9) | 99.4 (98.4) |
| Multiplicity | 3.3 (2.9) | 4.1 (3.4) |
| Refinement | | |
| Resolution (Å) | 20.-3.4 | 20.-3.4 |
| No. reflections work/free | 17658/1902 | 17458/1886 |
| $R_{work}/R_{free}$ | 0.216/0.269 | 0.226/0.279 |
| No. atoms | 4905 | 4887 |
| Average B values (Å$^2$) | | |
| Receptor | 156. | 187. |
| Fab5 | 67. | 91. |
| Overall anisotropic B (Å$^2$) | | |
| $B_{11}/B_{22}/B_{33}/B_{13}$ | −27.1/31.3/−4.2/4.4 | −16.8/20.4/−3.5/12.4 |
| R.m.s deviations | | |
| Bond lengths (Å) | 0.007 | 0.008 |
| Bond angles (°) | 1.4 | 1.5 |
| Ramachandran plot** receptor/Fab5 | | |
| % most favored | 76.3/71.5 | 75.8/71.8 |
| allowed | 22.1/27.2 | 22.1/26.6 |
| generously allowed | 1.6/1.3 | 2.1/1.6 |
| disallowed | 0.0/0.0 | 0.0/0.0 |

*Highest resolution shell is shown in parenthesis.
**As defined in PROCHECK

ESRF data were processed with MOSFLM and SCALA (Collaborative Computational Project, N. Acta Cryst. 1994 D50, 760-763) and data measured at the APS were processed with HKL2000 (Otwinowski et al, Methods Enzymol. 1997 276, 307-326). In many cases it was necessary to reindex the crystal after moving to a new position on the crystal, which may have been due to bending of the frozen crystals such that the indexing matrix from the previous volume could not accurately predict the diffraction pattern from a new volume. This problem precluded global postrefinement of the unit cell parameters. The unit cell parameters used for subsequent analysis (Table 1) were obtained from initial indexing and refinement from one wedge of the ESRF data, and were subsequently found to be sufficient for processing the remaining data without unit cell constant refinement. Using a partial specific volume of 1.21 Å$^3$/Da for protein, the unit cell would have 66% lipid, detergent and aqueous solvent for is one $\beta_2$AR-Fab5 complex in the asymmetric unit.

EXAMPLE 7

Structure Solution and Refinement

The structure of the $\beta_2$AR365-Fab5 complex was solved by molecular replacement, by searching with separate constant and variable domain models against a low resolution (4.1 Å) data set measured at ESRF beamline ID-13. The Fab was derived from a murine IgG antibody containing a κ light chain and γ1 heavy chain. At the time of these calculations the sequence of the heavy chain was not known, and the crystal structure of a Fab containing a □ light chain but □2 heavy chain (PDB code 1IGT) was used as a search model. The program PHASER (McCoy, Acta Crystallogr D. Biol. Crystallogr. 2007 63: 32-41) was used to place the constant domain, then the variable domain, using data between 12 and 4.5 Å. The constant domain model retained all side chains, whereas the variable domain was reduced to polyalanine. All atomic temperature factors were set to 50 Å$^2$. The best solution had rotation and translation function Z scores of 5.3 and 10.6 for the constant domain, and 4.5 and 21.7 for the variable domain. An electron density map calculated to 6 Å from this solution revealed rods of density corresponding to the TM helices of the receptor. A model of the transmembrane portion of rhodopsin made by removing the cytoplasmic and extracellular loops, retinal, and water molecules, and replacing those residues non-identical with $\beta_2$AR with alanine could be manually placed into this density. To obtain a convenient starting model for building the receptor, the molecular replacement calculation was re-run to include the rhodopsin transmembrane helices model as a third search model after placing the two Fab domains. Although the top solution was not very strong statistically (rotation function Z=2.5, translation function Z=7.0), after rigid body refinement the rhodopsin model was very close to that placed manually into the 6 Å map. This molecular replacement solution was then subjected to rigid-body refinement between 20 and 5 Å in CNS (Brünger et al, Acta Cryst. 1998 D54: 905-921), using five rigid bodies (the Fab constant domain light and heavy chains, the variable domain light and heavy chains, and rhodopsin). This gave R and $R_{free}$ values of 0.447 and 0.452, respectively.

Figure 5A:
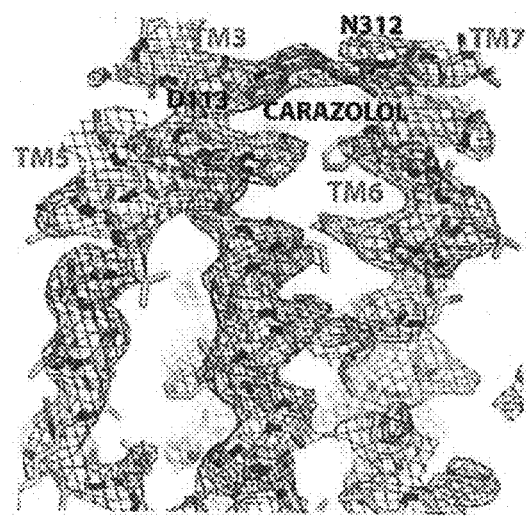
FIGS. 5A-5C. Views of the electron density. The final $2F_o$-$F_c$ map contoured at 0.7σ (blue mesh) is shown in three regions of the structure. Note that this contour level is required to visualize the receptor molecule, as it is much more poorly ordered than the Fab. The receptor carbon atoms are gold, with red, blue and green atoms representing oxygen, nitrogen, and sulfur. 5A) TM segments 3, 5, 6, 7 near the extracellular side of the receptor. 5B) The Fab-Intercellular loop 3 interface. The Fab5 light chain carbon atoms are shown in red, heavy chain carbon atoms in light blue. Selected side chains are labeled. 5C) The DRY region of TM6 and surroundings.
Figure 5B:
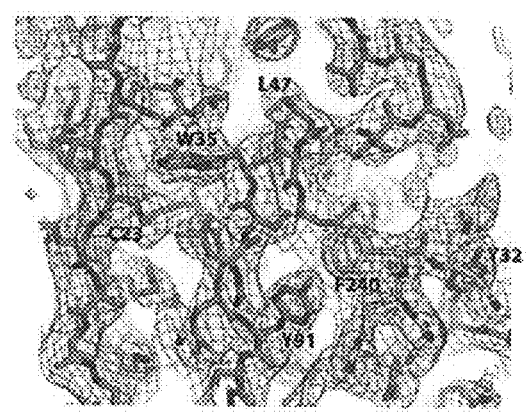
Figure 5C:
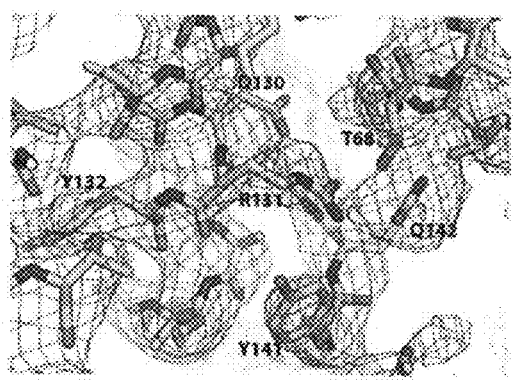

Electron density maps made with phases either from the Fab model alone or the rigid-body refined Fab+minimal rhodopsin model indicated significant differences between rhodopsin and $\beta_2$AR, and extensive manual rebuilding was required to refine the structure. The structure was initially refined at 4.1 Å resolution. The test set from the 4.1 Å set was transferred to the higher-resolution $\beta_2$AR365-Fab5 set measured at the ESRF (Table 1) and additional test set reflections added in the 4.1-3.4 Å range. Multiple rounds of manual rebuilding, positional and grouped temperature factor refinement were performed using the maximum likelihood amplitude target in CNS. The electron density of the Fab is very well defined due to its tight packing in the crystal, whereas the receptor is poorly packed and has much higher temperature factors (FIG. 5 and Table 1). Because the receptor density is poor, we also refined against a second data set from a single crystal of a the $\beta_2$AR24/365-Fab5 complex (Table 1), to ensure that any densities observed in the receptor region are not due to noise in the first data set. The $\beta_2$AR24/365-Fab5 data set was obtained from 225° of data measured using a 4-micron×6-micron beam at beamline 23ID-B of the APS. Although there is electron density in the extracellular region, the final model retains only those residues that could be unambiguously assigned (FIG. 1).

The Fab represents 50% of the scattering mass and, because of its better order, contributes even more to the total scattering, and so represents a significant source of phase information independent of the receptor. Simulated annealing omit maps confirmed the interpretation presented here. Moreover, alternative sequence registers or backbone paths were considered in several portions of the receptor, but these models could be eliminated based on inspection of $\sigma_A$ weighted 2Fo-Fc and Fo-Fc electron density maps.

Based on the average F/$\sigma$(F) of reflections near the three crystallographic axes (as defined by the program TRUNCATE Whorton et al, Proc. Natl. Acad. Sci. 2007 104: 7682-7), we estimate the effective resolution to be 3.4 Å within the plane of the membrane and 3.7 Å perpendicular to the membrane for the $\beta_2$AR365-Fab5 structure, and 3.4 Å/3.8 Å for the $\beta_2$AR24/365-Fab5 structure.

EXAMPLE 8

Crystallization and Structure Solution

In an effort to provide conformational stability while increasing the polar surface available for crystal contacts, we generated a monoclonal antibody (Mab5) that binds to the third intracellular loop of native, but not denatured receptor protein. Mab5 was generated by immunizing mice with purified $\beta_2$AR reconstituted into phospholipid vesicles at a high protein to lipid ratio. Binding of Mab5 to the $\beta_2$AR does not alter agonist or antagonist binding affinities, and does not prevent agonist-induced conformational changes; therefore, it does not significantly alter the native structure of the receptor. Purified, deglycosylated $\beta_2$AR bound to carazolol (an inverse agonist) forms a complex with the Fab generated from Mab5 (Fab5) in detergent, and the $\beta_2$AR-Fab5 complex can be isolated by size exclusion chromatography.

Crystals of the carazolol-bound $\beta_2$AR-Fab5 complex were grown in DMPC bicelles Faham et al, Protein Sci. 2005 14: 836-40) using ammonium sulfate as a precipitant. The size and uniformity of the crystals were improved by removing 48 amino acids from the unstructured carboxyl terminus ($\beta_2$AR365, FIG. 1). Crystals of the $\beta_2$AR365-Fab5 complex grew as long, thin plates up to 300 µm long, approximately 30 µm wide, and less than 10 µm thick. Data collection was done using microbeam technology where X-ray beams are either focused (ID-13 and ID23-2 beamlines, European Synchrotron Radiation Facility, Grenoble) or moderately focused and then further collimated (23ID-B GM/CA-CAT beamline, Advanced Photon Source) to diameters between 5 and 10 µm. The initial images from the best crystals showed diffraction to 3.0 Å; however, resolution decreased in sequential images from the same crystal volume. Nevertheless, we obtained a complete data set from a single crystal, and determined the structure by molecular replacement using immunoglobulin domain search models for the Fab. The diffraction is anisotropic, with diffraction extending to 3.4 Å in the plane of the membrane and 3.7 Å perpendicular to the plane of the membrane.

EXAMPLE 9

Crystal Structure of the $\beta_2$AR-Fab5 Complex

Figures 2A, 2B, 2C:
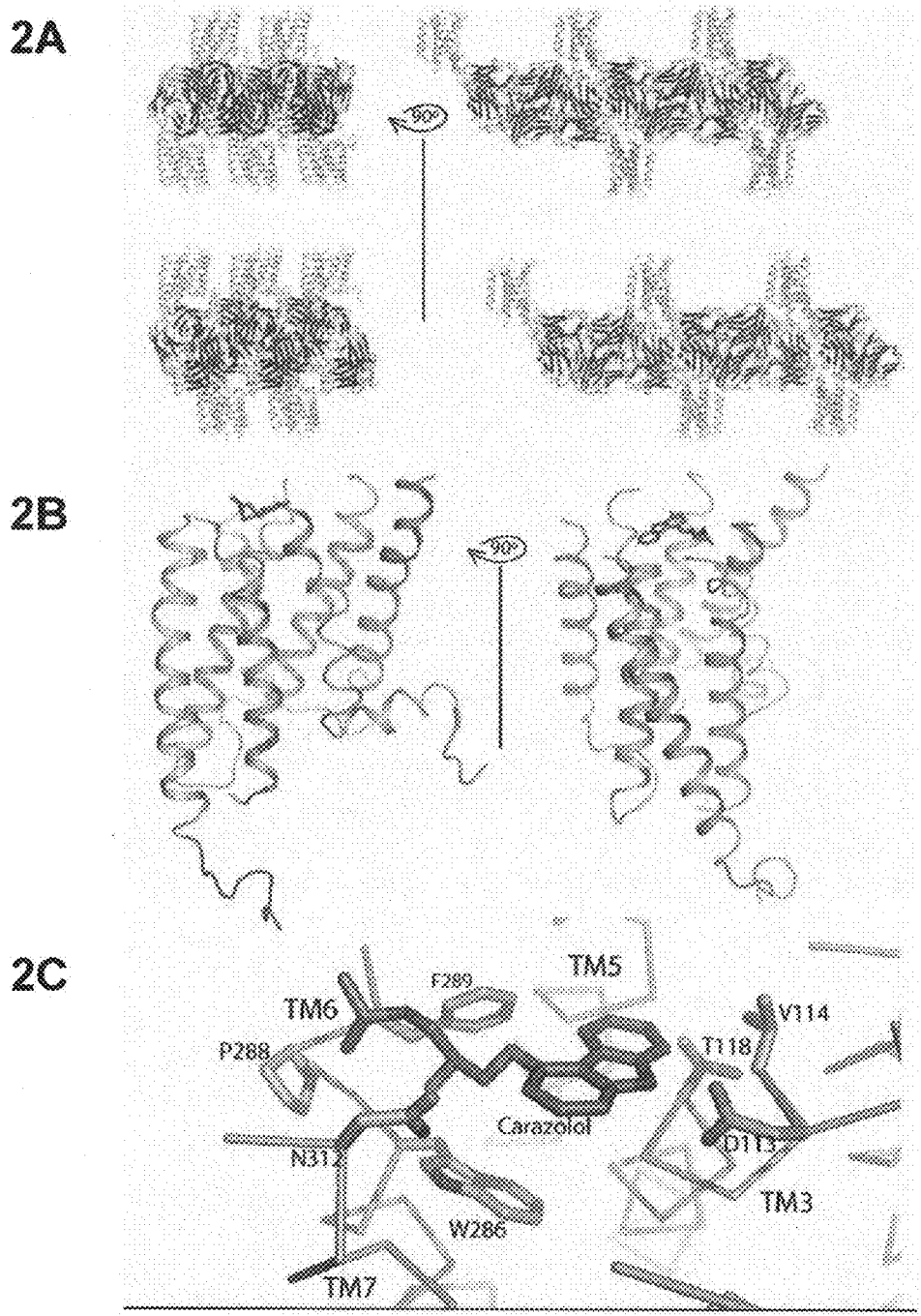
FIGS. 2A-2C. Structure of the β₂AR365-Fab5 complex. 2A, Packing of β₂AR365-Fab5 complex in crystals formed in DMPC bicelles (β₂AR—gold, heavy chain—blue, light chain—red). 2B, Structure of the β₂AR showing sites of the interactions with Fab5. Sites of specific (idiotypic) interactions between Fab5 and the β₂AR are shown in green. Sites of interactions between the β₂AR and the constant region of Fab5 of the symmetry mate are shown in magenta. Dotted gray lines indicate predicted membrane boundaries. Solid black lines indicate extracellular connections between transmembrane segments. 2C, $F_o$-$F_c$ map contoured at 2.0σ surround by residues know to be involved in ligand binding.

FIG. 2A shows the packing of the $\beta_2$AR365-Fab5 complex in the crystals. The crystals appear to be formed from stacks of two-dimensional crystals as previously reported for bacteriorhodopsin crystallized in bicelles. There are few contacts between adjacent receptor molecules within a bicelle layer, indicating that the receptor is monomeric in the crystal. Purified $\beta_2$AR exists as a monomer, and monomeric $\beta_2$AR reconstituted into recombinant high density lipoprotein particles couples efficiently to Gs, it's preferred heterotrimeric G protein.

Figure 6:
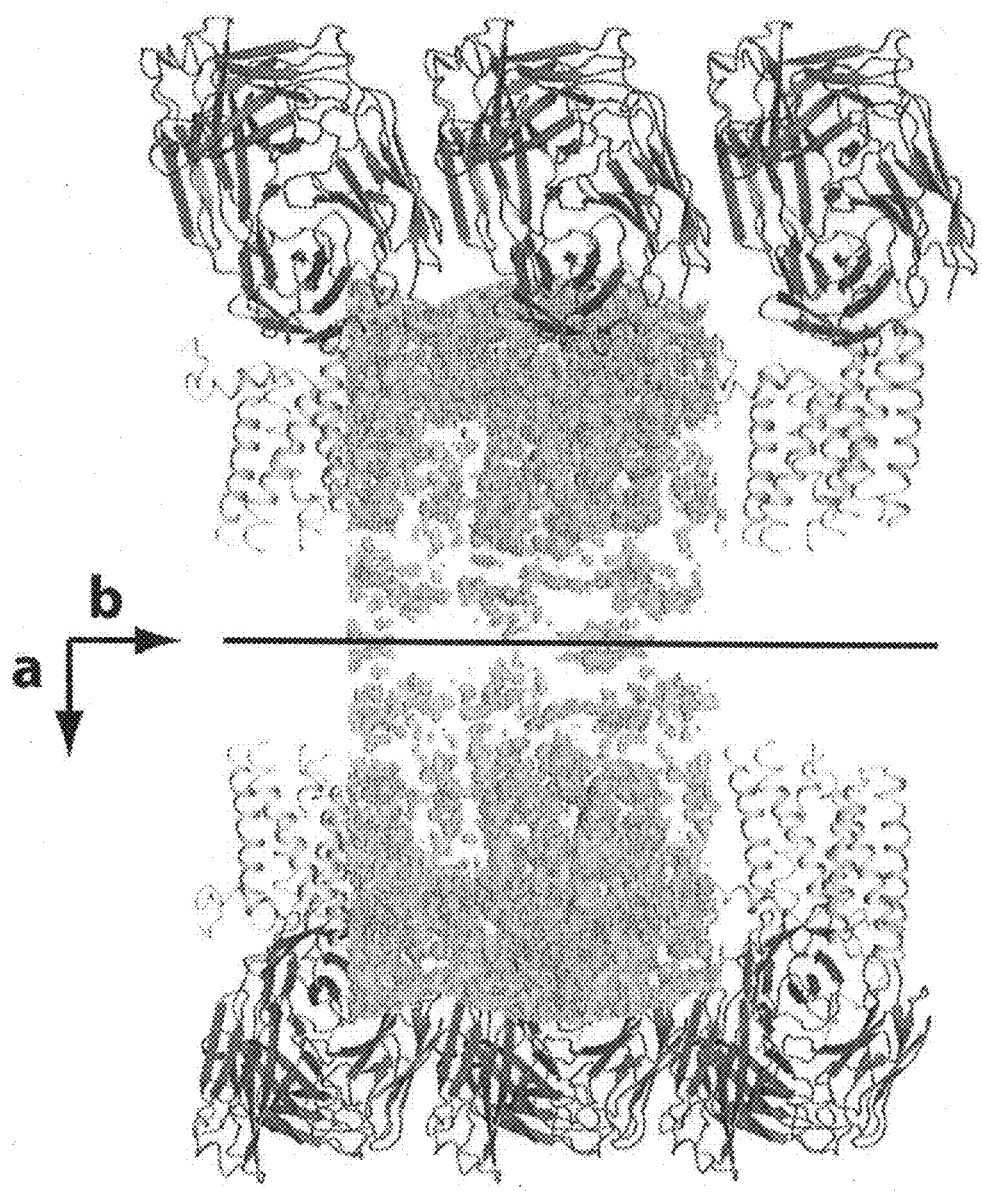
FIG. 6. Weak electron density in the extracellular region of the β₂AR. The final $2F_o$-$F_c$ map (grey mesh, contoured at 0.7σ) around two receptor molecules packed across the crystallographic twofold (b) axis (horizontal line). The view is the same as the left panel of FIG. 2A.

The best resolved regions of the crystal are the Fab5 fragments and cytoplasmic ends of the TM segments of the receptor (FIG. 5). In contrast to the cytoplasmic side of the receptor, the electron density is poor in the extracellular domain (FIG. 6), even though this region of two receptor molecules packs together in a head-to-head manner around the crystallographic twofold axis. The poor packing in this interface likely explains the significant anisotropy and overall low resolution of the crystals. In an effort to improve the order of the extracellular domains, we further modified $\beta_2$AR365 by inserting a TEV cleavage site after amino acid 24 ($\beta_2$AR24/365, FIG. 1). However, crystals of this construct are isomorphous to those made with $\beta_2$AR365, and the structure (Table 1) is virtually identical to that obtained from $\beta_2$AR365-Fab5.

As expected, the overall structure of the $\beta_2$AR (FIG. 2b) is similar to rhodopsin with seven TM helices and an eighth helix that runs parallel to the cytoplasmic face of the membrane. Several of the TM helices are broken by non-helical kinks, most prominently TM7. Residues not included in the $\beta_2$AR model due to absent or uninterpretable electron density are indicated in FIG. 1. In the transmembrane helices, the majority of the missing side chains face the lipid environment. The loss of electron density occurs just above the ligand-binding site near the predicted lipid-water interface, suggesting that ligand binding and/or the lipid environment contributes to the order of the TM segments. Specific interactions between the variable domains of Fab5 and the $\beta_2$AR occur over a sequence of nine amino acids at the amino terminal end of intercellular loop 3 (I233-V242 of SEQ ID NO:1) and two amino acids at the carboxyl terminal end (L266 and K270 of SEQ ID NO:1) (shown in green in FIG. 2b). Therefore, Fab5 recognizes a three-dimensional epitope on the $\beta_2$AR, which is in agreement with the observation that Fab5 binds to native, but not denatured $\beta_2$AR protein. Additional lattice contacts occur between the constant domain of a symmetry-related Fab5 molecule and the second intracellular loop of $\beta_2$AR (shown in magenta in FIG. 2b).

EXAMPLE 10

Implications of the Carazolol-Bound $\beta_2$AR Structure for Receptor Activation The ligand-binding site can be identified by an extended flat feature in the electron density maps close to the extracellular side of the transmembrane helices (FIGS. 2B and 2C). This is the only large feature in residual electron density maps and is adjacent to Asp113, V114, Phe 289, Phe290 and Asn 312 of SEQ ID NO:1, residues identified from mutagenesis studies as being involved in ligand binding in the $\beta_2$AR. This region corresponds to the retinal-binding site of rhodopsin. The weak electron density in this region precludes definitive modeling of carazolol. It is unlikely that the crystallization conditions resulted in dissociation of carazolol from $\beta_2$AR. Carazolol bound to the $\beta_2$AR has a distinct fluorescence emission spectrum, and $\beta_2$AR crystals and associated protein precipitate harvested from equilibrated hanging-drops showed no significant loss of carazolol binding as detected fluorescence spectroscopy (data not shown).

Figures 3A, 3B:
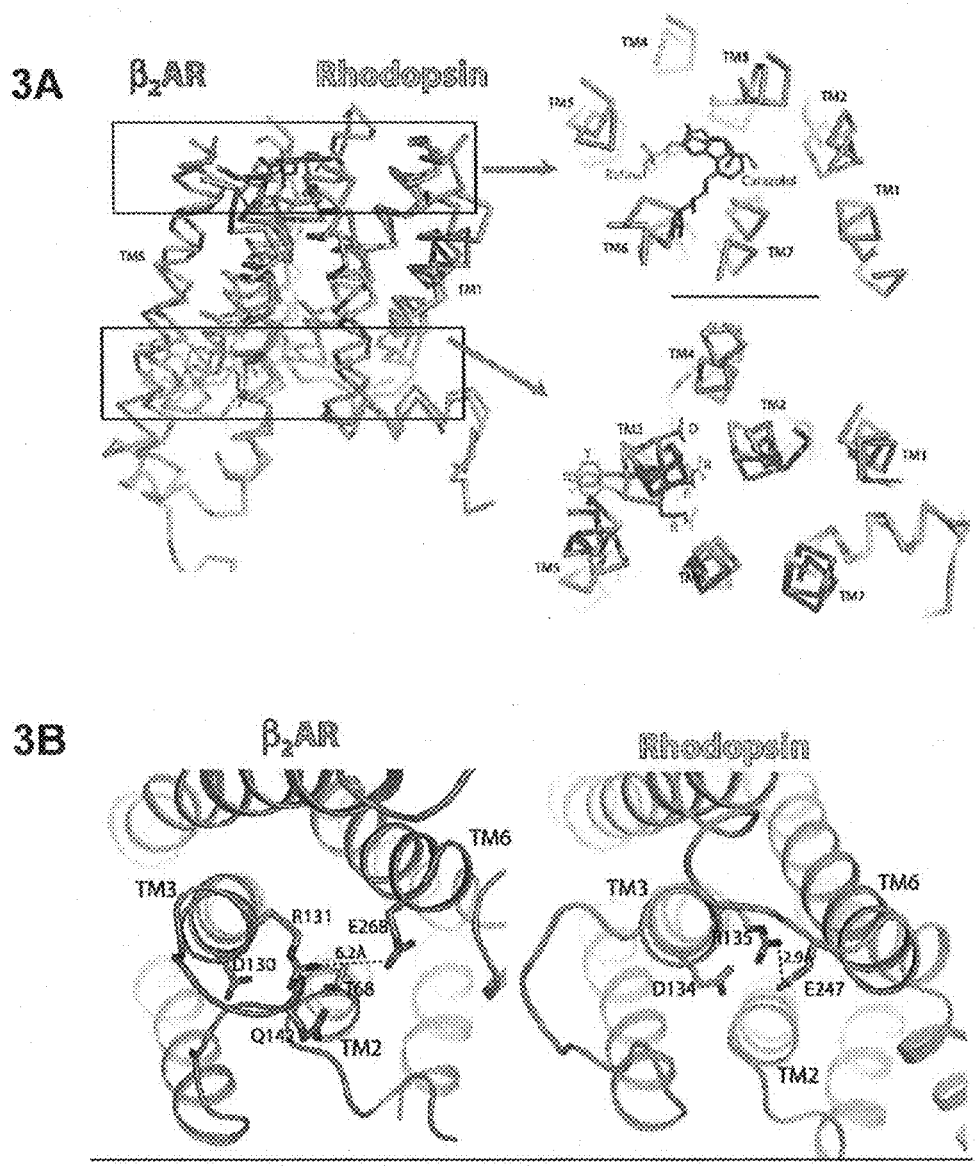
FIGS. 3A and 3B. Comparison of β₂AR and rhodopsin structures. 3A, The β₂AR is superimposed with the homologous structure of rhodopsin. Retinal is shown in purple and the electron density in the putative ligand binding site is shown as a green mesh. Structures were aligned using all seven TM segments. 3B, Comparison of the β₂AR with structures of inactive rhodopsin and light activated rhodopsin around the conserved E/DRY sequence in TM3. A dashed line shows the distance between the homologous arginine in TM3 and glutamate in TM6. To facilitate comparison of the E/DRY regions, the structures were aligned by superimposing TM3 only.
Figure 8:
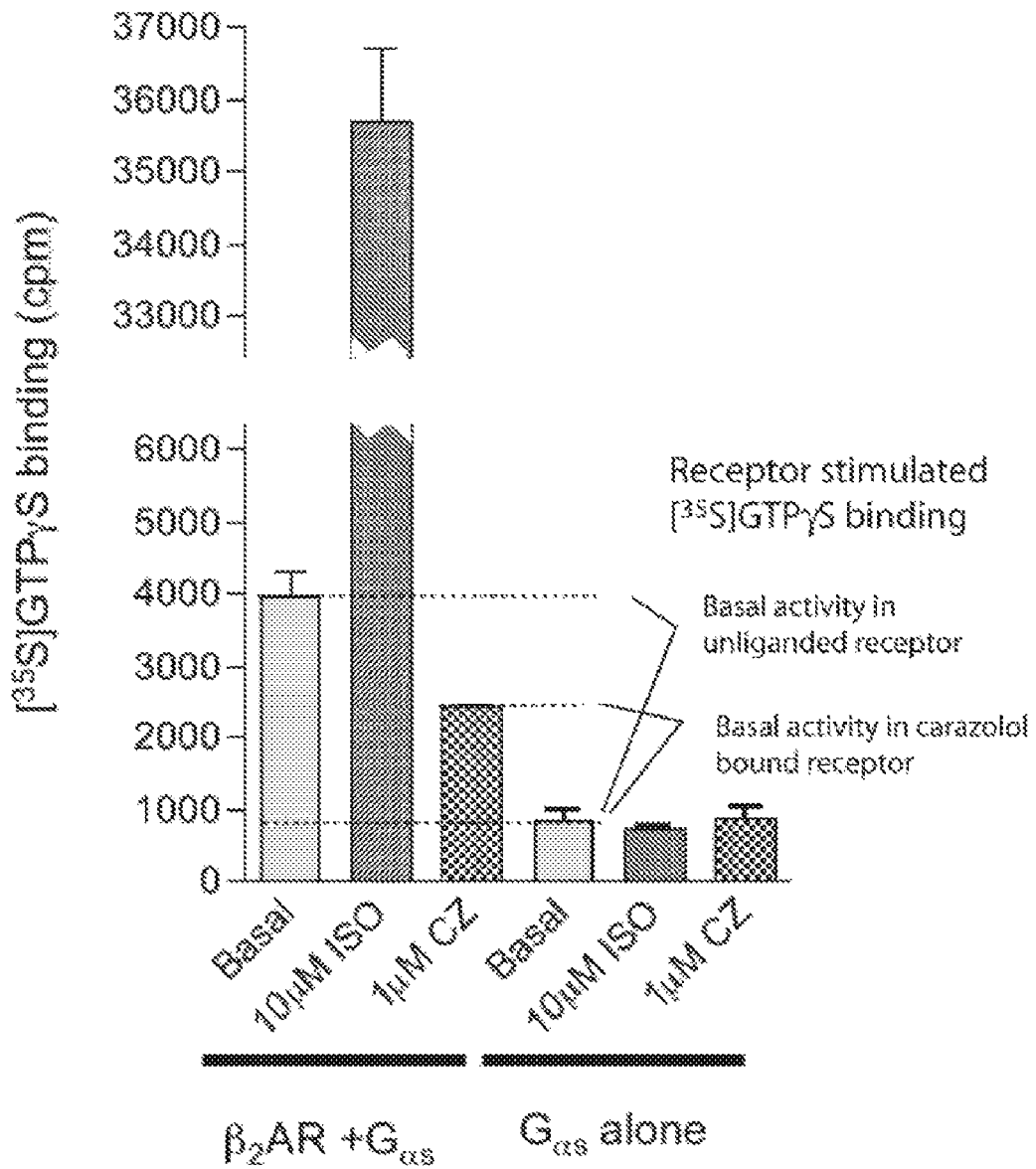
FIG. 8. Basal activity of carazolol-bound $\beta_2$AR. Purified Gs was reconstituted into phospholipid vesicles in the presence and absence of purified $\beta_2$AR. [$^{35}$S]GTPγS binding was measured in the absence of ligand, the presence of the agonist isoproterenol or the inverse agonist carazolol. Basal activity is determined relative to [$^{35}$S]GTPγS binding to Gs in the absence of $\beta_2$AR.

FIG. 3 shows a comparison of transmembrane segments of the $\beta_2$AR superimposed with the homologous structure of rhodopsin. The root mean square deviation for the alpha carbon backbone of the TM segments is 1.56 Å. While the overall arrangement of the TM segments is similar, the $\beta_2$AR has a more open structure. The difference in the arrangement of the cytoplasmic ends of the TM segments of $\beta_2$AR and rhodopsin may provide structural insights into basal receptor activity. Rhodopsin has no detectable basal activity, a feature essential for vision. In contrast, even when bound to the inverse agonist carazolol, the comparatively high basal activity of the $\beta_2$AR is suppressed by only 50% (FIG. 8). Therefore, the carazolol bound $\beta_2$AR is not functionally equivalent to dark rhodopsin. FIG. 3b compares the $\beta_2$AR and two rhodopsin structures at the level of the conserved (E/D)R(Y/W) sequence (found in 72% of rhodopsin family members).

In the high resolution structure of inactive (dark) rhodopsin, E134 and R135 in TM3 and E247 in TM6 form a network of hydrogen bonds and charge interactions referred to as the ionic lock (Ballesteros et al, J. Biol. Chem. 2001 276, 29171-7). These interactions maintain rhodopsin in an inactive conformation. The ionic lock residues appear to play a similar role in the β$_2$AR as mutations of these amino acids in the β$_2$AR or other adrenergic receptors lead to constitutive activity (Ballesteros et al, J. Biol. Chem. 2001 276, 29171-7; Scheer et al, Mol. Pharmacol. 2000 57: 219-31). Moreover, evidence from biophysical studies suggests that movement of the cytoplasmic end of TM3 relative to TM6 upon activation is similar for the β$_2$AR and rhodopsin. However, as shown in FIG. 3b, the TM segments of the β$_2$AR have a more open structure in this region, and R131 in carazolol-bound β$_2$AR is not close enough to E268 to form a hydrogen bond. The structure of carazolol bound β$_2$AR around the ionic lock is more similar to the structure of light activated rhodopsin (FIG. 3b), where R135 and E247 are separated by 4.1 Å. This light activated rhodopsin structure may not represent the fully active conformation, since the spectral properties of these crystals are similar, but not identical to those of metarhodopsin II. Nevertheless, given the role of TM3, TM6 and the adjacent cytoplasmic loops in G protein coupling, the more open structure of the β$_2$AR may account for the residual basal activity of the β$_2$AR bound to the inverse agonist carazolol.

It is unlikely that the observed structural differences between the β$_2$AR and rhodopsin are due to distortion of the β$_2$AR due to interactions between Fab5 and the third intracellular loop, since binding of Fab5 had no effect on agonist or antagonist binding affinity, and does not effect agonist-induced movement of TM3 relative to TM6. However, we cannot exclude the possibility that crystal packing interactions between Fab5 and the second extracellular loop (FIG. 2b) contribute to these structural differences.

Figure 4:
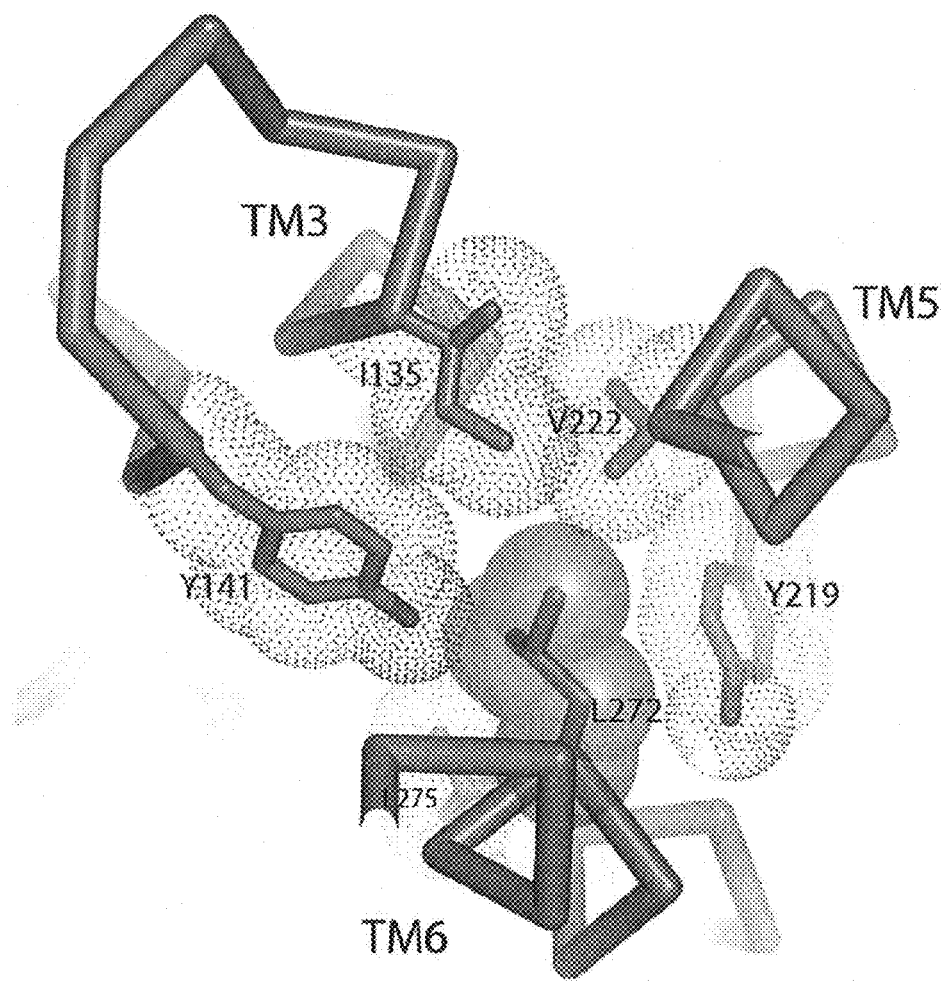
FIG. 4. Side chain interactions between Leu 272 and residues in TM3, TM5 and intracellular loop 2. Packing interactions are reflected in lower B-factors for these amino acids. The average B value of residues 136, 141, 219, 222, 272, and 275 is 117 Å², compared to 157 Å² for the receptor as a whole.
Figure 7A:
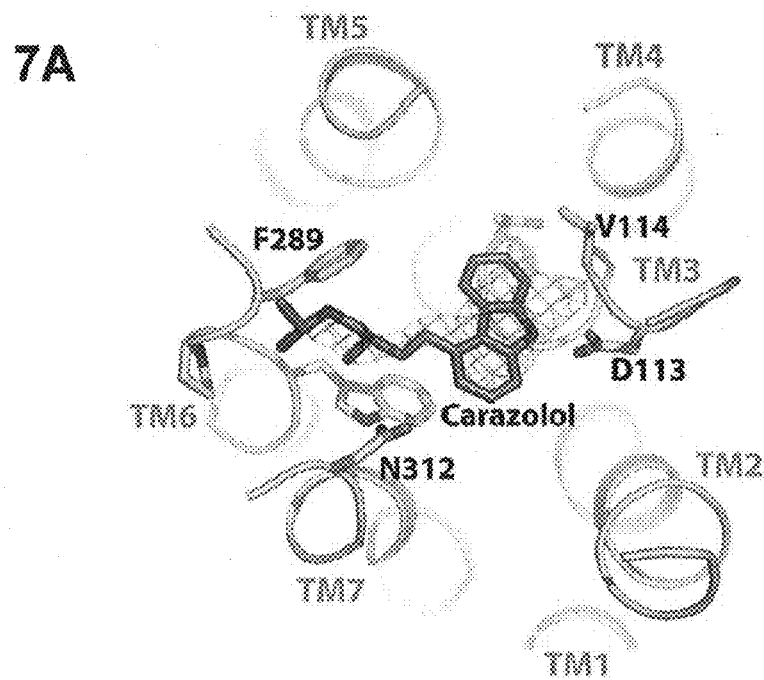
FIGS. 7A and 7B. $F_o$-$F_c$ omit map, contoured at 2.7σ, made by deleting all side chain atoms from D130, R131 and E268 and refining the structure.
Figure 7B:
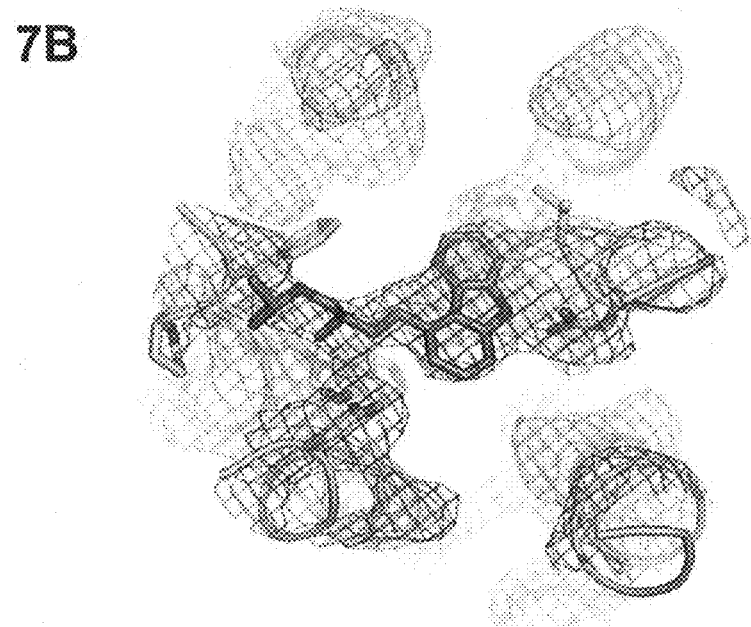

Another set of intramolecular interactions known to be important for minimizing the basal activity of the β$_2$AR involve L272 in TM6. Mutation of L272 to alanine was the first reported constitutively active mutant of the β$_2$AR (Samama et al, J. Biol. Chem. 1993 268, 4625-36). As seen in FIG. 4, L272 forms extensive van der Waals interactions with 1135 in TM3, V222, F223 and Y219 in TM5, and Y141 in intracellular loop 2 (FIG. 4, FIG. 7). Since L272 is adjacent to E268, disruption of the packing interactions by mutation to alanine may have an effect similar to disruption of the ionic lock in rhodopsin. It is likely that this mutation would produce a more loosely packed, dynamic structure in this region, shifting the equilibrium towards a more active state.

Packing interactions around L272 are observed while the ionic lock interactions appear to be absent. Since mutation of either E268 or L272 leads to elevated basal activity, it is likely that both are involved in maintaining the basal state of the receptor. From the current structure we can conclude that formation of the ionic lock and the tight packing of L272 are not interdependent, and might even be structurally incompatible. In certain cases it is possible that the ionic lock and L272 interactions stabilize two of several distinct substrates in the unliganded β$_2$AR, and that these two substrates have lower activity towards Gs than the others. Carazolol binding may further stabilize the substrates favoring packing around L272 and therefore reduce basal activity relative to the ensemble of substrates in the unliganded receptor. The residual activity in the carazolol bound receptor may be due to the failure to stabilize ionic lock interactions.

---

What is claimed is:

1. A method comprising:
   generating a three dimensional model of a human β₂ adrenoreceptor using a physical computer readable medium comprising the atomic coordinates for said human β₂ adrenoreceptor as set forth in Table 2;
   computationally identifying a compound that binds to the ligand binding site of said human β₂ adrenoreceptor using said three dimensional model, wherein said ligand binding site contains Asp113, V114, Phe 289, Phe290 and Asn 312 of SEQ ID NO:1
   synthesizing said compound;
   testing said compound to determine if it modulates an activity of said receptor.

2. The method of claim 1, wherein said testing comprises testing said compound to determine if it activates said human β₂ adrenoreceptor.

3. The method of claim 1, wherein said testing comprises testing said compound to determine if it inhibits said human β₂ adrenoreceptor.

4. The method of claim 1, wherein said computationally identifying employs a docking program that computationally tests known compounds for binding to said human β₂ adrenoreceptor.

5. The method of claim 1, wherein said computationally identifying comprises designing a compound that binds to said human β₂ adrenoreceptor.

6. The method of claim 1, wherein said computationally identifying comprises computationally testing a known ligand of human β2 adrenoreceptor for binding to said human β₂ adrenoreceptor.

* * * * *

UNITED STATES PATENT AND TRADEMARK OFFICE
CERTIFICATE OF CORRECTION

PATENT NO. : 7,912,654 B2
APPLICATION NO. : 12/283988
DATED : March 22, 2011
INVENTOR(S) : Brian K. Kobilka It is certified that error appears in the above-identified patent and that said Letters Patent is hereby corrected as shown below:

In the Specification:

- In column 1 lines 5-11: Please delete the paragraph starting with "This work" ending with "in this invention." and replace with the following paragraph:

--This invention was made with Government support under contracts GM082028, GM056169 and under contract NS028471 awarded by the National Institutes of Health. The Government has certain rights in this invention.--

Signed and Sealed this
Twenty-eighth Day of August, 2012

David J. Kappos
*Director of the United States Patent and Trademark Office*

SEQUENCE LISTING

```
<160> NUMBER OF SEQ ID NOS: 3

<210> SEQ ID NO 1
<211> LENGTH: 216
<212> TYPE: PRT
<213> ORGANISM: Artificial Sequence
<220> FEATURE:
<223> OTHER INFORMATION: Synthetic protein

<400> SEQUENCE: 1

Gly Ile Ala Ala Ser Ala Ile Val Ala Ala Val Ala Gly Asn Val
 1               5                  10                  15

Ala Val Ile Thr Ala Ile Ala Phe Glu Arg Leu Gln Thr Val Thr Asn
                20                  25                  30

Tyr Phe Ile Ala Ser Leu Ala Cys Ala Asp Leu Val Met Gly Leu Ala
            35                  40                  45

Val Val Pro Phe Gly Phe Ala Thr Ser Ala Asp Val Leu Cys Val Thr
        50                  55                  60

Ala Ser Ile Ala Thr Leu Cys Val Ile Ala Val Asp Arg Tyr Phe Ala
65                  70                  75                  80

Ile Thr Ser Pro Phe Lys Tyr Gln Ser Leu Leu Thr Ala Asn Lys Ala
                85                  90                  95

Arg Ala Ala Ala Ala Val Ala Ile Val Ser Gly Leu Thr Ser Ser
                100                 105                 110

Ile Val Ser Phe Ala Val Pro Leu Val Ile Met Val Phe Val Tyr Ser
            115                 120                 125

Arg Val Phe Gln Glu Ala Lys Arg Gln Leu Gln Lys Ile Asp Lys Ser
```

```
                130                 135                 140
Glu Gly Arg Phe His Val Phe Cys Leu Lys Glu His Lys Ala Leu Lys
145                 150                 155                 160

Thr Leu Gly Ile Ile Met Gly Thr Phe Thr Leu Cys Trp Leu Pro Phe
                165                 170                 175

Phe Ile Leu Asn Ala Ile Gly Tyr Val Ala Ala Gly Ala Asn Pro Leu
                180                 185                 190

Ala Ala Cys Arg Ser Pro Asp Ala Arg Ile Ala Phe Gln Glu Leu Leu
                195                 200                 205

Cys Leu Arg Arg Ser Ser Leu Lys
210                 215

<210> SEQ ID NO 2
<211> LENGTH: 217
<212> TYPE: PRT
<213> ORGANISM: Mus musculus

<400> SEQUENCE: 2

Glu Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ile Phe Thr Asp Tyr
                20                  25                  30

Tyr Ile Asn Trp Val Arg Gln Arg Thr Gly Gln Gly Phe Glu Trp Ile
                35                  40                  45

Gly Glu Ile Tyr Pro Gly Ser Gly Asn Ile Asp Tyr Asn Glu Arg Phe
            50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Val Arg Gly Phe Gly Tyr Trp Gly Gln Gly Thr Thr Leu Thr Val Ser
                100                 105                 110

Ser Ala Lys Thr Thr Pro Pro Ser Val Tyr Pro Leu Ala Pro Gly Ser
                115                 120                 125

Ala Ala Gln Thr Asn Ser Ala Val Thr Leu Gly Cys Leu Val Lys Gly
            130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
                180                 185                 190

Val Thr Cys Asn Val Ala His Pro Ala Ser Ser Thr Lys Val Asp Lys
                195                 200                 205

Lys Ile Val Pro Arg Asp Cys Gly Cys
            210                 215

<210> SEQ ID NO 3
<211> LENGTH: 214
<212> TYPE: PRT
<213> ORGANISM: Mus musculus

<400> SEQUENCE: 3

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30
```

-continued

```
Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ile Gly
    50                  55                  60

Thr Gly Ser Gly Gln Asp Tyr Ser Leu Thr Ile Ser Ser Leu Asp Tyr
65                  70                  75                  80

Ala Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
        195                 200                 205

Phe Asn Arg Asn Glu Cys
        210
```